(12) United States Patent
Ernst et al.

(10) Patent No.: US 7,947,277 B2
(45) Date of Patent: May 24, 2011

(54) WNT ANTAGONISTS AND THEIR USE IN THE DIAGNOSIS AND TREATMENT OF WNT-MEDIATED DISORDERS

(75) Inventors: James A. Ernst, San Francisco, CA (US); Paul Polakis, Mill Valley, CA (US); Bonnee Rubinfeld, Danville, CA (US); Venita I. DeAlmeida, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 11/851,596

(22) Filed: Sep. 7, 2007

(65) Prior Publication Data

US 2008/0299136 A1      Dec. 4, 2008

Related U.S. Application Data

(60) Provisional application No. 60/951,175, filed on Jul. 20, 2007, provisional application No. 60/825,063, filed on Sep. 8, 2006.

(51) Int. Cl.
*A61K 38/01*   (2006.01)
*A61K 38/00*   (2006.01)
*C07K 19/00*   (2006.01)
*A61K 39/385*  (2006.01)

(52) U.S. Cl. .................. 424/179.1; 424/194.1; 514/19.3; 530/389.7

(58) Field of Classification Search ........................ None
See application file for complete search history.

(56) References Cited

U.S. PATENT DOCUMENTS

| | | |
|---|---|---|
| 6,433,155 B1 | 8/2002 | Umansky et al. |
| 6,660,843 B1 | 12/2003 | Feige et al. |
| 7,091,321 B2 | 8/2006 | Gillies et al. |
| 7,723,477 B2 | 5/2010 | Gurney et al. |
| 7,803,783 B2 | 9/2010 | Lee et al. |
| 2002/0187502 A1 | 12/2002 | Waterman et al. |
| 2003/0040051 A1 | 2/2003 | Bhanot et al. |
| 2004/0171559 A1* | 9/2004 | Weissman et al. .............. 514/27 |
| 2004/0203003 A1 | 10/2004 | Rhee et al. |
| 2004/0247593 A1 | 12/2004 | He et al. |
| 2005/0096263 A1 | 5/2005 | Keay et al. |
| 2005/0191673 A1 | 9/2005 | Schlegel et al. |
| 2008/0194457 A1 | 8/2008 | Wands et al. |
| 2009/0074777 A1 | 3/2009 | Wands et al. |

FOREIGN PATENT DOCUMENTS

| | | |
|---|---|---|
| WO | 01/98354 A2 | 12/2001 |
| WO | 02/088081 | 11/2002 |
| WO | 02/092635 A2 | 11/2002 |
| WO | 03/004045 | 1/2003 |
| WO | 2004/032838 A2 | 4/2004 |
| WO | 2004/042028 A1 | 5/2004 |
| WO | 2006/034328 | 3/2006 |
| WO | 2006/036173 A2 | 4/2006 |
| WO | 2006/036175 | 4/2006 |
| WO | 2006055635 | 5/2006 |

OTHER PUBLICATIONS

Hsieh et al., Biochemical characterization of Wnt-Frizzled interactions using a soluble, biologically active vertebrate Wnt protein, Proc. Natl. Acad. Sci. USA vol. 96, 3546-3551, 1999.*
Recombinant mouse frizzled-4/Fc chimera description from R&D Systems (Cat No. 194-FZ, Nov. 10, 2005).*
Blumenthal et al., "The Wingless homolog WNT5A and its receptor Frizzled-5 regulate inflammatory responses of human mononuclear cells induced by microbial stimulation" *Blood Journal* 1(3):965-973 (Aug. 1, 2006).
Yamashita et al, "Prospective identification of cardiac progenitors by a novel single cell-based cardiomyocyte induction" *FASEB Journal* 19(9):1-29 (Jul. 2005).
Yamashita et al., "Prospective identification of cardiac progenitors by a novel single cell-based cardiomyocyte induction" *The FASEB Journal- FJ Express* 19(9):1534-1536 (Sep. 2005).
De Almeida, et al., "The soluble wnt receptor Frizzled8CRD-FC inhibits the growth of teratocarcinomas in vivo" *Cancer Research* 67(11):5371-5379 (Jun. 2007).
Kawano, et al., "Secreted anatagonists of the Wnt signaling pathway" *J Cell Science* 116:2627-2634 (2003).
Kirikoshi et al., "Molecular Cloning and Characterization of Human Frizzled-4 on Chromosome 11q14-q21" *Biochem. & Biophys. Res. Comm.* 264:955-961 (Nov. 1999).
Zi, et al., "Expression of Frzb/Secreted Frizzled-Related Protein 3, a secreted Wnt antagonist, in human androgen-independent prostate cancer PC-3 cells suppresses tumor growth and cellular invasiveness" *Cancer Research* 65(21):9762-9770 (Nov. 2005).
Anonymous, "Recombinant Mouse Frizzled-1/Fc Chimera, Catalog No. 1120-FZ" *R&D Systems Product Sheet* (*Online*) (Retrived from the internet: http://rndsystems.com/pdf/1120-fz.pdg) (Mar. 20, 2006).
Holcombe et al., "Expression of Wnt ligands and frizzled receptors in colonic mucosa and in colon carcinoma" *Molecular Pathology* 55(4):220-226 (Aug. 2002).
Milovanovic et al., "Expression of Wnt genes and frizzled 1 and 2 receptors in normal breast epithelium and infiltrating breast carcinoma" *International Journal of Oncology* 25(5):1337-1342 (Nov. 2004).
Nakamura et al., "A Wnt- and beta-catenin-dependent pathway for mammalian cardiac myogenesis" *Proceedings of the National Academy of Sciences of USA, National Academy of Science*, Washington, DC 100(10):5834-5839 (May 13, 2003).
PCT/ISA *International Search Report* pp. 1-9 (Sep. 19, 2008) for PCT/US2007/077845, Jun. 23, 2009.
Polakis, Paul, ""Evidence for Wnt Signalling in Cancers lacking Genetic Defects" Therapeutic Opportunities of the Wnt Signalling Pathway in Cancer" *NYAS eBriefings Online Adobe Flash Presentation* (http://nyas.org/ebriefreps/ebrief/00541/presentations/polakis/player.html) pp. 1-54 (Oct. 25, 2005).

* cited by examiner

*Primary Examiner* — Elly-Gerald Stoica

(57) ABSTRACT

The present invention provides for chimeric Wnt antagonists comprising a Frz domain component derived from a Frizzled protein, a secreted Frizzled related protein or Ror protein and an Fc immunoglobulin component, and their use in the treatment and diagnostic detection of cellular Wnt signaling and Wnt-mediated disorders, including cancer.

13 Claims, 59 Drawing Sheets

Alignment of Pro-Frz Extracellular Domains

Alignment of Mature Frz Extracellular Domains

FIG. 3B-2

Frz (173)-Fc Construct

MEWGYLLEVTSLLAALAVLQRSSGAAAASAKELACQEITVPLCKGIGYNYTYMPN
QFNHDTQDEAGLEVHQFWPLVEIQCSPDLKFFLCSMYTPICLEDYKKPLPPCRSV
CERAKAGCAPLMRQYGFAWPDRMRCDRLPEQGNPDTLCMDYNRTD LTTAAPSPPR
RLPPPPP LESGGGGVT DKTHTCPPCPAPELLGGPSVFLFPPKPKDTLMISRTPE
VTCVVVDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRWQQGNVF
SCSVMHEALHNHYTQKSLSLSPGK

FIG. 4A

Frz (156)-Fc Construct

MEWGYLLEVTSLLAALAVLQRSSGAAAASAKELACQEITVPLCKGIGYNYTYMPN
QFNHDTQDEAGLEVHQFWPLVEIQCSPDLKFFLCSMYTPICLEDYKKPLPPCRSV
CERAKAGCAPLMRQYGFAWPDRMRCDRLPEQGNPDTLCMDYNRTDLESGGGGVTD
KTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNHYTQKSL
SLSPGK

FIG. 4B

Frz1-Fc (SEQ ID NO: 115)
ATGGGGGGACTGCCGCCAGGTTGGGGGCCGTGATTTGTTTGTCGTCATAGTGGGCCTCCGCGGCAAAATGATGAGGAGGCAGCGGGGACCCGG
TGGCCGCCGCCGCCAGTTGACCCCCGGCCAGTTGGGCCCGCTGCTGCCCGCGCCCAGCAGCAACAGAGAGCGGGCAACAGCAGTACAACCTGCTGGAGAGGCCGAGCGGGGCATCTCCGTC
CGGGCCAGGGGCCAGGCCAGGGGCCTATTGCCAGGCTGCCAGCCATCTCCATCCGCTGTGCACGGACATCCGTGAGCTCCAACTCATGCCCAGCTACAACCAGCCATCATGCCCGTGCTCCGTGGGCCACACAGACCAGGAGGACGC
CGGCCACGGCACGGCTATTGCCAGGCTGCCACCAGTTCTACCCCTCTAGTGAAGTGCAGTGTTCCGCTGAGCTCAAGTTCTTCCTGTGCTCCATGTACGCCGTGTGCACCGTGCTAGAGC
AGGCGCTGCGCGCCGCCCTGCCCGTCCCGTGCGCGAGCGCGCGCCAGGGCTGCGAGGCCGACAAGGCTGCCCGAGAACAAGTTCGGCTTCCAGTGGCCCAGACACGCTCAAGTGTGAGAAG
TTCCCGGTGCACGGCCGCCGGCGAGCTGTGCGTGGGCGACCGTCAGTCTTCCTCTTCCCCCAAAACCAAGGACACCTCCAATGCGACCCTCATGACTCCGAAGACAAAGCCGGCGTCACATGCGTGG
ACCGTGCCCAGCGTGAGCGCACGGACCCTGAACTCCTGGGAGGTCAAGTTCAACTGGTACGTGGACGGCGTGGAGGTGCATAATGCCAAGACGAAGCCGCGGGAGGA
TGGTGGACGTGTGGTGGTCAGCGTGCTGACCGTCCTGCACCAGGACTGGCTGAATGGCAAGGAGTACAAGTGCAAGGTCTCCAACAAAGCCCTCCCAGCCCCCATCGAGAA
AACCATCTCAAAGGCCAAAGGCCAGCCCCGAGAACCACAGGTGTACACCCTGCCCCCATCCCGGGAGAGATGACCAAGAACCAGGTCAGCCTGACCTGCCTGGTCA
AAGGCTTCTATCCCAGCGACATCGCTGTGGAGTGGGAGAGCAATGGGCAGCCGGAGAACAACTACAAGACCACGCCTCCCGTGCTGGACTCCGACGGCTCCTTCTTC
CTCTACAGCAAGCTCACCGTGGACAAGAGCAGGTGGCAGCAGGGGAACGTCTTCTCATGCTCCGTGATGCATGAGGCTCTGCACAACCACTACACGCAGAAGAGCCCT
CTCCCTGTCTCCGGGTAAA

Frz2-Fc (SEQ ID NO: 116)
ATGGGGGGACTGCCGCCCAGGTTGGGGGCCGTGATTTGTTTGTCGTCATAGTGGGCCCTCCATGGGTCCGCGGCAAAATGATGCTGAGGGGCCAGTTCCACGG
GGAGAAGGGCCATTCCGAGAGGGCCTTCCCCGGACACCGGAATCCCGCTGTGCACGGACATCCGCTGCTACAACCAGACCATCCTCGCCGACACCATCATGCCCAGCTTCTGGGCC
ACACGAACCAGGAGGACGCCAGGCCTAGAGGTTGCACCAGGCGCCTCTATCGCTGGTCAGGTGCAGTGCTCGCCCGAACCTGCGCTTCTCGCTCCATGTACCGCACCC
GTGTGCACCGTGCTGGAACAGGCGACATCCGCCATCCCGGCGCGCGCCAGGGTCGCTCAGTCAGTTCTTCCTCTTTCCCTCTTCCCCAAAAACCCAAGGACACCCCTCATGATCTCCCGGACCCCTGAG
CTACTCGTGGTGCGTGGTGTGCCCTGTGAAGGTCAGCGGGCACCGGTGGACGGCGTGAAGGTCCATGAATGCCAAGACAAAGCCGCGGGAGGA
GTCACATGCCGTGGTGGTCAGCCATGCTGACCGTCCTGCACCAGGACTGGCTGAATGGCAAGGAGTACAAGTGCAAGGTCTCCAACAAGCCCCCTCCCAG
GCAGTACACAACAGCACGTACCCGTGTGCCAAAGCCAAAGGGCCAGCCCCGGAGAACCACACGGTCATACCCCGGGAAGAGATGACCAAGAACCAGGTCAGCCTG
ACCTGCCTGGTCAAAGGCTTCCTTCCTACAGCGACATCCGCAGTGAGTGGGAGAGCAATGGCGCAGCCGGGAGAACAACTACAAGACCACGCCTCCCGTGCTGGACTCCGA
CGGCTCCTTCTTCCTCTACAGCAAGCTCACCGTGGACAAGAGCAGGTGGCAGCAGGGAACGTCTTCTCATGCTCCGTGATGCATGAGGCTCTGCACAACCACTACA
CGCAGAAGAGCCCTCTCCCTGTCTCCGGGTAAA

*FIG. 5A*

Frz3-Fc (SEQ ID NO: 117)

```
ATGGGGGGACTGCCGCCAGGTTGGGGCCGTGATTTTGTTTGTCGTCATAGTGGCCTCCATGGGTCCGCGGCAAAATCGATGCTCGAGGCCACTCCCTGTTCAG
CTGTGAGCCAATCACCCTTCGAATGTGCAGGATCTGCCTTCATGCTCCTAATCTGCTCAATCACTACGAGCCAGCAAACTGCTGCCTTGGCAATGG
AGCCCTTCCACCCTATGGTCAACCTGGACTGTAGCAGGACTTACAGTGGAGTCAGCAGCTTACAGTGGAGTGAGTCTGGACATTGTGTAGGAGTACGGCCGTGACATTGCCT
TGTAGGAGGCTGTGTCAGCGAGCTTACAGTGGAGTGCAGCAAACTTATGGAAACTGTTTGGCGTCCCCTGGCCAGAAGATATGGAGTGCAGTCGGTTCCAGACTGTGA
CGAGGCCATAACCTAGACTGGTTGATCTCCTCGAGTCAGGAGGACACCCCTCATGATCTCCCGGACAAAGCGCGGGAGGAGCAGCCCTCCCCAGGACCCCGTGGGGGAC
CGTCAGTCTTCCTCTTCCCCAAAACCAAGGACTGTGAGGCGTGGACGCCGTGGACGGCCACGAAGACCCTGAGGTC
AAGTTCAACTGGTACGTGGACGGCGTGGAATGGCAAGGAGTACAAGTGCAAGGTGCATAATGCCAAGACAAAGCCGCGGGAGGAGCAGTACAACAGCACGTAC
GCACCAGGACTGGCTGAATGGCAAGGAGTACAAGTGCAAGGTCTCCAACAAAGCCCTCCCAGCCCCCATCGAGAAAACCATCTCCAAAGCCAAAGGGCAGCCCCGAG
AACCACAGGTGTACACCCTGCCCCCATCCCGGGAGGAGATGACCAAGAACCAGGTCAGCCTGACCTGCCTGGTCAAAGGCTTCTATCCCAGCGATATCGCCGTGGAG
TGGGAGAGCAATGGGCAGCCGGAGAACAACTACAAGACCACGCCTCCCGTGCTGGACTCCGACGGCTCCTTCTTCCTCTACAGCAAGCTCACCGTGGACAAGAGCAGG
TGGCAGCAGGGGAACGTCTTCTCATGCTCCGTGATGCATGAGGCTCTGCACAACCACTACACGCAGAAGAGCCTCTCCCTGTCTCCGGGTAAA
```

Frz4-Fc (SEQ ID NO: 118)

```
ATGGCGGGGACTGCCCGCCAGGTTGGGGCCGTGATTTTTGTTTGTCGTCATAGTGGCCTCCATGGGTCCGCGGCAAAATCGATGCTCGAGGGTTCGGGGACGAGGA
AGAGCGGGCGGCTGCGACAACTTTCACACCGCTCATCCAGTGTCTTTCAGTCGTGTGAACCCGTCCAGCTGCCAGCCTCCAGCGCTCGCAGTTCTTCCTTTGTTCTGTTTATGTGCCAATGTGCACAGAGAAGATCAACATC
CCCATTGGGCCATGCGGGCACCACAGAACGACCACGAAGCCTGTGAACCCGTCGACAAGCTGCCGCGCTCTCTACTCTGTGCCACCGT
GCCCCACAGAACGACCACGAAGGACCGTCAGCGCTCAGTTCAACTGCCACCAAGGAGCCGGCAGCCAGCTGAGCTGGAGCAGCCCCGGAGACGCTGGTGGTG
GACGTGAGCCACGAAGACCCTGAGGTCAAGTTCAACTGGTACGTGGACGGCGTGGAAGTGCATAATGCCAAGACAAAGCCGCGGGAGGAGCAGTACAACAGCACGTA
CCGTGTGGTGAGCGTCCTCACCGTCCTGCACCAGGACTGGCTGAATGGCAAGGAGTACAAGTGCAAGGTCTCCAACAAAGCCCTCCCAGCCCCCATCGAGAAAACCA
TCTCCAAAGCCAAAGGGCAGCCCCGAGAACCACAGGTGTACACCCTGCCCCCATCCCGGGATGAGCTGACCAAGAACCAGGTCAGCCTGACCTGCCTGGTCAAAGGC
TTCTATCCCAGCGATATCGCCGTGGAGTGGGAGAGCAATGGGCAGCCGGAGAACAACTACAAGACCACGCCTCCCGTGCTGGACTCCGACGGCTCCTTCTTCCTCTA
CAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCC
TGTCTCCGGGTAAA
```

*FIG. 5B*

Frz5-Fc (SEQ ID NO: 119)

ATGGGGGGACTGCGCCAGTTGGGGGCCGTGATTTTGTGTTTGTCGTCATAGTGGGCCCTCATGGGTCCGCGGCAAAATGCTGATGCTGAGGGGCGTCCAAGGCCCC
GGTGTGCCAGGAAATCACGCTGCCCATGTGCCGCGCACATGCCAACCAGTTCAACCACGACACAGCTTCCGGCTGCCGATCACGCGCCATCTGTCCGACTACACAAGCGCTG
TGCACCAGTTCTGGCCGCTGGTGCCTGTGGAGATCAATGTCTCGCCCGGGACCTCGCCGCTTCTGCCGCTTCCTATGTCTACACGGCTTCGCCTGGCTGGACAAAGCTGCGGACGGCCCTCCCGGT
CCGCCCAGTTCTCGCCGCTCGGTGTGCGAGTGCGAGAGCTGCTCGCCGTGATGCGCAGTACGGCTTCGCGTGATGAGCTGCGGACGACTCGTGCCCACCGTGCC
GCTGCACCTCGACGCCGAGGTCCTCGATGGATTACAACCGACGAGGCGGGCGTCCAGGTACACCGACAAAGCTGCGCCGCTCTACTCTGTGCCACCGTGCC
CAGGCACCTGAACTCTGGGGGACCCGTCAGTCTTCCTCTCCCCCCAAAACCAAGGACACCCTCATGATCTCCCCGGACACCCTGAGGTCACATGCGTGGTGGTGGAC
GTGAGCCACGAAGACCCTGAGGTCAAGTTCAACTGGTACGTGGACGGCGTGGAGGTGCATAATGCCAAGACGCGGGAGGAGCAGTACAACAGCACGTACCG
TGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATCT
CCAAAGCCAAAGGGCAGCCCCGAGAACCACAGGTGTACACCCTGCCCCCATCCCGGGATGAGCTGACCAAGAACCAGGTCAGCCTGACCTGCCTGGTCAAAGGCTTC
TATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTACAG
CAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGT
CTCCGGGTAAA

Frz6-Fc (SEQ ID NO: 120)

ATGGAAATGTTTACATTTTTGTTGACGTGCTATTTTTCTACCCCTCCTAAGAGGGCACAGTCTCTTCACCTGTGAACCAATTACTGTTCCCAGATGTATGAAAATGGGC
CTACAACATGACGTTTTCCTAATCTGATGGGTCATTATGACCAGAGTATTGCCGGCGTGAAATGGAGCATTTCTTCCTCTCGTGAACCAATTACTGTTCCTCGAAATCTGGAATGTTCACCAA
ACATTGAAACTTCCTCTGCAAAGCATTTGTACCAACCTGCATAGAACTGCGATAGAACAAATTCATGTCGTAAACTTTGTCGTAAACTTTGTGTAAACTTTCTGAGAAAAGTATATTCTGATTGCAAA
AAATTAATTGACACTTTTGGGATCCAGACTTGTGAATGTGACAGATTACAATACTGTCATGAGACTCGTTCCTGTAACTGTTTCTCGAGTCAGGAGGAGG
AGGAGTCACCGACAAAACTCACACATGCCCACCGTGCCCAGCACCTGAACTCTGGGGGGACCCGTCAGTCTTCCTCTTCCCCCCAAAAACCCAAGGACACCCTCATGA
TCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAG
ACAAAGCCGCGGGAGGAGCAGTACAACAGCACGTACCGTGTGGTCAGCGTCCTCACCGTCCTGCACCAGGACTGGCTGAATGGCAAGGAGTACAAGTGCAAGGTCTC
CAACAAAGCCCTCCCAGCCCCCATCGAGAAAACCATCTCCAAAGCCAAAGGGCAGCCCCGAGAACCACAGGTGTACACCCTGCCCCCATCCCGGGATGAGCTGACCA
AGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCT
CCCGTGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGC
TCTGCACAACCACTACACGCAGAAGAGCCTCTCCCTGTCTCCGGGTAAA

*FIG. 5C*

Frz7-Fc (SEQ ID NO: 121)

ATGCGGGACCCCGGCGCGGCCGCTCCGCTTTCGTCCCTGGTGCTCCTGTCCCTTGGTGCTCTGGGCGCTGCTGGGCGCTGTCCGCGGGGCGCCCGGGGCGCAGCCGTACCA
CGGAGAGAAGGGCCATCCCGTGCCGGACCACGGTTCTGCCAGCCTGTGCACGGACATCGCCTACAACCAGACCATCCTGCCCAACCTGCTGG
GCCACACCAAGAGGACGCGGGCCTCGAGGTGCACCAGTTCTACCCGCTGGTGAAGGTGCAGTGTTCTCCCGAACTCCGCTTTTTCTTATGCTCCATGTATGCG
CCCGTGTGCGACCCTGTCGATCAGGCTCGATCGAGAACTTCCCGGTGCACGGTGCGGGCTGCGGAGATCTGCCTGGGCAGAACAGTTGCGCTTCCAGTGCC
CGAGCGGCTGCCGTGCCACTGCACAACATGCCCACCGTGCCCAGCACCTGCCGAGTCTTCCCCCCAAAACCCAAGGACACCCTCATGATCTCCGGGACCCT
AAACTCACACATGCGTGGTGGTGGACGTGAGCCACGAAGACCCTGAGGTCAAGTTCAACTGGTACGTGGACGGCGTGGAGGTGCATAATGCCAAGACGCCGGGA
GGAGCAGTACAACAGCACGTACCGTGTGGTCAGCGTCCTCACCGTCCTGCACCAGGACTGGCTGAATGGCAAGGAGTACAAGTGCAAGGTCTCCAACAAAGCCCTCC
CAGCCCCCATCGAGAAAACCATCTCAAAGCCAAAGGGCAGCCCCGAGAACCACAGGTGTACACCCTGCCCCCATCCCGGGATGAGCTGACCAAGAACCAGGTCAGC
CTGACCTGCCTGGTCAAAGGCTTCTATCCCAGCGATATCGCCGTGGAGTGGGAGAGCAATGGGCAGCCGGAGAACAACTACAAGACCACGCCTCCCGTGCTGGACTC
CGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACAACCACT
ACACGCAGAAGAGCCTCTCCCTGTCTCCGGGTAAA

Frz8-Fc (SEQ ID NO: 122)

ATGGAGTGGGGGTTACCTGTGTTGGAAGTGACCTCGCTGTTGGAGACCTGACCCTCGCTCCGGCTGCGGCTGCGCTCTAGCGGCGCTGCCGTCCGCCAGT
AGAGATCACGGTGCCGTTGTGCAAGATACAGTGCTCTCCCCGGACATCGGTTACAACTACACTTACAACATGCCCAAGACACGACAACGCCAAGATGAGGCGCTAGAGGTGCACCAGT
TTTGGCCGCTGGTGGTGAGGAGATACAGTGCTCTCCCCGGACATCGGTTACAACTACACTTACAACATGCCCAAGACACGACAACGCCAAGATGACTACAAGAAGCCTCGCCGCTTGT
CGCTCTGTGTGTGAACGGCCAAGGCTGGACTGCAGGGCAAGCGGCTGCCAAGGCCGGCTGCGCCCAGTACGGCTTGCTTGGCCTGACCTGCCCATGCCGATCGGTTGCCGAGCAGGCAA
CCCGGACACTCTGTGCATGCAGTCTTCCTCTTCCCCCAAACCCAAGGACACCCCCTGAGGTCACATGCGTGGTGGTGGACGTGAGCCACGAAGAC
CCTGAGGTCAAGTTCAACTGGTACGTGGACGGCGTGGAGGTGCATAATGCCAAGACGCCCCCCGGGAGGAGCAGTACAACAGCACGTACCGTGTGGTCAGCGTCCT
CACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGGGC
AGCCCCGAGAACCACAGGTGTACACCCTGCCCCCATCCCGGGATGAGCTGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGA
CAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAA

*FIG. 5D*

Frz9-Fc (SEQ ID NO: 123)

ATGGCCGTGGCGCCTCGCGGGGCGCCTGCTGTGGCAGCTGCTGGCGGCGGCGGCACTGGAGATCGGCGCCGCTTCGACCCGGAGCGCGGCGGCGGGGC
TGCGCCCGTGCCAGGCGGTGGAGATCCCCGGCGACCTGCCGGCCTACAACCTGACCTGCTGGCCACACGTCGCAGGGCGGAGGCGGCTGCCG
AGCTAGCGGAGTTCGCGGCCTGGTGCAGTACGGCAGGCGGCTGCCACCTGCGCTACGCGCCATGTGCTCAGCCCATGTGCACCGACCAGGTCTCGACGCCC
ATTCCCGCCTGCCGCCCATGCGCAGGCGGCGCCTGCGCCGCTGCACGTCAACTTCGGCTGGCCGGACTCGTCACACAAACTCACACATGCCCACGTGCC
CACGCGCAACCTGAACTCCTGGGGAGACCGCGTCAGTTCAAGGTCAGACCCTCAAAACCCCCAAGGTCACACCCCTGAGGTCACATGCGTGGTGGAC
CAGCACCTGAACTCCTGGGGGACCGTCAGTTCAACTGGTACGTGGACGGCGTGGAGGTGCATAATGCCAAGACAAAGCCGCGGGAGGAGCAGTACAACAGCACGTACCG
GTGAGCCACGAAGACCCTGAGGTCAAGTTCAACTGGTACGTGGACGGCGTGGAGGTGCATAATGCCAAGACAAAGCCGCGGGAGGAGCAGTACAACAGCACGTACCG
TGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATCT
CCAAAGCCAAAGGGCAGCCCCGAGAACCACAGGTGTACACCCTGCCCCCATCCCGGGAAGAGATGACCAAGAACCAGGTCAGCCTGACCTGCCTGGTCAAAGGCTTC
TATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTACAG
CAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGT
CTCCGGGTAAA

Frz10-Fc (SEQ ID NO: 124)

ATGCAGCGCGCCGGGCCCCGCTGGTCCTGCTGGTCGCAGGTGATGGCTCGTGTCCTGCGCCGCCATCAGCTCATGACATGGAGCGCCCGGGCGACGGCAAATGCCAGCC
CATCGAGATCCCGATGTGCAAGGACATCGGCTACAACATGACTCGTATGCCCAACCTGATGGGCCACGAGAACCAGCAGCGCGAGGCAGCCATCCAGTTGCACGAGTTCG
CGCCGCTGGTGTACGGCTGCCACGGCCATCTGCGCTTCTTCCTGTGCTCGCTGTACGCGCCCATGTGCACCGAGCAGGTCTCTACCCCATCCCGCTGCCGG
GTCATGTGCGAGCAGGCCCGGCTCAAGTGCTCCCCAACATGTCAAGTTCAACTTCAAGTGGCCGGACTGCCGGAAACTCCCAACAAGAACGACCC
CAACTACCTGTGCATGGAGGCGCCCAACCCCTCGCGTCGAGTCACGGAGGACACCCTGAGGTCACAATGCGTGGTGGACGTGAGCCACGAAGAC
CCTGAGGTCAAGTTCAACTGGTACGTGGACGGCGTGGAAGTGCATAATGCCAAGACAAAGCCGCGGGAGGAGCAGTACAACAGCACGTACCGTGTGGTCAGCGTCCT
CACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGGGC
AGCCCCGAGAACCACAGGTGTACACCCTGCCCCCATCCCGGGATGAGCTGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGA
CAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAA

*FIG. 5E* sFRP1-Fc (SEQ ID NO: 125)

ATGGGCATCGGGCGCAGCGGGGCGCCGCGGGGCAGCCCCTGGGCGCTGTGCTGCTGGGCGCGTTCTGCCTCGTGGGCGTCGGCAGCGAGTACGACTA
CGTGAGCTTCCAGTCGGACATCGGCCCGTACCAGAGCGGGCGCTTCTACACCAAGCCACCTCAGTGCGTGGACATCCCCGCGGACCTGCGCCTGTGCCACAACGTGG
GCTACAAGAAGATGGTGCTGCCCAACCTGCTCGAGCACGAGACCATGGCGGAGGTGAAGCAGCAGGCCAGCAGCTGGGTGCCCCTGCTCAACAAGAACTGCCACGCC
GGCACCCAGGTGTTCCTCTGCTCTCTCTTCGCGCCCGTGTGCCTGGACCGGCCCATCTACCCGTGCCGCTGGCTCTGCGAGGCCGTCGTGCGCAGCTGCGAGCCGGT
CATGCAGTTCTTCGGCTTCTACTGGCCCGAGATGCTTAAGTGTGACAAGTTCCCCGAGGGGGACGTCTGCATCGCCATGACCCCGCCCAATGCCTGGCGCCCCAGG
TCACCGACAAAGCTGCGCGCTTACTCTGTGCCCAGCACGGTGGAGTCCTGGGGGACGTCTGAGGTCAAGTTCAACTGGTACGTGGACGGCGTGGAGGTGCATAATGC
ATGATCCCGGACCCCCTGAGGTCACATGCGGTGGTGGACGTGAGCCACGAGGACCCTGAGGTCAAGTTCAACTGGTACGTGGACGGCGTGGAGGTGCATAATGC
CAAGACAAAGCCGCGGGAGGAGCAGTACAACAGCACGTACCGTGTGGTCAGCGTCCTCACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCCAAAGGGCAGCCCCGAGAACCACAGGTGTACACCCTGCCCCCATCCCGGGAAGAGATG
ACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCAC
GCCTCCCGTGCTGGACTCCGACGGCTCCTTCTTCCTCTACAGCAAGCTCACCGTGGACAAGAGCAGGTGGCAGCAGGGGAACGTCTTCTCATGCTCCGTGATGCATG
AGGCTCTGCACAACCACTACACGCAGAAGAGCCTCTCCCTGTCTCCGGGTAAA sFRP2-Fc (SEQ ID NO: 126)

ATGCTGCAGGGCCCTGGCTCGCTGCTCGCTCCTCGCCACTGCTGCCCTGCCCTCGCCGCCTGCGCGGCTCTTCCTCTTTGGCCAGCCCGACTTCTCCTACAA
GCGCAGCAATTGCAAGCCCATCCCTGCCAACCTGCAGCTGTGCCACGGCATCGAATACCAGAACATGCGGCTGCCCAACCTGCTGGGCCACGAGACCATGAAGGAGG
TGCTGGAGCAGGCCGGCGCCTGGATCCCGCTTGGATCCGTGGTCATGATGAAGCAGTGCCACCCGGACACCAAGAAGTTCCTGTGCTCTCTGTTCGCCCCCGTCTGC
GACGAGAGACCCATCCAGGACAACGACCTTTGCATCCCCGTCCGGTGCAGGTGAAGGACCGCTGCGCCCACTGGGCTGCTAGCAGCCCAAAACCAAGGACACTCCCGGAC
CCGTTTCCCCGACCCTGAACTCCTGGGGGGACGCCGTCAGTTCAACTGGTACGTGGACGGCGTGGAGGTGCATAATGCCAAGACAAAGCCGCGGGAGGAGCAGTACA
CAGCACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATCG
AGAAAACCATCTCCAAAGCCAAAGGGCAGCCCCGAGAACCACAGGTGTACACCCTGCCCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTT
CTTCCTCTACAGCAAGCTCACCGTGGACAAGAGCAGGTGGCAGCAGGGGAACGTCTTCTCATGCTCCGTGATGCATGAGGCTCTGCACAACCACTACACGCAGAAGA
GCCTCTCCCTGTCTCCGGGTAAA

*FIG. 5F* sFRP3-Fc (SEQ ID NO: 127)

ATGGGGGGACTGCCGCCAGGTTGGGCCGTGATTTGTTTGTGTCATAGTGGGCCTCCATGGGGTCCGGGGCAAAATCGATGCTCCGAGGGGCAGCCTGTGAGCC
CGTCCGCATCCCCCTGTGCAAGTCCCTGCCCAGCCCCATCCGACCTGGAACATGACTAAGATGCCAACCACCTGCACCACAGACTCAGGCACTGCACGCAACGCCAACCGCTGCCATCCTGGAGCAGTTCG
AAGGTCTGCTGGCCACCCACTGCAGCCCCCGGCCAGGGCCCCATCCTGTGCCATGTACCGCCACTCGTGCCGGAGAACCTGGCCTGCGAGGAGCTGCCAGTGTACGACAG
AAGTCTGTGTGCAATCTCCCCGAGGGCCATCGTTACTGGGCGCGCCGACAAAGCTGCGCGTCTACTCTGTGCCACCGTGCCCAGCGTGCACCAGTGCTCCGCGACCCT
GGGGGACCGCTCAGTCTTCCTTCCCCCAAAAACCAAGGACCACCCCTCATGATCTCCCGGACAGCCCTGAGGTCACATGCGTGGTGGTGGACGTGAGCCACGAAGACCCT
GAGGTCAAGTTCAACTGGTACGTGGACGGCGTGGAAGGTGCATAATGCCAAGACAAAGCCGCGGGAGGAGCAGTACAACAGCACGTACCGTGTGGTCAGCGTCCTCAC
CGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGGGCAGC
CCCGAGAACCACAGGTGTACACCCTGCCCCCATCCCGGGAAGATGACCAAGAACCAGGTCAGCCTGACCTGCCTGGTCAAAGGCTTCTATCCCAGCGACATCGCC
GTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGACAA
GAGCAGGTGGCAGCAGGGGAACGTCTTCTCATGCTCCGTGATGCATGAGGCTCTGCACAACCACTACACGCAGAAGAGCCTCTCCCTGTCTCCGGGTAAA sFRP4-Fc (SEQ ID NO: 128)

ATGTTCCTCCTCCATCCTAGTGGCGCTGTGCCGCTGGGCTGTGCCTGGGCCGGAGGCGGTGCGCCCTGCGAGGCGGCCATCCCTATGTGCCGGCACATGCC
CTGGAACATCACGCGGATGCCCAACCACCTGCACCACAGCACGCAGGAAACGCCATCCTGGCCATCCTGCGAGCAGTACGAGGAGCAGTTCCAGACCTTCCGCG
TGCTGCGCTTCTGTGCGAAGTGTACGCCATGCCATGTGCCACCCTGGAGTTCCTGCGACGAGCAGCCCATCAAGCCGTCGAAGTCGGTGCCAAGCCGTCGGCGGACGAC
TGCCGAGGCCCCTGAATCGAGAGATGTACAACCATCAGGAGGAGTCCCGGACAGCCCTGCCTGGAGCCTGCCACCATGCGTCGTGGTGGACGTGAGCCACGAAGCCATCGT
CACGCTCGAGTCAGGAGGACGCCCCTCATGATCTCCCGGACAGCCCTGAGGTCACATGCGTGGTGGTGGACGTGAGCCACGAAGACCCTGAGGTCAAGTTCAACTGGTACGTGGACGGC
GTGGAGGTGCATAATGCCAAGACAAAGCCGCGGGAGGAGCAGTACAACAGCACGTACCGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGAAAACCATCTCCAAAGCCAAAGGGCAGCCCCGAGAACCACAGGTGTACACCCTGCCCC
CATCCCGGGAAGATGACCAAGAACCAGGTCAGCCTGACCTGCCTGGTCAAAGGCTTCTATCCCAGCGACATCGCCGTGGAGTGGGAGAGCAATGGGCAGCCGGAG
AACAACTACAAGACCACGCCTCCCGTGCTGGACTCCGACGGCTCCTTCTTCCTCTACAGCAAGCTCACCGTGGACAAGAGCAGGTGGCAGCAGGGGAACGTCTTCTC
ATGCTCCGTGATGCATGAGGCTCTGCACAACCACTACACGCAGAAGAGCCTCTCCCTGTCTCCGGGTAAA

FIG. 5G sFRP5-Fc (SEQ ID NO: 129)

ATGGCGGGCGGCGGCGGGGGGCGGGGGGCGTGCGGAGACGGCCGCGCTGGGCGCTGCTGCTGGGGGCGCCGCCGGCGCTGGCACTGGGCGCCTGCGGAGGAGTACGACTACTATGG
CTGGCAGGCCGAGCCGCTGCACGGCCGCCTCCTACTCCTCAAGCCGCCAGTGCCTTGACATCCCTGCCGACCTCTGCCACACGGTGGGCTACAAGCGCATGC
GGCTGCCCAACCTGCTGGAGCACGAGAGCCTGGCCGAAGTGAAGCAGCAGGCCCTGGCTGCCAAGCGCTGCCACTCGGATACGCAGGTCTTC
CTGTGCTCGCTCTTTGCGCCCGTCTGTCTCGACCGGTCCACTGCGACATGCGCCTCTACCCGTGCCGCCATCGCCCCTGCCATCGCCCAGTGCCGCCACCTGCCGCCACCTGTGCGGGCCACCTGCAGTTCGGGCCACCTGTGGGCCGCCACCTGTGCGGGCCACCTGCAGTTCGGGCCACCTGTGGGCGCCACCTGTGCGGGCCACCTGCAGTTCGGGCCACCTGTGGGCGCCACCTGTGCGGGCCACCTGCAGTTCGGGCCACCTGTGGGCGCGC
CTTCCCCTGGCCTCTACTCTGTGCCCACCGTGCCCAGCACGACCTTCCCCCCCAAAACCCAAGGACACCCTCATGATCTCCCGG
CTGCGCGCTCTGTGCCCACCGTGCCCAGCACGACCTTCCCCCCCAAAACCCAAGGACACCCTCATGATCTCCCGG
ACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCC
GCGGGAGGAGCAGTACAACAGCACGTACCGTGTGGTCAGCGTCCTCACCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGGCAGCCCCGAGAACCACAGGTGTACACCCTGCCCCCATCCCGGGAAGATGACCAAGAACCAG
GTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCT
GGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACA
ACCACTACACGCAGAAGAGCCTCTCCCTGTCTCCGGGTAAA

FIG. 5H

Frizzled 1 (NP_003496) (SEQ ID NO: 1)
MAEEEAPKKSRAAGGGASWELCAGALSARLAEEGSGDAGGRRRPPVDPRRLARQLLLLIWLLEAPLLLGVRAQAAGQGPGQGPGQGPPPPQQQSGQQYNGERG
ISVPDHGYCQPISIPLCTDIAYNQTIMPNLLGHTNQEEDAGLEVHQFYPLVKVQCSAELKFFLCSMYAPVCTVLEQAIPPCRSLCERARQGCEALMNKFGFQWPDTLK
CEKFPVHGAGELCVGQNTSDKGTPTPSLLPEFWTSNPQHGGGHRGFPGGAGASERGKFSCPRALKVPSYLNYHFLGEKDCGAPCEPTKVGLMYFGPEELRFSRT
WIGIWSVLCCASTLFTVLTYLVDMRRFSYPERPIIFLSGCYTAVAVAYIAGFLLEDRVVCNDKFAEDGARTVAQGTKKEGCTILPMLYFFSMASSIWWVILSLTWF
LAAGMKWGHEAIEANSQYFHLAAWAVPAIKTITILAMGQVDGDVLSGVCFVGLNNVDALRGFVLAPLFVYLFIGTSFLLAGFVSLFRIRTIMKHDGTKTEKLEKLMV
RIGVFSVLYTVPATIVIACYFYEQAFRDQWERSWAQSCKSYAIPCPHLQAGGGAPHPPMSPDFTVFMIKYLMTLIVGITSGFWIWSGKTLNSWRKFYTRLTNSKQ
GETT Frizzled 2 (NP_001457) (SEQ ID NO: 2)
MRPRSALPRLLLPLLLLPAAGPAQFHGEKGISIPDHGFCQPISIPLCTDIAYNQTIMPNLLGHTNQEDAGLEVHQFYPLVKVQCSPELRFFLCSMYAPVCTVLEQAI
PPCRSICESARQGCEALMNKFGFQWPERLRCEHFPRHGAEQICVGQNHSEDGAPALLTTAPPEGLQPGAGGTPGGPGGGAPPRYATLEHPFHCPRVLKVFSYLSYK
FLGERDCAAPCEPARPDGSMFFSQEETRFARLWILTWSVLCCASTFPTVTTYLVDMQRFRYPERPIIFLSGCYTMVSVAYIAGFVLQERVVCNERFSEDGYRTVVQG
TKKEGCTILPMLYFFSMASSIWWVILSLTWFLAAGMKWGHEAIEANSQYFHLAAWAVPAVKTITILAMGQIDGDLLSGVCFVGLNSLDPLRGFVLAPLFVYLFIGT
SFLLAGFVSLFRIRTIMKHDGTKTEKLERLMVRIGVFSVLYTVPATIVIACYFYEQAFREHWERSWSQHCKSLAIPCPAHYTPRMSPDFTVYMIKYLMTLIVGITS
GFWIWSGKTLHSWRKFYTRLTNSRHGETTV Frizzled 3 (NP_059108) (SEQ ID NO: 3)
MAMTWIVFSLMPLITVFMGHIGGHSLFSCEPITILRMCQDLPYNTTFMPNLLNHYDQQTAALAMEPFHPMVNLDCSRDFRPFLCALYAPICMEYGRVTLPCRRLCQRAY
SECSKLMEMFGVPWPEDMECSRFPDCDEPYFPRLVDLNLAGEFTEGAPVAVQRDYGFWCPRELKIDPDLGYSFLHVRDCSPPCPNMYFREELSFARYFIGLISICL
SATLFTFLTFLIDVTRFRYPERPIIFYAVCYMMVSLIFFIGFLLEDRVACNASIPAQYKASTVTQGSHNKACTMLFMILYFFTMAGSVMWVILTITWFLAAVPKWGS
EAIEKKALLFHASAWGIPGTLTIILLAMNKIEGDNISGVCFVGLYDVDALRYFVLAPLCLYVVGVSLLLAGIISLNRVRIEIPLEKENQDKLVKFMRIGVFSILY
LVPLLVVIGCYFYEQAYRGIWETTWIQERCREYHIPCPYQVTQMSRPDLILFLMKYLMALIVGIPSVFWVGSKKTCFEWASFFHGRRKKEIVNESRQVLQEPDFAQS
LLRDPNTPIIRKSRGTSTQGTSTHASSTQLAMVDDQRSKAGSIHSKVSSYHGSLHRSRDGRYTPCSYRGMEERLPHGSMSRLTDHSRHSSSHRLNEQSRHSSIRDLS
NNPMTHITHGTSMNRVIEEDGTSA Frizzled 4 (NP_036325) (SEQ ID NO: 4)
MAWRGAGPSVPGAPGGVGLSLGLLLQLLLLLLGPARGFGDEEERRCDPIRISMCQNLGYNVTKMPNLVGHELQTDAELQLTTFTPLIQYGCSSQLQFFLCSVYVPMCT
EKINIPIGPCGGMCLSVKRRCEPVLKEFGFAWPESLNCSKFPQNDHNHMCMEGPGDEEVPLPHKTPIQPGEECHSVGTNSDQYIWVKRSLNCVLKCGYDAGLYSRS
AKEFTDIWMAVWASLCFISTAFTVLTFLIDSSRFSYPERPIIFLSMCYNIYSIAYIVRLTVGRERISCDFEEAAEPVLIQEGLKNTGCAIIFLLMYFFGMASSIWWV
ILTLTWFLAAGLKWGHEAIEMHSSYFHIAAWAIPAVKTIVILIMRLVDADELTGLCYVGNQNLDALTGFVPVAPLFTYLVIGTLFIAAGLVALFKIRSNLQKDGTKTD
KLERLMVKIGVFSVLYTVPATCVIACYFYEISNWALFRYSADDSNMAVEMLKIFMSLLVGITSGMWIWSAKTLHTWQKCSNRLVNSGKVKREKRGNGWVKPGKGSET
VV

FIG. 6A

Frizzled 5 (NP_003459) (SEQ ID NO: 5)
MARPDPSAPPSLLLLLAQLVGRAAAASKAPVCQEITVPMCRGIGYNLTHMPNQFNHDTQDEAGLEVHQFWPLIVEIQCSPDLRFFLCSMYTPICLPDYHKPLPPCRS
VCERAKAGCSPLMRQYGFAWPERMSCDRLPVLGRDAEVLCMDYNRSEATTAPPRFPAKPTLPGPPGAPASGGECPAGGPFVCKCREPFVPILKESHPLYNKVRTGQ
VPNCAVPCYQPSFSADERTFATFWIGLWSVLCFISTSTTVATFLIDMERFRYPERPIIFLSACYLCVSLGFLVRLVVGHASVACSREHNHIHYETTGPALCTIVFLL
VYFFGMASSIWWVILSLTWFLAAGMKWGNEAIAGYAQYFHLAAWLIPSVKSITALALSSVDGPVAGICYVGNQNLNSLRGFVLGPLVLYLLVGTLFLLAGFVSLFR
IRSVIKQGGTKTDKLEKLMIRIGIFTLLYTVPASIVVACYLYEQHYRESWEAALTCACPGHDTGQPRAKPEYWVLMLKYFMCLVVGITSGVWIWSGKTVESWRRFTS
RCCCRPRRGHKSGGAMAAGDYPEASAALTGRTGPPGPAATYHKQVSLSHV Frizzled 6 (NP_003497) (SEQ ID NO: 6)
MEMFTLLTCIFLPLLRGHSLFTCEPITVPRCMKMAYNMTFPNLMGHYDQSIAAVEMEHFLPLANLECSPNIETFLCKAFVPTCIEQIHVVPPCRKLCEKVYSDCK
KLIDTFGIRWPEELECDRLQYCDETVPVTFDPHTEFLGPQKKTEQVQRDIGFWCPRHLKTSGQGYKFLGIDQCAPPCPNMYFKSDELEFAKSFIGTVSIFCLCATL
FTFLTFLIDVRRFRYPERPIIYYSVCYSIVSLMYFIGFLLGDSTACNKADEKLELGDTVVLGSQNKACTVLFMLLIYFFMAGTVWWVILTITWFLAAGRKWSCEAIE
QKAVWFHAVAWGTPGFLTVMLLAAMNKVEGDNISGVCFVGLYLDLDASRYFVLLPLCLCVFVGLSLLLAGIISLNHVRQVIQHDGRNQEKLKKFMIRIGVFSGLYLVPL
VTLLGCYVYEQVNRITWEITWVSDHCRQYHIPCPYQAKARPELALFMIKYLMIVLIVGISAVFWVGSKKTCTEWAGFFKRNRKRDFISESRRVLQESCEFFLKHNS
KVKHKKHYKPSSHKLKVISKSMGTSTGATANHGTSAVAITTSHDYLGQETLTEIQTSPETSMREVKADGASTPRLREQDCGEPASPAASISRLSGEQVDGKQAGSV
SESARSEGRISPKSDITDTGLAQSNNLQVPSSEPSSLKGSTSLLVHPSGVRKEQGGGCHSDT Frizzled 7 (NP_003498) (SEQ ID NO: 7)
MRDPGAAAPLSSLGLCALVLALLGALSAGAGAQPYHGEKGISVPDHGFCQPISIPLCTDIAYNQTILPNLLGHTNQEDAGLEVHQFYPLVKVQCSPELRFFLCSMYA
PVCTVLDQAIPPCRSLCERARQGCEALMNKFGFQWPERLRCENFPVHGAGEICVGQNTSDGSGGPGGGPTAYPTAPYLPDLPFTALPPGASDGRGRPAFFSCPRQL
KVPPYLGYRFLGERDCGAPCEPGCRANGLMYFKEEERRFARLWVGVWSVLCCASTLFTVLTIVLDMRRFSYPERPIIFLSGCYFMVAVAHVAGFLLEDRAVCVERFSD
DGYRTVAQGTKKEGCTILFMVLYFFGMASSIWWVILSLTWFLAAGMKWGHEAIEANSQYFHLAAWAVPAVKTITILAMGQVDGDLLSGVCYVGLSSVDALRGFVLAP
LFVYLFIGTSFLLAGFVSLFRIRTIMKHDGTKTEKLEKLMVRIGVFSVLYTVPATIVLACYFYEQAFREHWERTWLLQTCKSYAVPCPPGHFPPMSPDFTVFMIKYL
MTMIVGITTGFWIWSGKTLQSWRRFYHRLSHSSKGETAV Frizzled 8 (NP_114072) (SEQ ID NO: 8)
MEWGYLLEVTSLLAALALLQRSSGAAAASAKELACQEITVPLCKGIGYNYTYMPNQFNHDTQDEAGLEVHQFWPLVEIQCSPDLKFFLCSMYTPICLEDYKKPLPPC
RSVCERAKAGCAPLMRQYGFAWPDRMRCDRLPEQGNPDTLCMDYNRTDLTTAAPSPPRRLPPPPGEQPPSGSGHGRPGARPPHRGGGRGGGGDAAAPPARGGGG
GGKARPPGGGAAPCEPGCQCRAPMVSVSSERHPLYNRVKTGQIANCALPCHNPFFSQDERAFTVFWIGLWSVLCFVSTFATVSTFLIDMERFKYPERPIIFLSACYL
FVSVGYLVRLIVAGHEKVACSGGAPCEGGAPGEAGAGAGAEAAGAGAGAGPGGRGEYEELGAVEQHVRYETTGPALCTVVFLLVYFGMASSIWWVILSLTWFLAAGMK
WGNEAIAGYSQYFHLAAWLVPSVKSIAVLALSSVDGPVAGICYVGNQSLDNLRGFVLAPLVIVLFIGTMFLLAGFVSLFRIRSVIKQQDGPTKTHKLEKLMIRLGL
FTVLYTVPAAVVVACLFYEQHNRPRWEATHNCPCLRDLQPDQARRPDYAVFMLKYFMCLVVGITSGVWVWSGKTLESWRSLCTRCCWASKGAAVGGGAGATAAGGGG
GPGGGGGGGGGPGGGGGSLYSDVSTGLTWRSGTASSVSYPKQMPLSQV

FIG. 6B

Frizzled 9 (NP_003499) (SEQ ID NO: 9)

MAVAPLRGALLLMQLLAAGGAALEIGRFDPERGRGAAPCQAVEIPMCRGIGYNLTRMPNLLGHTSQGEAAAELAEFAPLVQYGCHSHLRFFLCSLYAPMCTDQVSTP
IPACRPMCEQARLRCAPIMEQFNFGWPDSLDCARLPTRNDPHALCMEAPENATAGPAEPHKGLGMLPVAFRPARPPGDLGPGAGGSGTCENPEKFQYVEKSRSCAPR
CGPGVEVFWSRRDKDFALVWMAVWSALCFFSTAFTVLTFLLEPHRFQYPERPIIFLSMCYNVYSLAFLIRAVAGAQSVACDQEAGALYVIQEGLENTGCTLVFLLLY
YFGMASSIWWVVLTLTWFLAAGKKWGHEAIEAHGSYFHMAAWGLPALKTIVILTLIRRKVAGDELTGLCYVASTDAAALTGFVLVPLSGYLVLGSSFLLTGFVALFHIR
KIMKTGGTNTEKLEKLMVKIGVFSILYTVPATCVIVCYVYERLNMDFWNRLRATEQPCAAAAGPGGRRDCSLPGGSVPTVAVFMLKIFMSLVVGITSGVWWSSKTFQ
TWQSLCYRKIAAGRARAKACRAPGSYGRGTHCHYKAPTVVLHMTKTDPSLENPTHL

Frizzled 10 (NP_009128) (SEQ ID NO: 10)

MQRPGPRLWLVLQVMGSCAAISSMDMERPGDGKCQPIEIPMCKDIGYNMTRMPNLMGHENQREAAIQLHEFAPLVEYGCHGHLRFFLCSLYAPMCTEQVSTPIPACR
VMCEQARLKCSPIMEQFNFKWPDSLDCRKLPNKNDPNYLCMEAPNNGSDEPTRGSGLFPPLFRPQRPHSAQEHPLKDGGPGRGGCDNPGKFHHVEKSASCAPLCTPG
VDVYWSREDKRFAVVWLAIWAVLCFFSSAPTVLTFLIDPARFRYPERPIIFLSMCYCVISVGYLIRLFAGAESIACDRDSGQLYVIQEGLESTGCTLVFLVLIYFGM
ASSLWWVVLTLTWFLAAGKKWGHEAIEANSSYFHLAAWAIPAVKTILILVMRRVAGDELTGVCYVGSMDVNALTGFVLIPLACYLVIGTSFILSGFVALFHIRRVMK
TGGENTDKLEKLMVRIGLFSVLYTVPATCVIACYFYERLNMDYWKILAAQHKCKMNNQTKTLDCLMAASIPAVEIFMVKIFMLLVGITSGMWIWTSKTLQSWQQVC
SRRLKKKSRRKPASVITSGGIYKKAQHPQKTHHGKYEIPAQSPTCV sFrp1 (NP_003003) (SEQ ID NO: 11)

MGIGRSEGGRRGAALGVLLALGAALLAVGSASEYDYVSFQSDIGPYQSGRFYTKPPQCVDIPADLRLCHNVGYKKMVLPNLLEHETMAEVKQQASSWVPLLNKNCHA
GTQVFLCSLFAPVCLDRPIYPCRWLCEAVRDSCEPVMQFFGFYWPEMLKCDKFPEGDVCIAMTPNATEASKPQGTTVCPPCDNELKSEAIIEHLCASEFALRMKIK
EVKKENGDKKIVPKKKKPLKLGPIKKKDLKKLVLYLKNGADCPCHQLDNLSHHFLIMGRKVKSQYLLTAIHKWDKKNKEFKNFMKKMKNHECPTFQSVFK sFrp2 (NP_003004) (SEQ ID NO: 12)

MLQGPGSLLLLFLASHCCLGSARGLFLFGQPDFSYKRSNCKPIPANLQLCHGIEYQNMRLPNLLGHETMKEVLEQAGAWIPLVMKQCHPDTKKFLCSLFAPVCLDDL
DETIQPCHSLCVQVKDRCAPVMSAFGFPWPDMLECDRFPQDNDLCIPLASSDHLLPATEEAPKVCEACKNKNDDNDIMETLCKNDFALKIKVKEITYINRDTKIIL
ETKSKTIYKLNGVSERDLKKSVLWLKDSLQCTCEEMNDINAPYLVMGQKQGGELVITSVKRWQKQREFKRISRSIRKLQC

FIG. 6C sFrp3 (FRZB) (NP_001454) (SEQ ID NO: 13)

MVCGSPGGMLLRAGLLLAALCLLRVPGARAAACEPVRIPLCKSLPWNMTKMPNHLHHSTQANAILAIEQFEGLLGTHCSPDLLFFLCAMYAPICTIDFQHEPIKP
CKSVCERARQGCEPILIKYRHSWPENLACEELPVYDRGVCISPEAIVTADGADFPMDSSNGNCRGASSERCKCKPIRATQKTYFRNNYNYVIRAKVKEIKTKCHDVT
AVVEVKEILKSSLVNIPRDTVNLYTSSGCLCPPLNVNEEYIIMGYEDEERSRLLLVEGSIAEKWKDRLGKKVKRWDMKLRHLGLSKSDSSNSDSTQSQKSGRNSNPR
QARN sFrp4 (NP_003005) (SEQ ID NO: 14)

MFLSILVALCLMLHLALGVRGAPCEAVRIPMCRHMPWNITRMPNHLHHSTQENAILAIEQYEELVDVNCSAVLRFFFCAMYAPICTLEFLHDPIKPCKSVCQRARDD
CEPLMKMYNHSWPESLACEDELPVYDRGVCISPEAIVTDLPEDVKWIDITPDMNVQERPLDVCKRLSPDRCKCKKVKPTLATYLSKNYSYVIHAKIKAVQRSGCNEV
TTVVDVKEIFKSSSPIPRTQVFLITNSSCQCPHILPHQDVLIMCYEWRSRAMLLENCLVEKWRDQLSKRSIQWEERLQEQRRTVQDKKTAGRTSRSNPPKPKGKPP
APKPASPEKNIKTRSAQKRTNPKRV sFrp5 (NP_003006) (SEQ ID NO: 15)

MRAAAAGGVRTAALALILGALHWAPARCEEYDYYGWQAEPLHGRSYSKPPQCLDIPADLPLCHTVGYKRMRLPNLLEHESLAEVKQQASSWLPLLAKRCHSDTQVF
LCSLFAPVCLDRPIYPCRSLCEAVRAGCAPLMEAVGFPWPEMLHCHKFPLDNDLCIAVQFGHLPATAPPVTKICAQCEMEHSADGLMEQMCSSDFVKMRIKEIKIE
NGDRKLIGAQKKKLLKPGPLKRKDTKRLVLHMKNGAGCPCPQLDSLAGSFLVMGRKVDGQLLMAVYRWDKNKEMKFAVKFMFSYPCSLYYPFFYGAAEPH

Ror1 (NP_005003) (SEQ ID NO: 16)

MHRPRRRGTRPPLLALLAAILLAARGAAAQETELSVSAELVPTSSWNISSELNKDSYLTLDEPMNNITTSLGQTAELHCKVSGNPPPTIRWFKNDAPVQEPRRLSF
RSTIYGSRLRIRNLDTTDTGYFQCVATNGKEVVSSTGVLFVKFGPPPTASPGYSDEYEEDGFCQPYRGIACARFIGNRTVYMESLHMQGEIENQITAAFTMIGTSSH
LSDKCSQFAIPSLCHYAFPYCDETSSVKPRDLCRDECEILENVLCQTEYIFARSNPMILMRLKLPNCEDLPQPESPEAANCIRIGIPMADPINKNHKCYNSTGVDY
RGTVSVTKSGRQCQPWNSQYPHTHTFTALRFPELNGGHSYCRNPGNQKEAPWCFTLDENFKSDLCDIPACDSKDSKEKNKMEILYILVPSVAIPLAIALLFFICVC
RNNQKSSSAPVQRQPKHVRGQNVEMSMLNAYKPKSKAKELPLSAVRFMEELGECAFGKIYKGHLYLPGMDHAQLVAIKTLKDYNNPQQWMEFQQEASLMAELHHPNI
VCLLGAVTQEQPVCMLFEYINQGDLHEFLIMRSPHSDVGCSSDEDGTVKSSLDHGDPLHIAIQIAAGMEYLSSHFFVHKDLAARNILIGEQLHVKISDLGLSREIYS
ADYYRVQSKSLLPIRWMPPEAIMYGKFSSDSDIWSFGVVLWEIFSFGLQPYYGFSNQEVIEMVRKRQLLPCSEDCPPRMYSLMTECWNEIPSRRPRFKDIHVRLRSW
EGLSSHTSSTTPSGGNATTQTTSLSASPVSNLSNPRYPNYMFPSQGITPQGQIAGFIGPPIPQNQRFIPINGYPIPPGYAAFPAAHYQPTGPPRVIQHCPPPKSRSP
SSASGSTSTGHVTSLPSSGSNQEANIPLLPHMSIPNHPGGMGITVFGNKSQKPYKIDSKQASLLGDANIHGHTESMISAEL

FIG. 6D

Ror2 (NP_004551) (SEQ ID NO: 17)

MARGSALPRRPLLCIPAVWAAAALLLSVSRTSGEVEVLDPNDPLGPLDGQDGPIPTLKGYFLNFLEPVNNITIVQGQTAILHCKVAGNPPPNVRWLKNDAPVVQEPR
RIIIRKTEYGSRLRIQDLDTTDTGYYQCVATNGMKTITATGVLFVRLGPTHSPNHNFQDDYHEDGFCQPVRGIACARFIGNRTIYVDSLQMQGEIENRITAAFTMIG
TSTHLSDQCSQFAIPSFCHFVFPLCDARSRTPKPRELCRDECEVLESDLCRQEYTIARSNPLILMRLQLPKCEALPMPESPDAANCMRIGIPAERLGRYHQCYNGSG
MDYRGTASTTKSGHQCQPWALQHPHSHHLSSTDFPELGGGHAYCRNPGGQMEGPWCFTQNKNVRMELCDVPSCSPRDSSKMGILYILYLVPSIAIPLVIACLFFLVCMC
RNKQKASASTPQRRQLMASPSQDMEMPLINQHKQAKLKEISLSAVRFMEELGEDRFGKVYKGHLFGPAPGEQTQAVAIKTLKDKAEGPLREEFRHEAMLRARLQHPN
VVCLLGVVTKDQPLSMIFSYCSHGDLHEFLVMRSPHSDVGSTDDDRTVKSALEPPDFVHLVAQIAAGMEVLSSHHVVHKDLATRNVLVYDKLNVKISDLGLFREVYA
ADYYKLLGNSLLPIRWMAPEAIMYGKFSIDSDIWSYGVVIWEVFSYGLQPYCGYSNQDVVEMIRNRQVLPCPDDCPAWVYALMIECWNEFPSRRPFKDIHSRLRAW
GNLSNYNSSAQTSGASNTTQTSSLSTSPVSNVSNARYVGPKQKAPFFPQPQFIPMKGQIRPMVPPPQLYVPVNGYQPVPAYGAYLPNFYPVQIPMQMAPQQVPPQMV
PKPSSSHHSGSGSTSTGYVTTAPSNTSMADRAALLSEGADDTQNAPEDGAQSTVQEAEEEEGSVPETELLGDCDTLQVDEAQVQLEA

FIG. 6E

Frz1-Fc (SEQ ID NO: 76)

MGGTAARLGAVILFVVIVGLHGVRGKIDEEGSGDAGGRRAPPVDPRRLARQLLLIIMLLEAPLLLGVRAQAAGQGPGQGPGPGQQPPPPQQQQSGQYNGERGISV
PDHGYCQPESDLCTDIAVNQTIMPNLLGHTNQEDAGLEVHQFYPIVKVQCSAELKFFLCSMYAPVCTVLEQALPPCRSICERARQGCEALMNKFGFQWPDTLKCEK
FPVHGAGELCVGQNTSDKARGRAQVTEQAIQCLCVGQNHSEDGRAQVTDKAARSTLCPPCPAPELLGGPSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPGK

Frz2-Fc (SEQ ID NO: 77)

MGGTAARLGAVILFVVIVGLHGVRGKIDARGAQFHGEKGESIPDHGFQPESIPLCTDIAYNQHIMPNLLGHTNQEDAGLEVHQFYPIVKVQCSPELRFFLCSMYAP
VCTVLEQAIPPCRSICERAQGCEALMNKFGFQWPERIRCEHFPRHGAEQICVGQNHSEDGRAQVTDKAARSTLCPPCPAPELLGGPSVFLFPPKPKDTLMISRTPE
VTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSVMHEALHNHYTQKSLSLSPGK

Frz3-Fc (SEQ ID NO: 78)

MGGTAARLGAVILFVVIVGLHGVRGKIDARGHSIFSCEPITLRMCQDLEYNTTEMPNLLNHYDQQTAALAMEPHPMVNLDCSRDFRPFLCALYAPICMEYGRVFLP
CRRLCQRAYSECGMCLSVKRRCEPVLKEFGFAWEESLNCSKFPQNDHNHMCMEGPGDEEGRAQVTDKAARSTLCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK

Frz4-Fc (SEQ ID NO: 79)

MGGTAARLGAVILFVVIVGLHGVRGKIDARGFGDEEERRCDPERISMCQNIGYNVEKMPNLVGHELQTDARLQLTTFEPLIQYGCSSQIQFFLCSVYVPMCTEKINI
PIGFCGGMCLSVKRRCEPVLKEFGFAWEESLNCSKFPQNDHNHMCMEGPGDEEGRAQVTDKAARSTLCPPCPAPELLGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKG
FYPSDIAVEWESNGQPENNYKTTPPVLDSDGSFFLYSKLTVDKSRWQQGNVFSCSVMHEALHNHYTQKSLSLSPGK

Frz5-Fc (SEQ ID NO: 75)

MGGTAARLGAVILFVVIVGLHGVRGKIDARGASKAPVCQEITVPMCRGIGYNLTHMPNQFNHDTQDEAGLEVHQFWPIVEEQCSPDLRFFLCSMYEPICLPDYHKPL
PPCRSVCERAKAGCSPLMRQYGFAWPERMSCDRLPVLGRDAEVLCMDYNRSEAGRAQVEDKAARSTLCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVFSCSVMHEALHNHYTQKSLSLSPGK

*FIG. 7A*

Frz6-Fc (SEQ ID NO: 80)

MEMFTFLLTC-FLPLLRGHSLFTCEPITVPRCMKMAYNMTFPNLMGHYDQS-AAVEMEHFLPLANLECSPN-ETFLCKAFVPTCTEQIHVPPCRKLCEKVYSDCK
KLIDTFGIRWPEEIECDRLQYCDETVPVTFLESGGGVTDKTHTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPGK

Frz7-Fc (SEQ ID NO: 81)

MRDPGAAAPISSIGLCAINLALLGALSAGAGAQPYHGEKGISVPDHGFCQPISIPLCTDIAYNQTILPNLLGHTNQEDAGLEVHQFYPLVKVQCSPELRFFLCSMYA
PVCTVLDQAIPPCRSICERARQGCEALMNKFGFQWPERLRCENFPVHGAGEICVGQNTSDGLESGGGGVTDKTHTCPPCPAPELLGGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVDKSRWQQGNVFSCSVMHEALHNHYTQKSLSLSPGK

Frz8-Fc (SEQ ID NO: 74)

MEWGYLLEVTSLLAALAVLQRSSGAAAASAKELACQEITVPLCKGIGYNYTVMPNQFNHDTQDEAGLEVHQFWPLVEIQCSPDLKFFLCSMYTP-CLEDYKKRPLPPC
RSVCERAKAGCAPIMRQYGFAWPDRMRCDRLPEQGNPDTLCMDYNRTDLESGGGGVTDKTHTCPPCPAPELLGGPSVFLFPPKPKDTLMISRTPEVTCVVVDSHED
PEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLSLSPGK

Frz9-Fc (SEQ ID NO: 82)

MAVAPLRGALLIWQLLAAGGAALEIGRFDPERGRGAAPCQAVEIPMCRGIGVNITRMPNLLGHTSQGEAAAELAEFAPLVQYGCHSHLRFFLCSLVAPMCTDQVSTP
IPACRPMCEQARLRCAPIMEQFNFWGWPDSLDCARLPTRNDPHAICMEAPENAPLESGGGGVTDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVFSCSVMHEALHNHYTQKSLSLSPGK

Frz10-Fc (SEQ ID NO: 83)

MQRPGPRLWLVLQVMGSCAAISSMDMERPGDGKCQPIEIPMCKDIGYNMTRMPNLMGHENQREAAIQLHEFAPLVEYGCHGHLRFFLCSLYAPMCTEQVSTPIPACR
VMCEQARLKCSPIMEQFNFWPDSLDCRKLPNKNDPNYLCMEAPNNGSLESGGGGVTDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLSLSPGK

FIG. 7B sFRP1-Fc (SEQ ID NO: 84)

MGIGRSEGGRRGAALGVLLALGAALLAVGSASEYDYVSFQSD-IGPYQSGRFYTKPPQCVDIPADLRLCHNVGYKKMVLPNLLEHETMAEVKQQASSWVPLLNKNCHA
GTQVFLCSLFAPVCLDRPIYPCRWLCEAVRDSCE-VMQFFGFWPEMLKCDKFPEGDVCIAM PPNAWRAQVT DKAARSTLCPPCPAPELLGGPSVFLFPPKPKDTL
MISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQQGNVFSCSVMHEALHNHYTQKSLSLSPGK sFRP2-Fc (SEQ ID NO: 85)

MLQG-GSLLLFLASHCCLGSARGLFLFGQPDFSYKRSNCKPIPANLQLCHG-EYQNMRLPNLLGHETMKEVLEQGAWIPLVMKQCHPDTKKELCSLFAPVCLDDL
DETIQPCHSLCVQVKDRCAPVMSAFGFPWPDMLECDRFPQDNDLCIPLASSDHWRAQVTDKAARSTLCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVFSCSVMHEALHNHYTQKSLSLSPGK sFRP3-Fc (SEQ ID NO: 86)

MGGTAARLIGAVILFVTIVGLHGVRGKIDARGAACEPVR-PLCKSLPWNMTKMPNHLHHSTQANAILAIEQFEGLLGTHCSPDLLFFICAMYAPICTIDFQHEPIKPC
KSVCERARQGCEPILIKYRHSWPENLACEELPVDRGVCISPEAIV GRAQVTDKAARSTLCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSPGK sFRP4-Fc (SEQ ID NO: 87)

MFLSIIVALCLMLHLALGVRGAPCEAVRIPMCRHMPWNIFRMPNHLHHSTQENAILAIEQYEELVDVNCSAVLRFFCAMYAP-CTLEFLHDPIKPCKSVCQRARDD
CEPIMKMYNHSWPESLACEDELPVDRGVCISPEAIVTLESGGGVTDKTHTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK sFRP5-Fc (SEQ ID NO: 88)

MRAAAAGGVRTAALALILLGALHWAPARCEEYDYVGWQAEPLHGRSVSKPPQCLDIPADLPLCHTVGYKRMRLPNLLEHESLAEVKQQASSWLPILAKRCHSDTQVF
LCSLFAPVCLDRPIYPCRSICEAVRAGCAPLMEAVGFPWPEMLHCHKFPLDNDLCIAVQFGHLNRAQVTDKAARSTLCPPCPAPELLGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQGNVFSCSVMHEALHNHYTQKSLSLSPGK

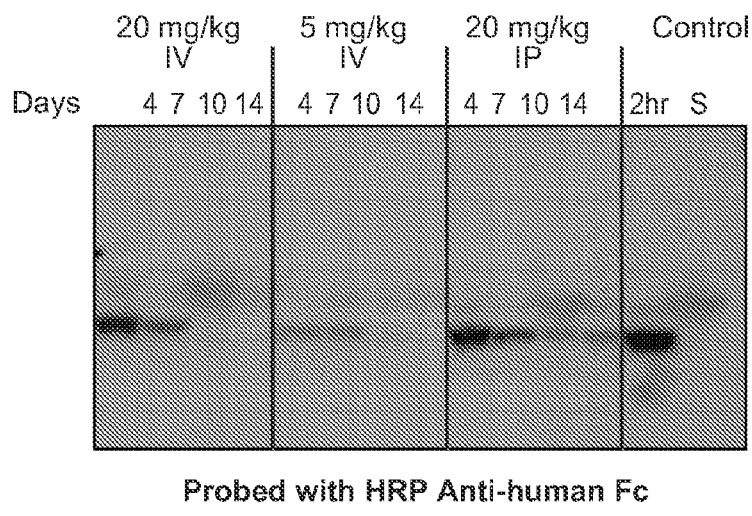
FIG. 13A
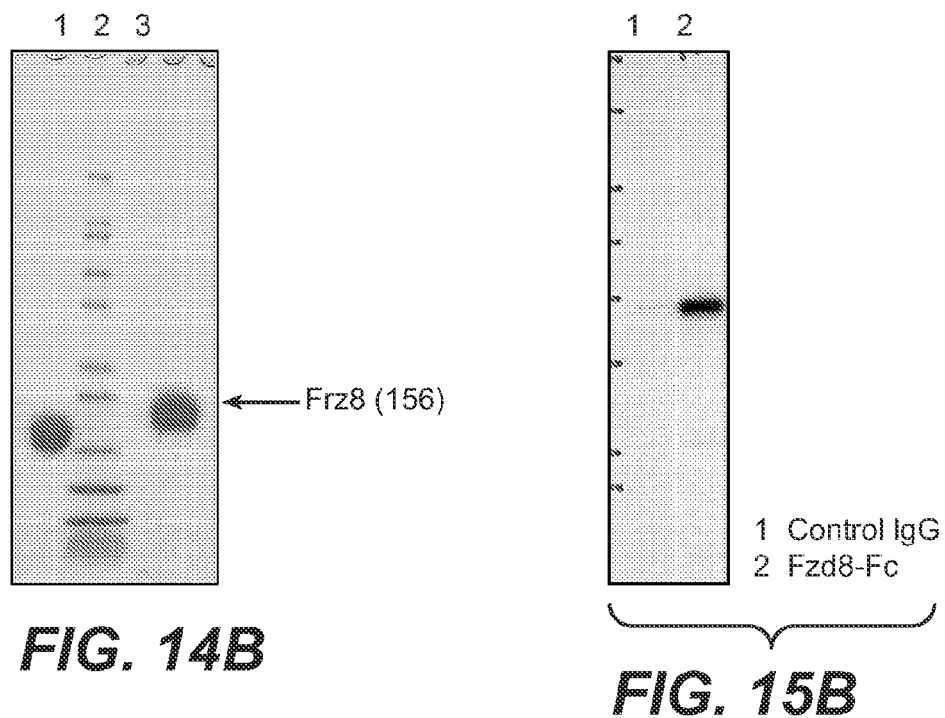
FIG. 14B
FIG. 15B

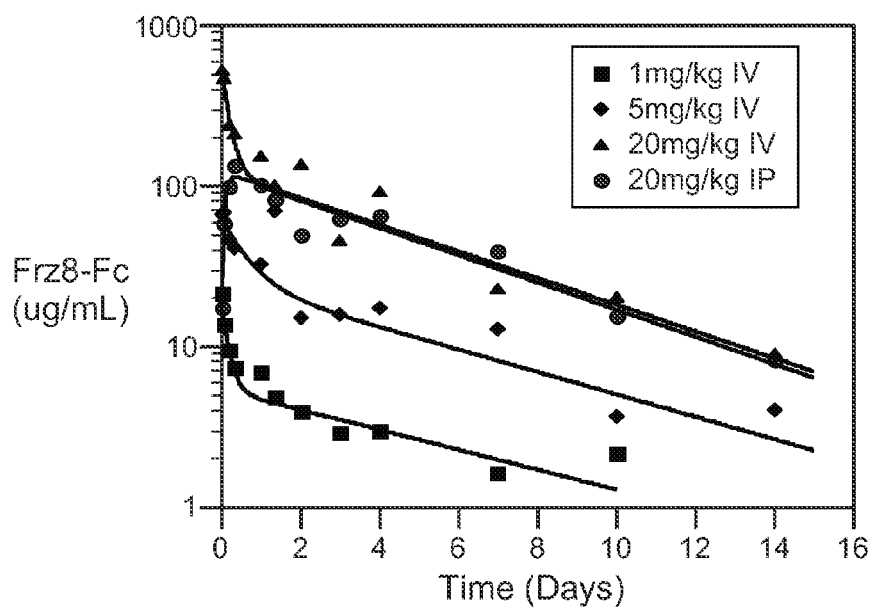
FIG. 13B  Symbols = Observed  Lines = Predicted
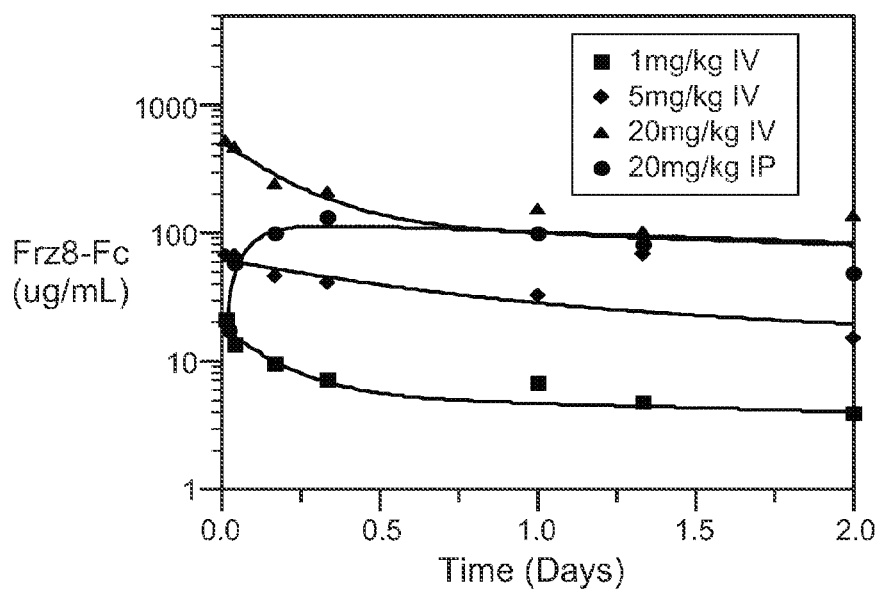
FIG. 13C  Symbols = Observed  Lines = Predicted

|  | Frz8-Fc 1mg/kg IV | Frz8-Fc 5mg/kg IV | Frz8-Fc 20mg/kg IV | Frz8-Fc 20mg/kg IP |
| --- | --- | --- | --- | --- |
| AUC (day*ug/mL) | 39.7 | 179 | 687 | 633 |
| CL or CL/F (mL/day/kg) | 25.2 | 28.0 | 29.1 | 31.6 |
| Alpha HL (Hours) | 2.76 | 10.0 | 3.29 | |
| T1/2 (Days) | 4.86 | 4.32 | 3.52 | 3.62 |
| Tmax (Hours) | | | | 8.38 |
| Cmax (ug/mL) | 18.3 | 62.4 | 515 | 113 |
| V1 (ml/kg) | 54.6 | 80.1 | 38.8 | |
| Vss or V/F (ml/kg) | 167 | 154 | 133 | 165 |

*FIG. 13D*

| Gene Name | Accession No. | Forward Primer | Reverse Primer | Probe Sequence |
|---|---|---|---|---|
| Lefty1 (B) | NM_020997 | CTAAGCACTTACATGTGGAGATACTG (SEQ ID NO: 89) | ACAGGACAAGTAAACAATGACACA (SEQ ID NO: 90) | AACCTGAGGGCAGAAAGCCCAA (SEQ ID NO: 91) |
| Lefty2 (A) | NM_003240 | TTCCCACACTGTCTTAGAGAACTT (SEQ ID NO: 92) | TTCTGAGTATCTACATTCAATTGCTTTT (SEQ ID NO: 93) | AAACATGCAAATACATGTGGTTTCTGGTGAC (SEQ ID NO: 94) |
| Gad1 | NM_000817 | TGACTCGCTTAGCTGAAACCT (SEQ ID NO: 95) | TGAGCCTGGTCACTTTATCTGA (SEQ ID NO: 96) | TCAGAAGGTCTTCGGAAATGTTGCCT (SEQ ID NO: 97) |
| APCDD1 | NM_153000 | TGTGGTTGCAGCCTGTCT (SEQ ID NO: 98) | AACCAACTCTGCATTGGATTC (SEQ ID NO: 99) | CCTTTGAAATTGTTTTACTCTCTGAGTTTATATGCTG (SEQ ID NO: 100) |
| Axin2 | NM_004655 | CTCCGTGTGTGCCTAT (SEQ ID NO: 101) | CATGACAAAGTCATTGAGTACAAGA (SEQ ID NO: 102) | TTGAGGGCTTCAAGCTTTCCCTTGT (SEQ ID NO: 103) |
| Sax1 | XM_372331 | GAACCTCGCGCTGTCTCT (SEQ ID NO: 104) | ACTTGGTCCTGCGATTCTG (SEQ ID NO: 105) | AGCCTCACCGAGACGCAGGTC (SEQ ID NO: 106) |
| Fzd5 | NM_003468 | GGCAACAATTTACCTTTGCTT (SEQ ID NO: 107) | GAACCAAGTGGAACTTCATTACA (SEQ ID NO: 108) | CGCCAACCTTAGGATTGTAAAGCCC (SEQ ID NO: 109) |
| sFRP1 | NM_003012 | CAGATACACAGGACATGGATGA (SEQ ID NO: 110) | CAAAGCTTTTGTAAGAGACTTAGGAT (SEQ ID NO: 111) | CCGTTTCCTCTAGTTTCTTCCTGTAGTACTCCTCT (SEQ ID NO: 112) |

FIG. 20

Mean Tumor Volumes

| Day | PBS ip | | CD4 ip | | Frz ip | |
|---|---|---|---|---|---|---|
| | Mean | SEM | Mean | SEM | Mean | SEM |
| 0 | 225.93 | 9.61 | 226.89 | 9.64 | 226.91 | 10.43 |
| 4 | 204.15 | 14.75 | 175.55 | 16.55 | 219.03 | 15.48 |
| 7 | 277.53 | 43.16 | 259.37 | 25.02 | 191.11 | 29.50 |
| 11 | 457.82 | 122.93 | 429.21 | 85.56 | 140.81 | 11.93 |
| 14 | 1031.84 | 333.62 | 1112.39 | 238.44 | 113.56 | 12.62 |
| 18 | 1767.01 | 513.69 | 1935.97 | 404.77 | 67.31 | 7.48 |

Mean % Change in Tumor Volume

| Day | PBS ip | | CD4 ip | | Frz ip | |
|---|---|---|---|---|---|---|
| | Mean | SEM | Mean | SEM | Mean | SEM |
| 4 | -8.07 | 7.36 | -22.91 | 5.76 | -3.66 | 4.79 |
| 7 | 28.57 | 23.12 | 14.51 | 10.51 | -16.76 | 11.34 |
| 11 | 116.03 | 61.46 | 90.58 | 41.23 | -37.28 | 5.31 |
| 14 | 396.12 | 165.30 | 388.61 | 105.48 | -49.84 | 5.25 |
| 18 | 736.95 | 252.59 | 766.50 | 189.04 | -69.67 | 3.51 |

Mean Tumor Volumes

| Day | PBS iv | | CD4 iv | | Frz iv | | Frz iv High Group | |
|---|---|---|---|---|---|---|---|---|
| | Mean | SEM | Mean | SEM | Mean | SEM | Mean | SEM |
| 0 | 225.77 | 10.49 | 225.61 | 10.09 | 225.95 | 9.97 | 376.03 | 13.90 |
| 4 | 181.27 | 12.97 | 202.13 | 13.68 | 178.60 | 10.86 | 225.50 | 16.47 |
| 7 | 196.93 | 16.02 | 224.70 | 18.96 | 137.38 | 7.15 | 161.01 | 10.29 |
| 11 | 268.38 | 41.88 | 371.32 | 62.94 | 97.76 | 11.03 | 107.32 | 7.90 |
| 14 | 504.20 | 122.01 | 592.14 | 161.73 | 89.54 | 10.45 | 88.39 | 8.27 |
| 18 | 1324.53 | 381.24 | 1224.00 | 315.88 | 73.27 | 7.01 | 52.66 | 7.52 |

Mean % Change in Tumor Volume

| Day | PBS iv | | CD4 iv | | Frz iv | | Frz iv High Group | |
|---|---|---|---|---|---|---|---|---|
| | Mean | SEM | Mean | SEM | Mean | SEM | Mean | SEM |
| 4 | -19.75 | 4.49 | -9.94 | 5.18 | -20.97 | 3.31 | -39.19 | 5.19 |
| 7 | -12.72 | 6.13 | 3.06 | 11.85 | -38.25 | 3.92 | -56.90 | 2.88 |
| 11 | 16.07 | 15.71 | 71.13 | 30.63 | -57.08 | 4.51 | -71.22 | 2.23 |
| 14 | 110.70 | 45.68 | 177.25 | 75.09 | -60.25 | 4.63 | -76.15 | 2.15 |
| 18 | 440.18 | 143.18 | 477.62 | 150.60 | -67.10 | 3.14 | -85.64 | 2.17 |

*FIG. 23B*

Mean Tumor Volume

| | A-PBS | | B-CD4 | | C-Frzd8 | | D-Frzd8 Hi | |
|---|---|---|---|---|---|---|---|---|
| Day | Mean | SEM | Mean | SEM | Mean | SEM | Mean | SEM |
| 0 | 201.87 | 4.77 | 201.47 | 4.71 | 201.25 | 4.55 | 336.13 | 16.41 |
| 4 | 244.09 | 8.03 | 240.31 | 11.73 | 193.57 | 7.70 | 228.07 | 9.67 |
| 8 | 324.51 | 17.62 | 340.32 | 17.84 | 220.08 | 11.21 | 258.18 | 15.24 |
| 11 | 472.56 | 30.40 | 460.39 | 32.42 | 278.11 | 16.03 | 384.99 | 35.34 |
| 15 | 785.50 | 64.09 | 785.44 | 55.64 | 439.92 | 19.18 | 503.53 | 72.39 |
| 18 | 993.47 | 81.81 | 968.94 | 82.53 | 591.65 | 29.83 | 541.90 | 92.76 |

*FIG. 26D*

Mean % Change in Tumor Volume

| | A-PBS | | B-CD4 | | C-Frzd8 | | D-Frzd8 Hi | |
|---|---|---|---|---|---|---|---|---|
| Day | Mean | SEM | Mean | SEM | Mean | SEM | Mean | SEM |
| 4 | 21.73 | 4.17 | 20.27 | 6.24 | -3.01 | 4.42 | -30.82 | 4.37 |
| 8 | 62.19 | 9.63 | 71.92 | 10.91 | 9.84 | 5.71 | -21.16 | 6.81 |
| 11 | 136.08 | 16.35 | 131.68 | 17.58 | 38.88 | 8.53 | 14.16 | 8.50 |
| 15 | 293.50 | 34.54 | 295.91 | 30.72 | 119.74 | 10.17 | 48.53 | 18.47 |
| 18 | 398.22 | 46.14 | 387.96 | 44.41 | 195.07 | 40.24 | 58.76 | 25.38 |

*FIG. 26E*

Mean Tumor Volume

| | A-PBS | | B-CD4 | | C-Frz8-Fc | |
|---|---|---|---|---|---|---|
| Day | Mean | SEM | Mean | SEM | Mean | SEM |
| 26 | 167.5 | 9.6 | 167.8 | 9.6 | 167.2 | 9.1 |
| 30 | 113.4 | 12.0 | 110.6 | 8.9 | 106.5 | 10.5 |
| 32 | 273.5 | 26.5 | 221.8 | 16.4 | 232.5 | 18.4 |
| 36 | 334.4 | 35.0 | 349.4 | 27.5 | 253.4 | 25.9 |
| 39 | 426.1 | 46.0 | 413.0 | 30.5 | 275.3 | 26.5 |
| 43 | 508.3 | 68.3 | 520.2 | 50.6 | 314.4 | 37.0 |
| 46 | 652.4 | 98.9 | 653.8 | 65.9 | 352.7 | 54.5 |
| 50 | 803.5 | 140.7 | 786.3 | 90.3 | 387.2 | 64.7 |
| 53 | 989.8 | 184.9 | 872.4 | 102.9 | 460.9 | 81.8 |
| 57 | 1170.0 | 232.2 | 1074.1 | 134.0 | 531.8 | 109.1 |

FIG. 28D

Mean % Change in Tumor Volume

| | A-PBS | | B-CD4 | | C-Frz8-Fc | |
|---|---|---|---|---|---|---|
| Day | Mean | SEM | Mean | SEM | Mean | SEM |
| 30 | -33.5 | 5.3 | -34.3 | 3.6 | -37.4 | 3.5 |
| 32 | 61.5 | 11.6 | 32.6 | 7.7 | 38.7 | 6.3 |
| 36 | 96.8 | 16.2 | 108.8 | 12.6 | 49.1 | 9.5 |
| 39 | 152.5 | 22.6 | 155.4 | 18.4 | 62.7 | 10.0 |
| 43 | 197.7 | 35.1 | 223.2 | 32.2 | 84.9 | 14.4 |
| 46 | 279.9 | 50.8 | 304.0 | 38.7 | 104.6 | 22.2 |
| 50 | 363.8 | 68.8 | 385.7 | 52.6 | 123.2 | 28.7 |
| 53 | 476.1 | 96.8 | 443.3 | 61.1 | 164.8 | 35.5 |
| 57 | 579.2 | 121.2 | 562.7 | 72.6 | 203.1 | 49.2 |

FIG. 28E

Wnt-1 Expression in Human Tumors
Normal

Wnt-1 Expression in Human Tumors
Low Grade

Wnt-1 Expression in Human Tumors
High Grade

Nuclear and Cytoplasmic Localization
of β-catenin in Breast Cancer Patients
Nuclear + Cytoplasmic β-catenin IHC Nuclear and Cytoplasmic Localization
of β-catenin in Breast Cancer Patients
Plasma Membrane β-catenin IHC

SEQUENCE LISTING

<160> NUMBER OF SEQ ID NOS: 129

<210> SEQ ID NO 1
<211> LENGTH: 646
<212> TYPE: PRT
<213> ORGANISM: Homo sapiens

<400> SEQUENCE: 1

Met Ala Glu Glu Ala Pro Lys Lys Ser Arg Ala Ala Gly Gly Gly
1               5                   10                  15

Ala Ser Trp Glu Leu Cys Ala Gly Ala Leu Ser Ala Arg Leu Ala Glu
            20                  25                  30

Glu Gly Ser Gly Asp Ala Gly Gly Arg Arg Pro Pro Val Asp Pro
        35                  40                  45

Arg Arg Leu Ala Arg Gln Leu Leu Leu Leu Trp Leu Leu Glu Ala
50                  55                  60

Pro Leu Leu Gly Val Arg Ala Gln Ala Gly Gln Gly Pro Gly
65                  70                  75                  80

Gln Gly Pro Gly Pro Gly Gln Gln Pro Pro Pro Gln Gln Gln
            85                  90                  95

Gln Ser Gly Gln Gln Tyr Asn Gly Glu Arg Gly Ile Ser Val Pro Asp
            100                 105                 110

His Gly Tyr Cys Gln Pro Ile Ser Ile Pro Leu Cys Thr Asp Ile Ala
        115                 120                 125

Tyr Asn Gln Thr Ile Met Pro Asn Leu Leu Gly His Thr Asn Gln Glu
    130                 135                 140

Asp Ala Gly Leu Glu Val His Gln Phe Tyr Pro Leu Val Lys Val Gln
145                 150                 155                 160

Cys Ser Ala Glu Leu Lys Phe Phe Leu Cys Ser Met Tyr Ala Pro Val
                165                 170                 175

Cys Thr Val Leu Glu Gln Ala Leu Pro Pro Cys Arg Ser Leu Cys Glu
            180                 185                 190

Arg Ala Arg Gln Gly Cys Glu Ala Leu Met Asn Lys Phe Gly Phe Gln
        195                 200                 205

Trp Pro Asp Thr Leu Lys Cys Glu Lys Phe Pro Val His Gly Ala Gly
    210                 215                 220

Glu Leu Cys Val Gly Gln Asn Thr Ser Asp Lys Gly Thr Pro Thr Pro
225                 230                 235                 240

Ser Leu Leu Pro Glu Phe Trp Thr Ser Asn Pro Gln His Gly Gly Gly
                245                 250                 255

Gly His Arg Gly Gly Phe Pro Gly Gly Ala Gly Ala Ser Glu Arg Gly
            260                 265                 270

Lys Phe Ser Cys Pro Arg Ala Leu Lys Val Pro Ser Tyr Leu Asn Tyr
        275                 280                 285

His Phe Leu Gly Glu Lys Asp Cys Gly Ala Pro Cys Glu Pro Thr Lys
    290                 295                 300

Val Tyr Gly Leu Met Tyr Phe Gly Pro Glu Glu Leu Arg Phe Ser Arg
305                 310                 315                 320

Thr Trp Ile Gly Ile Trp Ser Val Leu Cys Cys Ala Ser Thr Leu Phe
                325                 330                 335

Thr Val Leu Thr Tyr Leu Val Asp Met Arg Arg Phe Ser Tyr Pro Glu
            340                 345                 350

Arg Pro Ile Ile Phe Leu Ser Gly Cys Tyr Thr Ala Val Ala Val Ala
        355                 360                 365

```
Tyr Ile Ala Gly Phe Leu Leu Glu Asp Arg Val Val Cys Asn Asp Lys
    370                 375                 380

Phe Ala Glu Asp Gly Ala Arg Thr Val Ala Gln Gly Thr Lys Lys Glu
385                 390                 395                 400

Gly Cys Thr Ile Leu Phe Met Met Leu Tyr Phe Phe Ser Met Ala Ser
                405                 410                 415

Ser Ile Trp Trp Val Ile Leu Ser Leu Thr Trp Phe Leu Ala Ala Gly
            420                 425                 430

Met Lys Trp Gly His Glu Ala Ile Glu Ala Asn Ser Gln Tyr Phe His
        435                 440                 445

Leu Ala Ala Trp Ala Val Pro Ala Ile Lys Thr Ile Thr Ile Leu Ala
    450                 455                 460

Leu Gly Gln Val Asp Gly Asp Val Leu Ser Gly Val Cys Phe Val Gly
465                 470                 475                 480

Leu Asn Asn Val Asp Ala Leu Arg Gly Phe Val Leu Ala Pro Leu Phe
                485                 490                 495

Val Tyr Leu Phe Ile Gly Thr Ser Phe Leu Leu Ala Gly Phe Val Ser
            500                 505                 510

Leu Phe Arg Ile Arg Thr Ile Met Lys His Asp Gly Thr Lys Thr Glu
        515                 520                 525

Lys Leu Glu Lys Leu Met Val Arg Ile Gly Val Phe Ser Val Leu Tyr
    530                 535                 540

Thr Val Pro Ala Thr Ile Val Ile Ala Cys Tyr Phe Tyr Glu Gln Ala
545                 550                 555                 560

Phe Arg Asp Gln Trp Glu Arg Ser Trp Val Ala Gln Ser Cys Lys Ser
                565                 570                 575

Tyr Ala Ile Pro Cys Pro His Leu Gln Ala Gly Gly Ala Pro Pro
            580                 585                 590

His Pro Pro Met Ser Pro Asp Phe Thr Val Phe Met Ile Lys Tyr Leu
        595                 600                 605

Met Thr Leu Ile Val Gly Ile Thr Ser Gly Phe Trp Ile Trp Ser Gly
    610                 615                 620

Lys Thr Leu Asn Ser Trp Arg Lys Phe Tyr Thr Arg Leu Thr Asn Ser
625                 630                 635                 640

Lys Gln Gly Glu Thr Thr
                645

<210> SEQ ID NO 2
<211> LENGTH: 565
<212> TYPE: PRT
<213> ORGANISM: Homo sapiens

<400> SEQUENCE: 2

Met Arg Pro Arg Ser Ala Leu Pro Arg Leu Leu Leu Pro Leu Leu Leu
1               5                   10                  15

Leu Pro Ala Ala Gly Pro Ala Gln Phe His Gly Glu Lys Gly Ile Ser
                20                  25                  30

Ile Pro Asp His Gly Phe Cys Gln Pro Ile Ser Ile Pro Leu Cys Thr
            35                  40                  45

Asp Ile Ala Tyr Asn Gln Thr Ile Met Pro Asn Leu Leu Gly His Thr
    50                  55                  60

Asn Gln Glu Asp Ala Gly Leu Glu Val His Gln Phe Tyr Pro Leu Val
65                  70                  75                  80

Lys Val Gln Cys Ser Pro Glu Leu Arg Phe Phe Leu Cys Ser Met Tyr
                85                  90                  95
```

```
Ala Pro Val Cys Thr Val Leu Glu Gln Ala Ile Pro Pro Cys Arg Ser
            100                 105                 110
Ile Cys Glu Ser Ala Arg Gln Gly Cys Glu Ala Leu Met Asn Lys Phe
        115                 120                 125
Gly Phe Gln Trp Pro Glu Arg Leu Arg Cys Glu His Phe Pro Arg His
    130                 135                 140
Gly Ala Glu Gln Ile Cys Val Gly Gln Asn His Ser Glu Asp Gly Ala
145                 150                 155                 160
Pro Ala Leu Leu Thr Thr Ala Pro Pro Gly Leu Gln Pro Gly Ala
                165                 170                 175
Gly Gly Thr Pro Gly Gly Pro Gly Gly Gly Ala Pro Pro Arg Tyr
            180                 185                 190
Ala Thr Leu Glu His Pro Phe His Cys Pro Arg Val Leu Lys Val Pro
            195                 200                 205
Ser Tyr Leu Ser Tyr Lys Phe Leu Gly Glu Arg Asp Cys Ala Ala Pro
    210                 215                 220
Cys Glu Pro Ala Arg Pro Asp Gly Ser Met Phe Phe Ser Gln Glu Glu
225                 230                 235                 240
Thr Arg Phe Ala Arg Leu Trp Ile Leu Thr Trp Ser Val Leu Cys Cys
                245                 250                 255
Ala Ser Thr Phe Phe Thr Val Thr Thr Tyr Leu Val Asp Met Gln Arg
            260                 265                 270
Phe Arg Tyr Pro Glu Arg Pro Ile Ile Phe Leu Ser Gly Cys Tyr Thr
        275                 280                 285
Met Val Ser Val Ala Tyr Ile Ala Gly Phe Val Leu Gln Glu Arg Val
    290                 295                 300
Val Cys Asn Glu Arg Phe Ser Glu Asp Gly Tyr Arg Thr Val Val Gln
305                 310                 315                 320
Gly Thr Lys Lys Glu Gly Cys Thr Ile Leu Phe Met Met Leu Tyr Phe
                325                 330                 335
Phe Ser Met Ala Ser Ser Ile Trp Trp Val Ile Leu Ser Leu Thr Trp
            340                 345                 350
Phe Leu Ala Ala Gly Met Lys Trp Gly His Glu Ala Ile Glu Ala Asn
        355                 360                 365
Ser Gln Tyr Phe His Leu Ala Ala Trp Ala Val Pro Ala Val Lys Thr
    370                 375                 380
Ile Thr Ile Leu Ala Met Gly Gln Ile Asp Gly Asp Leu Leu Ser Gly
385                 390                 395                 400
Val Cys Phe Val Gly Leu Asn Ser Leu Asp Pro Leu Arg Gly Phe Val
                405                 410                 415
Leu Ala Pro Leu Phe Val Tyr Leu Phe Ile Gly Thr Ser Phe Leu Leu
            420                 425                 430
Ala Gly Phe Val Ser Leu Phe Arg Ile Arg Thr Ile Met Lys His Asp
        435                 440                 445
Gly Thr Lys Thr Glu Lys Leu Glu Arg Leu Met Val Arg Ile Gly Val
    450                 455                 460
Phe Ser Val Leu Tyr Thr Val Pro Ala Thr Ile Val Ile Ala Cys Tyr
465                 470                 475                 480
Phe Tyr Glu Gln Ala Phe Arg Glu His Trp Glu Arg Ser Trp Val Ser
                485                 490                 495
Gln His Cys Lys Ser Leu Ala Ile Pro Cys Pro Ala His Tyr Thr Pro
            500                 505                 510
Arg Met Ser Pro Asp Phe Thr Val Tyr Met Ile Lys Tyr Leu Met Thr
```

```
                515                 520                 525
Leu Ile Val Gly Ile Thr Ser Gly Phe Trp Ile Trp Ser Gly Lys Thr
            530                 535                 540
Leu His Ser Trp Arg Lys Phe Tyr Thr Arg Leu Thr Asn Ser Arg His
545                 550                 555                 560
Gly Glu Thr Thr Val
            565

<210> SEQ ID NO 3
<211> LENGTH: 666
<212> TYPE: PRT
<213> ORGANISM: Homo sapiens

<400> SEQUENCE: 3

Met Ala Met Thr Trp Ile Val Phe Ser Leu Trp Pro Leu Thr Val Phe
1               5                   10                  15
Met Gly His Ile Gly Gly His Ser Leu Phe Ser Cys Glu Pro Ile Thr
            20                  25                  30
Leu Arg Met Cys Gln Asp Leu Pro Tyr Asn Thr Thr Phe Met Pro Asn
        35                  40                  45
Leu Leu Asn His Tyr Asp Gln Gln Thr Ala Ala Leu Ala Met Glu Pro
    50                  55                  60
Phe His Pro Met Val Asn Leu Asp Cys Ser Arg Asp Phe Arg Pro Phe
65                  70                  75                  80
Leu Cys Ala Leu Tyr Ala Pro Ile Cys Met Glu Tyr Gly Arg Val Thr
                85                  90                  95
Leu Pro Cys Arg Arg Leu Cys Gln Arg Ala Tyr Ser Glu Cys Ser Lys
            100                 105                 110
Leu Met Glu Met Phe Gly Val Pro Trp Pro Glu Asp Met Glu Cys Ser
        115                 120                 125
Arg Phe Pro Asp Cys Asp Glu Pro Tyr Pro Arg Leu Val Asp Leu Asn
    130                 135                 140
Leu Ala Gly Glu Pro Thr Glu Gly Ala Pro Val Ala Val Gln Arg Asp
145                 150                 155                 160
Tyr Gly Phe Trp Cys Pro Arg Glu Leu Lys Ile Asp Pro Asp Leu Gly
                165                 170                 175
Tyr Ser Phe Leu His Val Arg Asp Cys Ser Pro Pro Cys Pro Asn Met
            180                 185                 190
Tyr Phe Arg Arg Glu Glu Leu Ser Phe Ala Arg Tyr Phe Ile Gly Leu
        195                 200                 205
Ile Ser Ile Ile Cys Leu Ser Ala Thr Leu Phe Thr Phe Leu Thr Phe
    210                 215                 220
Leu Ile Asp Val Thr Arg Phe Arg Tyr Pro Glu Arg Pro Ile Ile Phe
225                 230                 235                 240
Tyr Ala Val Cys Tyr Met Met Val Ser Leu Ile Phe Phe Ile Gly Phe
                245                 250                 255
Leu Leu Glu Asp Arg Val Ala Cys Asn Ala Ser Ile Pro Ala Gln Tyr
            260                 265                 270
Lys Ala Ser Thr Val Thr Gln Gly Ser His Asn Lys Ala Cys Thr Met
        275                 280                 285
Leu Phe Met Ile Leu Tyr Phe Phe Thr Met Ala Gly Ser Val Trp Trp
    290                 295                 300
Val Ile Leu Thr Ile Thr Trp Phe Leu Ala Ala Val Pro Lys Trp Gly
305                 310                 315                 320
Ser Glu Ala Ile Glu Lys Lys Ala Leu Leu Phe His Ala Ser Ala Trp
```

```
                     325                 330                 335
Gly Ile Pro Gly Thr Leu Thr Ile Ile Leu Ala Met Asn Lys Ile
                340                 345                 350

Glu Gly Asp Asn Ile Ser Gly Val Cys Phe Val Gly Leu Tyr Asp Val
            355                 360                 365

Asp Ala Leu Arg Tyr Phe Val Leu Ala Pro Leu Cys Leu Tyr Val Val
    370                 375                 380

Val Gly Val Ser Leu Leu Leu Ala Gly Ile Ile Ser Leu Asn Arg Val
385                 390                 395                 400

Arg Ile Glu Ile Pro Leu Glu Lys Glu Asn Gln Asp Lys Leu Val Lys
                405                 410                 415

Phe Met Ile Arg Ile Gly Val Phe Ser Ile Leu Tyr Leu Val Pro Leu
                420                 425                 430

Leu Val Val Ile Gly Cys Tyr Phe Tyr Glu Gln Ala Tyr Arg Gly Ile
            435                 440                 445

Trp Glu Thr Thr Trp Ile Gln Glu Arg Cys Arg Glu Tyr His Ile Pro
    450                 455                 460

Cys Pro Tyr Gln Val Thr Gln Met Ser Arg Pro Asp Leu Ile Leu Phe
465                 470                 475                 480

Leu Met Lys Tyr Leu Met Ala Leu Ile Val Gly Ile Pro Ser Val Phe
                485                 490                 495

Trp Val Gly Ser Lys Lys Thr Cys Phe Glu Trp Ala Ser Phe Phe His
                500                 505                 510

Gly Arg Arg Lys Lys Glu Ile Val Asn Glu Ser Arg Gln Val Leu Gln
            515                 520                 525

Glu Pro Asp Phe Ala Gln Ser Leu Leu Arg Asp Pro Asn Thr Pro Ile
    530                 535                 540

Ile Arg Lys Ser Arg Gly Thr Ser Thr Gln Gly Thr Ser Thr His Ala
545                 550                 555                 560

Ser Ser Thr Gln Leu Ala Met Val Asp Asp Gln Arg Ser Lys Ala Gly
                565                 570                 575

Ser Ile His Ser Lys Val Ser Ser Tyr His Gly Ser Leu His Arg Ser
                580                 585                 590

Arg Asp Gly Arg Tyr Thr Pro Cys Ser Tyr Arg Gly Met Glu Glu Arg
            595                 600                 605

Leu Pro His Gly Ser Met Ser Arg Leu Thr Asp His Ser Arg His Ser
    610                 615                 620

Ser Ser His Arg Leu Asn Glu Gln Ser Arg His Ser Ser Ile Arg Asp
625                 630                 635                 640

Leu Ser Asn Asn Pro Met Thr His Ile Thr His Gly Thr Ser Met Asn
                645                 650                 655

Arg Val Ile Glu Glu Asp Gly Thr Ser Ala
            660                 665

<210> SEQ ID NO 4
<211> LENGTH: 537
<212> TYPE: PRT
<213> ORGANISM: Homo sapiens

<400> SEQUENCE: 4

Met Ala Trp Arg Gly Ala Gly Pro Ser Val Pro Gly Ala Pro Gly Gly
1               5                   10                  15

Val Gly Leu Ser Leu Gly Leu Leu Gln Leu Leu Leu Leu Leu Leu Gly
            20                  25                  30

Pro Ala Arg Gly Phe Gly Asp Glu Glu Glu Arg Arg Cys Asp Pro Ile
```

-continued

```
                35                  40                  45
Arg Ile Ser Met Cys Gln Asn Leu Gly Tyr Asn Val Thr Lys Met Pro
 50                  55                  60
Asn Leu Val Gly His Glu Leu Gln Thr Asp Ala Glu Leu Gln Leu Thr
 65                  70                  75                  80
Thr Phe Thr Pro Leu Ile Gln Tyr Gly Cys Ser Ser Gln Leu Gln Phe
                 85                  90                  95
Phe Leu Cys Ser Val Tyr Val Pro Met Cys Thr Glu Lys Ile Asn Ile
                100                 105                 110
Pro Ile Gly Pro Cys Gly Gly Met Cys Leu Ser Val Lys Arg Arg Cys
                115                 120                 125
Glu Pro Val Leu Lys Glu Phe Gly Phe Ala Trp Pro Glu Ser Leu Asn
130                 135                 140
Cys Ser Lys Phe Pro Pro Gln Asn Asp His Asn His Met Cys Met Glu
145                 150                 155                 160
Gly Pro Gly Asp Glu Glu Val Pro Leu Pro His Lys Thr Pro Ile Gln
                165                 170                 175
Pro Gly Glu Glu Cys His Ser Val Gly Thr Asn Ser Asp Gln Tyr Ile
                180                 185                 190
Trp Val Lys Arg Ser Leu Asn Cys Val Leu Lys Cys Gly Tyr Asp Ala
                195                 200                 205
Gly Leu Tyr Ser Arg Ser Ala Lys Glu Phe Thr Asp Ile Trp Met Ala
                210                 215                 220
Val Trp Ala Ser Leu Cys Phe Ile Ser Thr Ala Phe Thr Val Leu Thr
225                 230                 235                 240
Phe Leu Ile Asp Ser Ser Arg Phe Ser Tyr Pro Glu Arg Pro Ile Ile
                245                 250                 255
Phe Leu Ser Met Cys Tyr Asn Ile Tyr Ser Ile Ala Tyr Ile Val Arg
                260                 265                 270
Leu Thr Val Gly Arg Glu Arg Ile Ser Cys Asp Phe Glu Glu Ala Ala
                275                 280                 285
Glu Pro Val Leu Ile Gln Glu Gly Leu Lys Asn Thr Gly Cys Ala Ile
290                 295                 300
Ile Phe Leu Leu Met Tyr Phe Phe Gly Met Ala Ser Ser Ile Trp Trp
305                 310                 315                 320
Val Ile Leu Thr Leu Thr Trp Phe Leu Ala Ala Gly Leu Lys Trp Gly
                325                 330                 335
His Glu Ala Ile Glu Met His Ser Ser Tyr Phe His Ile Ala Ala Trp
                340                 345                 350
Ala Ile Pro Ala Val Lys Thr Ile Val Ile Leu Ile Met Arg Leu Val
                355                 360                 365
Asp Ala Asp Glu Leu Thr Gly Leu Cys Tyr Val Gly Asn Gln Asn Leu
                370                 375                 380
Asp Ala Leu Thr Gly Phe Val Val Ala Pro Leu Phe Thr Tyr Leu Val
385                 390                 395                 400
Ile Gly Thr Leu Phe Ile Ala Ala Gly Leu Val Ala Leu Phe Lys Ile
                405                 410                 415
Arg Ser Asn Leu Gln Lys Asp Gly Thr Lys Thr Asp Lys Leu Glu Arg
                420                 425                 430
Leu Met Val Lys Ile Gly Val Phe Ser Val Leu Tyr Thr Val Pro Ala
                435                 440                 445
Thr Cys Val Ile Ala Cys Tyr Phe Tyr Glu Ile Ser Asn Trp Ala Leu
450                 455                 460
```

```
Phe Arg Tyr Ser Ala Asp Asp Ser Asn Met Ala Val Glu Met Leu Lys
465                 470                 475                 480

Ile Phe Met Ser Leu Leu Val Gly Ile Thr Ser Gly Met Trp Ile Trp
                485                 490                 495

Ser Ala Lys Thr Leu His Thr Trp Gln Lys Cys Ser Asn Arg Leu Val
            500                 505                 510

Asn Ser Gly Lys Val Lys Arg Glu Lys Arg Gly Asn Gly Trp Val Lys
        515                 520                 525

Pro Gly Lys Gly Ser Glu Thr Val Val
        530                 535

<210> SEQ ID NO 5
<211> LENGTH: 585
<212> TYPE: PRT
<213> ORGANISM: Homo sapiens

<400> SEQUENCE: 5

Met Ala Arg Pro Asp Pro Ser Ala Pro Ser Leu Leu Leu Leu Leu Leu
1               5                   10                  15

Leu Ala Gln Leu Val Gly Arg Ala Ala Ala Ser Lys Ala Pro Val
            20                  25                  30

Cys Gln Glu Ile Thr Val Pro Met Cys Arg Gly Ile Gly Tyr Asn Leu
        35                  40                  45

Thr His Met Pro Asn Gln Phe Asn His Asp Thr Gln Asp Glu Ala Gly
    50                  55                  60

Leu Glu Val His Gln Phe Trp Pro Leu Val Glu Ile Gln Cys Ser Pro
65                  70                  75                  80

Asp Leu Arg Phe Phe Leu Cys Ser Met Tyr Thr Pro Ile Cys Leu Pro
                85                  90                  95

Asp Tyr His Lys Pro Leu Pro Pro Cys Arg Ser Val Cys Glu Arg Ala
            100                 105                 110

Lys Ala Gly Cys Ser Pro Leu Met Arg Gln Tyr Gly Phe Ala Trp Pro
        115                 120                 125

Glu Arg Met Ser Cys Asp Arg Leu Pro Val Leu Gly Arg Asp Ala Glu
    130                 135                 140

Val Leu Cys Met Asp Tyr Asn Arg Ser Glu Ala Thr Thr Ala Pro Pro
145                 150                 155                 160

Arg Pro Phe Pro Ala Lys Pro Thr Leu Pro Gly Pro Pro Gly Ala Pro
                165                 170                 175

Ala Ser Gly Gly Glu Cys Pro Ala Gly Gly Pro Phe Val Cys Lys Cys
            180                 185                 190

Arg Glu Pro Phe Val Pro Ile Leu Lys Glu Ser His Pro Leu Tyr Asn
        195                 200                 205

Lys Val Arg Thr Gly Gln Val Pro Asn Cys Ala Val Pro Cys Tyr Gln
    210                 215                 220

Pro Ser Phe Ser Ala Asp Glu Arg Thr Phe Ala Thr Phe Trp Ile Gly
225                 230                 235                 240

Leu Trp Ser Val Leu Cys Phe Ile Ser Thr Thr Val Ala Thr
                245                 250                 255

Phe Leu Ile Asp Met Glu Arg Phe Arg Tyr Pro Glu Arg Pro Ile Ile
                260                 265                 270

Phe Leu Ser Ala Cys Tyr Leu Cys Val Ser Leu Gly Phe Leu Val Arg
            275                 280                 285

Leu Val Val Gly His Ala Ser Val Ala Cys Ser Arg Glu His Asn His
        290                 295                 300
```

```
Ile His Tyr Glu Thr Thr Gly Pro Ala Leu Cys Thr Ile Val Phe Leu
305                 310                 315                 320

Leu Val Tyr Phe Phe Gly Met Ala Ser Ser Ile Trp Trp Val Ile Leu
                325                 330                 335

Ser Leu Thr Trp Phe Leu Ala Ala Gly Met Lys Trp Gly Asn Glu Ala
            340                 345                 350

Ile Ala Gly Tyr Ala Gln Tyr Phe His Leu Ala Ala Trp Leu Ile Pro
        355                 360                 365

Ser Val Lys Ser Ile Thr Ala Leu Ala Leu Ser Ser Val Asp Gly Asp
    370                 375                 380

Pro Val Ala Gly Ile Cys Tyr Val Gly Asn Gln Asn Leu Asn Ser Leu
385                 390                 395                 400

Arg Gly Phe Val Leu Gly Pro Leu Val Leu Tyr Leu Leu Val Gly Thr
                405                 410                 415

Leu Phe Leu Leu Ala Gly Phe Val Ser Leu Phe Arg Ile Arg Ser Val
            420                 425                 430

Ile Lys Gln Gly Gly Thr Lys Thr Asp Lys Leu Glu Lys Leu Met Ile
        435                 440                 445

Arg Ile Gly Ile Phe Thr Leu Leu Tyr Thr Val Pro Ala Ser Ile Val
    450                 455                 460

Val Ala Cys Tyr Leu Tyr Glu Gln His Tyr Arg Glu Ser Trp Glu Ala
465                 470                 475                 480

Ala Leu Thr Cys Ala Cys Pro Gly His Asp Thr Gly Gln Pro Arg Ala
                485                 490                 495

Lys Pro Glu Tyr Trp Val Leu Met Leu Lys Tyr Phe Met Cys Leu Val
            500                 505                 510

Val Gly Ile Thr Ser Gly Val Trp Ile Trp Ser Gly Lys Thr Val Glu
        515                 520                 525

Ser Trp Arg Arg Phe Thr Ser Arg Cys Cys Cys Arg Pro Arg Arg Gly
    530                 535                 540

His Lys Ser Gly Gly Ala Met Ala Ala Gly Asp Tyr Pro Glu Ala Ser
545                 550                 555                 560

Ala Ala Leu Thr Gly Arg Thr Gly Pro Pro Gly Pro Ala Ala Thr Tyr
                565                 570                 575

His Lys Gln Val Ser Leu Ser His Val
            580                 585

<210> SEQ ID NO 6
<211> LENGTH: 706
<212> TYPE: PRT
<213> ORGANISM: Homo sapiens

<400> SEQUENCE: 6

Met Glu Met Phe Thr Phe Leu Leu Thr Cys Ile Phe Leu Pro Leu Leu
1               5                   10                  15

Arg Gly His Ser Leu Phe Thr Cys Glu Pro Ile Thr Val Pro Arg Cys
                20                  25                  30

Met Lys Met Ala Tyr Asn Met Thr Phe Phe Pro Asn Leu Met Gly His
            35                  40                  45

Tyr Asp Gln Ser Ile Ala Ala Val Glu Met Glu His Phe Leu Pro Leu
        50                  55                  60

Ala Asn Leu Glu Cys Ser Pro Asn Ile Glu Thr Phe Leu Cys Lys Ala
65                  70                  75                  80

Phe Val Pro Thr Cys Ile Glu Gln Ile His Val Val Pro Pro Cys Arg
                85                  90                  95
```

-continued

```
Lys Leu Cys Glu Lys Val Tyr Ser Asp Cys Lys Lys Leu Ile Asp Thr
            100                 105                 110
Phe Gly Ile Arg Trp Pro Glu Leu Glu Cys Asp Arg Leu Gln Tyr
        115                 120                 125
Cys Asp Glu Thr Val Pro Val Thr Phe Asp Pro His Thr Glu Phe Leu
130                 135                 140
Gly Pro Gln Lys Lys Thr Glu Gln Val Gln Arg Asp Ile Gly Phe Trp
145                 150                 155                 160
Cys Pro Arg His Leu Lys Thr Ser Gly Gly Gln Gly Tyr Lys Phe Leu
                165                 170                 175
Gly Ile Asp Gln Cys Ala Pro Pro Cys Pro Asn Met Tyr Phe Lys Ser
            180                 185                 190
Asp Glu Leu Glu Phe Ala Lys Ser Phe Ile Gly Thr Val Ser Ile Phe
        195                 200                 205
Cys Leu Cys Ala Thr Leu Phe Thr Phe Leu Thr Phe Leu Ile Asp Val
    210                 215                 220
Arg Arg Phe Arg Tyr Pro Glu Arg Pro Ile Ile Tyr Tyr Ser Val Cys
225                 230                 235                 240
Tyr Ser Ile Val Ser Leu Met Tyr Phe Ile Gly Phe Leu Leu Gly Asp
                245                 250                 255
Ser Thr Ala Cys Asn Lys Ala Asp Glu Lys Leu Glu Leu Gly Asp Thr
            260                 265                 270
Val Val Leu Gly Ser Gln Asn Lys Ala Cys Thr Val Leu Phe Met Leu
        275                 280                 285
Leu Tyr Phe Phe Thr Met Ala Gly Thr Val Trp Trp Val Ile Leu Thr
    290                 295                 300
Ile Thr Trp Phe Leu Ala Ala Gly Arg Lys Trp Ser Cys Glu Ala Ile
305                 310                 315                 320
Glu Gln Lys Ala Val Trp Phe His Ala Val Ala Trp Gly Thr Pro Gly
                325                 330                 335
Phe Leu Thr Val Met Leu Leu Ala Met Asn Lys Val Glu Gly Asp Asn
            340                 345                 350
Ile Ser Gly Val Cys Phe Val Gly Leu Tyr Asp Leu Asp Ala Ser Arg
        355                 360                 365
Tyr Phe Val Leu Leu Pro Leu Cys Leu Cys Val Phe Val Gly Leu Ser
    370                 375                 380
Leu Leu Leu Ala Gly Ile Ile Ser Leu Asn His Val Arg Gln Val Ile
385                 390                 395                 400
Gln His Asp Gly Arg Asn Gln Glu Lys Leu Lys Lys Phe Met Ile Arg
                405                 410                 415
Ile Gly Val Phe Ser Gly Leu Tyr Leu Val Pro Leu Val Thr Leu Leu
            420                 425                 430
Gly Cys Tyr Val Tyr Glu Gln Val Asn Arg Ile Thr Trp Glu Ile Thr
        435                 440                 445
Trp Val Ser Asp His Cys Arg Gln Tyr His Ile Pro Cys Pro Tyr Gln
    450                 455                 460
Ala Lys Ala Lys Ala Arg Pro Glu Leu Ala Leu Phe Met Ile Lys Tyr
465                 470                 475                 480
Leu Met Thr Leu Ile Val Gly Ile Ser Ala Val Phe Trp Val Gly Ser
                485                 490                 495
Lys Lys Thr Cys Thr Glu Trp Ala Gly Phe Phe Lys Arg Asn Arg Lys
            500                 505                 510
Arg Asp Pro Ile Ser Glu Ser Arg Arg Val Leu Gln Glu Ser Cys Glu
        515                 520                 525
```

```
Phe Phe Leu Lys His Asn Ser Lys Val Lys His Lys Lys Lys His Tyr
    530                 535                 540
Lys Pro Ser Ser His Lys Leu Lys Val Ile Ser Lys Ser Met Gly Thr
545                 550                 555                 560
Ser Thr Gly Ala Thr Ala Asn His Gly Thr Ser Ala Val Ala Ile Thr
                565                 570                 575
Ser His Asp Tyr Leu Gly Gln Glu Thr Leu Thr Glu Ile Gln Thr Ser
            580                 585                 590
Pro Glu Thr Ser Met Arg Glu Val Lys Ala Asp Gly Ala Ser Thr Pro
        595                 600                 605
Arg Leu Arg Glu Gln Asp Cys Gly Glu Pro Ala Ser Pro Ala Ala Ser
    610                 615                 620
Ile Ser Arg Leu Ser Gly Glu Gln Val Asp Gly Lys Gly Gln Ala Gly
625                 630                 635                 640
Ser Val Ser Glu Ser Ala Arg Ser Glu Gly Arg Ile Ser Pro Lys Ser
                645                 650                 655
Asp Ile Thr Asp Thr Gly Leu Ala Gln Ser Asn Asn Leu Gln Val Pro
            660                 665                 670
Ser Ser Ser Glu Pro Ser Ser Leu Lys Gly Ser Thr Ser Leu Leu Val
        675                 680                 685
His Pro Val Ser Gly Val Arg Lys Glu Gln Gly Gly Cys His Ser
    690                 695                 700
Asp Thr
705

<210> SEQ ID NO 7
<211> LENGTH: 574
<212> TYPE: PRT
<213> ORGANISM: Homo sapiens

<400> SEQUENCE: 7

Met Arg Asp Pro Gly Ala Ala Ala Pro Leu Ser Ser Leu Gly Leu Cys
1               5                   10                  15
Ala Leu Val Leu Ala Leu Leu Gly Ala Leu Ser Ala Gly Ala Gly Ala
                20                  25                  30
Gln Pro Tyr His Gly Glu Lys Gly Ile Ser Val Pro Asp His Gly Phe
            35                  40                  45
Cys Gln Pro Ile Ser Ile Pro Leu Cys Thr Asp Ile Ala Tyr Asn Gln
        50                  55                  60
Thr Ile Leu Pro Asn Leu Leu Gly His Thr Asn Gln Glu Asp Ala Gly
65                  70                  75                  80
Leu Glu Val His Gln Phe Tyr Pro Leu Val Lys Val Gln Cys Ser Pro
                85                  90                  95
Glu Leu Arg Phe Phe Leu Cys Ser Met Tyr Ala Pro Val Cys Thr Val
            100                 105                 110
Leu Asp Gln Ala Ile Pro Pro Cys Arg Ser Leu Cys Glu Arg Ala Arg
        115                 120                 125
Gln Gly Cys Glu Ala Leu Met Asn Lys Phe Gly Phe Gln Trp Pro Glu
    130                 135                 140
Arg Leu Arg Cys Glu Asn Phe Pro Val His Gly Ala Gly Glu Ile Cys
145                 150                 155                 160
Val Gly Gln Asn Thr Ser Asp Gly Ser Gly Gly Pro Gly Gly Gly Pro
                165                 170                 175
Thr Ala Tyr Pro Thr Ala Pro Tyr Leu Pro Asp Leu Pro Phe Thr Ala
            180                 185                 190
```

```
Leu Pro Pro Gly Ala Ser Asp Gly Arg Gly Arg Pro Ala Phe Pro Phe
            195                 200                 205

Ser Cys Pro Arg Gln Leu Lys Val Pro Pro Tyr Leu Gly Tyr Arg Phe
        210                 215                 220

Leu Gly Glu Arg Asp Cys Gly Ala Pro Cys Pro Gly Arg Ala Asn
225                 230                 235                 240

Gly Leu Met Tyr Phe Lys Glu Glu Arg Arg Phe Ala Arg Leu Trp
                245                 250                 255

Val Gly Val Trp Ser Val Leu Cys Cys Ala Ser Thr Leu Phe Thr Val
            260                 265                 270

Leu Thr Tyr Leu Val Asp Met Arg Arg Phe Ser Tyr Pro Glu Arg Pro
        275                 280                 285

Ile Ile Phe Leu Ser Gly Cys Tyr Phe Met Val Ala Val Ala His Val
        290                 295                 300

Ala Gly Phe Leu Leu Glu Asp Arg Ala Val Cys Val Glu Arg Phe Ser
305                 310                 315                 320

Asp Asp Gly Tyr Arg Thr Val Ala Gln Gly Thr Lys Lys Glu Gly Cys
                325                 330                 335

Thr Ile Leu Phe Met Val Leu Tyr Phe Phe Gly Met Ala Ser Ser Ile
                340                 345                 350

Trp Trp Val Ile Leu Ser Leu Thr Trp Phe Leu Ala Ala Gly Met Lys
            355                 360                 365

Trp Gly His Glu Ala Ile Glu Ala Asn Ser Gln Tyr Phe His Leu Ala
        370                 375                 380

Ala Trp Ala Val Pro Ala Val Lys Thr Ile Thr Ile Leu Ala Met Gly
385                 390                 395                 400

Gln Val Asp Gly Asp Leu Leu Ser Gly Val Cys Tyr Val Gly Leu Ser
                405                 410                 415

Ser Val Asp Ala Leu Arg Gly Phe Val Leu Ala Pro Leu Phe Val Tyr
            420                 425                 430

Leu Phe Ile Gly Thr Ser Phe Leu Leu Ala Gly Phe Val Ser Leu Phe
        435                 440                 445

Arg Ile Arg Thr Ile Met Lys His Asp Gly Thr Lys Thr Glu Lys Leu
        450                 455                 460

Glu Lys Leu Met Val Arg Ile Gly Val Phe Ser Val Leu Tyr Thr Val
465                 470                 475                 480

Pro Ala Thr Ile Val Leu Ala Cys Tyr Phe Tyr Glu Gln Ala Phe Arg
                485                 490                 495

Glu His Trp Glu Arg Thr Trp Leu Leu Gln Thr Cys Lys Ser Tyr Ala
            500                 505                 510

Val Pro Cys Pro Pro Gly His Phe Pro Pro Met Ser Pro Asp Phe Thr
        515                 520                 525

Val Phe Met Ile Lys Tyr Leu Met Thr Met Ile Val Gly Ile Thr Thr
        530                 535                 540

Gly Phe Trp Ile Trp Ser Gly Lys Thr Leu Gln Ser Trp Arg Arg Phe
545                 550                 555                 560

Tyr His Arg Leu Ser His Ser Ser Lys Gly Glu Thr Ala Val
                565                 570

<210> SEQ ID NO 8
<211> LENGTH: 694
<212> TYPE: PRT
<213> ORGANISM: Homo sapiens

<400> SEQUENCE: 8
```

-continued

```
Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
        20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
        50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
            85                  90                  95

Leu Glu Asp Tyr Lys Lys Pro Leu Pro Pro Cys Arg Ser Val Cys Glu
                100                 105                 110

Arg Ala Lys Ala Gly Cys Ala Pro Leu Met Arg Gln Tyr Gly Phe Ala
            115                 120                 125

Trp Pro Asp Arg Met Arg Cys Asp Arg Leu Pro Glu Gln Gly Asn Pro
        130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Gly Glu Gln Pro
                165                 170                 175

Pro Ser Gly Ser Gly His Gly Arg Pro Pro Gly Ala Arg Pro Pro His
            180                 185                 190

Arg Gly Gly Gly Arg Gly Gly Gly Gly Asp Ala Ala Pro Pro
            195                 200                 205

Ala Arg Gly Gly Gly Gly Gly Lys Ala Arg Pro Pro Gly Gly Gly
            210                 215                 220

Ala Ala Pro Cys Glu Pro Gly Cys Gln Cys Arg Ala Pro Met Val Ser
225                 230                 235                 240

Val Ser Ser Glu Arg His Pro Leu Tyr Asn Arg Val Lys Thr Gly Gln
                245                 250                 255

Ile Ala Asn Cys Ala Leu Pro Cys His Asn Pro Phe Phe Ser Gln Asp
            260                 265                 270

Glu Arg Ala Phe Thr Val Phe Trp Ile Gly Leu Trp Ser Val Leu Cys
        275                 280                 285

Phe Val Ser Thr Phe Ala Thr Val Ser Thr Phe Leu Ile Asp Met Glu
        290                 295                 300

Arg Phe Lys Tyr Pro Glu Arg Pro Ile Ile Phe Leu Ser Ala Cys Tyr
305                 310                 315                 320

Leu Phe Val Ser Val Gly Tyr Leu Val Arg Leu Val Ala Gly His Glu
                325                 330                 335

Lys Val Ala Cys Ser Gly Gly Ala Pro Gly Ala Gly Gly Ala Gly Gly
            340                 345                 350

Ala Gly Gly Ala Ala Ala Gly Ala Gly Ala Gly Ala Gly Ala Gly
        355                 360                 365

Gly Pro Gly Gly Arg Gly Glu Tyr Glu Glu Leu Gly Ala Val Glu Gln
        370                 375                 380

His Val Arg Tyr Glu Thr Thr Gly Pro Ala Leu Cys Thr Val Val Phe
385                 390                 395                 400

Leu Leu Val Tyr Phe Phe Gly Met Ala Ser Ser Ile Trp Trp Val Ile
                405                 410                 415

Leu Ser Leu Thr Trp Phe Leu Ala Ala Gly Met Lys Trp Gly Asn Glu
```

```
                     420               425               430
Ala Ile Ala Gly Tyr Ser Gln Tyr Phe His Leu Ala Ala Trp Leu Val
                435               440               445

Pro Ser Val Lys Ser Ile Ala Val Leu Ala Leu Ser Ser Val Asp Gly
            450               455               460

Asp Pro Val Ala Gly Ile Cys Tyr Val Gly Asn Gln Ser Leu Asp Asn
465               470               475               480

Leu Arg Gly Phe Val Leu Ala Pro Leu Val Ile Tyr Leu Phe Ile Gly
                485               490               495

Thr Met Phe Leu Leu Ala Gly Phe Val Ser Leu Phe Arg Ile Arg Ser
            500               505               510

Val Ile Lys Gln Gln Asp Gly Pro Thr Lys Thr His Lys Leu Glu Lys
        515               520               525

Leu Met Ile Arg Leu Gly Leu Phe Thr Val Leu Tyr Thr Val Pro Ala
    530               535               540

Ala Val Val Val Ala Cys Leu Phe Tyr Glu Gln His Asn Arg Pro Arg
545               550               555               560

Trp Glu Ala Thr His Asn Cys Pro Cys Leu Arg Asp Leu Gln Pro Asp
                565               570               575

Gln Ala Arg Arg Pro Asp Tyr Ala Val Phe Met Leu Lys Tyr Phe Met
            580               585               590

Cys Leu Val Val Gly Ile Thr Ser Gly Val Trp Val Trp Ser Gly Lys
        595               600               605

Thr Leu Glu Ser Trp Arg Ser Leu Cys Thr Arg Cys Cys Trp Ala Ser
    610               615               620

Lys Gly Ala Ala Val Gly Gly Ala Gly Ala Thr Ala Ala Gly Gly
625               630               635               640

Gly Gly Gly Pro Gly Gly Gly Gly Gly Pro Gly Gly Gly Gly
                645               650               655

Gly Pro Gly Gly Gly Gly Ser Leu Tyr Ser Asp Val Ser Thr Gly
            660               665               670

Leu Thr Trp Arg Ser Gly Thr Ala Ser Ser Val Ser Tyr Pro Lys Gln
    675               680               685

Met Pro Leu Ser Gln Val
    690

<210> SEQ ID NO 9
<211> LENGTH: 591
<212> TYPE: PRT
<213> ORGANISM: Homo sapiens

<400> SEQUENCE: 9

Met Ala Val Ala Pro Leu Arg Gly Ala Leu Leu Leu Trp Gln Leu Leu
1               5                   10                  15

Ala Ala Gly Gly Ala Ala Leu Glu Ile Gly Arg Phe Asp Pro Glu Arg
                20                  25                  30

Gly Arg Gly Ala Ala Pro Cys Gln Ala Val Glu Ile Pro Met Cys Arg
            35                  40                  45

Gly Ile Gly Tyr Asn Leu Thr Arg Met Pro Asn Leu Leu Gly His Thr
        50                  55                  60

Ser Gln Gly Glu Ala Ala Ala Glu Leu Ala Glu Phe Ala Pro Leu Val
65                  70                  75                  80

Gln Tyr Gly Cys His Ser His Leu Arg Phe Phe Leu Cys Ser Leu Tyr
                85                  90                  95

Ala Pro Met Cys Thr Asp Gln Val Ser Thr Pro Ile Pro Ala Cys Arg
```

-continued

```
               100                 105                 110
Pro Met Cys Glu Gln Ala Arg Leu Arg Cys Ala Pro Ile Met Glu Gln
        115                 120                 125

Phe Asn Phe Gly Trp Pro Asp Ser Leu Asp Cys Ala Arg Leu Pro Thr
        130                 135                 140

Arg Asn Asp Pro His Ala Leu Cys Met Glu Ala Pro Glu Asn Ala Thr
145                 150                 155                 160

Ala Gly Pro Ala Glu Pro His Lys Gly Leu Gly Met Leu Pro Val Ala
                165                 170                 175

Pro Arg Pro Ala Arg Pro Pro Gly Asp Leu Gly Pro Gly Ala Gly Gly
                180                 185                 190

Ser Gly Thr Cys Glu Asn Pro Glu Lys Phe Gln Tyr Val Glu Lys Ser
        195                 200                 205

Arg Ser Cys Ala Pro Arg Cys Gly Pro Gly Val Glu Val Phe Trp Ser
210                 215                 220

Arg Arg Asp Lys Asp Phe Ala Leu Val Trp Met Ala Val Trp Ser Ala
225                 230                 235                 240

Leu Cys Phe Phe Ser Thr Ala Phe Thr Val Leu Thr Phe Leu Leu Glu
                245                 250                 255

Pro His Arg Phe Gln Tyr Pro Glu Arg Pro Ile Ile Phe Leu Ser Met
                260                 265                 270

Cys Tyr Asn Val Tyr Ser Leu Ala Phe Leu Ile Arg Ala Val Ala Gly
        275                 280                 285

Ala Gln Ser Val Ala Cys Asp Gln Glu Ala Gly Ala Leu Tyr Val Ile
        290                 295                 300

Gln Glu Gly Leu Glu Asn Thr Gly Cys Thr Leu Val Phe Leu Leu Leu
305                 310                 315                 320

Tyr Tyr Phe Gly Met Ala Ser Ser Leu Trp Trp Val Val Leu Thr Leu
                325                 330                 335

Thr Trp Phe Leu Ala Ala Gly Lys Lys Trp Gly His Glu Ala Ile Glu
                340                 345                 350

Ala His Gly Ser Tyr Phe His Met Ala Ala Trp Gly Leu Pro Ala Leu
        355                 360                 365

Lys Thr Ile Val Ile Leu Thr Leu Arg Lys Val Ala Gly Asp Glu Leu
        370                 375                 380

Thr Gly Leu Cys Tyr Val Ala Ser Thr Asp Ala Ala Leu Thr Gly
385                 390                 395                 400

Phe Val Leu Val Pro Leu Ser Gly Tyr Leu Val Leu Gly Ser Ser Phe
                405                 410                 415

Leu Leu Thr Gly Phe Val Ala Leu Phe His Ile Arg Lys Ile Met Lys
                420                 425                 430

Thr Gly Gly Thr Asn Thr Glu Lys Leu Glu Lys Leu Met Val Lys Ile
        435                 440                 445

Gly Val Phe Ser Ile Leu Tyr Thr Val Pro Ala Thr Cys Val Ile Val
        450                 455                 460

Cys Tyr Val Tyr Glu Arg Leu Asn Met Asp Phe Trp Arg Leu Arg Ala
465                 470                 475                 480

Thr Glu Gln Pro Cys Ala Ala Ala Gly Pro Gly Arg Arg Asp
                485                 490                 495

Cys Ser Leu Pro Gly Gly Ser Val Pro Thr Val Ala Val Phe Met Leu
                500                 505                 510

Lys Ile Phe Met Ser Leu Val Val Gly Ile Thr Ser Gly Val Trp Val
        515                 520                 525
```

```
Trp Ser Ser Lys Thr Phe Gln Thr Trp Gln Ser Leu Cys Tyr Arg Lys
        530                 535                 540

Ile Ala Ala Gly Arg Ala Arg Ala Lys Ala Cys Arg Ala Pro Gly Ser
545                 550                 555                 560

Tyr Gly Arg Gly Thr His Cys His Tyr Lys Ala Pro Thr Val Val Leu
                565                 570                 575

His Met Thr Lys Thr Asp Pro Ser Leu Glu Asn Pro Thr His Leu
            580                 585                 590

<210> SEQ ID NO 10
<211> LENGTH: 581
<212> TYPE: PRT
<213> ORGANISM: Homo sapiens

<400> SEQUENCE: 10

Met Gln Arg Pro Gly Pro Arg Leu Trp Leu Val Leu Gln Val Met Gly
1               5                   10                  15

Ser Cys Ala Ala Ile Ser Ser Met Asp Met Glu Arg Pro Gly Asp Gly
            20                  25                  30

Lys Cys Gln Pro Ile Glu Ile Pro Met Cys Lys Asp Ile Gly Tyr Asn
        35                  40                  45

Met Thr Arg Met Pro Asn Leu Met Gly His Glu Asn Gln Arg Glu Ala
50                  55                  60

Ala Ile Gln Leu His Glu Phe Ala Pro Leu Val Glu Tyr Gly Cys His
65                  70                  75                  80

Gly His Leu Arg Phe Phe Leu Cys Ser Leu Tyr Ala Pro Met Cys Thr
                85                  90                  95

Glu Gln Val Ser Thr Pro Ile Pro Ala Cys Arg Val Met Cys Glu Gln
            100                 105                 110

Ala Arg Leu Lys Cys Ser Pro Ile Met Glu Gln Phe Asn Phe Lys Trp
        115                 120                 125

Pro Asp Ser Leu Asp Cys Arg Lys Leu Pro Asn Lys Asn Asp Pro Asn
130                 135                 140

Tyr Leu Cys Met Glu Ala Pro Asn Asn Gly Ser Asp Glu Pro Thr Arg
145                 150                 155                 160

Gly Ser Gly Leu Phe Pro Pro Leu Phe Arg Pro Gln Arg Pro His Ser
                165                 170                 175

Ala Gln Glu His Pro Leu Lys Asp Gly Gly Pro Gly Arg Gly Gly Cys
            180                 185                 190

Asp Asn Pro Gly Lys Phe His His Val Glu Lys Ser Ala Ser Cys Ala
        195                 200                 205

Pro Leu Cys Thr Pro Gly Val Asp Val Tyr Trp Ser Arg Glu Asp Lys
210                 215                 220

Arg Phe Ala Val Val Trp Leu Ala Ile Trp Ala Val Leu Cys Phe Phe
225                 230                 235                 240

Ser Ser Ala Phe Thr Val Leu Thr Phe Leu Ile Asp Pro Ala Arg Phe
                245                 250                 255

Arg Tyr Pro Glu Arg Pro Ile Ile Phe Leu Ser Met Cys Tyr Cys Val
            260                 265                 270

Tyr Ser Val Gly Tyr Leu Ile Arg Leu Phe Ala Gly Ala Glu Ser Ile
        275                 280                 285

Ala Cys Asp Arg Asp Ser Gly Gln Leu Tyr Val Ile Gln Glu Gly Leu
290                 295                 300

Glu Ser Thr Gly Cys Thr Leu Val Phe Leu Val Leu Tyr Tyr Phe Gly
305                 310                 315                 320
```

```
Met Ala Ser Ser Leu Trp Trp Val Val Leu Thr Leu Thr Trp Phe Leu
            325                 330                 335

Ala Ala Gly Lys Lys Trp Gly His Glu Ala Ile Glu Ala Asn Ser Ser
            340                 345                 350

Tyr Phe His Leu Ala Ala Trp Ala Ile Pro Ala Val Lys Thr Ile Leu
            355                 360                 365

Ile Leu Val Met Arg Arg Val Ala Gly Asp Glu Leu Thr Gly Val Cys
            370                 375                 380

Tyr Val Gly Ser Met Asp Val Asn Ala Leu Thr Gly Phe Val Leu Ile
385                 390                 395                 400

Pro Leu Ala Cys Tyr Leu Val Ile Gly Thr Ser Phe Ile Leu Ser Gly
            405                 410                 415

Phe Val Ala Leu Phe His Ile Arg Arg Val Met Lys Thr Gly Gly Glu
            420                 425                 430

Asn Thr Asp Lys Leu Glu Lys Leu Met Val Arg Ile Gly Leu Phe Ser
            435                 440                 445

Val Leu Tyr Thr Val Pro Ala Thr Cys Val Ile Ala Cys Tyr Phe Tyr
        450                 455                 460

Glu Arg Leu Asn Met Asp Tyr Trp Lys Ile Leu Ala Ala Gln His Lys
465                 470                 475                 480

Cys Lys Met Asn Asn Gln Thr Lys Thr Leu Asp Cys Leu Met Ala Ala
            485                 490                 495

Ser Ile Pro Ala Val Glu Ile Phe Met Val Lys Ile Phe Met Leu Leu
            500                 505                 510

Val Val Gly Ile Thr Ser Gly Met Trp Ile Trp Thr Ser Lys Thr Leu
            515                 520                 525

Gln Ser Trp Gln Gln Val Cys Ser Arg Arg Leu Lys Lys Lys Ser Arg
            530                 535                 540

Arg Lys Pro Ala Ser Val Ile Thr Ser Gly Gly Ile Tyr Lys Lys Ala
545                 550                 555                 560

Gln His Pro Gln Lys Thr His His Gly Lys Tyr Glu Ile Pro Ala Gln
            565                 570                 575

Ser Pro Thr Cys Val
            580

<210> SEQ ID NO 11
<211> LENGTH: 314
<212> TYPE: PRT
<213> ORGANISM: Homo sapiens

<400> SEQUENCE: 11

Met Gly Ile Gly Arg Ser Glu Gly Gly Arg Gly Ala Ala Leu Gly
1                5                  10                  15

Val Leu Leu Ala Leu Gly Ala Ala Leu Leu Ala Val Gly Ser Ala Ser
            20                  25                  30

Glu Tyr Asp Tyr Val Ser Phe Gln Ser Asp Ile Gly Pro Tyr Gln Ser
            35                  40                  45

Gly Arg Phe Tyr Thr Lys Pro Pro Gln Cys Val Asp Ile Pro Ala Asp
        50                  55                  60

Leu Arg Leu Cys His Asn Val Gly Tyr Lys Lys Met Val Leu Pro Asn
65                  70                  75                  80

Leu Leu Glu His Glu Thr Met Ala Glu Val Lys Gln Gln Ala Ser Ser
            85                  90                  95

Trp Val Pro Leu Leu Asn Lys Asn Cys His Ala Gly Thr Gln Val Phe
            100                 105                 110
```

Leu Cys Ser Leu Phe Ala Pro Val Cys Leu Asp Arg Pro Ile Tyr Pro
            115                 120                 125

Cys Arg Trp Leu Cys Glu Ala Val Arg Asp Ser Cys Glu Pro Val Met
130                 135                 140

Gln Phe Gly Phe Tyr Trp Pro Glu Met Leu Lys Cys Asp Lys Phe
145                 150                 155                 160

Pro Glu Gly Asp Val Cys Ile Ala Met Thr Pro Pro Asn Ala Thr Glu
                165                 170                 175

Ala Ser Lys Pro Gln Gly Thr Thr Val Cys Pro Pro Cys Asp Asn Glu
            180                 185                 190

Leu Lys Ser Glu Ala Ile Ile Glu His Leu Cys Ala Ser Glu Phe Ala
        195                 200                 205

Leu Arg Met Lys Ile Lys Glu Val Lys Glu Asn Gly Asp Lys Lys
210                 215                 220

Ile Val Pro Lys Lys Lys Pro Leu Lys Leu Gly Pro Ile Lys Lys
225                 230                 235                 240

Lys Asp Leu Lys Lys Leu Val Leu Tyr Leu Lys Asn Gly Ala Asp Cys
                245                 250                 255

Pro Cys His Gln Leu Asp Asn Leu Ser His His Phe Leu Ile Met Gly
            260                 265                 270

Arg Lys Val Lys Ser Gln Tyr Leu Leu Thr Ala Ile His Lys Trp Asp
        275                 280                 285

Lys Lys Asn Lys Glu Phe Lys Asn Phe Met Lys Lys Met Lys Asn His
    290                 295                 300

Glu Cys Pro Thr Phe Gln Ser Val Phe Lys
305                 310

<210> SEQ ID NO 12
<211> LENGTH: 295
<212> TYPE: PRT
<213> ORGANISM: Homo sapiens

<400> SEQUENCE: 12

Met Leu Gln Gly Pro Gly Ser Leu Leu Leu Leu Phe Leu Ala Ser His
1               5                   10                  15

Cys Cys Leu Gly Ser Ala Arg Gly Leu Phe Leu Phe Gly Gln Pro Asp
                20                  25                  30

Phe Ser Tyr Lys Arg Ser Asn Cys Lys Pro Ile Pro Ala Asn Leu Gln
            35                  40                  45

Leu Cys His Gly Ile Glu Tyr Gln Asn Met Arg Leu Pro Asn Leu Leu
        50                  55                  60

Gly His Glu Thr Met Lys Glu Val Leu Glu Gln Ala Gly Ala Trp Ile
65                  70                  75                  80

Pro Leu Val Met Lys Gln Cys His Pro Asp Thr Lys Lys Phe Leu Cys
                85                  90                  95

Ser Leu Phe Ala Pro Val Cys Leu Asp Asp Leu Asp Glu Thr Ile Gln
            100                 105                 110

Pro Cys His Ser Leu Cys Val Gln Val Lys Asp Arg Cys Ala Pro Val
        115                 120                 125

Met Ser Ala Phe Gly Phe Pro Trp Pro Asp Met Leu Glu Cys Asp Arg
130                 135                 140

Phe Pro Gln Asp Asn Asp Leu Cys Ile Pro Leu Ala Ser Ser Asp His
145                 150                 155                 160

Leu Leu Pro Ala Thr Glu Glu Ala Pro Lys Val Cys Glu Ala Cys Lys
                165                 170                 175

```
Asn Lys Asn Asp Asp Asp Asn Asp Ile Met Glu Thr Leu Cys Lys Asn
            180                 185                 190
Asp Phe Ala Leu Lys Ile Lys Val Lys Glu Ile Thr Tyr Ile Asn Arg
            195                 200                 205
Asp Thr Lys Ile Ile Leu Glu Thr Lys Ser Lys Thr Ile Tyr Lys Leu
            210                 215                 220
Asn Gly Val Ser Glu Arg Asp Leu Lys Lys Ser Val Leu Trp Leu Lys
225                 230                 235                 240
Asp Ser Leu Gln Cys Thr Cys Glu Glu Met Asn Asp Ile Asn Ala Pro
            245                 250                 255
Tyr Leu Val Met Gly Gln Lys Gln Gly Gly Leu Val Ile Thr Ser
            260                 265                 270
Val Lys Arg Trp Gln Lys Gly Gln Arg Glu Phe Lys Arg Ile Ser Arg
            275                 280                 285
Ser Ile Arg Lys Leu Gln Cys
            290                 295

<210> SEQ ID NO 13
<211> LENGTH: 325
<212> TYPE: PRT
<213> ORGANISM: Homo sapiens

<400> SEQUENCE: 13

Met Val Cys Gly Ser Pro Gly Gly Met Leu Leu Leu Arg Ala Gly Leu
1               5                   10                  15
Leu Ala Leu Ala Ala Leu Cys Leu Leu Arg Val Pro Gly Ala Arg Ala
            20                  25                  30
Ala Ala Cys Glu Pro Val Arg Ile Pro Leu Cys Lys Ser Leu Pro Trp
            35                  40                  45
Asn Met Thr Lys Met Pro Asn His Leu His His Ser Thr Gln Ala Asn
            50                  55                  60
Ala Ile Leu Ala Ile Glu Gln Phe Glu Gly Leu Leu Gly Thr His Cys
65                  70                  75                  80
Ser Pro Asp Leu Leu Phe Phe Leu Cys Ala Met Tyr Ala Pro Ile Cys
            85                  90                  95
Thr Ile Asp Phe Gln His Glu Pro Ile Lys Pro Cys Lys Ser Val Cys
            100                 105                 110
Glu Arg Ala Arg Gln Gly Cys Glu Pro Ile Leu Ile Lys Tyr Arg His
            115                 120                 125
Ser Trp Pro Glu Asn Leu Ala Cys Glu Glu Leu Pro Val Tyr Asp Arg
            130                 135                 140
Gly Val Cys Ile Ser Pro Glu Ala Ile Val Thr Ala Asp Gly Ala Asp
145                 150                 155                 160
Phe Pro Met Asp Ser Ser Asn Gly Asn Cys Arg Gly Ala Ser Ser Glu
            165                 170                 175
Arg Cys Lys Cys Lys Pro Ile Arg Ala Thr Gln Lys Thr Tyr Phe Arg
            180                 185                 190
Asn Asn Tyr Asn Tyr Val Ile Arg Ala Lys Val Lys Glu Ile Lys Thr
            195                 200                 205
Lys Cys His Asp Val Thr Ala Val Val Glu Val Lys Glu Ile Leu Lys
            210                 215                 220
Ser Ser Leu Val Asn Ile Pro Arg Asp Thr Val Asn Leu Tyr Thr Ser
225                 230                 235                 240
Ser Gly Cys Leu Cys Pro Pro Leu Asn Val Asn Glu Glu Tyr Ile Ile
            245                 250                 255
```

```
Met Gly Tyr Glu Asp Glu Arg Ser Arg Leu Leu Val Gly
            260                 265                 270

Ser Ile Ala Glu Lys Trp Lys Asp Arg Leu Gly Lys Lys Val Lys Arg
        275                 280                 285

Trp Asp Met Lys Leu Arg His Leu Gly Leu Ser Lys Ser Asp Ser Ser
290                 295                 300

Asn Ser Asp Ser Thr Gln Ser Gln Lys Ser Gly Arg Asn Ser Asn Pro
305                 310                 315                 320

Arg Gln Ala Arg Asn
                325

<210> SEQ ID NO 14
<211> LENGTH: 346
<212> TYPE: PRT
<213> ORGANISM: Homo sapiens

<400> SEQUENCE: 14

Met Phe Leu Ser Ile Leu Val Ala Leu Cys Leu Trp Leu His Leu Ala
1               5                   10                  15

Leu Gly Val Arg Gly Ala Pro Cys Glu Ala Val Arg Ile Pro Met Cys
            20                  25                  30

Arg His Met Pro Trp Asn Ile Thr Arg Met Pro Asn His Leu His His
        35                  40                  45

Ser Thr Gln Glu Asn Ala Ile Leu Ala Ile Glu Gln Tyr Glu Glu Leu
    50                  55                  60

Val Asp Val Asn Cys Ser Ala Val Leu Arg Phe Phe Phe Cys Ala Met
65                  70                  75                  80

Tyr Ala Pro Ile Cys Thr Leu Glu Phe Leu His Asp Pro Ile Lys Pro
                85                  90                  95

Cys Lys Ser Val Cys Gln Arg Ala Arg Asp Asp Cys Glu Pro Leu Met
            100                 105                 110

Lys Met Tyr Asn His Ser Trp Pro Glu Ser Leu Ala Cys Asp Glu Leu
        115                 120                 125

Pro Val Tyr Asp Arg Gly Val Cys Ile Ser Pro Glu Ala Ile Val Thr
    130                 135                 140

Asp Leu Pro Glu Asp Val Lys Trp Ile Asp Ile Thr Pro Asp Met Met
145                 150                 155                 160

Val Gln Glu Arg Pro Leu Asp Val Asp Cys Lys Arg Leu Ser Pro Asp
                165                 170                 175

Arg Cys Lys Cys Lys Lys Val Leu Pro Thr Leu Ala Thr Tyr Leu Ser
            180                 185                 190

Lys Asn Tyr Ser Tyr Val Ile His Ala Lys Ile Lys Ala Val Gln Arg
        195                 200                 205

Ser Gly Cys Asn Glu Val Thr Thr Val Val Asp Val Lys Glu Ile Phe
    210                 215                 220

Lys Ser Ser Ser Pro Ile Pro Arg Thr Gln Val Pro Leu Ile Thr Asn
225                 230                 235                 240

Ser Ser Cys Gln Cys Pro His Ile Leu Pro His Gln Asp Val Leu Ile
                245                 250                 255

Met Cys Tyr Glu Trp Arg Ser Arg Met Met Leu Leu Glu Asn Cys Leu
            260                 265                 270

Val Glu Lys Trp Arg Asp Gln Leu Ser Lys Arg Ser Ile Gln Trp Glu
        275                 280                 285

Glu Arg Leu Gln Glu Gln Arg Arg Thr Val Gln Asp Lys Lys Lys Thr
    290                 295                 300
```

```
Ala Gly Arg Thr Ser Arg Ser Asn Pro Pro Lys Pro Lys Gly Lys Pro
305                 310                 315                 320

Pro Ala Pro Lys Pro Ala Ser Pro Lys Lys Asn Ile Lys Thr Arg Ser
                325                 330                 335

Ala Gln Lys Arg Thr Asn Pro Lys Arg Val
            340                 345

<210> SEQ ID NO 15
<211> LENGTH: 317
<212> TYPE: PRT
<213> ORGANISM: Homo sapiens

<400> SEQUENCE: 15

Met Arg Ala Ala Ala Ala Gly Gly Val Arg Thr Ala Ala Leu Ala
1               5                   10                  15

Leu Leu Leu Gly Ala Leu His Trp Ala Pro Ala Arg Cys Glu Glu Tyr
                20                  25                  30

Asp Tyr Tyr Gly Trp Gln Ala Glu Pro Leu His Gly Arg Ser Tyr Ser
                35                  40                  45

Lys Pro Pro Gln Cys Leu Asp Ile Pro Ala Asp Leu Pro Leu Cys His
    50                  55                  60

Thr Val Gly Tyr Lys Arg Met Arg Leu Pro Asn Leu Leu Glu His Glu
65                  70                  75                  80

Ser Leu Ala Glu Val Lys Gln Gln Ala Ser Ser Trp Leu Pro Leu Leu
                85                  90                  95

Ala Lys Arg Cys His Ser Asp Thr Gln Val Phe Leu Cys Ser Leu Phe
                100                 105                 110

Ala Pro Val Cys Leu Asp Arg Pro Ile Tyr Pro Cys Arg Ser Leu Cys
                115                 120                 125

Glu Ala Val Arg Ala Gly Cys Ala Pro Leu Met Glu Ala Tyr Gly Phe
    130                 135                 140

Pro Trp Pro Glu Met Leu His Cys His Lys Phe Pro Leu Asp Asn Asp
145                 150                 155                 160

Leu Cys Ile Ala Val Gln Phe Gly His Leu Pro Ala Thr Ala Pro Pro
                165                 170                 175

Val Thr Lys Ile Cys Ala Gln Cys Glu Met Glu His Ser Ala Asp Gly
                180                 185                 190

Leu Met Glu Gln Met Cys Ser Ser Asp Phe Val Val Lys Met Arg Ile
            195                 200                 205

Lys Glu Ile Lys Ile Glu Asn Gly Asp Arg Lys Leu Ile Gly Ala Gln
    210                 215                 220

Lys Lys Lys Lys Leu Leu Lys Pro Gly Pro Leu Lys Arg Lys Asp Thr
225                 230                 235                 240

Lys Arg Leu Val Leu His Met Lys Asn Gly Ala Gly Cys Pro Cys Pro
                245                 250                 255

Gln Leu Asp Ser Leu Ala Gly Ser Phe Leu Val Met Gly Arg Lys Val
                260                 265                 270

Asp Gly Gln Leu Leu Leu Met Ala Val Tyr Arg Trp Asp Lys Lys Asn
            275                 280                 285

Lys Glu Met Lys Phe Ala Val Lys Phe Met Phe Ser Tyr Pro Cys Ser
    290                 295                 300

Leu Tyr Tyr Pro Phe Phe Tyr Gly Ala Ala Glu Pro His
305                 310                 315

<210> SEQ ID NO 16
<211> LENGTH: 937
```

<212> TYPE: PRT
<213> ORGANISM: Homo sapiens

<400> SEQUENCE: 16

```
Met His Arg Pro Arg Arg Gly Thr Arg Pro Pro Leu Leu Ala Leu
1               5                   10                  15

Leu Ala Ala Leu Leu Ala Ala Arg Gly Ala Ala Ala Gln Glu Thr
                20                  25                  30

Glu Leu Ser Val Ser Ala Glu Leu Val Pro Thr Ser Ser Trp Asn Ile
            35                  40                  45

Ser Ser Glu Leu Asn Lys Asp Ser Tyr Leu Thr Leu Asp Glu Pro Met
        50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
                100                 105                 110

Gly Ser Arg Leu Arg Ile Arg Asn Leu Asp Thr Thr Asp Thr Gly Tyr
            115                 120                 125

Phe Gln Cys Val Ala Thr Asn Gly Lys Glu Val Val Ser Ser Thr Gly
    130                 135                 140

Val Leu Phe Val Lys Phe Gly Pro Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
    290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
    370                 375                 380

Leu Cys Asp Ile Pro Ala Cys Asp Ser Lys Asp Ser Lys Glu Lys Asn
385                 390                 395                 400
```

-continued

```
Lys Met Glu Ile Leu Tyr Ile Leu Val Pro Ser Val Ala Ile Pro Leu
            405                 410                 415

Ala Ile Ala Leu Leu Phe Phe Phe Ile Cys Val Cys Arg Asn Asn Gln
        420                 425                 430

Lys Ser Ser Ser Ala Pro Val Gln Arg Gln Pro Lys His Val Arg Gly
    435                 440                 445

Gln Asn Val Glu Met Ser Met Leu Asn Ala Tyr Lys Pro Lys Ser Lys
450                 455                 460

Ala Lys Glu Leu Pro Leu Ser Ala Val Arg Phe Met Glu Glu Leu Gly
465                 470                 475                 480

Glu Cys Ala Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
            500                 505                 510

Asn Pro Gln Gln Trp Met Glu Phe Gln Gln Glu Ala Ser Leu Met Ala
        515                 520                 525

Glu Leu His His Pro Asn Ile Val Cys Leu Leu Gly Ala Val Thr Gln
    530                 535                 540

Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
        595                 600                 605

His Phe Phe Val His Lys Asp Leu Ala Ala Arg Asn Ile Leu Ile Gly
    610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
                645                 650                 655

Arg Trp Met Pro Pro Glu Ala Ile Met Tyr Gly Lys Phe Ser Ser Asp
            660                 665                 670

Ser Asp Ile Trp Ser Phe Gly Val Val Leu Trp Glu Ile Phe Ser Phe
        675                 680                 685

Gly Leu Gln Pro Tyr Tyr Gly Phe Ser Asn Gln Glu Val Ile Glu Met
    690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
            740                 745                 750

Ser Ser His Thr Ser Ser Thr Thr Pro Ser Gly Gly Asn Ala Thr Thr
        755                 760                 765

Gln Thr Thr Ser Leu Ser Ala Ser Pro Val Ser Asn Leu Ser Asn Pro
    770                 775                 780

Arg Tyr Pro Asn Tyr Met Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
                805                 810                 815

Ile Pro Ile Asn Gly Tyr Pro Ile Pro Pro Gly Tyr Ala Ala Phe Pro
            820                 825                 830
```

```
Ala Ala His Tyr Gln Pro Thr Gly Pro Pro Arg Val Ile Gln His Cys
            835                 840                 845

Pro Pro Pro Lys Ser Arg Ser Pro Ser Ser Ala Ser Gly Ser Thr Ser
        850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
            885                 890                 895

Met Gly Ile Thr Val Phe Gly Asn Lys Ser Gln Lys Pro Tyr Lys Ile
        900                 905                 910

Asp Ser Lys Gln Ala Ser Leu Leu Gly Asp Ala Asn Ile His Gly His
        915                 920                 925

Thr Glu Ser Met Ile Ser Ala Glu Leu
        930                 935

<210> SEQ ID NO 17
<211> LENGTH: 943
<212> TYPE: PRT
<213> ORGANISM: Homo sapiens

<400> SEQUENCE: 17

Met Ala Arg Gly Ser Ala Leu Pro Arg Pro Leu Leu Cys Ile Pro
1               5                   10                  15

Ala Val Trp Ala Ala Ala Leu Leu Leu Ser Val Ser Arg Thr Ser
            20                  25                  30

Gly Glu Val Glu Val Leu Asp Pro Asn Asp Pro Leu Gly Pro Leu Asp
            35                  40                  45

Gly Gln Asp Gly Pro Ile Pro Thr Leu Lys Gly Tyr Phe Leu Asn Phe
    50                  55                  60

Leu Glu Pro Val Asn Asn Ile Thr Ile Val Gln Gly Gln Thr Ala Ile
65                  70                  75                  80

Leu His Cys Lys Val Ala Gly Asn Pro Pro Pro Asn Val Arg Trp Leu
                85                  90                  95

Lys Asn Asp Ala Pro Val Val Gln Glu Pro Arg Arg Ile Ile Ile Arg
            100                 105                 110

Lys Thr Glu Tyr Gly Ser Arg Leu Arg Ile Gln Asp Leu Asp Thr Thr
        115                 120                 125

Asp Thr Gly Tyr Tyr Gln Cys Val Ala Thr Asn Gly Met Lys Thr Ile
    130                 135                 140

Thr Ala Thr Gly Val Leu Phe Val Arg Leu Gly Pro Thr His Ser Pro
145                 150                 155                 160

Asn His Asn Phe Gln Asp Asp Tyr His Glu Asp Gly Phe Cys Gln Pro
                165                 170                 175

Tyr Arg Gly Ile Ala Cys Ala Arg Phe Ile Gly Asn Arg Thr Ile Tyr
            180                 185                 190

Val Asp Ser Leu Gln Met Gln Gly Glu Ile Glu Asn Arg Ile Thr Ala
        195                 200                 205

Ala Phe Thr Met Ile Gly Thr Ser Thr His Leu Ser Asp Gln Cys Ser
    210                 215                 220

Gln Phe Ala Ile Pro Ser Phe Cys His Phe Val Phe Pro Leu Cys Asp
225                 230                 235                 240

Ala Arg Ser Arg Thr Pro Lys Pro Arg Glu Leu Cys Arg Asp Glu Cys
                245                 250                 255

Glu Val Leu Glu Ser Asp Leu Cys Arg Gln Glu Tyr Thr Ile Ala Arg
            260                 265                 270
```

```
Ser Asn Pro Leu Ile Leu Met Arg Leu Gln Leu Pro Lys Cys Glu Ala
        275                 280                 285

Leu Pro Met Pro Glu Ser Pro Asp Ala Ala Asn Cys Met Arg Ile Gly
        290                 295                 300

Ile Pro Ala Glu Arg Leu Gly Arg Tyr His Gln Cys Tyr Asn Gly Ser
305                 310                 315                 320

Gly Met Asp Tyr Arg Gly Thr Ala Ser Thr Thr Lys Ser Gly His Gln
                325                 330                 335

Cys Gln Pro Trp Ala Leu Gln His Pro His Ser His His Leu Ser Ser
                340                 345                 350

Thr Asp Phe Pro Glu Leu Gly Gly His Ala Tyr Cys Arg Asn Pro
        355                 360                 365

Gly Gly Gln Met Glu Gly Pro Trp Cys Phe Thr Gln Asn Lys Asn Val
        370                 375                 380

Arg Met Glu Leu Cys Asp Val Pro Ser Cys Ser Pro Arg Asp Ser Ser
385                 390                 395                 400

Lys Met Gly Ile Leu Tyr Ile Leu Val Pro Ser Ile Ala Ile Pro Leu
                405                 410                 415

Val Ile Ala Cys Leu Phe Phe Leu Val Cys Met Cys Arg Asn Lys Gln
                420                 425                 430

Lys Ala Ser Ala Ser Thr Pro Gln Arg Arg Gln Leu Met Ala Ser Pro
                435                 440                 445

Ser Gln Asp Met Glu Met Pro Leu Ile Asn Gln His Lys Gln Ala Lys
        450                 455                 460

Leu Lys Glu Ile Ser Leu Ser Ala Val Arg Phe Met Glu Glu Leu Gly
465                 470                 475                 480

Glu Asp Arg Phe Gly Lys Val Tyr Lys Gly His Leu Phe Gly Pro Ala
                485                 490                 495

Pro Gly Glu Gln Thr Gln Ala Val Ala Ile Lys Thr Leu Lys Asp Lys
        500                 505                 510

Ala Glu Gly Pro Leu Arg Glu Glu Phe Arg His Glu Ala Met Leu Arg
        515                 520                 525

Ala Arg Leu Gln His Pro Asn Val Val Cys Leu Leu Gly Val Val Thr
        530                 535                 540

Lys Asp Gln Pro Leu Ser Met Ile Phe Ser Tyr Cys Ser His Gly Asp
545                 550                 555                 560

Leu His Glu Phe Leu Val Met Arg Ser Pro His Ser Asp Val Gly Ser
                565                 570                 575

Thr Asp Asp Asp Arg Thr Val Lys Ser Ala Leu Glu Pro Pro Asp Phe
                580                 585                 590

Val His Leu Val Ala Gln Ile Ala Ala Gly Met Glu Tyr Leu Ser Ser
        595                 600                 605

His His Val Val His Lys Asp Leu Ala Thr Arg Asn Val Leu Val Tyr
        610                 615                 620

Asp Lys Leu Asn Val Lys Ile Ser Asp Leu Gly Leu Phe Arg Glu Val
625                 630                 635                 640

Tyr Ala Ala Asp Tyr Tyr Lys Leu Leu Gly Asn Ser Leu Leu Pro Ile
                645                 650                 655

Arg Trp Met Ala Pro Glu Ala Ile Met Tyr Gly Lys Phe Ser Ile Asp
                660                 665                 670

Ser Asp Ile Trp Ser Tyr Gly Val Val Leu Trp Glu Val Phe Ser Tyr
        675                 680                 685

Gly Leu Gln Pro Tyr Cys Gly Tyr Ser Asn Gln Asp Val Val Glu Met
```

```
                690             695             700
Ile Arg Asn Arg Gln Val Leu Pro Cys Pro Asp Asp Cys Pro Ala Trp
705             710             715             720

Val Tyr Ala Leu Met Ile Glu Cys Trp Asn Glu Phe Pro Ser Arg Arg
            725             730             735

Pro Arg Phe Lys Asp Ile His Ser Arg Leu Arg Ala Trp Gly Asn Leu
            740             745             750

Ser Asn Tyr Asn Ser Ser Ala Gln Thr Ser Gly Ala Ser Asn Thr Thr
            755             760             765

Gln Thr Ser Ser Leu Ser Thr Ser Pro Val Ser Asn Val Ser Asn Ala
            770             775             780

Arg Tyr Val Gly Pro Lys Gln Lys Ala Pro Pro Phe Pro Gln Pro Gln
785             790             795             800

Phe Ile Pro Met Lys Gly Gln Ile Arg Pro Met Val Pro Pro Pro Gln
            805             810             815

Leu Tyr Val Pro Val Asn Gly Tyr Gln Pro Val Pro Ala Tyr Gly Ala
            820             825             830

Tyr Leu Pro Asn Phe Tyr Pro Val Gln Ile Pro Met Gln Met Ala Pro
            835             840             845

Gln Gln Val Pro Pro Gln Met Val Pro Lys Pro Ser Ser His His Ser
850             855             860

Gly Ser Gly Ser Thr Ser Thr Gly Tyr Val Thr Thr Ala Pro Ser Asn
865             870             875             880

Thr Ser Met Ala Asp Arg Ala Ala Leu Leu Ser Glu Gly Ala Asp Asp
            885             890             895

Thr Gln Asn Ala Pro Glu Asp Gly Ala Gln Ser Thr Val Gln Glu Ala
            900             905             910

Glu Glu Glu Glu Glu Gly Ser Val Pro Glu Thr Glu Leu Leu Gly Asp
            915             920             925

Cys Asp Thr Leu Gln Val Asp Glu Ala Gln Val Gln Leu Glu Ala
            930             935             940

<210> SEQ ID NO 18
<211> LENGTH: 127
<212> TYPE: PRT
<213> ORGANISM: Homo sapiens

<400> SEQUENCE: 18

Ser Val Pro Asp His Gly Tyr Cys Gln Pro Ile Ser Ile Pro Leu Cys
1               5               10              15

Thr Asp Ile Ala Tyr Asn Gln Thr Ile Met Pro Asn Leu Leu Gly His
            20              25              30

Thr Asn Gln Glu Asp Ala Gly Leu Glu Val His Gln Phe Tyr Pro Leu
            35              40              45

Val Lys Val Gln Cys Ser Ala Glu Leu Lys Phe Phe Leu Cys Ser Met
        50              55              60

Tyr Ala Pro Val Cys Thr Val Leu Glu Gln Ala Leu Pro Pro Cys Arg
65              70              75              80

Ser Leu Cys Glu Arg Ala Arg Gln Gly Cys Glu Ala Leu Met Asn Lys
            85              90              95

Phe Gly Phe Gln Trp Pro Asp Thr Leu Lys Cys Glu Lys Phe Pro Val
            100             105             110

His Gly Ala Gly Glu Leu Cys Val Gly Gln Asn Thr Ser Asp Lys
            115             120             125
```

```
<210> SEQ ID NO 19
<211> LENGTH: 127
<212> TYPE: PRT
<213> ORGANISM: Homo sapiens

<400> SEQUENCE: 19

Ser Ile Pro Asp His Gly Phe Cys Gln Pro Ile Ser Ile Pro Leu Cys
1               5                   10                  15

Thr Asp Ile Ala Tyr Asn Gln Thr Ile Met Pro Asn Leu Leu Gly His
            20                  25                  30

Thr Asn Gln Glu Asp Ala Gly Leu Glu Val His Gln Phe Tyr Pro Leu
        35                  40                  45

Val Lys Val Gln Cys Ser Pro Glu Leu Arg Phe Phe Leu Cys Ser Met
    50                  55                  60

Tyr Ala Pro Val Cys Thr Val Leu Glu Gln Ala Ile Pro Pro Cys Arg
65                  70                  75                  80

Ser Ile Cys Glu Ser Ala Arg Gln Gly Cys Glu Ala Leu Met Asn Lys
                85                  90                  95

Phe Gly Phe Gln Trp Pro Glu Arg Leu Arg Cys Glu His Phe Pro Arg
            100                 105                 110

His Gly Ala Glu Gln Ile Cys Val Gly Gln Asn His Ser Glu Asp
        115                 120                 125

<210> SEQ ID NO 20
<211> LENGTH: 119
<212> TYPE: PRT
<213> ORGANISM: Homo sapiens

<400> SEQUENCE: 20

His Ser Leu Phe Ser Cys Glu Pro Ile Thr Leu Arg Met Cys Gln Asp
1               5                   10                  15

Leu Pro Tyr Asn Thr Thr Phe Met Pro Asn Leu Leu Asn His Tyr Asp
            20                  25                  30

Gln Gln Thr Ala Ala Leu Ala Met Glu Pro Phe His Pro Met Val Asn
        35                  40                  45

Leu Asp Cys Ser Arg Asp Phe Arg Pro Phe Leu Cys Ala Leu Tyr Ala
    50                  55                  60

Pro Ile Cys Met Glu Tyr Gly Arg Val Thr Leu Pro Cys Arg Arg Leu
65                  70                  75                  80

Cys Gln Arg Ala Tyr Ser Glu Cys Ser Lys Leu Met Glu Met Phe Gly
                85                  90                  95

Val Pro Trp Pro Glu Asp Met Glu Cys Ser Arg Phe Pro Asp Cys Asp
            100                 105                 110

Glu Pro Tyr Pro Arg Leu Val
        115

<210> SEQ ID NO 21
<211> LENGTH: 125
<212> TYPE: PRT
<213> ORGANISM: Homo sapiens

<400> SEQUENCE: 21

Glu Arg Arg Cys Asp Pro Ile Arg Ile Ser Met Cys Gln Asn Leu Gly
1               5                   10                  15

Tyr Asn Val Thr Lys Met Pro Asn Leu Val Gly His Glu Leu Gln Thr
            20                  25                  30

Asp Ala Glu Leu Gln Leu Thr Thr Phe Thr Pro Leu Ile Gln Tyr Gly
        35                  40                  45
```

```
Cys Ser Ser Gln Leu Gln Phe Phe Leu Cys Ser Val Tyr Val Pro Met
     50                  55                  60

Cys Thr Glu Lys Ile Asn Ile Pro Ile Gly Pro Cys Gly Gly Met Cys
 65                  70                  75                  80

Leu Ser Val Lys Arg Arg Cys Glu Pro Val Leu Lys Glu Phe Gly Phe
                 85                  90                  95

Ala Trp Pro Glu Ser Leu Asn Cys Ser Lys Phe Pro Pro Gln Asn Asp
            100                 105                 110

His Asn His Met Cys Met Glu Gly Pro Gly Asp Glu Glu
            115                 120                 125

<210> SEQ ID NO 22
<211> LENGTH: 129
<212> TYPE: PRT
<213> ORGANISM: Homo sapiens

<400> SEQUENCE: 22

Ala Ser Lys Ala Pro Val Cys Gln Glu Ile Thr Val Pro Met Cys Arg
  1               5                  10                  15

Gly Ile Gly Tyr Asn Leu Thr His Met Pro Asn Gln Phe Asn His Asp
                 20                  25                  30

Thr Gln Asp Glu Ala Gly Leu Glu Val His Gln Phe Trp Pro Leu Val
             35                  40                  45

Glu Ile Gln Cys Ser Pro Asp Leu Arg Phe Phe Leu Cys Ser Met Tyr
         50                  55                  60

Thr Pro Ile Cys Leu Pro Asp Tyr His Lys Pro Leu Pro Pro Cys Arg
 65                  70                  75                  80

Ser Val Cys Glu Arg Ala Lys Ala Gly Cys Ser Pro Leu Met Arg Gln
                 85                  90                  95

Tyr Gly Phe Ala Trp Pro Glu Arg Met Ser Cys Asp Arg Leu Pro Val
            100                 105                 110

Leu Gly Arg Asp Ala Glu Val Leu Cys Met Asp Tyr Asn Arg Ser Glu
            115                 120                 125

Ala

<210> SEQ ID NO 23
<211> LENGTH: 119
<212> TYPE: PRT
<213> ORGANISM: Homo sapiens

<400> SEQUENCE: 23

His Ser Leu Phe Thr Cys Glu Pro Ile Thr Val Pro Arg Cys Met Lys
  1               5                  10                  15

Met Ala Tyr Asn Met Thr Phe Phe Pro Asn Leu Met Gly His Tyr Asp
                 20                  25                  30

Gln Ser Ile Ala Ala Val Glu Met Glu His Phe Leu Pro Leu Ala Asn
             35                  40                  45

Leu Glu Cys Ser Pro Asn Ile Glu Thr Phe Leu Cys Lys Ala Phe Val
         50                  55                  60

Pro Thr Cys Ile Glu Gln Ile His Val Val Pro Pro Cys Arg Lys Leu
 65                  70                  75                  80

Cys Glu Lys Val Tyr Ser Asp Cys Lys Lys Leu Ile Asp Thr Phe Gly
                 85                  90                  95

Ile Arg Trp Pro Glu Glu Leu Glu Cys Asp Arg Leu Gln Tyr Cys Asp
            100                 105                 110

Glu Thr Val Pro Val Thr Phe
            115
```

<210> SEQ ID NO 24
<211> LENGTH: 127
<212> TYPE: PRT
<213> ORGANISM: Homo sapiens

<400> SEQUENCE: 24

Ser Val Pro Asp His Gly Phe Cys Gln Pro Ile Ser Ile Pro Leu Cys
1               5                   10                  15

Thr Asp Ile Ala Tyr Asn Gln Thr Ile Leu Pro Asn Leu Leu Gly His
            20                  25                  30

Thr Asn Gln Glu Asp Ala Gly Leu Glu Val His Gln Phe Tyr Pro Leu
        35                  40                  45

Val Lys Val Gln Cys Ser Pro Glu Leu Arg Phe Phe Leu Cys Ser Met
50                  55                  60

Tyr Ala Pro Val Cys Thr Val Leu Asp Gln Ala Ile Pro Pro Cys Arg
65                  70                  75                  80

Ser Leu Cys Glu Arg Ala Arg Gln Gly Cys Glu Ala Leu Met Asn Lys
                85                  90                  95

Phe Gly Phe Gln Trp Pro Glu Arg Leu Arg Cys Glu Asn Phe Pro Val
            100                 105                 110

His Gly Ala Gly Glu Ile Cys Val Gly Gln Asn Thr Ser Asp Gly
        115                 120                 125

<210> SEQ ID NO 25
<211> LENGTH: 129
<212> TYPE: PRT
<213> ORGANISM: Homo sapiens

<400> SEQUENCE: 25

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu

<210> SEQ ID NO 26
<211> LENGTH: 125
<212> TYPE: PRT
<213> ORGANISM: Homo sapiens

<400> SEQUENCE: 26

Ala Ala Pro Cys Gln Ala Val Glu Ile Pro Met Cys Arg Gly Ile Gly
1               5                   10                  15

Tyr Asn Leu Thr Arg Met Pro Asn Leu Leu Gly His Thr Ser Gln Gly
            20                  25                  30

```
Glu Ala Ala Ala Glu Leu Ala Glu Phe Ala Pro Leu Val Gln Tyr Gly
                35                  40                  45

Cys His Ser His Leu Arg Phe Phe Leu Cys Ser Leu Tyr Ala Pro Met
 50                  55                  60

Cys Thr Asp Gln Val Ser Thr Pro Ile Pro Ala Cys Arg Pro Met Cys
 65                  70                  75                  80

Glu Gln Ala Arg Leu Arg Cys Ala Pro Ile Met Glu Gln Phe Asn Phe
                85                  90                  95

Gly Trp Pro Asp Ser Leu Asp Cys Ala Arg Leu Pro Thr Arg Asn Asp
                100                 105                 110

Pro His Ala Leu Cys Met Glu Ala Pro Glu Asn Ala Thr
                115                 120                 125

<210> SEQ ID NO 27
<211> LENGTH: 125
<212> TYPE: PRT
<213> ORGANISM: Homo sapiens

<400> SEQUENCE: 27

Asp Gly Lys Cys Gln Pro Ile Glu Ile Pro Met Cys Lys Asp Ile Gly
 1               5                  10                  15

Tyr Asn Met Thr Arg Met Pro Asn Leu Met Gly His Glu Asn Gln Arg
                20                  25                  30

Glu Ala Ala Ile Gln Leu His Glu Phe Ala Pro Leu Val Glu Tyr Gly
                35                  40                  45

Cys His Gly His Leu Arg Phe Phe Leu Cys Ser Leu Tyr Ala Pro Met
 50                  55                  60

Cys Thr Glu Gln Val Ser Thr Pro Ile Pro Ala Cys Arg Val Met Cys
 65                  70                  75                  80

Glu Gln Ala Arg Leu Lys Cys Ser Pro Ile Met Glu Gln Phe Asn Phe
                85                  90                  95

Lys Trp Pro Asp Ser Leu Asp Cys Arg Lys Leu Pro Asn Lys Asn Asp
                100                 105                 110

Pro Asn Tyr Leu Cys Met Glu Ala Pro Asn Asn Gly Ser
                115                 120                 125

<210> SEQ ID NO 28
<211> LENGTH: 124
<212> TYPE: PRT
<213> ORGANISM: Homo sapiens

<400> SEQUENCE: 28

Phe Tyr Thr Lys Pro Pro Gln Cys Val Asp Ile Pro Ala Asp Leu Arg
 1               5                  10                  15

Leu Cys His Asn Val Gly Tyr Lys Lys Met Val Leu Pro Asn Leu Leu
                20                  25                  30

Glu His Glu Thr Met Ala Glu Val Lys Gln Gln Ala Ser Ser Trp Val
                35                  40                  45

Pro Leu Leu Asn Lys Asn Cys His Ala Gly Thr Gln Val Phe Leu Cys
 50                  55                  60

Ser Leu Phe Ala Pro Val Cys Leu Asp Arg Pro Ile Tyr Pro Cys Arg
 65                  70                  75                  80

Trp Leu Cys Glu Ala Val Arg Asp Ser Cys Glu Pro Val Met Gln Phe
                85                  90                  95

Phe Gly Phe Tyr Trp Pro Glu Met Leu Lys Cys Asp Lys Phe Pro Glu
                100                 105                 110
```

Gly Asp Val Cys Ile Ala Met Thr Pro Pro Asn Ala
            115                 120

<210> SEQ ID NO 29
<211> LENGTH: 128
<212> TYPE: PRT
<213> ORGANISM: Homo sapiens

<400> SEQUENCE: 29

Phe Ser Tyr Lys Arg Ser Asn Cys Lys Pro Ile Pro Ala Asn Leu Gln
1               5                   10                  15

Leu Cys His Gly Ile Glu Tyr Gln Asn Met Arg Leu Pro Asn Leu Leu
            20                  25                  30

Gly His Glu Thr Met Lys Glu Val Leu Glu Gln Ala Gly Ala Trp Ile
        35                  40                  45

Pro Leu Val Met Lys Gln Cys His Pro Asp Thr Lys Lys Phe Leu Cys
    50                  55                  60

Ser Leu Phe Ala Pro Val Cys Leu Asp Asp Leu Asp Glu Thr Ile Gln
65                  70                  75                  80

Pro Cys His Ser Leu Cys Val Gln Val Lys Asp Arg Cys Ala Pro Val
                85                  90                  95

Met Ser Ala Phe Gly Phe Pro Trp Pro Asp Met Leu Glu Cys Asp Arg
            100                 105                 110

Phe Pro Gln Asp Asn Asp Leu Cys Ile Pro Leu Ala Ser Ser Asp His
        115                 120                 125

<210> SEQ ID NO 30
<211> LENGTH: 123
<212> TYPE: PRT
<213> ORGANISM: Homo sapiens

<400> SEQUENCE: 30

Ala Ala Cys Glu Pro Val Arg Ile Pro Leu Cys Lys Ser Leu Pro Trp
1               5                   10                  15

Asn Met Thr Lys Met Pro Asn His Leu His His Ser Thr Gln Ala Asn
            20                  25                  30

Ala Ile Leu Ala Ile Glu Gln Phe Glu Gly Leu Leu Gly Thr His Cys
        35                  40                  45

Ser Pro Asp Leu Leu Phe Phe Leu Cys Ala Met Tyr Ala Pro Ile Cys
    50                  55                  60

Thr Ile Asp Phe Gln His Glu Pro Ile Lys Pro Cys Lys Ser Val Cys
65                  70                  75                  80

Glu Arg Ala Arg Gln Gly Cys Glu Pro Ile Leu Ile Lys Tyr Arg His
                85                  90                  95

Ser Trp Pro Glu Asn Leu Ala Cys Glu Glu Leu Pro Val Tyr Asp Arg
            100                 105                 110

Gly Val Cys Ile Ser Pro Glu Ala Ile Val Thr
        115                 120

<210> SEQ ID NO 31
<211> LENGTH: 126
<212> TYPE: PRT
<213> ORGANISM: Homo sapiens

<400> SEQUENCE: 31

Val Arg Gly Ala Pro Cys Glu Ala Val Arg Ile Pro Met Cys Arg His
1               5                   10                  15

Met Pro Trp Asn Ile Thr Arg Met Pro Asn His Leu His His Ser Thr
            20                  25                  30

```
Gln Glu Asn Ala Ile Leu Ala Ile Glu Gln Tyr Glu Glu Leu Val Asp
                35                  40                  45

Val Asn Cys Ser Ala Val Leu Arg Phe Phe Cys Ala Met Tyr Ala
 50                  55                  60

Pro Ile Cys Thr Leu Glu Phe Leu His Asp Pro Ile Lys Pro Cys Lys
 65                  70                  75                  80

Ser Val Cys Gln Arg Ala Arg Asp Asp Cys Glu Pro Leu Met Lys Met
                 85                  90                  95

Tyr Asn His Ser Trp Pro Glu Ser Leu Ala Cys Asp Glu Leu Pro Val
                100                 105                 110

Tyr Asp Arg Gly Val Cys Ile Ser Pro Glu Ala Ile Val Thr
                115                 120                 125

<210> SEQ ID NO 32
<211> LENGTH: 125
<212> TYPE: PRT
<213> ORGANISM: Homo sapiens

<400> SEQUENCE: 32

Ser Tyr Ser Lys Pro Pro Gln Cys Leu Asp Ile Pro Ala Asp Leu Pro
 1               5                  10                  15

Leu Cys His Thr Val Gly Tyr Lys Arg Met Arg Leu Pro Asn Leu Leu
                20                  25                  30

Glu His Glu Ser Leu Ala Glu Val Lys Gln Gln Ala Ser Ser Trp Leu
                35                  40                  45

Pro Leu Leu Ala Lys Arg Cys His Ser Asp Thr Gln Val Phe Leu Cys
 50                  55                  60

Ser Leu Phe Ala Pro Val Cys Leu Asp Arg Pro Ile Tyr Pro Cys Arg
 65                  70                  75                  80

Ser Leu Cys Glu Ala Val Arg Ala Gly Cys Ala Pro Leu Met Glu Ala
                 85                  90                  95

Tyr Gly Phe Pro Trp Pro Glu Met Leu His Cys His Lys Phe Pro Leu
                100                 105                 110

Asp Asn Asp Leu Cys Ile Ala Val Gln Phe Gly His Leu
                115                 120                 125

<210> SEQ ID NO 33
<211> LENGTH: 142
<212> TYPE: PRT
<213> ORGANISM: Homo sapiens

<400> SEQUENCE: 33

Glu Tyr Glu Glu Asp Gly Phe Cys Gln Pro Tyr Arg Gly Ile Ala Cys
 1               5                  10                  15

Ala Arg Phe Ile Gly Asn Arg Thr Val Tyr Met Glu Ser Leu His Met
                20                  25                  30

Gln Gly Glu Ile Glu Asn Gln Ile Thr Ala Ala Phe Thr Met Ile Gly
                35                  40                  45

Thr Ser Ser His Leu Ser Asp Lys Cys Ser Gln Phe Ala Ile Pro Ser
 50                  55                  60

Leu Cys His Tyr Ala Phe Pro Tyr Cys Asp Glu Thr Ser Ser Val Pro
 65                  70                  75                  80

Lys Pro Arg Asp Leu Cys Arg Asp Glu Cys Glu Ile Leu Glu Asn Val
                 85                  90                  95

Leu Cys Gln Thr Glu Tyr Ile Phe Ala Arg Ser Asn Pro Met Ile Leu
                100                 105                 110
```

```
Met Arg Leu Lys Leu Pro Asn Cys Glu Asp Leu Pro Gln Pro Glu Ser
        115                 120                 125

Pro Glu Ala Ala Asn Cys Ile Arg Ile Gly Ile Pro Met Ala
    130                 135                 140

<210> SEQ ID NO 34
<211> LENGTH: 142
<212> TYPE: PRT
<213> ORGANISM: Homo sapiens

<400> SEQUENCE: 34

Asp Tyr His Glu Asp Gly Phe Cys Gln Pro Tyr Arg Gly Ile Ala Cys
1               5                   10                  15

Ala Arg Phe Ile Gly Asn Arg Thr Ile Tyr Val Asp Ser Leu Gln Met
            20                  25                  30

Gln Gly Glu Ile Glu Asn Arg Ile Thr Ala Ala Phe Thr Met Ile Gly
        35                  40                  45

Thr Ser Thr His Leu Ser Asp Gln Cys Ser Gln Phe Ala Ile Pro Ser
    50                  55                  60

Phe Cys His Phe Val Phe Pro Leu Cys Asp Ala Arg Ser Arg Thr Pro
65                  70                  75                  80

Lys Pro Arg Glu Leu Cys Arg Asp Glu Cys Glu Val Leu Glu Ser Asp
                85                  90                  95

Leu Cys Arg Gln Glu Tyr Thr Ile Ala Arg Ser Asn Pro Leu Ile Leu
            100                 105                 110

Met Arg Leu Gln Leu Pro Lys Cys Glu Ala Leu Pro Met Pro Glu Ser
        115                 120                 125

Pro Asp Ala Ala Asn Cys Met Arg Ile Gly Ile Pro Ala Glu
    130                 135                 140

<210> SEQ ID NO 35
<211> LENGTH: 235
<212> TYPE: PRT
<213> ORGANISM: Homo sapiens

<400> SEQUENCE: 35

Met Ala Glu Glu Ala Pro Lys Lys Ser Arg Ala Ala Gly Gly Gly
1               5                   10                  15

Ala Ser Trp Glu Leu Cys Ala Gly Ala Leu Ser Ala Arg Leu Ala Glu
            20                  25                  30

Glu Gly Ser Gly Asp Ala Gly Gly Arg Arg Pro Pro Val Asp Pro
        35                  40                  45

Arg Arg Leu Ala Arg Gln Leu Leu Leu Leu Trp Leu Leu Glu Ala
    50                  55                  60

Pro Leu Leu Leu Gly Val Arg Ala Gln Ala Ala Gly Gln Gly Pro Gly
65                  70                  75                  80

Gln Gly Pro Gly Pro Gly Gln Gln Pro Pro Pro Gln Gln Gln
                85                  90                  95

Gln Ser Gly Gln Gln Tyr Asn Gly Glu Arg Gly Ile Ser Val Pro Asp
            100                 105                 110

His Gly Tyr Cys Gln Pro Ile Ser Ile Pro Leu Cys Thr Asp Ile Ala
        115                 120                 125

Tyr Asn Gln Thr Ile Met Pro Asn Leu Leu Gly His Thr Asn Gln Glu
    130                 135                 140

Asp Ala Gly Leu Glu Val His Gln Phe Tyr Pro Leu Val Lys Val Gln
145                 150                 155                 160

Cys Ser Ala Glu Leu Lys Phe Phe Leu Cys Ser Met Tyr Ala Pro Val
```

```
                165                 170                 175
Cys Thr Val Leu Glu Gln Ala Leu Pro Pro Cys Arg Ser Leu Cys Glu
        180                 185                 190

Arg Ala Arg Gln Gly Cys Glu Ala Leu Met Asn Lys Phe Gly Phe Gln
        195                 200                 205

Trp Pro Asp Thr Leu Lys Cys Glu Lys Phe Pro Val His Gly Ala Gly
        210                 215                 220

Glu Leu Cys Val Gly Gln Asn Thr Ser Asp Lys
225                 230                 235

<210> SEQ ID NO 36
<211> LENGTH: 158
<212> TYPE: PRT
<213> ORGANISM: Homo sapiens

<400> SEQUENCE: 36

Met Arg Pro Arg Ser Ala Leu Pro Arg Leu Leu Leu Pro Leu Leu Leu
1               5                   10                  15

Leu Pro Ala Ala Gly Pro Ala Gln Phe His Gly Glu Lys Gly Ile Ser
            20                  25                  30

Ile Pro Asp His Gly Phe Cys Gln Pro Ile Ser Ile Pro Leu Cys Thr
        35                  40                  45

Asp Ile Ala Tyr Asn Gln Thr Ile Met Pro Asn Leu Leu Gly His Thr
    50                  55                  60

Asn Gln Glu Asp Ala Gly Leu Glu Val His Gln Phe Tyr Pro Leu Val
65                  70                  75                  80

Lys Val Gln Cys Ser Pro Glu Leu Arg Phe Phe Leu Cys Ser Met Tyr
                85                  90                  95

Ala Pro Val Cys Thr Val Leu Glu Gln Ala Ile Pro Pro Cys Arg Ser
            100                 105                 110

Ile Cys Glu Ser Ala Arg Gln Gly Cys Glu Ala Leu Met Asn Lys Phe
        115                 120                 125

Gly Phe Gln Trp Pro Glu Arg Leu Arg Cys Glu His Phe Pro Arg His
    130                 135                 140

Gly Ala Glu Gln Ile Cys Val Gly Gln Asn His Ser Glu Asp
145                 150                 155

<210> SEQ ID NO 37
<211> LENGTH: 141
<212> TYPE: PRT
<213> ORGANISM: Homo sapiens

<400> SEQUENCE: 37

Met Ala Met Thr Trp Ile Val Phe Ser Leu Trp Pro Leu Thr Val Phe
1               5                   10                  15

Met Gly His Ile Gly Gly His Ser Leu Phe Ser Cys Glu Pro Ile Thr
            20                  25                  30

Leu Arg Met Cys Gln Asp Leu Pro Tyr Asn Thr Thr Phe Met Pro Asn
        35                  40                  45

Leu Leu Asn His Tyr Asp Gln Gln Thr Ala Ala Leu Ala Met Glu Pro
    50                  55                  60

Phe His Pro Met Val Asn Leu Asp Cys Ser Arg Asp Phe Arg Pro Phe
65                  70                  75                  80

Leu Cys Ala Leu Tyr Ala Pro Ile Cys Met Glu Tyr Gly Arg Val Thr
                85                  90                  95

Leu Pro Cys Arg Arg Leu Cys Gln Arg Ala Tyr Ser Glu Cys Ser Lys
            100                 105                 110
```

Leu Met Glu Met Phe Gly Val Pro Trp Pro Glu Asp Met Glu Cys Ser
            115                 120                 125

Arg Phe Pro Asp Cys Asp Glu Pro Tyr Pro Arg Leu Val
    130                 135                 140

<210> SEQ ID NO 38
<211> LENGTH: 166
<212> TYPE: PRT
<213> ORGANISM: Homo sapiens

<400> SEQUENCE: 38

Met Ala Trp Arg Gly Ala Gly Pro Ser Val Pro Gly Ala Pro Gly Gly
1               5                   10                  15

Val Gly Leu Ser Leu Gly Leu Leu Gln Leu Leu Leu Leu Leu Leu Gly
            20                  25                  30

Pro Ala Arg Gly Phe Gly Asp Glu Glu Arg Arg Cys Asp Pro Ile
            35                  40                  45

Arg Ile Ser Met Cys Gln Asn Leu Gly Tyr Asn Val Thr Lys Met Pro
    50                  55                  60

Asn Leu Val Gly His Glu Leu Gln Thr Asp Ala Glu Leu Gln Leu Thr
65                  70                  75                  80

Thr Phe Thr Pro Leu Ile Gln Tyr Gly Cys Ser Ser Gln Leu Gln Phe
                85                  90                  95

Phe Leu Cys Ser Val Tyr Val Pro Met Cys Thr Glu Lys Ile Asn Ile
                100                 105                 110

Pro Ile Gly Pro Cys Gly Gly Met Cys Leu Ser Val Lys Arg Arg Cys
            115                 120                 125

Glu Pro Val Leu Lys Glu Phe Gly Phe Ala Trp Pro Glu Ser Leu Asn
    130                 135                 140

Cys Ser Lys Phe Pro Pro Gln Asn Asp His Asn His Met Cys Met Glu
145                 150                 155                 160

Gly Pro Gly Asp Glu Glu
                165

<210> SEQ ID NO 39
<211> LENGTH: 155
<212> TYPE: PRT
<213> ORGANISM: Homo sapiens

<400> SEQUENCE: 39

Met Ala Arg Pro Asp Pro Ser Ala Pro Pro Ser Leu Leu Leu Leu Leu
1               5                   10                  15

Leu Ala Gln Leu Val Gly Arg Ala Ala Ala Ala Ser Lys Ala Pro Val
            20                  25                  30

Cys Gln Glu Ile Thr Val Pro Met Cys Arg Gly Ile Gly Tyr Asn Leu
            35                  40                  45

Thr His Met Pro Asn Gln Phe Asn His Asp Thr Gln Asp Glu Ala Gly
    50                  55                  60

Leu Glu Val His Gln Phe Trp Pro Leu Val Glu Ile Gln Cys Ser Pro
65                  70                  75                  80

Asp Leu Arg Phe Phe Leu Cys Ser Met Tyr Thr Pro Ile Cys Leu Pro
                85                  90                  95

Asp Tyr His Lys Pro Leu Pro Pro Cys Arg Ser Val Cys Glu Arg Ala
                100                 105                 110

Lys Ala Gly Cys Ser Pro Leu Met Arg Gln Tyr Gly Phe Ala Trp Pro
            115                 120                 125

```
Glu Arg Met Ser Cys Asp Arg Leu Pro Val Leu Gly Arg Asp Ala Glu
        130                 135                 140

Val Leu Cys Met Asp Tyr Asn Arg Ser Glu Ala
145                 150                 155

<210> SEQ ID NO 40
<211> LENGTH: 137
<212> TYPE: PRT
<213> ORGANISM: Homo sapiens

<400> SEQUENCE: 40

Met Glu Met Phe Thr Phe Leu Leu Thr Cys Ile Phe Leu Pro Leu Leu
1               5                   10                  15

Arg Gly His Ser Leu Phe Thr Cys Glu Pro Ile Thr Val Pro Arg Cys
                20                  25                  30

Met Lys Met Ala Tyr Asn Met Thr Phe Phe Pro Asn Leu Met Gly His
            35                  40                  45

Tyr Asp Gln Ser Ile Ala Ala Val Glu Met Glu His Phe Leu Pro Leu
        50                  55                  60

Ala Asn Leu Glu Cys Ser Pro Asn Ile Glu Thr Phe Leu Cys Lys Ala
65                  70                  75                  80

Phe Val Pro Thr Cys Ile Glu Gln Ile His Val Val Pro Pro Cys Arg
                85                  90                  95

Lys Leu Cys Glu Lys Val Tyr Ser Asp Cys Lys Lys Leu Ile Asp Thr
            100                 105                 110

Phe Gly Ile Arg Trp Pro Glu Glu Leu Glu Cys Asp Arg Leu Gln Tyr
        115                 120                 125

Cys Asp Glu Thr Val Pro Val Thr Phe
    130                 135

<210> SEQ ID NO 41
<211> LENGTH: 168
<212> TYPE: PRT
<213> ORGANISM: Homo sapiens

<400> SEQUENCE: 41

Met Arg Asp Pro Gly Ala Ala Pro Leu Ser Ser Leu Gly Leu Cys
1               5                   10                  15

Ala Leu Val Leu Ala Leu Leu Gly Ala Leu Ser Ala Gly Ala Gly Ala
                20                  25                  30

Gln Pro Tyr His Gly Glu Lys Gly Ile Ser Val Pro Asp His Gly Phe
            35                  40                  45

Cys Gln Pro Ile Ser Ile Pro Leu Cys Thr Asp Ile Ala Tyr Asn Gln
        50                  55                  60

Thr Ile Leu Pro Asn Leu Leu Gly His Thr Asn Gln Glu Asp Ala Gly
65                  70                  75                  80

Leu Glu Val His Gln Phe Tyr Pro Leu Val Lys Val Gln Cys Ser Pro
                85                  90                  95

Glu Leu Arg Phe Phe Leu Cys Ser Met Tyr Ala Pro Val Cys Thr Val
            100                 105                 110

Leu Asp Gln Ala Ile Pro Pro Cys Arg Ser Leu Cys Glu Arg Ala Arg
        115                 120                 125

Gln Gly Cys Glu Ala Leu Met Asn Lys Phe Gly Phe Gln Trp Pro Glu
    130                 135                 140

Arg Leu Arg Cys Glu Asn Phe Pro Val His Gly Ala Gly Glu Ile Cys
145                 150                 155                 160

Val Gly Gln Asn Thr Ser Asp Gly
```

<210> SEQ ID NO 42
<211> LENGTH: 156
<212> TYPE: PRT
<213> ORGANISM: Homo sapiens

<400> SEQUENCE: 42

```
Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
130                 135                 140

Asp Thr Leu Cys Met Asp Tyr Asn Arg Thr Asp Leu
145                 150                 155
```

<210> SEQ ID NO 43
<211> LENGTH: 160
<212> TYPE: PRT
<213> ORGANISM: Homo sapiens

<400> SEQUENCE: 43

```
Met Ala Val Ala Pro Leu Arg Gly Ala Leu Leu Leu Trp Gln Leu Leu
1               5                   10                  15

Ala Ala Gly Gly Ala Ala Leu Glu Ile Gly Arg Phe Asp Pro Glu Arg
            20                  25                  30

Gly Arg Gly Ala Ala Pro Cys Gln Ala Val Glu Ile Pro Met Cys Arg
        35                  40                  45

Gly Ile Gly Tyr Asn Leu Thr Arg Met Pro Asn Leu Leu Gly His Thr
50                  55                  60

Ser Gln Gly Glu Ala Ala Ala Glu Leu Ala Glu Phe Ala Pro Leu Val
65                  70                  75                  80

Gln Tyr Gly Cys His Ser His Leu Arg Phe Phe Leu Cys Ser Leu Tyr
                85                  90                  95

Ala Pro Met Cys Thr Asp Gln Val Ser Thr Pro Ile Pro Ala Cys Arg
            100                 105                 110

Pro Met Cys Glu Gln Ala Arg Leu Arg Cys Ala Pro Ile Met Glu Gln
        115                 120                 125

Phe Asn Phe Gly Trp Pro Asp Ser Leu Asp Cys Ala Arg Leu Pro Thr
130                 135                 140

Arg Asn Asp Pro His Ala Leu Cys Met Glu Ala Pro Glu Asn Ala Thr
145                 150                 155                 160
```

<210> SEQ ID NO 44

```
<211> LENGTH: 155
<212> TYPE: PRT
<213> ORGANISM: Homo sapiens

<400> SEQUENCE: 44

Met Gln Arg Pro Gly Pro Arg Leu Trp Leu Val Leu Gln Val Met Gly
1               5                   10                  15

Ser Cys Ala Ala Ile Ser Ser Met Asp Met Glu Arg Pro Gly Asp Gly
            20                  25                  30

Lys Cys Gln Pro Ile Glu Ile Pro Met Cys Lys Asp Ile Gly Tyr Asn
        35                  40                  45

Met Thr Arg Met Pro Asn Leu Met Gly His Glu Asn Gln Arg Glu Ala
    50                  55                  60

Ala Ile Gln Leu His Glu Phe Ala Pro Leu Val Glu Tyr Gly Cys His
65                  70                  75                  80

Gly His Leu Arg Phe Phe Leu Cys Ser Leu Tyr Ala Pro Met Cys Thr
                85                  90                  95

Glu Gln Val Ser Thr Pro Ile Pro Ala Cys Arg Val Met Cys Glu Gln
            100                 105                 110

Ala Arg Leu Lys Cys Ser Pro Ile Met Glu Gln Phe Asn Phe Lys Trp
        115                 120                 125

Pro Asp Ser Leu Asp Cys Arg Lys Leu Pro Asn Lys Asn Asp Pro Asn
    130                 135                 140

Tyr Leu Cys Met Glu Ala Pro Asn Asn Gly Ser
145                 150                 155

<210> SEQ ID NO 45
<211> LENGTH: 174
<212> TYPE: PRT
<213> ORGANISM: Homo sapiens

<400> SEQUENCE: 45

Met Gly Ile Gly Arg Ser Glu Gly Gly Arg Gly Ala Ala Leu Gly
1               5                   10                  15

Val Leu Leu Ala Leu Gly Ala Ala Leu Leu Ala Val Gly Ser Ala Ser
            20                  25                  30

Glu Tyr Asp Tyr Val Ser Phe Gln Ser Asp Ile Gly Pro Tyr Gln Ser
        35                  40                  45

Gly Arg Phe Tyr Thr Lys Pro Pro Gln Cys Val Asp Ile Pro Ala Asp
    50                  55                  60

Leu Arg Leu Cys His Asn Val Gly Tyr Lys Lys Met Val Leu Pro Asn
65                  70                  75                  80

Leu Leu Glu His Glu Thr Met Ala Glu Val Lys Gln Gln Ala Ser Ser
                85                  90                  95

Trp Val Pro Leu Leu Asn Lys Asn Cys His Ala Gly Thr Gln Val Phe
            100                 105                 110

Leu Cys Ser Leu Phe Ala Pro Val Cys Leu Asp Arg Pro Ile Tyr Pro
        115                 120                 125

Cys Arg Trp Leu Cys Glu Ala Val Arg Asp Ser Cys Glu Pro Val Met
    130                 135                 140

Gln Phe Phe Gly Phe Tyr Trp Pro Glu Met Leu Lys Cys Asp Lys Phe
145                 150                 155                 160

Pro Glu Gly Asp Val Cys Ile Ala Met Thr Pro Pro Asn Ala
                165                 170

<210> SEQ ID NO 46
<211> LENGTH: 160
```

```
<212> TYPE: PRT
<213> ORGANISM: Homo sapiens

<400> SEQUENCE: 46

Met Leu Gln Gly Pro Gly Ser Leu Leu Leu Phe Leu Ala Ser His
1               5                   10                  15

Cys Cys Leu Gly Ser Ala Arg Gly Leu Phe Leu Phe Gly Gln Pro Asp
            20                  25                  30

Phe Ser Tyr Lys Arg Ser Asn Cys Lys Pro Ile Pro Ala Asn Leu Gln
        35                  40                  45

Leu Cys His Gly Ile Glu Tyr Gln Asn Met Arg Leu Pro Asn Leu Leu
    50                  55                  60

Gly His Glu Thr Met Lys Glu Val Leu Glu Gln Ala Gly Ala Trp Ile
65                  70                  75                  80

Pro Leu Val Met Lys Gln Cys His Pro Asp Thr Lys Lys Phe Leu Cys
                85                  90                  95

Ser Leu Phe Ala Pro Val Cys Leu Asp Asp Leu Asp Glu Thr Ile Gln
                100                 105                 110

Pro Cys His Ser Leu Cys Val Gln Val Lys Asp Arg Cys Ala Pro Val
            115                 120                 125

Met Ser Ala Phe Gly Phe Pro Trp Pro Asp Met Leu Glu Cys Asp Arg
        130                 135                 140

Phe Pro Gln Asp Asn Asp Leu Cys Ile Pro Leu Ala Ser Ser Asp His
145                 150                 155                 160

<210> SEQ ID NO 47
<211> LENGTH: 155
<212> TYPE: PRT
<213> ORGANISM: Homo sapiens

<400> SEQUENCE: 47

Met Val Cys Gly Ser Pro Gly Gly Met Leu Leu Leu Arg Ala Gly Leu
1               5                   10                  15

Leu Ala Leu Ala Ala Leu Cys Leu Leu Arg Val Pro Gly Ala Arg Ala
            20                  25                  30

Ala Ala Cys Glu Pro Val Arg Ile Pro Leu Cys Lys Ser Leu Pro Trp
        35                  40                  45

Asn Met Thr Lys Met Pro Asn His Leu His His Ser Thr Gln Ala Asn
    50                  55                  60

Ala Ile Leu Ala Ile Glu Gln Phe Glu Gly Leu Leu Gly Thr His Cys
65                  70                  75                  80

Ser Pro Asp Leu Leu Phe Phe Leu Cys Ala Met Tyr Ala Pro Ile Cys
                85                  90                  95

Thr Ile Asp Phe Gln His Glu Pro Ile Lys Pro Cys Lys Ser Val Cys
                100                 105                 110

Glu Arg Ala Arg Gln Gly Cys Glu Pro Ile Leu Ile Lys Tyr Arg His
            115                 120                 125

Ser Trp Pro Glu Asn Leu Ala Cys Glu Glu Leu Pro Val Tyr Asp Arg
        130                 135                 140

Gly Val Cys Ile Ser Pro Glu Ala Ile Val Thr
145                 150                 155

<210> SEQ ID NO 48
<211> LENGTH: 144
<212> TYPE: PRT
<213> ORGANISM: Homo sapiens

<400> SEQUENCE: 48
```

```
Met Phe Leu Ser Ile Leu Val Ala Leu Cys Leu Trp Leu His Leu Ala
1               5                   10                  15

Leu Gly Val Arg Gly Ala Pro Cys Glu Ala Val Arg Ile Pro Met Cys
            20                  25                  30

Arg His Met Pro Trp Asn Ile Thr Arg Met Pro Asn His Leu His His
            35                  40                  45

Ser Thr Gln Glu Asn Ala Ile Leu Ala Ile Glu Gln Tyr Glu Glu Leu
    50                  55                  60

Val Asp Val Asn Cys Ser Ala Val Leu Arg Phe Phe Cys Ala Met
65                  70                  75                  80

Tyr Ala Pro Ile Cys Thr Leu Glu Phe Leu His Asp Pro Ile Lys Pro
                85                  90                  95

Cys Lys Ser Val Cys Gln Arg Ala Arg Asp Asp Cys Glu Pro Leu Met
            100                 105                 110

Lys Met Tyr Asn His Ser Trp Pro Glu Ser Leu Ala Cys Asp Glu Leu
            115                 120                 125

Pro Val Tyr Asp Arg Gly Val Cys Ile Ser Pro Glu Ala Ile Val Thr
            130                 135                 140
```

<210> SEQ ID NO 49
<211> LENGTH: 170
<212> TYPE: PRT
<213> ORGANISM: Homo sapiens

<400> SEQUENCE: 49

```
Met Arg Ala Ala Ala Ala Gly Gly Val Arg Thr Ala Ala Leu Ala
1               5                   10                  15

Leu Leu Leu Gly Ala Leu His Trp Ala Pro Ala Arg Cys Glu Glu Tyr
            20                  25                  30

Asp Tyr Tyr Gly Trp Gln Ala Glu Pro Leu His Gly Arg Ser Tyr Ser
            35                  40                  45

Lys Pro Pro Gln Cys Leu Asp Ile Pro Ala Asp Leu Pro Leu Cys His
    50                  55                  60

Thr Val Gly Tyr Lys Arg Met Arg Leu Pro Asn Leu Leu Glu His Glu
65                  70                  75                  80

Ser Leu Ala Glu Val Lys Gln Gln Ala Ser Ser Trp Leu Pro Leu Leu
                85                  90                  95

Ala Lys Arg Cys His Ser Asp Thr Gln Val Phe Leu Cys Ser Leu Phe
            100                 105                 110

Ala Pro Val Cys Leu Asp Arg Pro Ile Tyr Pro Cys Arg Ser Leu Cys
            115                 120                 125

Glu Ala Val Arg Ala Gly Cys Ala Pro Leu Met Glu Ala Tyr Gly Phe
            130                 135                 140

Pro Trp Pro Glu Met Leu His Cys His Lys Phe Pro Leu Asp Asn Asp
145                 150                 155                 160

Leu Cys Ile Ala Val Gln Phe Gly His Leu
            165                 170
```

<210> SEQ ID NO 50
<211> LENGTH: 163
<212> TYPE: PRT
<213> ORGANISM: Homo sapiens

<400> SEQUENCE: 50

```
Gln Ala Ala Gly Gln Gly Pro Gly Gln Gly Pro Gly Pro Gly Gln Gln
1               5                   10                  15
```

Pro Pro Pro Pro Pro Gln Gln Gln Ser Gly Gln Gln Tyr Asn Gly
            20                  25                  30

Glu Arg Gly Ile Ser Val Pro Asp His Gly Tyr Cys Gln Pro Ile Ser
         35                  40                  45

Ile Pro Leu Cys Thr Asp Ile Ala Tyr Asn Gln Thr Ile Met Pro Asn
 50                  55                  60

Leu Leu Gly His Thr Asn Gln Glu Asp Ala Gly Leu Glu Val His Gln
 65                  70                  75                  80

Phe Tyr Pro Leu Val Lys Val Gln Cys Ser Ala Glu Leu Lys Phe Phe
                 85                  90                  95

Leu Cys Ser Met Tyr Ala Pro Val Cys Thr Val Leu Glu Gln Ala Leu
            100                 105                 110

Pro Pro Cys Arg Ser Leu Cys Glu Arg Ala Arg Gln Gly Cys Glu Ala
            115                 120                 125

Leu Met Asn Lys Phe Gly Phe Gln Trp Pro Asp Thr Leu Lys Cys Glu
            130                 135                 140

Lys Phe Pro Val His Gly Ala Gly Glu Leu Cys Val Gly Gln Asn Thr
145                 150                 155                 160

Ser Asp Lys

<210> SEQ ID NO 51
<211> LENGTH: 136
<212> TYPE: PRT
<213> ORGANISM: Homo sapiens

<400> SEQUENCE: 51

Ala Gln Phe His Gly Glu Lys Gly Ile Ser Ile Pro Asp His Gly Phe
1               5                  10                  15

Cys Gln Pro Ile Ser Ile Pro Leu Cys Thr Asp Ile Ala Tyr Asn Gln
            20                  25                  30

Thr Ile Met Pro Asn Leu Leu Gly His Thr Asn Gln Glu Asp Ala Gly
         35                  40                  45

Leu Glu Val His Gln Phe Tyr Pro Leu Val Lys Val Gln Cys Ser Pro
 50                  55                  60

Glu Leu Arg Phe Phe Leu Cys Ser Met Tyr Ala Pro Val Cys Thr Val
 65                  70                  75                  80

Leu Glu Gln Ala Ile Pro Pro Cys Arg Ser Ile Cys Glu Ser Ala Arg
                 85                  90                  95

Gln Gly Cys Glu Ala Leu Met Asn Lys Phe Gly Phe Gln Trp Pro Glu
            100                 105                 110

Arg Leu Arg Cys Glu His Phe Pro Arg His Gly Ala Glu Gln Ile Cys
            115                 120                 125

Val Gly Gln Asn His Ser Glu Asp
            130                 135

<210> SEQ ID NO 52
<211> LENGTH: 119
<212> TYPE: PRT
<213> ORGANISM: Homo sapiens

<400> SEQUENCE: 52

His Ser Leu Phe Ser Cys Glu Pro Ile Thr Leu Arg Met Cys Gln Asp
1               5                  10                  15

Leu Pro Tyr Asn Thr Thr Phe Met Pro Asn Leu Leu Asn His Tyr Asp
            20                  25                  30

Gln Gln Thr Ala Ala Leu Ala Met Glu Pro Phe His Pro Met Val Asn
         35                  40                  45

Leu Asp Cys Ser Arg Asp Phe Arg Pro Phe Leu Cys Ala Leu Tyr Ala
    50                  55                  60

Pro Ile Cys Met Glu Tyr Gly Arg Val Thr Leu Pro Cys Arg Arg Leu
65                  70                  75                  80

Cys Gln Arg Ala Tyr Ser Glu Cys Ser Lys Leu Met Glu Met Phe Gly
                85                  90                  95

Val Pro Trp Pro Glu Asp Met Cys Ser Arg Phe Pro Asp Cys Asp
                100                 105                 110

Glu Pro Tyr Pro Arg Leu Val
        115

<210> SEQ ID NO 53
<211> LENGTH: 130
<212> TYPE: PRT
<213> ORGANISM: Homo sapiens

<400> SEQUENCE: 53

Phe Gly Asp Glu Glu Arg Arg Cys Asp Pro Ile Arg Ile Ser Met
1               5                   10                  15

Cys Gln Asn Leu Gly Tyr Asn Val Thr Lys Met Pro Asn Leu Val Gly
                20                  25                  30

His Glu Leu Gln Thr Asp Ala Glu Leu Gln Leu Thr Thr Phe Thr Pro
            35                  40                  45

Leu Ile Gln Tyr Gly Cys Ser Ser Gln Leu Gln Phe Phe Leu Cys Ser
    50                  55                  60

Val Tyr Val Pro Met Cys Thr Glu Lys Ile Asn Ile Pro Ile Gly Pro
65                  70                  75                  80

Cys Gly Gly Met Cys Leu Ser Val Lys Arg Arg Cys Glu Pro Val Leu
                85                  90                  95

Lys Glu Phe Gly Phe Ala Trp Pro Glu Ser Leu Asn Cys Ser Lys Phe
            100                 105                 110

Pro Pro Gln Asn Asp His Asn His Met Cys Met Glu Gly Pro Gly Asp
    115                 120                 125

Glu Glu
    130

<210> SEQ ID NO 54
<211> LENGTH: 129
<212> TYPE: PRT
<213> ORGANISM: Homo sapiens

<400> SEQUENCE: 54

Ala Ser Lys Ala Pro Val Cys Gln Glu Ile Thr Val Pro Met Cys Arg
1               5                   10                  15

Gly Ile Gly Tyr Asn Leu Thr His Met Pro Asn Gln Phe Asn His Asp
                20                  25                  30

Thr Gln Asp Glu Ala Gly Leu Glu Val His Gln Phe Trp Pro Leu Val
            35                  40                  45

Glu Ile Gln Cys Ser Pro Asp Leu Arg Phe Phe Leu Cys Ser Met Tyr
    50                  55                  60

Thr Pro Ile Cys Leu Pro Asp Tyr His Lys Pro Leu Pro Pro Cys Arg
65                  70                  75                  80

Ser Val Cys Glu Arg Ala Lys Ala Gly Cys Ser Pro Leu Met Arg Gln
                85                  90                  95

Tyr Gly Phe Ala Trp Pro Glu Arg Met Ser Cys Asp Arg Leu Pro Val
            100                 105                 110

```
Leu Gly Arg Asp Ala Glu Val Leu Cys Met Asp Tyr Asn Arg Ser Glu
        115                 120                 125
Ala

<210> SEQ ID NO 55
<211> LENGTH: 119
<212> TYPE: PRT
<213> ORGANISM: Homo sapiens

<400> SEQUENCE: 55

His Ser Leu Phe Thr Cys Glu Pro Ile Thr Val Pro Arg Cys Met Lys
1               5                   10                  15

Met Ala Tyr Asn Met Thr Phe Phe Pro Asn Leu Met Gly His Tyr Asp
            20                  25                  30

Gln Ser Ile Ala Ala Val Glu Met Glu His Phe Leu Pro Leu Ala Asn
        35                  40                  45

Leu Glu Cys Ser Pro Asn Ile Glu Thr Phe Leu Cys Lys Ala Phe Val
    50                  55                  60

Pro Thr Cys Ile Glu Gln Ile His Val Val Pro Pro Cys Arg Lys Leu
65                  70                  75                  80

Cys Glu Lys Val Tyr Ser Asp Cys Lys Lys Leu Ile Asp Thr Phe Gly
                85                  90                  95

Ile Arg Trp Pro Glu Glu Leu Glu Cys Asp Arg Leu Gln Tyr Cys Asp
            100                 105                 110

Glu Thr Val Pro Val Thr Phe
        115

<210> SEQ ID NO 56
<211> LENGTH: 136
<212> TYPE: PRT
<213> ORGANISM: Homo sapiens

<400> SEQUENCE: 56

Gln Pro Tyr His Gly Glu Lys Gly Ile Ser Val Pro Asp His Gly Phe
1               5                   10                  15

Cys Gln Pro Ile Ser Ile Pro Leu Cys Thr Asp Ile Ala Tyr Asn Gln
            20                  25                  30

Thr Ile Leu Pro Asn Leu Leu Gly His Thr Asn Gln Glu Asp Ala Gly
        35                  40                  45

Leu Glu Val His Gln Phe Tyr Pro Leu Val Lys Val Gln Cys Ser Pro
    50                  55                  60

Glu Leu Arg Phe Phe Leu Cys Ser Met Tyr Ala Pro Val Cys Thr Val
65                  70                  75                  80

Leu Asp Gln Ala Ile Pro Pro Cys Arg Ser Leu Cys Glu Arg Ala Arg
                85                  90                  95

Gln Gly Cys Glu Ala Leu Met Asn Lys Phe Gly Phe Gln Trp Pro Glu
            100                 105                 110

Arg Leu Arg Cys Glu Asn Phe Pro Val His Gly Ala Gly Glu Ile Cys
        115                 120                 125

Val Gly Gln Asn Thr Ser Asp Gly
    130                 135

<210> SEQ ID NO 57
<211> LENGTH: 129
<212> TYPE: PRT
<213> ORGANISM: Homo sapiens

<400> SEQUENCE: 57
```

```
Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
            115                 120                 125

Leu

<210> SEQ ID NO 58
<211> LENGTH: 139
<212> TYPE: PRT
<213> ORGANISM: Homo sapiens

<400> SEQUENCE: 58

Ala Leu Glu Ile Gly Arg Phe Asp Pro Glu Arg Gly Arg Gly Ala Ala
1               5                   10                  15

Pro Cys Gln Ala Val Glu Ile Pro Met Cys Arg Gly Ile Gly Tyr Asn
            20                  25                  30

Leu Thr Arg Met Pro Asn Leu Leu Gly His Thr Ser Gln Gly Glu Ala
        35                  40                  45

Ala Ala Glu Leu Ala Glu Phe Ala Pro Leu Val Gln Tyr Gly Cys His
50                  55                  60

Ser His Leu Arg Phe Phe Leu Cys Ser Leu Tyr Ala Pro Met Cys Thr
65                  70                  75                  80

Asp Gln Val Ser Thr Pro Ile Pro Ala Cys Arg Pro Met Cys Glu Gln
                85                  90                  95

Ala Arg Leu Arg Cys Ala Pro Ile Met Glu Gln Phe Asn Phe Gly Trp
            100                 105                 110

Pro Asp Ser Leu Asp Cys Ala Arg Leu Pro Thr Arg Asn Asp Pro His
            115                 120                 125

Ala Leu Cys Met Glu Ala Pro Glu Asn Ala Thr
        130                 135

<210> SEQ ID NO 59
<211> LENGTH: 135
<212> TYPE: PRT
<213> ORGANISM: Homo sapiens

<400> SEQUENCE: 59

Ile Ser Ser Met Asp Met Glu Arg Pro Gly Asp Gly Lys Cys Gln Pro
1               5                   10                  15

Ile Glu Ile Pro Met Cys Lys Asp Ile Gly Tyr Asn Met Thr Arg Met
            20                  25                  30

Pro Asn Leu Met Gly His Glu Asn Gln Arg Glu Ala Ala Ile Gln Leu
        35                  40                  45

His Glu Phe Ala Pro Leu Val Glu Tyr Gly Cys His Gly His Leu Arg
50                  55                  60
```

Phe Phe Leu Cys Ser Leu Tyr Ala Pro Met Cys Thr Glu Gln Val Ser
65                  70                  75                  80

Thr Pro Ile Pro Ala Cys Arg Val Met Cys Glu Gln Ala Arg Leu Lys
                85                  90                  95

Cys Ser Pro Ile Met Glu Gln Phe Asn Phe Lys Trp Pro Asp Ser Leu
            100                 105                 110

Asp Cys Arg Lys Leu Pro Asn Lys Asn Asp Pro Asn Tyr Leu Cys Met
        115                 120                 125

Glu Ala Pro Asn Asn Gly Ser
        130                 135

<210> SEQ ID NO 60
<211> LENGTH: 144
<212> TYPE: PRT
<213> ORGANISM: Homo sapiens

<400> SEQUENCE: 60

Ala Ser Glu Tyr Asp Tyr Val Ser Phe Gln Ser Asp Ile Gly Pro Tyr
1               5                   10                  15

Gln Ser Gly Arg Phe Tyr Thr Lys Pro Pro Gln Cys Val Asp Ile Pro
            20                  25                  30

Ala Asp Leu Arg Leu Cys His Asn Val Gly Tyr Lys Lys Met Val Leu
        35                  40                  45

Pro Asn Leu Leu Glu His Glu Thr Met Ala Glu Val Lys Gln Gln Ala
    50                  55                  60

Ser Ser Trp Val Pro Leu Leu Asn Lys Asn Cys His Ala Gly Thr Gln
65                  70                  75                  80

Val Phe Leu Cys Ser Leu Phe Ala Pro Val Cys Leu Asp Arg Pro Ile
                85                  90                  95

Tyr Pro Cys Arg Trp Leu Cys Glu Ala Val Arg Asp Ser Cys Glu Pro
            100                 105                 110

Val Met Gln Phe Phe Gly Phe Tyr Trp Pro Glu Met Leu Lys Cys Asp
        115                 120                 125

Lys Phe Pro Glu Gly Asp Val Cys Ile Ala Met Thr Pro Pro Asn Ala
    130                 135                 140

<210> SEQ ID NO 61
<211> LENGTH: 142
<212> TYPE: PRT
<213> ORGANISM: Homo sapiens

<400> SEQUENCE: 61

Leu Gly Ser Ala Arg Gly Leu Phe Leu Phe Gly Gln Pro Asp Phe Ser
1               5                   10                  15

Tyr Lys Arg Ser Asn Cys Lys Pro Ile Pro Ala Asn Leu Gln Leu Cys
            20                  25                  30

His Gly Ile Glu Tyr Gln Asn Met Arg Leu Pro Asn Leu Leu Gly His
        35                  40                  45

Glu Thr Met Lys Glu Val Leu Glu Gln Ala Gly Ala Trp Ile Pro Leu
    50                  55                  60

Val Met Lys Gln Cys His Pro Asp Thr Lys Lys Phe Leu Cys Ser Leu
65                  70                  75                  80

Phe Ala Pro Val Cys Leu Asp Asp Leu Asp Glu Thr Ile Gln Pro Cys
                85                  90                  95

His Ser Leu Cys Val Gln Val Lys Asp Arg Cys Ala Pro Val Met Ser
            100                 105                 110

```
Ala Phe Gly Phe Pro Trp Pro Asp Met Leu Glu Cys Asp Arg Phe Pro
        115                 120                 125

Gln Asp Asn Asp Leu Cys Ile Pro Leu Ala Ser Ser Asp His
        130                 135                 140

<210> SEQ ID NO 62
<211> LENGTH: 123
<212> TYPE: PRT
<213> ORGANISM: Homo sapiens

<400> SEQUENCE: 62

Ala Ala Cys Glu Pro Val Arg Ile Pro Leu Cys Lys Ser Leu Pro Trp
1               5                   10                  15

Asn Met Thr Lys Met Pro Asn His Leu His His Ser Thr Gln Ala Asn
            20                  25                  30

Ala Ile Leu Ala Ile Glu Gln Phe Glu Gly Leu Leu Gly Thr His Cys
        35                  40                  45

Ser Pro Asp Leu Leu Phe Phe Leu Cys Ala Met Tyr Ala Pro Ile Cys
    50                  55                  60

Thr Ile Asp Phe Gln His Glu Pro Ile Lys Pro Cys Lys Ser Val Cys
65                  70                  75                  80

Glu Arg Ala Arg Gln Gly Cys Glu Pro Ile Leu Ile Lys Tyr Arg His
                85                  90                  95

Ser Trp Pro Glu Asn Leu Ala Cys Glu Glu Leu Pro Val Tyr Asp Arg
            100                 105                 110

Gly Val Cys Ile Ser Pro Glu Ala Ile Val Thr
        115                 120

<210> SEQ ID NO 63
<211> LENGTH: 126
<212> TYPE: PRT
<213> ORGANISM: Homo sapiens

<400> SEQUENCE: 63

Val Arg Gly Ala Pro Cys Glu Ala Val Arg Ile Pro Met Cys Arg His
1               5                   10                  15

Met Pro Trp Asn Ile Thr Arg Met Pro Asn His Leu His His Ser Thr
            20                  25                  30

Gln Glu Asn Ala Ile Leu Ala Ile Glu Gln Tyr Glu Glu Leu Val Asp
        35                  40                  45

Val Asn Cys Ser Ala Val Leu Arg Phe Phe Phe Cys Ala Met Tyr Ala
    50                  55                  60

Pro Ile Cys Thr Leu Glu Phe Leu His Asp Pro Ile Lys Pro Cys Lys
65                  70                  75                  80

Ser Val Cys Gln Arg Ala Arg Asp Asp Cys Glu Pro Leu Met Lys Met
                85                  90                  95

Tyr Asn His Ser Trp Pro Glu Ser Leu Ala Cys Asp Glu Leu Pro Val
            100                 105                 110

Tyr Asp Arg Gly Val Cys Ile Ser Pro Glu Ala Ile Val Thr
        115                 120                 125

<210> SEQ ID NO 64
<211> LENGTH: 143
<212> TYPE: PRT
<213> ORGANISM: Homo sapiens

<400> SEQUENCE: 64

Arg Cys Glu Glu Tyr Asp Tyr Tyr Gly Trp Gln Ala Glu Pro Leu His
1               5                   10                  15
```

-continued

Gly Arg Ser Tyr Ser Lys Pro Pro Gln Cys Leu Asp Ile Pro Ala Asp
            20                  25                  30

Leu Pro Leu Cys His Thr Val Gly Tyr Lys Arg Met Arg Leu Pro Asn
        35                  40                  45

Leu Leu Glu His Glu Ser Leu Ala Glu Val Lys Gln Gln Ala Ser Ser
    50                  55                  60

Trp Leu Pro Leu Leu Ala Lys Arg Cys His Ser Asp Thr Gln Val Phe
65                  70                  75                  80

Leu Cys Ser Leu Phe Ala Pro Val Cys Leu Asp Arg Pro Ile Tyr Pro
                85                  90                  95

Cys Arg Ser Leu Cys Glu Ala Val Arg Ala Gly Cys Ala Pro Leu Met
            100                 105                 110

Glu Ala Tyr Gly Phe Pro Trp Pro Glu Met Leu His Cys His Lys Phe
        115                 120                 125

Pro Leu Asp Asn Asp Leu Cys Ile Ala Val Gln Phe Gly His Leu
    130                 135                 140

<210> SEQ ID NO 65
<211> LENGTH: 162
<212> TYPE: PRT
<213> ORGANISM: Homo sapiens

<400> SEQUENCE: 65

Thr Gly Val Leu Phe Val Lys Phe Gly Pro Pro Thr Ala Ser Pro
1               5                   10                  15

Gly Tyr Ser Asp Glu Tyr Glu Asp Gly Phe Cys Gln Pro Tyr Arg
            20                  25                  30

Gly Ile Ala Cys Ala Arg Phe Ile Gly Asn Arg Thr Val Tyr Met Glu
        35                  40                  45

Ser Leu His Met Gln Gly Glu Ile Asn Gln Ile Thr Ala Ala Phe
    50                  55                  60

Thr Met Ile Gly Thr Ser Ser His Leu Ser Asp Lys Cys Ser Gln Phe
65                  70                  75                  80

Ala Ile Pro Ser Leu Cys His Tyr Ala Phe Pro Tyr Cys Asp Glu Thr
                85                  90                  95

Ser Ser Val Pro Lys Pro Arg Asp Leu Cys Arg Asp Glu Cys Glu Ile
            100                 105                 110

Leu Glu Asn Val Leu Cys Gln Thr Glu Tyr Ile Phe Ala Arg Ser Asn
        115                 120                 125

Pro Met Ile Leu Met Arg Leu Lys Leu Pro Asn Cys Gly Asp Leu Pro
    130                 135                 140

Gln Pro Glu Ser Pro Glu Ala Ala Asn Cys Ile Arg Ile Gly Ile Pro
145                 150                 155                 160

Met Ala

<210> SEQ ID NO 66
<211> LENGTH: 162
<212> TYPE: PRT
<213> ORGANISM: Homo sapiens

<400> SEQUENCE: 66

Thr Gly Val Leu Phe Val Arg Leu Gly Pro Thr His Ser Pro Asn His
1               5                   10                  15

Asn Phe Gln Asp Asp Tyr His Glu Asp Gly Phe Cys Gln Pro Tyr Arg
            20                  25                  30

Gly Ile Ala Cys Ala Arg Phe Ile Gly Asn Arg Thr Ile Tyr Val Asp

```
                35                  40                  45
Ser Leu Gln Met Gln Gly Glu Ile Glu Asn Arg Ile Thr Ala Ala Phe
 50                  55                  60

Thr Met Ile Gly Thr Ser Thr His Leu Ser Asp Gln Cys Ser Gln Phe
 65                  70                  75                  80

Ala Ile Pro Ser Phe Cys His Phe Val Phe Pro Leu Cys Asp Ala Arg
                 85                  90                  95

Ser Arg Thr Pro Lys Pro Arg Glu Leu Cys Arg Asp Glu Cys Glu Val
                100                 105                 110

Leu Glu Ser Asp Leu Cys Arg Gln Glu Tyr Thr Ile Ala Arg Ser Asn
                115                 120                 125

Pro Leu Ile Leu Met Arg Leu Gln Leu Pro Lys Cys Glu Ala Leu Pro
                130                 135                 140

Met Pro Glu Ser Pro Asp Ala Ala Asn Cys Met Arg Ile Gly Ile Pro
145                 150                 155                 160

Ala Glu

<210> SEQ ID NO 67
<211> LENGTH: 227
<212> TYPE: PRT
<213> ORGANISM: Homo sapiens

<400> SEQUENCE: 67

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
                 35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Glu Glu Met Thr Lys Asn Gln Val Ser
                130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
                210                 215                 220

Pro Gly Lys
225

<210> SEQ ID NO 68
```

```
<211> LENGTH: 230
<212> TYPE: PRT
<213> ORGANISM: Homo sapiens

<400> SEQUENCE: 68

Asp Lys Ala Ala Arg Ser Thr Leu Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225                 230

<210> SEQ ID NO 69
<211> LENGTH: 8
<212> TYPE: PRT
<213> ORGANISM: Artificial sequence
<220> FEATURE:
<223> OTHER INFORMATION: Peptide linker

<400> SEQUENCE: 69

Glu Ser Gly Gly Gly Gly Val Thr
1               5

<210> SEQ ID NO 70
<211> LENGTH: 9
<212> TYPE: PRT
<213> ORGANISM: Artificial sequence
<220> FEATURE:
<223> OTHER INFORMATION: Peptide linker

<400> SEQUENCE: 70

Leu Glu Ser Gly Gly Gly Gly Val Thr
1               5

<210> SEQ ID NO 71
<211> LENGTH: 6
```

```
<212> TYPE: PRT
<213> ORGANISM: Artificial sequence
<220> FEATURE:
<223> OTHER INFORMATION: Peptide linker

<400> SEQUENCE: 71

Gly Arg Ala Gln Val Thr
1               5

<210> SEQ ID NO 72
<211> LENGTH: 6
<212> TYPE: PRT
<213> ORGANISM: Artificial Sequence
<220> FEATURE:
<223> OTHER INFORMATION: Peptide linker

<400> SEQUENCE: 72

Trp Arg Ala Gln Val Thr
1               5

<210> SEQ ID NO 73
<211> LENGTH: 8
<212> TYPE: PRT
<213> ORGANISM: Artificial sequence
<220> FEATURE:
<223> OTHER INFORMATION: Peptide linker

<400> SEQUENCE: 73

Ala Arg Gly Arg Ala Gln Val Thr
1               5

<210> SEQ ID NO 74
<211> LENGTH: 391
<212> TYPE: PRT
<213> ORGANISM: Artificial sequence
<220> FEATURE:
<223> OTHER INFORMATION: Frz8-Fc chimeric protein

<400> SEQUENCE: 74

Met Glu Trp Gly Tyr Leu Leu Glu Val Thr Ser Leu Leu Ala Ala Leu
1               5                   10                  15

Ala Val Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
    50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Glu Ser Gly Gly
145                 150                 155                 160

Gly Gly Val Thr Asp Lys Thr His Thr Cys Pro Pro Cys Pro Ala Pro
                165                 170                 175

Glu Leu Leu Gly Gly Pro Ser Val Phe Leu Phe Pro Pro Lys Pro Lys
```

-continued

```
                180                 185                 190
Asp Thr Leu Met Ile Ser Arg Thr Pro Glu Val Thr Cys Val Val Val
            195                 200                 205

Asp Val Ser His Glu Asp Pro Glu Val Lys Phe Asn Trp Tyr Val Asp
        210                 215                 220

Gly Val Glu Val His Asn Ala Lys Thr Lys Pro Arg Glu Glu Gln Tyr
225                 230                 235                 240

Asn Ser Thr Tyr Arg Val Val Ser Val Leu Thr Val Leu His Gln Asp
                245                 250                 255

Trp Leu Asn Gly Lys Glu Tyr Lys Cys Lys Val Ser Asn Lys Ala Leu
            260                 265                 270

Pro Ala Pro Ile Glu Lys Thr Ile Ser Lys Ala Lys Gly Gln Pro Arg
        275                 280                 285

Glu Pro Gln Val Tyr Thr Leu Pro Pro Ser Arg Glu Glu Met Thr Lys
290                 295                 300

Asn Gln Val Ser Leu Thr Cys Leu Val Lys Gly Phe Tyr Pro Ser Asp
305                 310                 315                 320

Ile Ala Val Glu Trp Glu Ser Asn Gly Gln Pro Glu Asn Asn Tyr Lys
                325                 330                 335

Thr Thr Pro Pro Val Leu Asp Ser Asp Gly Ser Phe Phe Leu Tyr Ser
            340                 345                 350

Lys Leu Thr Val Asp Lys Ser Arg Trp Gln Gln Gly Asn Val Phe Ser
        355                 360                 365

Cys Ser Val Met His Glu Ala Leu His Asn His Tyr Thr Gln Lys Ser
370                 375                 380

Leu Ser Leu Ser Pro Gly Lys
385                 390

<210> SEQ ID NO 75
<211> LENGTH: 396
<212> TYPE: PRT
<213> ORGANISM: Artificial sequence
<220> FEATURE:
<223> OTHER INFORMATION: Frz5-Fc chimeric protein

<400> SEQUENCE: 75

Met Gly Gly Thr Ala Ala Arg Leu Gly Ala Val Ile Leu Phe Val Val
1               5                   10                  15

Ile Val Gly Leu His Gly Val Arg Gly Lys Ile Asp Ala Arg Gly Ala
            20                  25                  30

Ser Lys Ala Pro Val Cys Gln Glu Ile Thr Val Pro Met Cys Arg Gly
        35                  40                  45

Ile Gly Tyr Asn Leu Thr His Met Pro Asn Gln Phe Asn His Asp Thr
    50                  55                  60

Gln Asp Glu Ala Gly Leu Glu Val His Gln Phe Trp Pro Leu Val Glu
65                  70                  75                  80

Ile Gln Cys Ser Pro Asp Leu Arg Phe Phe Leu Cys Ser Met Tyr Thr
                85                  90                  95

Pro Ile Cys Leu Pro Asp Tyr His Lys Pro Leu Pro Pro Cys Arg Ser
            100                 105                 110

Val Cys Glu Arg Ala Lys Ala Gly Cys Ser Pro Leu Met Arg Gln Tyr
        115                 120                 125

Gly Phe Ala Trp Pro Glu Arg Met Ser Cys Asp Arg Leu Pro Val Leu
    130                 135                 140

Gly Arg Asp Ala Glu Val Leu Cys Met Asp Tyr Asn Arg Ser Glu Ala
145                 150                 155                 160
```

-continued

```
Gly Arg Ala Gln Val Thr Asp Lys Ala Ala Arg Ser Thr Leu Cys Pro
                165                 170                 175
Pro Cys Pro Ala Pro Glu Leu Leu Gly Gly Pro Ser Val Phe Leu Phe
            180                 185                 190
Pro Pro Lys Pro Lys Asp Thr Leu Met Ile Ser Arg Thr Pro Glu Val
        195                 200                 205
Thr Cys Val Val Val Asp Val Ser His Glu Asp Pro Glu Val Lys Phe
    210                 215                 220
Asn Trp Tyr Val Asp Gly Val Glu Val His Asn Ala Lys Thr Lys Pro
225                 230                 235                 240
Arg Glu Glu Gln Tyr Asn Ser Thr Tyr Arg Val Val Ser Val Leu Thr
                245                 250                 255
Val Leu His Gln Asp Trp Leu Asn Gly Lys Glu Tyr Lys Cys Lys Val
            260                 265                 270
Ser Asn Lys Ala Leu Pro Ala Pro Ile Glu Lys Thr Ile Ser Lys Ala
        275                 280                 285
Lys Gly Gln Pro Arg Glu Pro Gln Val Tyr Thr Leu Pro Pro Ser Arg
    290                 295                 300
Glu Glu Met Thr Lys Asn Gln Val Ser Leu Thr Cys Leu Val Lys Gly
305                 310                 315                 320
Phe Tyr Pro Ser Asp Ile Ala Val Glu Trp Glu Ser Asn Gly Gln Pro
                325                 330                 335
Glu Asn Asn Tyr Lys Thr Thr Pro Pro Val Leu Asp Ser Asp Gly Ser
            340                 345                 350
Phe Phe Leu Tyr Ser Lys Leu Thr Val Asp Lys Ser Arg Trp Gln Gln
        355                 360                 365
Gly Asn Val Phe Ser Cys Ser Val Met His Glu Ala Leu His Asn His
    370                 375                 380
Tyr Thr Gln Lys Ser Leu Ser Leu Ser Pro Gly Lys
385                 390                 395

<210> SEQ ID NO 76
<211> LENGTH: 470
<212> TYPE: PRT
<213> ORGANISM: Artificial sequence
<220> FEATURE:
<223> OTHER INFORMATION: Frz1-Fc chimeric protein

<400> SEQUENCE: 76

Met Gly Gly Thr Ala Ala Arg Leu Gly Ala Val Ile Leu Phe Val Val
1               5                   10                  15
Ile Val Gly Leu His Gly Val Arg Gly Lys Ile Asp Glu Glu Gly Ser
            20                  25                  30
Gly Asp Ala Gly Gly Arg Arg Arg Pro Pro Val Asp Pro Arg Arg Leu
        35                  40                  45
Ala Arg Gln Leu Leu Leu Leu Leu Trp Leu Leu Glu Ala Pro Leu Leu
    50                  55                  60
Leu Gly Val Arg Ala Gln Ala Ala Gly Gln Gly Pro Gly Gln Gly Pro
65                  70                  75                  80
Gly Pro Gly Gln Gln Pro Pro Pro Pro Gln Gln Gln Gln Gln Ser Gly
                85                  90                  95
Gln Gln Tyr Asn Gly Glu Arg Gly Ile Ser Val Pro Asp His Gly Tyr
            100                 105                 110
Cys Gln Pro Ile Ser Ile Pro Leu Cys Thr Asp Ile Ala Tyr Asn Gln
        115                 120                 125
```

```
Thr Ile Met Pro Asn Leu Leu Gly His Thr Asn Gln Glu Asp Ala Gly
            130                 135                 140

Leu Glu Val His Gln Phe Tyr Pro Leu Val Lys Val Gln Cys Ser Ala
145                 150                 155                 160

Glu Leu Lys Phe Phe Leu Cys Ser Met Tyr Ala Pro Val Cys Thr Val
                165                 170                 175

Leu Glu Gln Ala Leu Pro Pro Cys Arg Ser Leu Cys Glu Arg Ala Arg
                180                 185                 190

Gln Gly Cys Glu Ala Leu Met Asn Lys Phe Gly Phe Gln Trp Pro Asp
            195                 200                 205

Thr Leu Lys Cys Glu Lys Phe Pro Val His Gly Ala Gly Glu Leu Cys
210                 215                 220

Val Gly Gln Asn Thr Ser Asp Lys Ala Arg Gly Arg Ala Gln Val Thr
225                 230                 235                 240

Asp Lys Ala Ala Arg Ser Thr Leu Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 77
<211> LENGTH: 403
<212> TYPE: PRT
<213> ORGANISM: Artificial sequence
<220> FEATURE:
<223> OTHER INFORMATION: Frz2-Fc chimeric protein

<400> SEQUENCE: 77

Met Gly Gly Thr Ala Ala Arg Leu Gly Ala Val Ile Leu Phe Val Val
1               5                   10                  15

Ile Val Gly Leu His Gly Val Arg Gly Lys Ile Asp Ala Arg Gly Ala
```

```
                    20                  25                  30
Gln Phe His Gly Glu Lys Gly Ile Ser Ile Pro Asp His Gly Phe Cys
             35                  40                  45
Gln Pro Ile Ser Ile Pro Leu Cys Thr Asp Ile Ala Tyr Asn Gln Thr
         50                  55                  60
Ile Met Pro Asn Leu Leu Gly His Thr Asn Gln Glu Asp Ala Gly Leu
 65                  70                  75                  80
Glu Val His Gln Phe Tyr Pro Leu Val Lys Val Gln Cys Ser Pro Glu
                 85                  90                  95
Leu Arg Phe Phe Leu Cys Ser Met Tyr Ala Pro Val Cys Thr Val Leu
                100                 105                 110
Glu Gln Ala Ile Pro Pro Cys Arg Ser Ile Cys Glu Arg Ala Arg Gln
            115                 120                 125
Gly Cys Glu Ala Leu Met Asn Lys Phe Gly Phe Gln Trp Pro Glu Arg
        130                 135                 140
Leu Arg Cys Glu His Phe Pro Arg His Gly Ala Glu Gln Ile Cys Val
145                 150                 155                 160
Gly Gln Asn His Ser Glu Asp Gly Arg Ala Gln Val Thr Asp Lys Ala
                165                 170                 175
Ala Arg Ser Thr Leu Cys Pro Pro Cys Pro Ala Pro Glu Leu Leu Gly
                180                 185                 190
Gly Pro Ser Val Phe Leu Phe Pro Pro Lys Pro Lys Asp Thr Leu Met
            195                 200                 205
Ile Ser Arg Thr Pro Glu Val Thr Cys Val Val Val Asp Val Ser His
        210                 215                 220
Glu Asp Pro Glu Val Lys Phe Asn Trp Tyr Val Asp Gly Val Glu Val
225                 230                 235                 240
His Asn Ala Lys Thr Lys Pro Arg Glu Glu Gln Tyr Asn Ser Thr Tyr
                245                 250                 255
Arg Val Val Ser Val Leu Thr Val Leu His Gln Asp Trp Leu Asn Gly
                260                 265                 270
Lys Glu Tyr Lys Cys Lys Val Ser Asn Lys Ala Leu Pro Ala Pro Ile
            275                 280                 285
Glu Lys Thr Ile Ser Lys Ala Lys Gly Gln Pro Arg Glu Pro Gln Val
        290                 295                 300
Tyr Thr Leu Pro Pro Ser Arg Glu Glu Met Thr Lys Asn Gln Val Ser
305                 310                 315                 320
Leu Thr Cys Leu Val Lys Gly Phe Tyr Pro Ser Asp Ile Ala Val Glu
                325                 330                 335
Trp Glu Ser Asn Gly Gln Pro Glu Asn Asn Tyr Lys Thr Thr Pro Pro
                340                 345                 350
Val Leu Asp Ser Asp Gly Ser Phe Phe Leu Tyr Ser Lys Leu Thr Val
            355                 360                 365
Asp Lys Ser Arg Trp Gln Gln Gly Asn Val Phe Ser Cys Ser Val Met
        370                 375                 380
His Glu Ala Leu His Asn His Tyr Thr Gln Lys Ser Leu Ser Leu Ser
385                 390                 395                 400
Pro Gly Lys

<210> SEQ ID NO 78
<211> LENGTH: 388
<212> TYPE: PRT
<213> ORGANISM: Artificial sequence
<220> FEATURE:
<223> OTHER INFORMATION: Frz3-Fc chimeric protein
```

<400> SEQUENCE: 78

```
Met Gly Gly Thr Ala Ala Arg Leu Gly Ala Val Ile Leu Phe Val Val
1               5                   10                  15

Ile Val Gly Leu His Gly Val Arg Gly Lys Ile Asp Ala Arg Gly His
            20                  25                  30

Ser Leu Phe Ser Cys Glu Pro Ile Thr Leu Arg Met Cys Gln Asp Leu
        35                  40                  45

Pro Tyr Asn Thr Thr Phe Met Pro Asn Leu Leu Asn His Tyr Asp Gln
50                  55                  60

Gln Thr Ala Ala Leu Ala Met Glu Pro Phe His Pro Met Val Asn Leu
65                  70                  75                  80

Asp Cys Ser Arg Asp Phe Arg Pro Phe Leu Cys Ala Leu Tyr Ala Pro
                85                  90                  95

Ile Cys Met Glu Tyr Gly Arg Val Thr Leu Pro Cys Arg Arg Leu Cys
            100                 105                 110

Gln Arg Ala Tyr Ser Glu Cys Ser Lys Leu Met Glu Met Phe Gly Val
        115                 120                 125

Pro Trp Pro Glu Asp Met Glu Cys Ser Arg Phe Pro Asp Cys Asp Glu
130                 135                 140

Pro Tyr Pro Arg Leu Val Asp Leu Gly Arg Ala Gln Val Thr Asp Lys
145                 150                 155                 160

Ala Ala Arg Ser Thr Leu Cys Pro Pro Cys Pro Ala Pro Glu Leu Leu
                165                 170                 175

Gly Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
        195                 200                 205

His Glu Asp Pro Glu Val Lys Phe Asn Trp Tyr Val Asp Gly Val Glu
    210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Lys Val Ser Asn Lys Ala Leu Pro Ala Pro
            260                 265                 270

Ile Glu Lys Thr Ile Ser Lys Ala Lys Gly Gln Pro Arg Glu Pro Gln
        275                 280                 285

Val Tyr Thr Leu Pro Pro Ser Arg Glu Glu Met Thr Lys Asn Gln Val
290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Val Leu Asp Ser Asp Gly Ser Phe Phe Leu Tyr Ser Lys Leu Thr
            340                 345                 350

Val Asp Lys Ser Arg Trp Gln Gln Gly Asn Val Phe Ser Cys Ser Val
        355                 360                 365

Met His Glu Ala Leu His Asn His Tyr Thr Gln Lys Ser Leu Ser Leu
370                 375                 380

Ser Pro Gly Lys
385
```

<210> SEQ ID NO 79

```
<211> LENGTH: 397
<212> TYPE: PRT
<213> ORGANISM: Artificial sequence
<220> FEATURE:
<223> OTHER INFORMATION: Frz4-Fc chimeric protein

<400> SEQUENCE: 79

Met Gly Gly Thr Ala Ala Arg Leu Gly Ala Val Ile Leu Phe Val Val
1               5                   10                  15

Ile Val Gly Leu His Gly Val Arg Gly Lys Ile Asp Ala Arg Gly Phe
            20                  25                  30

Gly Asp Glu Glu Glu Arg Arg Cys Asp Pro Ile Arg Ile Ser Met Cys
        35                  40                  45

Gln Asn Leu Gly Tyr Asn Val Thr Lys Met Pro Asn Leu Val Gly His
    50                  55                  60

Glu Leu Gln Thr Asp Ala Glu Leu Gln Leu Thr Thr Phe Thr Pro Leu
65                  70                  75                  80

Ile Gln Tyr Gly Cys Ser Ser Gln Leu Gln Phe Phe Leu Cys Ser Val
                85                  90                  95

Tyr Val Pro Met Cys Thr Glu Lys Ile Asn Ile Pro Ile Gly Pro Cys
            100                 105                 110

Gly Gly Met Cys Leu Ser Val Lys Arg Arg Cys Glu Pro Val Leu Lys
        115                 120                 125

Glu Phe Gly Phe Ala Trp Pro Glu Ser Leu Asn Cys Ser Lys Phe Pro
    130                 135                 140

Pro Gln Asn Asp His Asn His Met Cys Met Glu Gly Pro Gly Asp Glu
145                 150                 155                 160

Glu Gly Arg Ala Gln Val Thr Asp Lys Ala Ala Arg Ser Thr Leu Cys
                165                 170                 175

Pro Pro Cys Pro Ala Pro Glu Leu Leu Gly Gly Pro Ser Val Phe Leu
            180                 185                 190

Phe Pro Pro Lys Pro Lys Asp Thr Leu Met Ile Ser Arg Thr Pro Glu
        195                 200                 205

Val Thr Cys Val Val Val Asp Val Ser His Glu Asp Pro Glu Val Lys
    210                 215                 220

Phe Asn Trp Tyr Val Asp Gly Val Glu Val His Asn Ala Lys Thr Lys
225                 230                 235                 240

Pro Arg Glu Glu Gln Tyr Asn Ser Thr Tyr Arg Val Val Ser Val Leu
                245                 250                 255

Thr Val Leu His Gln Asp Trp Leu Asn Gly Lys Glu Tyr Lys Cys Lys
            260                 265                 270

Val Ser Asn Lys Ala Leu Pro Ala Pro Ile Glu Lys Thr Ile Ser Lys
        275                 280                 285

Ala Lys Gly Gln Pro Arg Glu Pro Gln Val Tyr Thr Leu Pro Pro Ser
    290                 295                 300

Arg Glu Glu Met Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
                325                 330                 335

Pro Glu Asn Asn Tyr Lys Thr Thr Pro Pro Val Leu Asp Ser Asp Gly
            340                 345                 350

Ser Phe Phe Leu Tyr Ser Lys Leu Thr Val Asp Lys Ser Arg Trp Gln
        355                 360                 365

Gln Gly Asn Val Phe Ser Cys Ser Val Met His Glu Ala Leu His Asn
    370                 375                 380
```

His Tyr Thr Gln Lys Ser Leu Ser Leu Ser Pro Gly Lys
385                 390                 395

<210> SEQ ID NO 80
<211> LENGTH: 373
<212> TYPE: PRT
<213> ORGANISM: Artificial sequence
<220> FEATURE:
<223> OTHER INFORMATION: Frz6-Fc chimeric protein

<400> SEQUENCE: 80

Met Glu Met Phe Thr Phe Leu Leu Thr Cys Ile Phe Leu Pro Leu Leu
1               5                   10                  15

Arg Gly His Ser Leu Phe Thr Cys Glu Pro Ile Thr Val Pro Arg Cys
            20                  25                  30

Met Lys Met Ala Tyr Asn Met Thr Phe Phe Pro Asn Leu Met Gly His
        35                  40                  45

Tyr Asp Gln Ser Ile Ala Ala Val Glu Met Glu His Phe Leu Pro Leu
    50                  55                  60

Ala Asn Leu Glu Cys Ser Pro Asn Ile Glu Thr Phe Leu Cys Lys Ala
65                  70                  75                  80

Phe Val Pro Thr Cys Ile Glu Gln Ile His Val Val Pro Pro Cys Arg
                85                  90                  95

Lys Leu Cys Glu Lys Val Tyr Ser Asp Cys Lys Lys Leu Ile Asp Thr
            100                 105                 110

Phe Gly Ile Arg Trp Pro Glu Glu Leu Glu Cys Asp Arg Leu Gln Tyr
        115                 120                 125

Cys Asp Glu Thr Val Pro Val Thr Phe Leu Glu Ser Gly Gly Gly Gly
    130                 135                 140

Val Thr Asp Lys Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
        195                 200                 205

Glu Val His Asn Ala Lys Thr Lys Pro Arg Glu Glu Gln Tyr Asn Ser
    210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
            260                 265                 270

Gln Val Tyr Thr Leu Pro Pro Ser Arg Glu Glu Met Thr Lys Asn Gln
        275                 280                 285

Val Ser Leu Thr Cys Leu Val Lys Gly Phe Tyr Pro Ser Asp Ile Ala
    290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Lys Leu
                325                 330                 335

Thr Val Asp Lys Ser Arg Trp Gln Gln Gly Asn Val Phe Ser Cys Ser
            340                 345                 350

Val Met His Glu Ala Leu His Asn His Tyr Thr Gln Lys Ser Leu Ser

```
            355                 360                 365

Leu Ser Pro Gly Lys
        370

<210> SEQ ID NO 81
<211> LENGTH: 404
<212> TYPE: PRT
<213> ORGANISM: Artificial sequence
<220> FEATURE:
<223> OTHER INFORMATION: Frz7-Fc chimeric protein

<400> SEQUENCE: 81

Met Arg Asp Pro Gly Ala Ala Ala Pro Leu Ser Ser Leu Gly Leu Cys
1               5                   10                  15

Ala Leu Val Leu Ala Leu Leu Gly Ala Leu Ser Ala Gly Ala Gly Ala
            20                  25                  30

Gln Pro Tyr His Gly Glu Lys Gly Ile Ser Val Pro Asp His Gly Phe
        35                  40                  45

Cys Gln Pro Ile Ser Ile Pro Leu Cys Thr Asp Ile Ala Tyr Asn Gln
    50                  55                  60

Thr Ile Leu Pro Asn Leu Leu Gly His Thr Asn Gln Glu Asp Ala Gly
65                  70                  75                  80

Leu Glu Val His Gln Phe Tyr Pro Leu Val Lys Val Gln Cys Ser Pro
                85                  90                  95

Glu Leu Arg Phe Phe Leu Cys Ser Met Tyr Ala Pro Val Cys Thr Val
            100                 105                 110

Leu Asp Gln Ala Ile Pro Pro Cys Arg Ser Leu Cys Glu Arg Ala Arg
        115                 120                 125

Gln Gly Cys Glu Ala Leu Met Asn Lys Phe Gly Phe Gln Trp Pro Glu
    130                 135                 140

Arg Leu Arg Cys Glu Asn Phe Pro Val His Gly Ala Gly Glu Ile Cys
145                 150                 155                 160

Val Gly Gln Asn Thr Ser Asp Gly Leu Glu Ser Gly Gly Gly Gly Val
                165                 170                 175

Thr Asp Lys Thr His Thr Cys Pro Pro Cys Pro Ala Pro Glu Leu Leu
            180                 185                 190

Gly Gly Pro Ser Val Phe Leu Phe Pro Pro Lys Pro Lys Asp Thr Leu
        195                 200                 205

Met Ile Ser Arg Thr Pro Glu Val Thr Cys Val Val Val Asp Val Ser
    210                 215                 220

His Glu Asp Pro Glu Val Lys Phe Asn Trp Tyr Val Asp Gly Val Glu
225                 230                 235                 240

Val His Asn Ala Lys Thr Lys Pro Arg Glu Glu Gln Tyr Asn Ser Thr
                245                 250                 255

Tyr Arg Val Val Ser Val Leu Thr Val Leu His Gln Asp Trp Leu Asn
            260                 265                 270

Gly Lys Glu Tyr Lys Cys Lys Val Ser Asn Lys Ala Leu Pro Ala Pro
        275                 280                 285

Ile Glu Lys Thr Ile Ser Lys Ala Lys Gly Gln Pro Arg Glu Pro Gln
    290                 295                 300

Val Tyr Thr Leu Pro Pro Ser Arg Glu Glu Met Thr Lys Asn Gln Val
305                 310                 315                 320

Ser Leu Thr Cys Leu Val Lys Gly Phe Tyr Pro Ser Asp Ile Ala Val
                325                 330                 335

Glu Trp Glu Ser Asn Gly Gln Pro Glu Asn Asn Tyr Lys Thr Thr Pro
            340                 345                 350
```

```
Pro Val Leu Asp Ser Asp Gly Ser Phe Phe Leu Tyr Ser Lys Leu Thr
            355                 360                 365

Val Asp Lys Ser Arg Trp Gln Gln Gly Asn Val Phe Ser Cys Ser Val
    370                 375                 380

Met His Glu Ala Leu His Asn His Tyr Thr Gln Lys Ser Leu Ser Leu
385                 390                 395                 400

Ser Pro Gly Lys

<210> SEQ ID NO 82
<211> LENGTH: 396
<212> TYPE: PRT
<213> ORGANISM: Artificial Sequence
<220> FEATURE:
<223> OTHER INFORMATION: Frz9-Fc chimeric protein

<400> SEQUENCE: 82

Met Ala Val Ala Pro Leu Arg Gly Ala Leu Leu Leu Trp Gln Leu Leu
1               5                   10                  15

Ala Ala Gly Gly Ala Ala Leu Glu Ile Gly Arg Phe Asp Pro Glu Arg
                20                  25                  30

Gly Arg Gly Ala Ala Pro Cys Gln Ala Val Glu Ile Pro Met Cys Arg
            35                  40                  45

Gly Ile Gly Tyr Asn Leu Thr Arg Met Pro Asn Leu Leu Gly His Thr
        50                  55                  60

Ser Gln Gly Glu Ala Ala Ala Glu Leu Ala Glu Phe Ala Pro Leu Val
65                  70                  75                  80

Gln Tyr Gly Cys His Ser His Leu Arg Phe Phe Leu Cys Ser Leu Tyr
                85                  90                  95

Ala Pro Met Cys Thr Asp Gln Val Ser Thr Pro Ile Pro Ala Cys Arg
            100                 105                 110

Pro Met Cys Glu Gln Ala Arg Leu Arg Cys Ala Pro Ile Met Glu Gln
        115                 120                 125

Phe Asn Phe Gly Trp Pro Asp Ser Leu Asp Cys Ala Arg Leu Pro Thr
    130                 135                 140

Arg Asn Asp Pro His Ala Leu Cys Met Glu Ala Pro Glu Asn Ala Thr
145                 150                 155                 160

Leu Glu Ser Gly Gly Gly Gly Val Thr Asp Lys Thr His Thr Cys Pro
                165                 170                 175

Pro Cys Pro Ala Pro Glu Leu Leu Gly Gly Pro Ser Val Phe Leu Phe
            180                 185                 190

Pro Pro Lys Pro Lys Asp Thr Leu Met Ile Ser Arg Thr Pro Glu Val
        195                 200                 205

Thr Cys Val Val Val Asp Val Ser His Glu Asp Pro Glu Val Lys Phe
    210                 215                 220

Asn Trp Tyr Val Asp Gly Val Glu Val His Asn Ala Lys Thr Lys Pro
225                 230                 235                 240

Arg Glu Glu Gln Tyr Asn Ser Thr Tyr Arg Val Val Ser Val Leu Thr
                245                 250                 255

Val Leu His Gln Asp Trp Leu Asn Gly Lys Glu Tyr Lys Cys Lys Val
            260                 265                 270

Ser Asn Lys Ala Leu Pro Ala Pro Ile Glu Lys Thr Ile Ser Lys Ala
        275                 280                 285

Lys Gly Gln Pro Arg Glu Pro Gln Val Tyr Thr Leu Pro Pro Ser Arg
    290                 295                 300

Glu Glu Met Thr Lys Asn Gln Val Ser Leu Thr Cys Leu Val Lys Gly
```

```
305                 310                 315                 320

Phe Tyr Pro Ser Asp Ile Ala Val Glu Trp Glu Ser Asn Gly Gln Pro
                325                 330                 335

Glu Asn Asn Tyr Lys Thr Thr Pro Val Leu Asp Ser Asp Gly Ser
            340                 345                 350

Phe Phe Leu Tyr Ser Lys Leu Thr Val Asp Lys Ser Arg Trp Gln Gln
            355                 360                 365

Gly Asn Val Phe Ser Cys Ser Val Met His Glu Ala Leu His Asn His
        370                 375                 380

Tyr Thr Gln Lys Ser Leu Ser Leu Ser Pro Gly Lys
385                 390                 395

<210> SEQ ID NO 83
<211> LENGTH: 391
<212> TYPE: PRT
<213> ORGANISM: Artificial sequence
<220> FEATURE:
<223> OTHER INFORMATION: Frz10-Fc chimeric protein

<400> SEQUENCE: 83

Met Gln Arg Pro Gly Pro Arg Leu Trp Leu Val Leu Gln Val Met Gly
1               5                   10                  15

Ser Cys Ala Ala Ile Ser Ser Met Asp Met Glu Arg Pro Gly Asp Gly
            20                  25                  30

Lys Cys Gln Pro Ile Glu Ile Pro Met Cys Lys Asp Ile Gly Tyr Asn
        35                  40                  45

Met Thr Arg Met Pro Asn Leu Met Gly His Glu Asn Gln Arg Glu Ala
    50                  55                  60

Ala Ile Gln Leu His Glu Phe Ala Pro Leu Val Glu Tyr Gly Cys His
65                  70                  75                  80

Gly His Leu Arg Phe Phe Leu Cys Ser Leu Tyr Ala Pro Met Cys Thr
                85                  90                  95

Glu Gln Val Ser Thr Pro Ile Pro Ala Cys Arg Val Met Cys Glu Gln
            100                 105                 110

Ala Arg Leu Lys Cys Ser Pro Ile Met Glu Gln Phe Asn Phe Lys Trp
        115                 120                 125

Pro Asp Ser Leu Asp Cys Arg Lys Leu Pro Asn Lys Asn Asp Pro Asn
    130                 135                 140

Tyr Leu Cys Met Glu Ala Pro Asn Asn Gly Ser Leu Glu Ser Gly Gly
145                 150                 155                 160

Gly Gly Val Thr Asp Lys Thr His Thr Cys Pro Pro Cys Pro Ala Pro
                165                 170                 175

Glu Leu Leu Gly Gly Pro Ser Val Phe Leu Phe Pro Pro Lys Pro Lys
            180                 185                 190

Asp Thr Leu Met Ile Ser Arg Thr Pro Glu Val Thr Cys Val Val Val
        195                 200                 205

Asp Val Ser His Glu Asp Pro Glu Val Lys Phe Asn Trp Tyr Val Asp
    210                 215                 220

Gly Val Glu Val His Asn Ala Lys Thr Lys Pro Arg Glu Glu Gln Tyr
225                 230                 235                 240

Asn Ser Thr Tyr Arg Val Val Ser Val Leu Thr Val Leu His Gln Asp
                245                 250                 255

Trp Leu Asn Gly Lys Glu Tyr Lys Cys Lys Val Ser Asn Lys Ala Leu
            260                 265                 270

Pro Ala Pro Ile Glu Lys Thr Ile Ser Lys Ala Lys Gly Gln Pro Arg
        275                 280                 285
```

```
Glu Pro Gln Val Tyr Thr Leu Pro Pro Ser Arg Glu Glu Met Thr Lys
        290                 295                 300

Asn Gln Val Ser Leu Thr Cys Leu Val Lys Gly Phe Tyr Pro Ser Asp
305                 310                 315                 320

Ile Ala Val Glu Trp Glu Ser Asn Gly Gln Pro Glu Asn Asn Tyr Lys
                325                 330                 335

Thr Thr Pro Pro Val Leu Asp Ser Asp Gly Ser Phe Phe Leu Tyr Ser
            340                 345                 350

Lys Leu Thr Val Asp Lys Ser Arg Trp Gln Gln Gly Asn Val Phe Ser
        355                 360                 365

Cys Ser Val Met His Glu Ala Leu His Asn His Tyr Thr Gln Lys Ser
370                 375                 380

Leu Ser Leu Ser Pro Gly Lys
385                 390

<210> SEQ ID NO 84
<211> LENGTH: 410
<212> TYPE: PRT
<213> ORGANISM: Artificial sequence
<220> FEATURE:
<223> OTHER INFORMATION: sFRP1-Fc chimeric protein

<400> SEQUENCE: 84

Met Gly Ile Gly Arg Ser Glu Gly Gly Arg Arg Gly Ala Ala Leu Gly
1               5                   10                  15

Val Leu Leu Ala Leu Gly Ala Ala Leu Leu Ala Val Gly Ser Ala Ser
            20                  25                  30

Glu Tyr Asp Tyr Val Ser Phe Gln Ser Asp Ile Gly Pro Tyr Gln Ser
        35                  40                  45

Gly Arg Phe Tyr Thr Lys Pro Pro Gln Cys Val Asp Ile Pro Ala Asp
    50                  55                  60

Leu Arg Leu Cys His Asn Val Gly Tyr Lys Lys Met Val Leu Pro Asn
65                  70                  75                  80

Leu Leu Glu His Glu Thr Met Ala Glu Val Lys Gln Gln Ala Ser Ser
                85                  90                  95

Trp Val Pro Leu Leu Asn Lys Asn Cys His Ala Gly Thr Gln Val Phe
            100                 105                 110

Leu Cys Ser Leu Phe Ala Pro Val Cys Leu Asp Arg Pro Ile Tyr Pro
        115                 120                 125

Cys Arg Trp Leu Cys Glu Ala Val Arg Asp Ser Cys Glu Pro Val Met
    130                 135                 140

Gln Phe Phe Gly Phe Tyr Trp Pro Glu Met Leu Lys Cys Asp Lys Phe
145                 150                 155                 160

Pro Glu Gly Asp Val Cys Ile Ala Met Thr Pro Pro Asn Ala Trp Arg
                165                 170                 175

Ala Gln Val Thr Asp Lys Ala Ala Arg Ser Thr Leu Cys Pro Pro Cys
            180                 185                 190

Pro Ala Pro Glu Leu Leu Gly Gly Pro Ser Val Phe Leu Phe Pro Pro
        195                 200                 205

Lys Pro Lys Asp Thr Leu Met Ile Ser Arg Thr Pro Glu Val Thr Cys
    210                 215                 220

Val Val Val Asp Val Ser His Glu Asp Pro Glu Val Lys Phe Asn Trp
225                 230                 235                 240

Tyr Val Asp Gly Val Glu Val His Asn Ala Lys Thr Lys Pro Arg Glu
                245                 250                 255
```

Glu Gln Tyr Asn Ser Thr Tyr Arg Val Val Ser Val Leu Thr Val Leu
                260                 265                 270

His Gln Asp Trp Leu Asn Gly Lys Glu Tyr Lys Cys Lys Val Ser Asn
            275                 280                 285

Lys Ala Leu Pro Ala Pro Ile Glu Lys Thr Ile Ser Lys Ala Lys Gly
        290                 295                 300

Gln Pro Arg Glu Pro Gln Val Tyr Thr Leu Pro Pro Ser Arg Glu Glu
305                 310                 315                 320

Met Thr Lys Asn Gln Val Ser Leu Thr Cys Leu Val Lys Gly Phe Tyr
                325                 330                 335

Pro Ser Asp Ile Ala Val Glu Trp Glu Ser Asn Gly Gln Pro Glu Asn
            340                 345                 350

Asn Tyr Lys Thr Thr Pro Pro Val Leu Asp Ser Asp Gly Ser Phe Phe
        355                 360                 365

Leu Tyr Ser Lys Leu Thr Val Asp Lys Ser Arg Trp Gln Gln Gly Asn
    370                 375                 380

Val Phe Ser Cys Ser Val Met His Glu Ala Leu His Asn His Tyr Thr
385                 390                 395                 400

Gln Lys Ser Leu Ser Leu Ser Pro Gly Lys
                405                 410

<210> SEQ ID NO 85
<211> LENGTH: 396
<212> TYPE: PRT
<213> ORGANISM: Artificial sequence
<220> FEATURE:
<223> OTHER INFORMATION: sFRP2-Fc chimeric protein

<400> SEQUENCE: 85

Met Leu Gln Gly Pro Gly Ser Leu Leu Leu Phe Leu Ala Ser His
1               5                   10                  15

Cys Cys Leu Gly Ser Ala Arg Gly Leu Phe Leu Phe Gly Gln Pro Asp
                20                  25                  30

Phe Ser Tyr Lys Arg Ser Asn Cys Lys Pro Ile Pro Ala Asn Leu Gln
            35                  40                  45

Leu Cys His Gly Ile Glu Tyr Gln Asn Met Arg Leu Pro Asn Leu Leu
        50                  55                  60

Gly His Glu Thr Met Lys Glu Val Leu Glu Gln Ala Gly Ala Trp Ile
65                  70                  75                  80

Pro Leu Val Met Lys Gln Cys His Pro Asp Thr Lys Lys Phe Leu Cys
                85                  90                  95

Ser Leu Phe Ala Pro Val Cys Leu Asp Asp Leu Asp Glu Thr Ile Gln
            100                 105                 110

Pro Cys His Ser Leu Cys Val Gln Val Lys Asp Arg Cys Ala Pro Val
        115                 120                 125

Met Ser Ala Phe Gly Phe Pro Trp Pro Asp Met Leu Glu Cys Asp Arg
130                 135                 140

Phe Pro Gln Asp Asn Asp Leu Cys Ile Pro Leu Ala Ser Ser Asp His
145                 150                 155                 160

Trp Arg Ala Gln Val Thr Asp Lys Ala Ala Arg Ser Thr Leu Cys Pro
                165                 170                 175

Pro Cys Pro Ala Pro Glu Leu Leu Gly Gly Pro Ser Val Phe Leu Phe
            180                 185                 190

Pro Pro Lys Pro Lys Asp Thr Leu Met Ile Ser Arg Thr Pro Glu Val
        195                 200                 205

Thr Cys Val Val Val Asp Val Ser His Glu Asp Pro Glu Val Lys Phe

```
                 210                 215                 220
Asn Trp Tyr Val Asp Gly Val Glu Val His Asn Ala Lys Thr Lys Pro
225                 230                 235                 240

Arg Glu Glu Gln Tyr Asn Ser Thr Tyr Arg Val Val Ser Val Leu Thr
                245                 250                 255

Val Leu His Gln Asp Trp Leu Asn Gly Lys Glu Tyr Lys Cys Lys Val
                260                 265                 270

Ser Asn Lys Ala Leu Pro Ala Pro Ile Glu Lys Thr Ile Ser Lys Ala
                275                 280                 285

Lys Gly Gln Pro Arg Glu Pro Gln Val Tyr Thr Leu Pro Pro Ser Arg
290                 295                 300

Glu Glu Met Thr Lys Asn Gln Val Ser Leu Thr Cys Leu Val Lys Gly
305                 310                 315                 320

Phe Tyr Pro Ser Asp Ile Ala Val Glu Trp Glu Ser Asn Gly Gln Pro
                325                 330                 335

Glu Asn Asn Tyr Lys Thr Thr Pro Pro Val Leu Asp Ser Asp Gly Ser
                340                 345                 350

Phe Phe Leu Tyr Ser Lys Leu Thr Val Asp Lys Ser Arg Trp Gln Gln
                355                 360                 365

Gly Asn Val Phe Ser Cys Ser Val Met His Glu Ala Leu His Asn His
                370                 375                 380

Tyr Thr Gln Lys Ser Leu Ser Leu Ser Pro Gly Lys
385                 390                 395

<210> SEQ ID NO 86
<211> LENGTH: 390
<212> TYPE: PRT
<213> ORGANISM: Artificial sequence
<220> FEATURE:
<223> OTHER INFORMATION: sFRP3-Fc chimeric construct

<400> SEQUENCE: 86

Met Gly Gly Thr Ala Ala Arg Leu Gly Ala Val Ile Leu Phe Val Val
1               5                   10                  15

Ile Val Gly Leu His Gly Val Arg Gly Lys Ile Asp Ala Arg Gly Ala
                20                  25                  30

Ala Cys Glu Pro Val Arg Ile Pro Leu Cys Lys Ser Leu Pro Trp Asn
                35                  40                  45

Met Thr Lys Met Pro Asn His Leu His His Ser Thr Gln Ala Asn Ala
50                  55                  60

Ile Leu Ala Ile Glu Gln Phe Glu Gly Leu Leu Gly Thr His Cys Ser
65                  70                  75                  80

Pro Asp Leu Leu Phe Phe Leu Cys Ala Met Tyr Ala Pro Ile Cys Thr
                85                  90                  95

Ile Asp Phe Gln His Glu Pro Ile Lys Pro Cys Lys Ser Val Cys Glu
                100                 105                 110

Arg Ala Arg Gln Gly Cys Glu Pro Ile Leu Ile Lys Tyr Arg His Ser
                115                 120                 125

Trp Pro Glu Asn Leu Ala Cys Glu Glu Leu Pro Val Tyr Asp Arg Gly
                130                 135                 140

Val Cys Ile Ser Pro Glu Ala Ile Val Thr Gly Arg Ala Gln Val Thr
145                 150                 155                 160

Asp Lys Ala Ala Arg Ser Thr Leu Cys Pro Pro Cys Pro Ala Pro Glu
                165                 170                 175

Leu Leu Gly Gly Pro Ser Val Phe Leu Phe Pro Pro Lys Pro Lys Asp
                180                 185                 190
```

```
Thr Leu Met Ile Ser Arg Thr Pro Glu Val Thr Cys Val Val Asp
        195                 200                 205

Val Ser His Glu Asp Pro Glu Val Lys Phe Asn Trp Tyr Val Asp Gly
210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
            245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
            275                 280                 285

Pro Gln Val Tyr Thr Leu Pro Pro Ser Arg Glu Glu Met Thr Lys Asn
            290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Leu Tyr Ser Lys
                340                 345                 350

Leu Thr Val Asp Lys Ser Arg Trp Gln Gln Gly Asn Val Phe Ser Cys
            355                 360                 365

Ser Val Met His Glu Ala Leu His Asn His Tyr Thr Gln Lys Ser Leu
            370                 375                 380

Ser Leu Ser Pro Gly Lys
385                 390

<210> SEQ ID NO 87
<211> LENGTH: 380
<212> TYPE: PRT
<213> ORGANISM: Artificial sequence
<220> FEATURE:
<223> OTHER INFORMATION: sFRP4-Fc chimeric protein

<400> SEQUENCE: 87

Met Phe Leu Ser Ile Leu Val Ala Leu Cys Leu Trp Leu His Leu Ala
1               5                   10                  15

Leu Gly Val Arg Gly Ala Pro Cys Glu Ala Val Arg Ile Pro Met Cys
            20                  25                  30

Arg His Met Pro Trp Asn Ile Thr Arg Met Pro Asn His Leu His His
            35                  40                  45

Ser Thr Gln Glu Asn Ala Ile Leu Ala Ile Glu Gln Tyr Glu Glu Leu
    50                  55                  60

Val Asp Val Asn Cys Ser Ala Val Leu Arg Phe Phe Phe Cys Ala Met
65                  70                  75                  80

Tyr Ala Pro Ile Cys Thr Leu Glu Phe Leu His Asp Pro Ile Lys Pro
                85                  90                  95

Cys Lys Ser Val Cys Gln Arg Ala Arg Asp Asp Cys Glu Pro Leu Met
            100                 105                 110

Lys Met Tyr Asn His Ser Trp Pro Glu Ser Leu Ala Cys Asp Glu Leu
            115                 120                 125

Pro Val Tyr Asp Arg Gly Val Cys Ile Ser Pro Glu Ala Ile Val Thr
        130                 135                 140

Leu Glu Ser Gly Gly Gly Gly Val Thr Asp Lys Thr His Thr Cys Pro
145                 150                 155                 160
```

```
Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
            195                 200                 205

Asn Trp Tyr Val Asp Gly Val Glu Val His Asn Ala Lys Thr Lys Pro
        210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
            275                 280                 285

Glu Glu Met Thr Lys Asn Gln Val Ser Leu Thr Cys Leu Val Lys Gly
        290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
        370                 375                 380

<210> SEQ ID NO 88
<211> LENGTH: 406
<212> TYPE: PRT
<213> ORGANISM: Artificial sequence
<220> FEATURE:
<223> OTHER INFORMATION: sFRP5-Fc chimeric protein

<400> SEQUENCE: 88

Met Arg Ala Ala Ala Ala Gly Gly Val Arg Thr Ala Ala Leu Ala
1               5                   10                  15

Leu Leu Leu Gly Ala Leu His Trp Ala Pro Ala Arg Cys Glu Glu Tyr
                20                  25                  30

Asp Tyr Tyr Gly Trp Gln Ala Glu Pro Leu His Gly Arg Ser Tyr Ser
            35                  40                  45

Lys Pro Pro Gln Cys Leu Asp Ile Pro Ala Asp Leu Pro Leu Cys His
    50                  55                  60

Thr Val Gly Tyr Lys Arg Met Arg Leu Pro Asn Leu Leu Glu His Glu
65                  70                  75                  80

Ser Leu Ala Glu Val Lys Gln Gln Ala Ser Ser Trp Leu Pro Leu Leu
                85                  90                  95

Ala Lys Arg Cys His Ser Asp Thr Gln Val Phe Leu Cys Ser Leu Phe
            100                 105                 110

Ala Pro Val Cys Leu Asp Arg Pro Ile Tyr Pro Cys Arg Ser Leu Cys
            115                 120                 125

Glu Ala Val Arg Ala Gly Cys Ala Pro Leu Met Glu Ala Tyr Gly Phe
        130                 135                 140

Pro Trp Pro Glu Met Leu His Cys His Lys Phe Pro Leu Asp Asn Asp
```

```
                145                 150                 155                 160
Leu Cys Ile Ala Val Gln Phe Gly His Leu Trp Arg Ala Gln Val Thr
                165                 170                 175

Asp Lys Ala Ala Arg Ser Thr Leu Cys Pro Pro Cys Pro Ala Pro Glu
            180                 185                 190

Leu Leu Gly Gly Pro Ser Val Phe Leu Phe Pro Pro Lys Pro Lys Asp
        195                 200                 205

Thr Leu Met Ile Ser Arg Thr Pro Glu Val Thr Cys Val Val Val Asp
    210                 215                 220

Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
                245                 250                 255

Ser Thr Tyr Arg Val Val Ser Val Leu Thr Val Leu His Gln Asp Trp
            260                 265                 270

Leu Asn Gly Lys Glu Tyr Lys Cys Lys Val Ser Asn Lys Ala Leu Pro
        275                 280                 285

Ala Pro Ile Glu Lys Thr Ile Ser Lys Ala Lys Gly Gln Pro Arg Glu
    290                 295                 300

Pro Gln Val Tyr Thr Leu Pro Pro Ser Arg Glu Glu Met Thr Lys Asn
305                 310                 315                 320

Gln Val Ser Leu Thr Cys Leu Val Lys Gly Phe Tyr Pro Ser Asp Ile
                325                 330                 335

Ala Val Glu Trp Glu Ser Asn Gly Gln Pro Glu Asn Asn Tyr Lys Thr
            340                 345                 350

Thr Pro Pro Val Leu Asp Ser Asp Gly Ser Phe Phe Leu Tyr Ser Lys
        355                 360                 365

Leu Thr Val Asp Lys Ser Arg Trp Gln Gln Gly Asn Val Phe Ser Cys
    370                 375                 380

Ser Val Met His Glu Ala Leu His Asn His Tyr Thr Gln Lys Ser Leu
385                 390                 395                 400

Ser Leu Ser Pro Gly Lys
            405

<210> SEQ ID NO 89
<211> LENGTH: 26
<212> TYPE: DNA
<213> ORGANISM: Artificial Sequence
<220> FEATURE:
<223> OTHER INFORMATION: PCR primer

<400> SEQUENCE: 89
ctaagcactt acatgtggag atactg                                        26

<210> SEQ ID NO 90
<211> LENGTH: 24
<212> TYPE: DNA
<213> ORGANISM: Artificial Sequence
<220> FEATURE:
<223> OTHER INFORMATION: PCR primer

<400> SEQUENCE: 90
acaggacaag taaacaatga caca                                          24

<210> SEQ ID NO 91
<211> LENGTH: 22
<212> TYPE: DNA
<213> ORGANISM: Artificial Sequence
<220> FEATURE:
```

<223> OTHER INFORMATION: Probe sequence

<400> SEQUENCE: 91
aacctgaggg cagaaagccc aa                                           22

<210> SEQ ID NO 92
<211> LENGTH: 24
<212> TYPE: DNA
<213> ORGANISM: Artificial Sequence
<220> FEATURE:
<223> OTHER INFORMATION: PCR primer

<400> SEQUENCE: 92
ttcccacact gtcttagaga actt                                         24

<210> SEQ ID NO 93
<211> LENGTH: 27
<212> TYPE: DNA
<213> ORGANISM: Artificial Sequence
<220> FEATURE:
<223> OTHER INFORMATION: PCR primer

<400> SEQUENCE: 93
ttctgagtat ctacattcaa ttgcttt                                      27

<210> SEQ ID NO 94
<211> LENGTH: 31
<212> TYPE: DNA
<213> ORGANISM: Artificial Sequence
<220> FEATURE:
<223> OTHER INFORMATION: Probe sequence

<400> SEQUENCE: 94
aaacatgcaa atacatgtgg tttctggtga c                                 31

<210> SEQ ID NO 95
<211> LENGTH: 21
<212> TYPE: DNA
<213> ORGANISM: Artificial Sequence
<220> FEATURE:
<223> OTHER INFORMATION: PCR primer

<400> SEQUENCE: 95
tgactcgctt agctgaaacc t                                            21

<210> SEQ ID NO 96
<211> LENGTH: 22
<212> TYPE: DNA
<213> ORGANISM: Artificial Sequence
<220> FEATURE:
<223> OTHER INFORMATION: PCR primer

<400> SEQUENCE: 96
tgagcctggt cactttatct ga                                           22

<210> SEQ ID NO 97
<211> LENGTH: 26
<212> TYPE: DNA
<213> ORGANISM: Artificial Sequence
<220> FEATURE:
<223> OTHER INFORMATION: Probe sequence

<400> SEQUENCE: 97
tcagaaggtc ttcggaaatg ttgcct                                       26

<210> SEQ ID NO 98

-continued

```
<211> LENGTH: 18
<212> TYPE: DNA
<213> ORGANISM: Artificial Sequence
<220> FEATURE:
<223> OTHER INFORMATION: PCR primer

<400> SEQUENCE: 98
tgtggttgca gcctgtct                                                 18

<210> SEQ ID NO 99
<211> LENGTH: 21
<212> TYPE: DNA
<213> ORGANISM: Artificial Sequence
<220> FEATURE:
<223> OTHER INFORMATION: PCR primer

<400> SEQUENCE: 99
aaccaactct gcattggatt c                                             21

<210> SEQ ID NO 100
<211> LENGTH: 38
<212> TYPE: DNA
<213> ORGANISM: Artificial Sequence
<220> FEATURE:
<223> OTHER INFORMATION: Probe sequence

<400> SEQUENCE: 100
cctttgaaat tgttttactc tctgagtttt atatgctg                           38

<210> SEQ ID NO 101
<211> LENGTH: 17
<212> TYPE: DNA
<213> ORGANISM: Artificial Sequence
<220> FEATURE:
<223> OTHER INFORMATION: PCR primer

<400> SEQUENCE: 101
ctccgtgtgt cgcctat                                                  17

<210> SEQ ID NO 102
<211> LENGTH: 26
<212> TYPE: DNA
<213> ORGANISM: Artificial Sequence
<220> FEATURE:
<223> OTHER INFORMATION: PCR primer

<400> SEQUENCE: 102
catgacaaaa gtcattgagt acaaga                                        26

<210> SEQ ID NO 103
<211> LENGTH: 24
<212> TYPE: DNA
<213> ORGANISM: Artificial Sequence
<220> FEATURE:
<223> OTHER INFORMATION: Probe sequence

<400> SEQUENCE: 103
ttgagggctc aagctttccc ttgt                                          24

<210> SEQ ID NO 104
<211> LENGTH: 18
<212> TYPE: DNA
<213> ORGANISM: Artificial Sequence
<220> FEATURE:
<223> OTHER INFORMATION: PCR primer

<400> SEQUENCE: 104
```
gaacctcgcg ctgtctct                                          18

<210> SEQ ID NO 105
<211> LENGTH: 19
<212> TYPE: DNA
<213> ORGANISM: Artificial Sequence
<220> FEATURE:
<223> OTHER INFORMATION: PCR primer

<400> SEQUENCE: 105
acttggtcct gcgattctg                                         19

<210> SEQ ID NO 106
<211> LENGTH: 21
<212> TYPE: DNA
<213> ORGANISM: Artificial Sequence
<220> FEATURE:
<223> OTHER INFORMATION: Probe sequence

<400> SEQUENCE: 106
agcctcaccg agacgcaggt c                                      21

<210> SEQ ID NO 107
<211> LENGTH: 21
<212> TYPE: DNA
<213> ORGANISM: Artificial Sequence
<220> FEATURE:
<223> OTHER INFORMATION: PCR primer

<400> SEQUENCE: 107
ggcaacaatt tacctttgct t                                      21

<210> SEQ ID NO 108
<211> LENGTH: 23
<212> TYPE: DNA
<213> ORGANISM: Artificial Sequence
<220> FEATURE:
<223> OTHER INFORMATION: PCR primer

<400> SEQUENCE: 108
gaaccaagtg gaacttcatt aca                                    23

<210> SEQ ID NO 109
<211> LENGTH: 25
<212> TYPE: DNA
<213> ORGANISM: Artificial Sequence
<220> FEATURE:
<223> OTHER INFORMATION: Probe sequence

<400> SEQUENCE: 109
cgccaacctt aggattgtaa agccc                                  25

<210> SEQ ID NO 110
<211> LENGTH: 22
<212> TYPE: DNA
<213> ORGANISM: Artificial sequence
<220> FEATURE:
<223> OTHER INFORMATION: PCR primer

<400> SEQUENCE: 110
cagatacaca ggacatggat ga                                     22

<210> SEQ ID NO 111
<211> LENGTH: 26
<212> TYPE: DNA
<213> ORGANISM: Artificial sequence
<220> FEATURE:

<223> OTHER INFORMATION: PCR primer

<400> SEQUENCE: 111
caaagctttt gtaagagact taggat                                              26

<210> SEQ ID NO 112
<211> LENGTH: 35
<212> TYPE: DNA
<213> ORGANISM: Artificial Sequence
<220> FEATURE:
<223> OTHER INFORMATION: Probe sequence

<400> SEQUENCE: 112
ccgtttcctc tagtttcttc ctgtagtact cctct                                    35

<210> SEQ ID NO 113
<211> LENGTH: 409
<212> TYPE: PRT
<213> ORGANISM: Artificial sequence
<220> FEATURE:
<223> OTHER INFORMATION: Frz8(1-173)-Fc chimeric protein

<400> SEQUENCE: 113

```
Met Glu Trp Gly Tyr Leu Leu Glu Val Thr Ser Leu Leu Ala Ala Leu
1               5                   10                  15

Ala Val Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
    50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Pro Leu Glu Ser
                165                 170                 175

Gly Gly Gly Gly Val Thr Asp Lys Thr His Thr Cys Pro Pro Cys Pro
            180                 185                 190

Ala Pro Glu Leu Leu Gly Gly Pro Ser Val Phe Leu Phe Pro Pro Lys
        195                 200                 205

Pro Lys Asp Thr Leu Met Ile Ser Arg Thr Pro Glu Val Thr Cys Val
    210                 215                 220

Val Val Asp Val Ser His Glu Asp Pro Glu Val Lys Phe Asn Trp Tyr
225                 230                 235                 240

Val Asp Gly Val Glu Val His Asn Ala Lys Thr Lys Pro Arg Glu Glu
                245                 250                 255

Gln Tyr Asn Ser Thr Tyr Arg Val Val Ser Val Leu Thr Val Leu His
            260                 265                 270

Gln Asp Trp Leu Asn Gly Lys Glu Tyr Lys Cys Lys Val Ser Asn Lys
```

```
                     275                 280                 285
Ala Leu Pro Ala Pro Ile Glu Lys Thr Ile Ser Lys Ala Lys Gly Gln
            290                 295                 300
Pro Arg Glu Pro Gln Val Tyr Thr Leu Pro Pro Ser Arg Glu Glu Met
305                 310                 315                 320
Thr Lys Asn Gln Val Ser Leu Thr Cys Leu Val Lys Gly Phe Tyr Pro
                325                 330                 335
Ser Asp Ile Ala Val Glu Trp Glu Ser Asn Gly Gln Pro Glu Asn Asn
            340                 345                 350
Tyr Lys Thr Thr Pro Pro Val Leu Asp Ser Asp Gly Ser Phe Phe Leu
        355                 360                 365
Tyr Ser Lys Leu Thr Val Asp Lys Ser Arg Trp Gln Gln Gly Asn Val
    370                 375                 380
Phe Ser Cys Ser Val Met His Glu Ala Leu His Asn His Tyr Thr Gln
385                 390                 395                 400
Lys Ser Leu Ser Leu Ser Pro Gly Lys
                405

<210> SEQ ID NO 114
<211> LENGTH: 388
<212> TYPE: PRT
<213> ORGANISM: Artificial sequence
<220> FEATURE:
<223> OTHER INFORMATION: Frz3-Fc chimeric protein

<400> SEQUENCE: 114

Met Gly Gly Thr Ala Ala Arg Leu Gly Ala Val Ile Leu Phe Val Val
1               5                   10                  15
Ile Val Gly Leu His Gly Val Arg Gly Lys Ile Asp Ala Arg Gly His
            20                  25                  30
Ser Leu Phe Ser Cys Glu Pro Ile Thr Leu Arg Met Cys Gln Asp Leu
        35                  40                  45
Pro Tyr Asn Thr Thr Phe Met Pro Asn Leu Leu Asn His Tyr Asp Gln
    50                  55                  60
Gln Thr Ala Ala Leu Ala Met Glu Pro Phe His Pro Met Val Asn Leu
65                  70                  75                  80
Asp Cys Ser Arg Asp Phe Arg Pro Phe Leu Cys Ala Leu Tyr Ala Pro
                85                  90                  95
Ile Cys Met Glu Tyr Gly Arg Val Thr Leu Pro Cys Arg Arg Leu Cys
            100                 105                 110
Gln Arg Ala Tyr Ser Glu Cys Ser Lys Leu Met Glu Met Phe Gly Val
        115                 120                 125
Pro Trp Pro Glu Asp Met Glu Cys Ser Arg Phe Pro Asp Cys Asp Glu
    130                 135                 140
Pro Tyr Pro Arg Leu Val Asp Leu Leu Glu Ser Gly Gly Gly Gly Val
145                 150                 155                 160
Thr Asp Lys Thr His Thr Cys Pro Pro Cys Pro Ala Pro Glu Leu Leu
                165                 170                 175
Gly Gly Pro Ser Val Phe Leu Phe Pro Pro Lys Pro Lys Asp Thr Leu
            180                 185                 190
Met Ile Ser Arg Thr Pro Glu Val Thr Cys Val Val Val Asp Val Ser
        195                 200                 205
His Glu Asp Pro Glu Val Lys Phe Asn Trp Tyr Val Asp Gly Val Glu
    210                 215                 220
Val His Asn Ala Lys Thr Lys Pro Arg Glu Glu Gln Tyr Asn Ser Thr
225                 230                 235                 240
```

Tyr Arg Val Val Ser Val Leu Thr Val Leu His Gln Asp Trp Leu Asn
            245                 250                 255

Gly Lys Glu Tyr Lys Cys Lys Val Ser Asn Lys Ala Leu Pro Ala Pro
        260                 265                 270

Ile Glu Lys Thr Ile Ser Lys Ala Lys Gly Gln Pro Arg Glu Pro Gln
    275                 280                 285

Val Tyr Thr Leu Pro Pro Ser Arg Glu Glu Met Thr Lys Asn Gln Val
290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Val Leu Asp Ser Asp Gly Ser Phe Phe Leu Tyr Ser Lys Leu Thr
            340                 345                 350

Val Asp Lys Ser Arg Trp Gln Gln Gly Asn Val Phe Ser Cys Ser Val
        355                 360                 365

Met His Glu Ala Leu His Asn His Tyr Thr Gln Lys Ser Leu Ser Leu
370                 375                 380

Ser Pro Gly Lys
385

<210> SEQ ID NO 115
<211> LENGTH: 1410
<212> TYPE: DNA
<213> ORGANISM: Artificial sequence
<220> FEATURE:
<223> OTHER INFORMATION: Frz1-Fc construct

<400> SEQUENCE: 115

| | | |
|---|---|---|
| atgggggga ctgccgccag gttgggggcc gtgattttgt ttgtcgtcat agtgggcctc | 60 |
| catgggtcc gcggcaaaat cgatgaggag ggcagcgggg acgccggtgg ccgccgccgc | 120 |
| ccgccagttg accccggcg attggcgcgc agctgctgc tgctgctttg gctgctggag | 180 |
| gctccgctgc tgctgggggt ccgggcccag gcggcgggcc aggggccagg ccaggggccc | 240 |
| gggccggggc agcaaccgcc gccgccgcct cagcagcaac agagcgggca gcagtacaac | 300 |
| ggcgagcggg gcatctccgt cccggaccac ggctattgcc agcccatctc catcccgctg | 360 |
| tgcacggaca tcgcgtacaa ccagaccatc atgcccaacc tgctgggcca cacgaaccag | 420 |
| gaggacgcgg gcctggaggt gcaccagttc taccctctag tgaaagtgca gtgttccgct | 480 |
| gagctcaagt tcttcctgtg ctccatgtac gcgcccgtgt gcaccgtgct agagcaggcg | 540 |
| ctgccgccct gccgctccct gtgcgagcgc gcgcgccagg gctgcgaggc gctcatgaac | 600 |
| aagttcggct tccagtggcc agacacgctc aagtgtgaga gttcccggt gcacggcgcc | 660 |
| ggcgagctgt gcgtgggcca gaacacgtcc gacaaggctc gagggcgcgc ccaggtcacc | 720 |
| gacaaagctg cgcgctctac tctgtgccca ccgtgcccag cacctgaact cctgggggga | 780 |
| ccgtcagtct tcctcttccc cccaaaaccc aaggacaccc tcatgatctc ccggaccct | 840 |
| gaggtcacat gcgtggtggt ggacgtgagc cacgaagacc ctgaggtcaa gttcaactgg | 900 |
| tacgtggacg gcgtggaggt gcataatgcc aagacaaagc cgcgggagga gcagtacaac | 960 |
| agcacgtacc gtgtggtcag cgtcctcacc gtcctgcacc aggactggct gaatggcaag | 1020 |
| gagtacaagt gcaaggtctc caacaaagcc ctcccagccc ccatcgagaa aaccatctcc | 1080 |
| aaagccaaag ggcagccccg agaaccacag gtgtacaccc tgcccccatc ccgggaagag | 1140 |
| atgaccaaga accaggtcag cctgacctgc ctggtcaaag gcttctatcc cagcgacatc | 1200 |

```
gccgtggagt gggagagcaa tgggcagccg gagaacaact acaagaccac gcctcccgtg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
cagaagagcc tctccctgtc tccgggtaaa                                    1410
```

<210> SEQ ID NO 116
<211> LENGTH: 1209
<212> TYPE: DNA
<213> ORGANISM: Artificial sequence
<220> FEATURE:
<223> OTHER INFORMATION: Frz2-Fc construct

<400> SEQUENCE: 116

```
atggggggga ctgccgccag gttgggggcc gtgattttgt tgtcgtcat agtgggcctc     60 catggggtcc gcggcaaaat cgatgctcga ggggcccagt ccacggggga aagggcatc    120 tccatcccgg accacggctt ctgccagccc atctccatcc cgctgtgcac ggacatcgcc   180
tacaaccaga ccatcatgcc caaccttctg gccacacga accaggagga cgcaggccta    240
gaggtgcacc agttctatcc gctggtgaag gtgcagtgct cgcccgaact gcgcttcttc   300
ctgtgctcca tgtacgcacc cgtgtgcacc gtgctggaac aggccatccc gccgtgccgc   360
tctatctgtg agcgcgcgcg ccaggggctgc gaagccctca tgaacaagtt cggttttcag   420
tggcccgagc gcctgcgctg cgagcacttc ccgcgccacg gcgccgagca gatctgcgtc    480
ggccagaacc actccgagga cgggcgcgcc caggtcaccg acaaagctgc gcgctctact   540
ctgtgcccac cgtgcccagc acctgaactc ctggggggac cgtcagtctt cctcttcccc    600
ccaaaaccca aggacaccct catgatctcc cggacccctg aggtcacatg cgtggtggtg    660
gacgtgagcc acgaagaccc tgaggtcaag ttcaactggt acgtggacgg cgtggaggtg    720
cataatgcca agacaaagcc gcgggaggag cagtacaaca gcacgtaccg tgtggtcagc    780
gtcctcaccg tcctgcacca ggactggctg aatggcaagg agtacaagtg caaggtctcc    840
aacaaagccc tcccagcccc catcgagaaa accatctcca aagccaaagg gcagccccga    900
gaaccacagg tgtacaccct gcccccatcc cgggaagaga tgaccaagaa ccaggtcagc    960
ctgacctgcc tggtcaaagg cttctatccc agcgacatcg ccgtggagtg ggagagcaat   1020
gggcagccgg agaacaacta caagaccacg cctcccgtgc tggactccga cggctccttc   1080
ttcctctaca gcaagctcac cgtggacaag agcaggtggc agcagggaa cgtcttctca   1140 tgctccgtga tgcatgaggc tctgcacaac cactacacgc agaagagcct ctccctgtct   1200
ccgggtaaa                                                           1209
```

<210> SEQ ID NO 117
<211> LENGTH: 1164
<212> TYPE: DNA
<213> ORGANISM: Artificial sequence
<220> FEATURE:
<223> OTHER INFORMATION: Frz3-Fc construct

<400> SEQUENCE: 117

```
atggggggga ctgccgccag gttgggggcc gtgattttgt tgtcgtcat agtgggcctc     60 catggggtcc gcggcaaaat cgatgctcga ggccactccc tgttcagctg tgagccaatc   120
acccttcgaa tgtgtcagga tctgccttac aataccacct tcatgcctaa tctgctcaat   180
cactacgacc agcaaactgc tgccttggca atggagccct ccacccctat ggtcaacctg   240
gactgtagca gggacttccg tccattttg tgtgccttgt atgcacctat ctgtatggag   300
```

```
tacggccgcg tgacattgcc ttgtaggagg ctgtgtcagc gagcttacag tgagtgcagc    360
aaacttatgg aaatgtttgg cgtcccctgg ccagaagata tggagtgcag tcggttccca    420
gactgtgacg agccataccc tagactggtt gatctcctcg agtcaggagg aggaggagtc    480
accgacaaaa ctcacacatg cccaccgtgc ccagcacctg aactcctggg gggaccgtca    540
gtcttcctct ccccccaaa acccaaggac accctcatga tctcccggac ccctgaggtc    600
acatgcgtgg tggtggacgt gagccacgaa gaccctgagg tcaagttcaa ctggtacgtg    660
gacggcgtgg aggtgcataa tgccaagaca aagccgcggg aggagcagta caacagcacg    720
taccgtgtgg tcagcgtcct caccgtcctg caccaggact ggctgaatgg caaggagtac    780
aagtgcaagg tctccaacaa agccctccca gcccccatcg agaaaaccat ctccaaagcc    840
aaagggcagc cccgagaacc acaggtgtac accctgcccc catcccggga agagatgacc    900
aagaaccagg tcagcctgac ctgcctggtc aaaggcttct atcccagcga catcgccgtg    960
gagtgggaga gcaatgggca gccggagaac aactacaaga ccacgcctcc cgtgctggac   1020
tccgacggct ccttcttcct ctacagcaag ctcaccgtgg acaagagcag gtggcagcag   1080
gggaacgtct tctcatgctc cgtgatgcat gaggctctgc acaaccacta cacgcagaag   1140
agcctctccc tgtctccggg taaa                                          1164

<210> SEQ ID NO 118
<211> LENGTH: 1191
<212> TYPE: DNA
<213> ORGANISM: Artificial sequence
<220> FEATURE:
<223> OTHER INFORMATION: Frz4-Fc construct

<400> SEQUENCE: 118
atggggggga ctgccgccag gttgggggcc gtgattttgt ttgtcgtcat agtgggcctc     60
catggggtcc gcggcaaaat cgatgctcga gggttcgggg acgaggaaga gcggcgctgc    120
gaccccatcc gcatctccat gtgccagaac ctcggctaca cgtgaccaa gatgcccaac    180 ctggttgggc acgagctgca gacggacgcc gagctgcagc tgacaacttt cacaccgctc    240
atccagtacg gctgctccag ccagctgcag ttcttccttt gttctgttta tgtgccaatg    300
tgcacagaga agatcaacat ccccattggc ccatgcggcg gcatgtgtct ttcagtcaag    360
agacgctgtg aacccgtcct gaaggaattt ggatttgcct ggccagagag tctgaactgc    420
agcaaattcc caccacagaa cgaccacaac cacatgtgca tggaagggcc aggtgatgaa    480
gaggggcgcg cccaggtcac cgacaaagct gcgcgctcta ctctgtgccc accgtgccca    540
gcacctgaac tcctgggggg accgtcagtc ttcctcttcc ccccaaaacc caaggacacc    600
ctcatgatct cccggacccc tgaggtcaca tgcgtggtgg tggacgtgag ccacgaagac    660
cctgaggtca agttcaactg gtacgtggac ggcgtggagg tgcataatgc caagacaaag    720
ccgcgggagg agcagtacaa cagcacgtac cgtgtggtca gcgtcctcac cgtcctgcac    780
caggactggc tgaatggcaa ggagtacaag tgcaaggtct ccaacaaagc cctcccagcc    840
cccatcgaga aaaccatctc caaagccaaa gggcagcccc gagaaccaca ggtgtacacc    900
ctgcccccat cccgggaaga gatgaccaag aaccaggtca gcctgacctg cctggtcaaa    960
ggcttctatc ccagcgacat cgccgtggag tgggagagca atgggcagcc ggagaacaac   1020
tacaagacca cgcctcccgt gctggactcc gacggctcct tcttcctcta cagcaagctc   1080
accgtggaca agagcaggtg gcagcagggg aacgtcttct catgctccgt gatgcatgag   1140
gctctgcaca accactacac gcagaagagc ctctccctgt ctccgggtaa a            1191
```

<210> SEQ ID NO 119
<211> LENGTH: 1188
<212> TYPE: DNA
<213> ORGANISM: Artificial sequence
<220> FEATURE:
<223> OTHER INFORMATION: Frz5-Fc construct

<400> SEQUENCE: 119

| | | | | | |
|---|---|---|---|---|---:|
| atggggggga | ctgccgccag | gttggggggcc | gtgattttgt | ttgtcgtcat | agtgggcctc | 60 |
| catggggtcc | gcggcaaaat | cgatgctcga | ggggcgtcca | aggcccccggt | gtgccaggaa | 120 |
| atcacggtgc | ccatgtgccg | cggcatcggc | tacaacctga | cgcacatgcc | caaccagttc | 180 |
| aaccacgaca | cgcaggacga | ggcgggcctg | gaggtgcacc | agttctggcc | gctggtggag | 240 |
| atccaatgct | cgccggacct | cgcgcttcttc | ctatgctcta | tgtacacgcc | catctgtctg | 300 |
| cccgactacc | acaagccgct | gccgccctgc | cgctcggtgt | gcgagcgcgc | caaggccggc | 360 |
| tgctcgccgc | tgatgcgcca | gtacggcttc | gcctggccccg | agcgcatgag | ctgcgaccgc | 420 |
| ctcccggtgc | tgggccgcga | cgccgaggtc | ctctgcatgg | attacaaccg | cagcgaggcc | 480 |
| gggcgcgccc | aggtcaccga | caaagctgcg | cgctctactc | tgtgcccacc | gtgcccagca | 540 |
| cctgaactcc | tggggggacc | gtcagtcttc | ctcttccccc | caaaacccaa | ggacaccctc | 600 |
| atgatctccc | ggacccctga | ggtcacatgc | gtggtggtgg | acgtgagcca | cgaagaccct | 660 |
| gaggtcaagt | tcaactggta | cgtggacggc | gtggaggtgc | ataatgccaa | gacaaagccg | 720 |
| cgggaggagc | agtacaacag | cacgtaccgt | gtggtcagcg | tcctcaccgt | cctgcaccag | 780 |
| gactggctga | atggcaagga | gtacaagtgc | aaggtctcca | caaagccct | cccagccccc | 840 |
| atcgagaaaa | ccatctccaa | agccaaaggg | cagccccgag | aaccacaggt | gtacaccctg | 900 |
| cccccatccc | gggaagagat | gaccaagaac | caggtcagcc | tgacctgcct | ggtcaaaggc | 960 |
| ttctatccca | gcgacatcgc | cgtggagtgg | gagagcaatg | ggcagccgga | gaacaactac | 1020 |
| aagaccacgc | ctcccgtgct | ggactccgac | ggctccttct | tcctctacag | caagctcacc | 1080 |
| gtggacaaga | gcaggtggca | gcaggggaac | gtcttctcat | gctccgtgat | gcatgaggct | 1140 |
| ctgcacaacc | actacacgca | gaagagcctc | tccctgtctc | cgggtaaa | | 1188 |

<210> SEQ ID NO 120
<211> LENGTH: 1119
<212> TYPE: DNA
<213> ORGANISM: Artificial sequence
<220> FEATURE:
<223> OTHER INFORMATION: Frz6-Fc construct

<400> SEQUENCE: 120

| | | | | | |
|---|---|---|---|---|---:|
| atggaaatgt | ttacattttt | gttgacgtgt | atttttctac | ccctcctaag | agggcacagt | 60 |
| ctcttcacct | gtgaaccaat | tactgttccc | agatgtatga | aaatggccta | caacatgacg | 120 |
| tttttcccta | atctgatggg | tcattatgac | cagagtattg | ccgcggtgga | aatggagcat | 180 |
| tttcttcctc | tcgcaaatct | ggaatgttca | ccaaacattg | aaactttcct | ctgcaaagca | 240 |
| tttgtaccaa | cctgcatagg | acaaattcat | gtggttccac | cttgtcgtaa | actttgtgag | 300 |
| aaagtatatt | ctgattgcaa | aaaattaatt | gacacttttg | ggatccgatg | gcctgaggag | 360 |
| cttaatgtgg | acagattaca | atactgtgat | gagactgttc | ctgtaacttt | tctcgagtca | 420 |
| ggaggaggag | gagtcaccga | caaaactcac | acatgcccac | cgtgcccagc | acctgaactc | 480 |
| ctgggggggac | cgtcagtctt | cctcttcccc | ccaaaaccca | aggacaccct | catgatctcc | 540 |
| cggacccctg | aggtcacatg | cgtggtggtg | gacgtgagcc | acgaagaccc | tgaggtcaag | 600 |

-continued

```
ttcaactggt acgtggacgg cgtggaggtg cataatgcca agacaaagcc gcgggaggag    660
cagtacaaca gcacgtaccg tgtggtcagc gtcctcaccg tcctgcacca ggactggctg    720
aatggcaagg agtacaagtg caaggtctcc aacaaagccc tcccagcccc catcgagaaa    780
accatctcca agccaaagg gcagccccga gaaccacagg tgtacaccct gcccccatcc    840
cgggaagaga tgaccaagaa ccaggtcagc ctgacctgcc tggtcaaagg cttctatccc    900
agcgacatcg ccgtggagtg ggagagcaat gggcagccgg agaacaacta caagaccacg    960
cctcccgtgc tggactccga cggctccttc ttcctctaca gcaagctcac cgtggacaag   1020
agcaggtggc agcaggggaa cgtcttctca tgctccgtga tgcatgaggc tctgcacaac   1080
cactacacgc agaagagcct ctccctgtct ccgggtaaa                          1119
```

<210> SEQ ID NO 121
<211> LENGTH: 1212
<212> TYPE: DNA
<213> ORGANISM: Artificial sequence
<220> FEATURE:
<223> OTHER INFORMATION: Frz7-Fc construct

<400> SEQUENCE: 121

```
atgcgggacc ccggcgcggc cgctccgctt cgtccctgg gcctctgtgc cctggtgctg     60
gcgctgctgg gcgcactgtc cgcgggcgcc ggggcgcagc cgtaccacgg agagaagggc   120
atctccgtgc cggaccacgg cttctgccag cccatctcca tcccgctgtg cacggacatc   180
gcctacaacc agaccatcct gcccaacctg ctgggccaca cgaaccaaga ggacgcgggc   240
ctcgaggtgc accagttcta cccgctggtg aaggtgcagt gttctcccga actccgcttt   300
ttcttatgct ccatgtatgc gcccgtgtgc accgtgctcg atcaggccat cccgccgtgt   360
cgttctctgt gcgagcgcgc ccgccagggc tgcgaggcgc tcatgaacaa gttcggcttc   420
cagtggcccg agcggctgcg ctgcgagaac ttcccggtgc acggtgcggg cgagatctgc   480
gtgggccaga acacgtcgga cggcctcgag tcaggaggag gaggagtcac cgacaaaact   540
cacacatgcc caccgtgccc agcacctgaa ctcctggggg gaccgtcagt cttcctcttc   600
cccccaaaac ccaaggacac cctcatgatc tcccggaccc ctgaggtcac atgcgtggtg   660
gtggacgtga gccacgaaga ccctgaggtc aagttcaact ggtacgtgga cggcgtggag   720
gtgcataatg ccaagacaaa gccgcgggag gagcagtaca acagcacgta ccgtgtggtc   780
agcgtcctca ccgtcctgca ccaggactgg ctgaatggca aggagtacaa gtgcaaggtc   840
tccaacaaag ccctcccagc ccccatcgag aaaaccatct ccaaagccaa agggcagccc   900
cgagaaccac aggtgtacac cctgccccca tcccgggaag atgaccaa gaaccaggtc    960 agcctgacct gcctggtcaa aggcttctat cccagcgaca tcgccgtgga gtgggagagc  1020
aatgggcagc cggagaacaa ctacaagacc acgcctcccg tgctggactc cgacggctcc  1080
ttcttcctct acagcaagct caccgtggac aagagcaggt ggcagcaggg gaacgtcttc  1140
tcatgctccg tgatgcatga ggctctgcac aaccactaca cgcagaagag cctctccctg  1200
tctccgggta aa                                                      1212
```

<210> SEQ ID NO 122
<211> LENGTH: 1176
<212> TYPE: DNA
<213> ORGANISM: Artificial sequence
<220> FEATURE:
<223> OTHER INFORMATION: Frz8-Fc chimeric construct

<400> SEQUENCE: 122

```
atggagtggg gttacctgtt ggaagtgacc tcgctcctag ccgccttggc ggtgctacag    60
cgctctagcg gcgctgccgc ggcttcggcc aaggagctgg cgtgccaaga gatcacggtg   120
ccgttgtgca aaggcatcgg ttacaactac acttacatgc ccaaccagtt caaccacgac   180
acgcaagatg aggcgggcct agaggtgcac cagttttggc cgctggtgga gatacagtgc   240
tccccggacc tcaagttctt tctgtgtagc atgtacacgc ccatctgcct ggaggactac   300
aagaagcctc tgccgccttg tcgctctgtg tgtgaacgcg ccaaggccgg ctgcgcgccg   360
ctcatgcgcc agtacggctt tgcttggcct gaccgcatgc gctgcgatcg gttgccggag   420
cagggcaacc cggacactct gtgcatggac tacaaccgca ccgacctcga gtcaggagga   480
ggaggagtca ccgacaaaac tcacacatgc ccaccgtgcc cagcacctga actcctgggg   540
ggaccgtcag tcttcctctt ccccccaaaa cccaaggaca cctcatgat  ctcccggacc   600 cctgaggtca catgcgtggt ggtggacgtg agccacgaag accctgaggt caagttcaac   660
tggtacgtgg acggcgtgga ggtgcataat gccaagacaa agccgcggga ggagcagtac   720
aacagcacgt accgtgtggt cagcgtcctc accgtcctgc accaggactg gctgaatggc   780
aaggagtaca agtgcaaggt ctccaacaaa gccctcccag cccccatcga gaaaaccatc   840
tccaaagcca aagggcagcc ccgagaacca caggtgtaca ccctgccccc atcccgggaa   900
gagatgacca agaaccaggt cagcctgacc tgcctggtca aaggcttcta tcccagcgac   960
atcgccgtgg agtgggagag caatgggcag ccggagaaca actacaagac cacgcctccc  1020
gtgctggact ccgacggctc cttcttcctc tacagcaagc tcaccgtgga caagagcagg  1080
tggcagcagg ggaacgtctt ctcatgctcc gtgatgcatg aggctctgca caaccactac  1140
acgcagaaga gcctctccct gtctccgggt aaatga                            1176

<210> SEQ ID NO 123
<211> LENGTH: 1188
<212> TYPE: DNA
<213> ORGANISM: Artificial sequence
<220> FEATURE:
<223> OTHER INFORMATION: Frz9-Fc construct

<400> SEQUENCE: 123
atggccgtgg cgcctctgcg gggggcgctg ctgctgtggc agctgctggc ggcgggcggc    60
gcggcactgg agatcggccg cttcgacccg gagcgcgggc gcggggctgc gccgtgccag   120
gcggtggaga tccccatgtg ccgcggcatc ggctacaacc tgacccgcat gcccaacctg   180
ctgggccaca cgtcgcaggg cgaggcggct gccgagctag cggagttcgc gccgctggtg   240
cagtacggct gccacagcca cctgcgcttc ttcctgtgct cgctctacgc gcccatgtgc   300
accgaccagg tctcgacgcc cattcccgcc tgccggccca tgtgcgagca ggcgcgcctg   360
cgctgcgcgc ccatcatgga gcagttcaac ttcggctggc cggactcgct cgactgcgcc   420
cggctgccca cgcgcaacga cccgcacgcg ctgtgcatgg aggcgcccga aacgccacg   480 ctcgagtcag gaggaggagg agtcaccgac aaaactcaca catgcccacc gtgcccagca   540
cctgaactcc tggggggacc gtcagtcttc ctcttccccc caaaacccaa ggacaccctc   600
atgatctccc ggaccctga  ggtcacatgc gtggtggtgg acgtgagcca cgaagaccct   660
gaggtcaagt tcaactggta cgtggacggc gtggaggtgc ataatgccaa gacaaagccg   720
cgggaggagc agtacaacag cacgtaccgt gtggtcagcg tcctcaccgt cctgcaccag   780
gactggctga atggcaagga gtacaagtgc aaggtctcca acaaagccct cccagccccc   840
atcgagaaaa ccatctccaa agccaaaggg cagccccgag aaccacaggt gtacaccctg   900
```

| | |
|---|---|
| ccccatccc gggaagagat gaccaagaac caggtcagcc tgacctgcct ggtcaaaggc | 960 |
| ttctatccca gcgacatcgc cgtggagtgg gagagcaatg ggcagccgga gaacaactac | 1020 |
| aagaccacgc ctcccgtgct ggactccgac ggctccttct ccctctacag caagctcacc | 1080 |
| gtggacaaga gcaggtggca gcaggggaac gtcttctcat gctccgtgat gcatgaggct | 1140 |
| ctgcacaacc actacacgca gaagagcctc tccctgtctc cgggtaaa | 1188 |

<210> SEQ ID NO 124
<211> LENGTH: 1173
<212> TYPE: DNA
<213> ORGANISM: Artificial sequence
<220> FEATURE:
<223> OTHER INFORMATION: Frz10-Fc construct

<400> SEQUENCE: 124

| | |
|---|---|
| atgcagcgcc cgggcccccg cctgtggctg gtcctgcagg tgatgggctc gtcgccgcc | 60 |
| atcagctcca tggacatgga gcgcccgggc gacggcaaat gccagcccat cgagatcccg | 120 |
| atgtgcaagg acatcggcta caacatgact cgtatgccca acctgatggg ccacgagaac | 180 |
| cagcgcgagg cagccatcca gttgcacgag ttcgcgccgc tggtggagta cggctgccac | 240 |
| ggccacctcc gcttcttcct gtgctcgctg tacgcgccga tgtgcaccga gcaggtctct | 300 |
| accccatcc ccgcctgccg ggtcatgtgc gagcaggccc ggctcaagtg ctccccgatt | 360 |
| atggagcagt tcaacttcaa gtggcccgac tccctggact gccggaaact ccccaacaag | 420 |
| aacgacccca ctacctgtg catggaggcg cccaacaacg ctcgctcga gtcaggagga | 480 |
| ggaggagtca ccgacaaaac tcacacatgc ccaccgtgcc cagcacctga actcctgggg | 540 |
| ggaccgtcag tcttcctctt cccccaaaa cccaaggaca cctcatgat ctcccggacc | 600 |
| cctgaggtca catgcgtggt ggtggacgtg agccacgaag accctgaggt caagttcaac | 660 |
| tggtacgtgg acggcgtgga ggtgcataat gccaagacaa agccgcggga ggagcagtac | 720 |
| aacagcacgt accgtgtggt cagcgtcctc accgtcctgc accaggactg gctgaatggc | 780 |
| aaggagtaca agtgcaaggt ctccaacaaa gccctcccag cccccatcga gaaaaccatc | 840 |
| tccaaagcca agggcagcc cgagaaccaa caggtgtaca ccctgccccc atcccgggaa | 900 |
| gagatgacca gaaccaggt cagcctgacc tgcctggtca aaggcttcta tcccagcgac | 960 |
| atcgccgtgg agtgggagag caatgggcag ccggagaaca actacaagac cacgcctccc | 1020 |
| gtgctggact ccgacggctc cttcttcctc tacagcaagc tcaccgtgga caagagcagg | 1080 |
| tggcagcagg ggaacgtctt ctcatgctcc gtgatgcatg aggctctgca caaccactac | 1140 |
| acgcagaaga gcctctccct gtctccgggt aaa | 1173 |

<210> SEQ ID NO 125
<211> LENGTH: 1230
<212> TYPE: DNA
<213> ORGANISM: Artificial sequence
<220> FEATURE:
<223> OTHER INFORMATION: sFRP1-Fc construct

<400> SEQUENCE: 125

| | |
|---|---|
| atgggcatcg gcgcagcga ggggggccgc cgcgggcag ccctgggcgt gctgctggcg | 60 |
| ctgggcgcgg cgcttctggc cgtgggctcg gccagcgagt acgactacgt gagcttccag | 120 |
| tcggacatcg gcccgtacca gagcgggcgc ttctacacca gccacctca gtgcgtggac | 180 |
| atccccgcgg acctgcggct gtgccacaac gtgggctaca gaagatggt gctgcccaac | 240 |
| ctgctggagc acgagaccat ggcggaggtg aagcagcagg ccagcagctg ggtgccctg | 300 |

```
ctcaacaaga actgccacgc cggcacccag gtcttcctct gctcgctctt cgcgcccgtc    360
tgcctggacc ggcccatcta cccgtgtcgc tggctctgcg aggccgtgcg cgactcgtgc    420
gagccggtca tgcagttctt cggcttctac tggcccgaga tgcttaagtg tgacaagttc    480
cccgaggggg acgtctgcat cgccatgacg ccgcccaatg cctggcgcgc ccaggtcacc    540
gacaaagctg cgcgctctac tctgtgccca ccgtgcccag cacctgaact cctgggggga    600
ccgtcagtct tcctcttccc cccaaaaccc aaggacaccc tcatgatctc ccggacccct    660
gaggtcacat gcgtggtggt ggacgtgagc cacgaagacc ctgaggtcaa gttcaactgg    720
tacgtggacg gcgtggaggt gcataatgcc aagacaaagc cgcgggagga gcagtacaac    780
agcacgtacc gtgtggtcag cgtcctcacc gtcctgcacc aggactggct gaatggcaag    840
gagtacaagt gcaaggtctc caacaaagcc ctcccagccc ccatcgagaa aaccatctcc    900
aaagccaaag gcagccccg agaaccacag gtgtacaccc tgcccccatc ccgggaagag    960
atgaccaaga accaggtcag cctgacctgc ctggtcaaag gcttctatcc cagcgacatc   1020
gccgtggagt gggagagcaa tgggcagccg gagaacaact acaagaccac gcctcccgtg   1080
ctggactccg acggctcctt cttcctctac agcaagctca ccgtggacaa gagcaggtgg   1140
cagcagggga acgtcttctc atgctccgtg atgcatgagg ctctgcacaa ccactacacg   1200
cagaagagcc tctccctgtc tccgggtaaa                                    1230

<210> SEQ ID NO 126
<211> LENGTH: 1188
<212> TYPE: DNA
<213> ORGANISM: Artificial sequence
<220> FEATURE:
<223> OTHER INFORMATION: sFRP2-Fc construct

<400> SEQUENCE: 126
atgctgcagg gccctggctc gctgctgctg ctcttcctcg cctcgcactg ctgcctgggc    60
tcggcgcgcg ggctcttcct cttTggccag cccgacttct cctacaagcg cagcaattgc   120
aagcccatcc ctgccaacct gcagctgtgc cacggcatcg aataccagaa catgcggctg   180
cccaacctgc tgggccacga gaccatgaag gaggtgctgg agcaggccgg cgcttggatc   240
ccgctggtca tgaagcagtg ccaccccgac accaagaagt tcctgtgctc gctcttcgcc   300
ccgtctgcc tcgatgacct agacgagacc atccagccat gccactcgct ctgcgtgcag   360
gtgaaggacc gctgcgcccc ggtcatgtcc gccttcggct cccctggcc cgacatgctt   420
gagtgcgacc gtttcccca ggacaacgac cttTgcatcc cctcgctag cagcgaccac   480
tggcgcgccc aggtcaccga caaagctgcg cgctctactc tgtgcccacc gtgcccagca   540
cctgaactcc tggggggacc gtcagtcttc ctcttccccc caaaacccaa ggacaccctc   600
atgatctccc ggacccctga ggtcacatgc gtggtggtgg acgtgagcca cgaagaccct   660
gaggtcaagt tcaactggta cgtggacggc gtggaggtgc ataatgccaa gacaaagccg   720
cgggaggagc agtacaacag cacgtaccgt gtggtcagcg tcctcaccgt cctgcaccag   780
gactggctga atggcaagga gtacaagtgc aaggtctcca acaaagccct cccagccccc   840
atcgagaaaa ccatctccaa agccaaaggg cagccccgag aaccacaggt gtacaccctg   900
cccccatccc gggaagagat gaccaagaac caggtcagcc tgacctgcct ggtcaaaggc   960
ttctatccca gcgacatcgc cgtggagtgg gagagcaatg ggcagccgga gaacaactac  1020
aagaccacgc ctcccgtgct ggactccgac ggctccttct tcctctacag caagctcacc  1080
gtggacaaga gcaggtggca gcaggggaac gtcttctcat gctccgtgat gcatgaggct  1140
```
ctgcacaacc actacacgca gaagagcctc tccctgtctc cgggtaaa         1188

<210> SEQ ID NO 127
<211> LENGTH: 1170
<212> TYPE: DNA
<213> ORGANISM: Artificial sequence
<220> FEATURE:
<223> OTHER INFORMATION: sFRP3-Fc construct

<400> SEQUENCE: 127

```
atggggggga ctgccgccag gttgggggcc gtgattttgt ttgtcgtcat agtgggcctc    60
catgggtcc  gcggcaaaat cgatgctcga ggggcagcct gtgagcccgt ccgcatcccc   120
ctgtgcaagt cccctgccctg gaacatgact aagatgccca accacctgca ccacagcact   180
caggccaacg ccatcctggc catcgagcag ttcgaaggtc tgctgggcac ccactgcagc   240
cccgatctgc tcttcttcct ctgtgccatg tacgcgccca tctgcaccat tgacttccag   300
cacgagccca tcaagccctg taagtctgtg tgcgagcggg cccggcaggg ctgtgagccc   360
atactcatca agtaccgcca ctcgtggccg gagaacctgg cctgcgagga gctgccagtg   420
tacgacaggg gcgtgtgcat ctctcccgag gccatcgtta ctgggcgcgc ccaggtcacc   480
gacaaagctg cgcgctctac tctgtgccca ccgtgcccag cacctgaact cctgggggga   540
ccgtcagtct tcctcttccc cccaaaaccc aaggacaccc tcatgatctc ccggacccct   600
gaggtcacat gcgtggtggt ggacgtgagc cacgaagacc ctgaggtcaa gttcaactgg   660
tacgtggacg gcgtggaggt gcataatgcc aagacaaagc cgcgggagga gcagtacaac   720
agcacgtacc gtgtggtcag cgtcctcacc gtcctgcacc aggactggct gaatggcaag   780
gagtacaagt gcaaggtctc caacaaagcc ctcccagccc ccatcgagaa aaccatctcc   840
aaagccaaag ggcagccccg agaaccacag gtgtacaccc tgcccccatc ccgggaagag   900
atgaccaaga accaggtcag cctgacctgc ctggtcaaag gcttctatcc cagcgacatc   960
gccgtggagt gggagagcaa tgggcagccg gagaacaact acaagaccac gcctcccgtg  1020
ctggactccg acggctcctt cttcctctac agcaagctca ccgtggacaa gagcaggtgg  1080
cagcagggga acgtcttctc atgctccgtg atgcatgagg ctctgcacaa ccactacacg  1140
cagaagagcc tctccctgtc tccgggtaaa                                    1170
```

<210> SEQ ID NO 128
<211> LENGTH: 1140
<212> TYPE: DNA
<213> ORGANISM: Artificial sequence
<220> FEATURE:
<223> OTHER INFORMATION: sFRP4-Fc construct

<400> SEQUENCE: 128

```
atgttcctct ccatcctagt ggcgctgtgc ctgtggctgc acctggcgct gggcgtgcgc    60
ggcgcgccct gcgaggcggt gcgcatccct atgtgccggc acatgccctg gaacatcacg   120
cggatgccca accacctgca ccacagcacg caggagaacg ccatcctggc catcgagcag   180
tacgaggagc tggtggacgt gaactgcagc gccgtgctgc gcttcttctt ctgtgccatg   240
tacgcgccca tttgcaccct ggagttcctg cacgaccctat caagccgtg caagtcggtg   300
tgccaacgcg cgcgcgacga ctgcgagccc ctcatgaaga tgtacaacca gctggccc    360
gaaagcctgg cctgcgacga gctgcctgtc tatgaccgtg gcgtgtgcat ttcgcctgaa   420
gccatcgtca cgctcgagtc aggaggagga ggagtcaccg acaaaactca cacatgccca   480
ccgtgcccag cacctgaact cctgggggga ccgtcagtct tcctcttccc cccaaaaccc   540
```

```
aaggacaccc tcatgatctc ccggacccct gaggtcacat gcgtggtggt ggacgtgagc      600
cacgaagacc ctgaggtcaa gttcaactgg tacgtggacg gcgtggaggt gcataatgcc      660
aagacaaagc cgcgggagga gcagtacaac agcacgtacc gtgtggtcag cgtcctcacc      720
gtcctgcacc aggactggct gaatggcaag gagtacaagt gcaaggtctc caacaaagcc      780
ctcccagccc ccatcgagaa aaccatctcc aaagccaaag gcagccccg agaaccacag      840 gtgtacaccc tgcccccatc ccgggaagag atgaccaaga accaggtcag cctgacctgc      900
ctggtcaaag gcttctatcc cagcgacatc gccgtggagt gggagagcaa tgggcagccg      960
gagaacaact acaagaccac gcctcccgtg ctggactccg acggctcctt cttcctctac     1020
agcaagctca ccgtggacaa gagcaggtgg cagcagggga acgtcttctc atgctccgtg     1080
atgcatgagg ctctgcacaa ccactacacg cagaagagcc tctccctgtc tccgggtaaa     1140

<210> SEQ ID NO 129
<211> LENGTH: 1218
<212> TYPE: DNA
<213> ORGANISM: Artificial sequence
<220> FEATURE:
<223> OTHER INFORMATION: sFRP5-Fc construct

<400> SEQUENCE: 129
atgcgggcgg cggcggcggc ggggggcgtg cggacggccg cgctggcgct gctgctgggg       60
gcgctgcact gggcgccggc gcgctgcgag gagtacgact actatggctg gcaggccgag      120
ccgctgcacg gccgctccta ctccaagccg ccgcagtgcc ttgacatccc tgccgacctg      180
ccgctctgcc acacggtggg ctacaagcgc atgcggctgc ccaacctgct ggagcacgag      240
agcctggccg aagtgaagca gcaggcgagc agctggctgc cgctgctggc caagcgctgc      300
cactcggata cgcaggtctt cctgtgctcg ctctttgcgc ccgtctgtct cgaccggccc      360
atctacccgt gccgctcgct gtgcgaggcc gtgcgcgccg gctgcgcgcc gctcatggag      420
gcctacggct tcccctggcc tgagatgctg cactgccaca agttccccct ggacaacgac      480
ctctgcatcg ccgtgcagtt cgggcacctg tgcgcgcccc aggtcaccga caaagctgcg      540
cgctctactc tgtgcccacc gtgcccagca cctgaactcc tggggggacc gtcagtcttc      600
ctcttccccc caaaacccaa ggacaccctc atgatctccc ggacccctga ggtcacatgc      660
gtggtggtgg acgtgagcca cgaagaccct gaggtcaagt tcaactggta cgtggacggc      720
gtggaggtgc ataatgccaa gacaaagccg cgggaggagc agtacaacag cacgtaccgt      780
gtggtcagcg tcctcaccgt cctgcaccag gactggctga atggcaagga gtacaagtgc      840
aaggtctcca acaaagccct cccagccccc atcgagaaaa ccatctccaa agccaaaggg      900
cagccccgag aaccacaggt gtacaccctg cccccatccc gggaagagat gaccaagaac      960
caggtcagcc tgacctgcct ggtcaaaggc ttctatccca gcgacatcgc cgtggagtgg     1020
gagagcaatg ggcagccgga gaacaactac aagaccacgc ctcccgtgct ggactccgac     1080
ggctccttct tcctctacag caagctcacc gtggacaaga gcaggtggca gcaggggaac     1140
gtcttctcat gctccgtgat gcatgaggct ctgcacaacc actacacgca gaagagcctc     1200
tccctgtctc cgggtaaa                                                    1218
```

WNT ANTAGONISTS AND THEIR USE IN THE DIAGNOSIS AND TREATMENT OF WNT-MEDIATED DISORDERS

RELATED APPLICATIONS

This application claims priority to and the benefit of U.S. Provisional Application Ser. No. 60/825,063, filed Sep. 8, 2006, and U.S. Provisional Application Ser. No. 60/951,175, filed Jul. 20, 2007, both of which are incorporated by reference in their entirety herein.

FIELD OF THE INVENTION

The present invention relates generally to the regulation of cell growth. More specifically, the present invention relates to inhibitors of the Wnt pathway as well as to their use in the diagnosis and treatment of disorders characterized by the activation of Wnt pathway signaling, as well as to the modulation of cellular events mediated by Wnt pathway signaling.

BACKGROUND OF THE INVENTION

The Wnt signaling pathway's association with carcinogenesis began as a result of early observations and experiments in certain murine mammary tumors. Wnt-1 proto-oncogene (Int-1) was originally identified from mammary tumors induced by mouse mammary tumor virus (MMTV) due to an insertion of a viral DNA sequence. Nusse et al., *Cell* 1982; 31: 99-109. The result of such viral integration was unregulated expression of Int-1 resulting in the formation of tumors. Vanooyen, A. et al., *Cell* 1984; 39: 233-240; Nusse, R. et al., *Nature* 1984; 307: 131-136; Tsukamoto et al., *Cell* 1988; 55: 619-625. Subsequent sequence analysis demonstrated that the Int-1 was a mammalian homolog of the *Drosophila* gene Wingless (Wg), which was implicated in development, and the terms were then combined to create "Wnt" to identify this family of proteins.

The human Wnt gene family of secreted ligands has now grown to at least 19 members (e.g., Wnt-1 (RefSeq.: NM_005430), Wnt-2 (RefSeq.: NM_003391), Wnt-2B (Wnt-13) (RefSeq.: NM_004185), Wnt-3 (ReSeq.: NM_030753), Wnt3a (RefSeq.: NM_033131), Wnt-4 (RefSeq.: NM_030761), Wnt-5A (RefSeq.: NM_003392), Wnt-5B (RefSeq.: NM_032642), Wnt-6 (RefSeq.: NM_006522), Wnt-7A (RefSeq.: NM_004625), Wnt-7B (RefSeq.: NM_058238), Wnt-8A (RefSeq.: NM_058244), Wnt-8B (RefSeq.: NM_003393), Wnt-9A (Wnt-14) (RefSeq.: NM_003395), Wnt-9B (Wnt-15) (RefSeq.: NM_003396), Wnt-10A (RefSeq.: NM_025216), Wnt-10B (RefSeq.: NM_003394), Wnt-11 (RefSeq.: NM_004626), Wnt-16 (RefSeq.: NM_016087)). Each member has varying degrees of sequence identity but all contain 23-24 conserved cysteine residues which show highly conserved spacing. McMahon, A P et al., *Trends Genet.* 1992; 8: 236-242; Miller, J R. *Genome Biol.* 2002; 3(1): 3001.1-3001.15. The Wnt proteins are small (i.e., 39-46 kD) acylated, secreted glycoproteins which play key roles in both embryogenesis and mature tissues. During embryological development, the expression of Wnt proteins is important in patterning through control of cell proliferation and determination of stem cell fate. The Wnt molecules are also palmitoylated, and thus are more hydrophobic than would be otherwise predicted by analysis of the amino acid sequence alone. Willert, K. et al, *Nature* 2003; 423: 448-52. The site or sites of palmitoylation are also believed to be essential for function.

The Wnt proteins act as ligands to activate the Frizzled (Frz) family of seven-pass transmembrane receptors. Ingham, P. W. *Trends Genet.* 1996; 12: 382-384; YangSnyder, J. et al., *Curr. Biol.* 1996; 6: 1302-1306; Bhanot, P. et al., *Nature* 1996; 382: 225-230. There are ten known members of the Frz family (e.g., Frz1, Frz2, Frz3 . . . . Frz10), each characterized by the presence of a cysteine rich domain (CRD). Huang et al., *Genome Biol.* 2004; 5: 234.1-234.8. There is a great degree of promiscuity between the various Wnt-Frizzled interactions, but Wnt-Frz binding must also incorporate the LDL receptor related proteins (LRP5 or LRP6) and the membrane and the cytoplasmic protein Dishevelled (Dsh) to form an active signaling complex.

The binding of Wnt to Frizzled can activate signaling via either the canonical Wnt signaling pathway, thereby resulting in stabilization and increased transcriptional activity of β-catenin [Peifer, M. et al., *Development* 1994; 120: 369-380; Papkoff, J. et al, *Mol. Cell Biol.* 1996; 16: 2128-2134] or non-canonical signaling, such as through the Wnt/planar cell polarity (Wnt/PCP) or Wnt-calcium (Wnt/Ca$^{2+}$) pathway. Veeman, M. T. et al., *Dev. Cell* 2003; 5: 367-377.

The canonical Wnt signaling pathway is the most relevant of the Wnt signaling pathways to the development of cancer. Ilyas, M. J. *Pathol.* 2005; 205: 130-144. Normal activation of this pathway begins a series of downstream events culminating in the stabilization and increased levels of the protein β-catenin. This protein is normally an inactive cytoplasmic protein, and is found at the cell membrane bound to proteins including e-cadherin. In the absence of Wnt ligand, phosphorylated cytoplasmic β-catenin is normally rapidly degraded. Upon activation of the canonical pathway, unphosphorylated β-catenin is transported to the nucleus where it further results in transcriptional activation of various target genes. The subsequent upregulation in transcription of these target genes leads to changes in the cell, and continuous, unregulated expression of such target genes results in tumor development. Since aberrant Wnt signaling appears to be a necessary precursor in carcinogenesis, effective inhibitors of Wnt signaling are of great interest as cancer therapeutics.

The use of soluble receptors as antagonists to ligand-receptor interactions is known in the art. Such molecules can be effective therapeutic antagonists if they bind the free ligand in a manner so as to prevent the initial receptor activation step of the signaling pathway. Soluble minimal extracellular domain (ECD) fragments of the cysteine-rich domain (CRD) of a Frizzled receptor which exhibit binding to Wnt have been identified, based on crystallography data. Dann et al., *Nature* 412: 86-90 (2001). However, while such Frizzled fragments did exhibit binding to Wnt ligand, such fragments are unsuitable for therapeutics because of their rapid degradation in vivo.

The use of a soluble Frizzled domain coupled to an immunoglobulin Fc as a potential Wnt antagonist has been proposed. Therapeutic Opportunities of the Wnt Signaling Pathway in Cancer, New York Academy of Sciences, Oct. 25, 2005; Hsieh, J-C. et al., *PNAS,* 96: 3546-3551 (1999). However, prior to the present invention, attempts at creating a soluble Frizzled receptor-Fc fusion therapeutic were not successful. For example, one such chimera based on residues 1-173 of the Frz8 CRD (Frz (173)-Fc, SEQ ID NO: 113) had suboptimal efficacy (FIG. 12), and was unstable in vivo (FIG. 11). Moreover, the Frz (173)-Fc chimera only reduced the rate of increase in tumor volume (as opposed to shrinking starting tumor volume). Additionally, while the creation of Fc fusions is generally known as one technique to improve the in vivo stability of the resulting construct, the creation of effective therapeutic Fc constructs can be difficult owing to a number of problems, including improper protein folding of the new protein construct and steric hindrance of the fusion construct to the target.

Thus, a need exits for a Wnt antagonist therapeutic with enhanced in vivo stability that acts to inhibit Wnt ligand induced cellular signaling.

SUMMARY OF THE INVENTION

The invention provides for compositions and their use in methods of diagnosing and treating Wnt-mediated disorder, such as cancer, and in inhibiting cellular Wnt signaling. Specifically, the invention provides for Wnt antagonists that are chimeric molecules comprising a Frizzled domain component, such as a polypeptide derived from a Frizzled (Frz) protein, a Frizzled related protein (sFRP) or another protein (e.g., Ror-1, -2, etc.), and an immunoglobulin Fc domain, and their use in methods of diagnosing and treating Wnt-mediated disorders and in inhibiting cellular Wnt signaling.

One aspect of the invention provides for a Wnt antagonist comprising a Frizzled domain component and a Fc domain. The Frizzled domain component of the Wnt antagonist comprises a polypeptide derived from a Frz protein, a FRP protein, or a Ror protein. In one embodiment, the Wnt antagonist is active in vivo for at least 1 hour. In another embodiment, the Wnt antagonist is active in vivo for at least 5 hours. In another embodiment, the Wnt antagonist has an in vivo half-life of at least 1 day. In yet another embodiment, the Wnt antagonist has an in vivo half-life of at least 2 days.

In a further embodiment, the Frizzled domain component comprises a minimal CRD (ECD) domain from a Frz polypeptide selected from the group consisting of hFrz1 (SEQ ID NO: 18), hFrz2 (SEQ ID NO: 19), hFrz3 (SEQ ID NO: 20), hFrz4 (SEQ ID NO: 21), hFrz5 (SEQ ID NO: 22), hFrz6 (SEQ ID NO: 23), hFrz7 (SEQ ID NO: 24), hFrz8 (SEQ ID NO: 25), hFrz9 (SEQ ID NO: 26), and hFrz10 (SEQ ID NO: 27), and active variants thereof. In yet a further embodiment, the Frizzled domain component comprises a minimal CRD (ECD) domain from a sFRP polypeptide selected from the group consisting of sFRP1 (SEQ ID NO: 28), sFRP2 (SEQ ID NO: 29), sFRP3 (SEQ ID NO: 30), sFRP4 (SEQ ID NO: 31), and sFRP5 (SEQ ID NO: 32), and active variants thereof. In yet a further embodiment, the Frizzled domain component comprises a minimal CRD (ECD) domain from a Ror polypeptide selected from the group consisting of hRor1 (SEQ ID NO: 33), and hRor2 (SEQ ID NO: 34), and active variants thereof.

In yet a further embodiment, the Frizzled domain component comprises a mature Frz polypeptide selected from the group consisting of hFrz1 (SEQ ID NO: 50), hFrz2 (SEQ ID NO: 51), hFrz3 (SEQ ID NO: 52), hFrz4 (SEQ ID NO: 53), hFrz5 (SEQ ID NO: 54), hFrz6 (SEQ ID NO: 55), hFrz7 (SEQ ID NO: 56), hFrz8 (SEQ ID NO: 57), hFrz9 (SEQ ID NO: 58), and hFrz10 (SEQ ID NO: 59), and active variants thereof, or a mature sFrp polypeptide selected from the group consisting of sFRP1 (SEQ ID NO: 60), sFRP2 (SEQ ID NO: 61), sFRP3 (SEQ ID NO: 62), sFRP4 (SEQ ID NO: 63), and sFRP5 (SEQ ID NO: 64), and active variants thereof, or a mature Ror polypeptide selected from the group consisting of hRor1 (SEQ ID NO: 65), and hRor2 (SEQ ID NO: 66), and active variants thereof.

In a still further embodiment, the Frizzled domain component comprises a pro-Frz polypeptide selected from the group consisting of hFrz1 (SEQ ID NO: 35), hFrz2 (SEQ ID NO: 36), hFrz3 (SEQ ID NO: 37), hFrz4 (SEQ ID NO: 38), hFrz5 (SEQ ID NO: 39), hFrz6 (SEQ ID NO: 40), hFrz7 (SEQ ID NO: 41), hFrz8 (SEQ ID NO: 42), hFrz9 (SEQ ID NO: 43), and hFrz10 (SEQ ID NO: 44), and active variants thereof, or a pro-sFrp polypeptide selected from the group consisting of sFRP1 (SEQ ID NO: 45), sFRP2 (SEQ ID NO: 46), sFRP3 (SEQ ID NO: 47), sFRP4 (SEQ ID NO: 48), and sFRP5 (SEQ ID NO: 49), and active variants thereof.

In one embodiment, the Wnt antagonist comprises a Fc component derived from an immunoglobulin selected from the group consisting of IgG1, IgG2, IgG3 and IgG4. In another embodiment, the Fc is derived from an IgG1 immunoglobulin. In yet another embodiment the Fc sequence comprises the Fc shown in SEQ ID NO: 67 or SEQ ID NO: 68.

In one embodiment, the Wnt antagonist further comprises a linker connecting the Frizzled domain component to the Fc domain. In one such embodiment, the linker is a peptide linker such as ESGGGGVT (SEQ ID NO: 69), LESGGGGVT (SEQ ID NO: 70), GRAQVT (SEQ ID NO: 71), WRAQVT (SEQ ID NO: 72), and ARGRAQVT (SEQ ID NO: 73).

In particular embodiments, the Wnt antagonist comprises a polypeptide selected from the group consisting of in Frz8-Fc (SEQ ID NO: 74), Frz5-Fc (SEQ ID NO: 75), Frz1-Fc (SEQ ID NO: 76), Frz2-Fc (SEQ ID NO: 77), Frz3-Fc (SEQ ID NO: 78), Frz4-Fc (SEQ ID NO: 79), Frz6-Fc (SEQ ID NO: 80), Frz7-Fc (SEQ ID NO: 81), Frz9-Fc (SEQ ID NO: 82), Frz10-Fc (SEQ ID NO: 83), sFRP1-Fc (SEQ ID NO: 84), sFRP2 (SEQ ID NO: 85), sFRP3-Fc (SEQ ID NO: 86), sFRP4-Fc (SEQ ID NO: 87), and sFRP5-Fc (SEQ ID NO: 88).

Another aspect of the invention provides for a composition comprising at least one pharmaceutically acceptable carrier or excipient and a Wnt antagonist as described above.

Yet another aspect of the invention provides for a nucleic acid sequence encoding any of the Wnt antagonists described above. In one embodiment, the nucleic acid encoding a Wnt antagonist further comprises a vector containing control sequences to which the nucleic acid is operably linked. In another embodiment, the vector is contained in host cells, such as a mammalian, insect, *E. coli* or yeast cell.

Another aspect of the invention provides for an article of manufacture comprising a composition comprising at least one pharmaceutically acceptable carrier or excipient and a Wnt antagonist as described above and a container, wherein the Wnt antagonist is contained within the container and the container further comprises (a) a label affixed to the container, or (b) a package insert inside the container referring to the use of the Wnt antagonist indicating use of the composition for the therapeutic treatment or diagnostic detection of a Wnt-mediated disorder.

Yet another aspect of the invention provides for a method of inhibiting Wnt signaling in a cell comprising contacting the cell with an effective amount of a Wnt antagonist comprising a Frizzled domain component and a Fc domain. The Frizzled domain component of the Wnt antagonist comprises a polypeptide derived from a Frz protein, a FRP protein, or a Ror protein. In one embodiment, the Wnt antagonist is active in vivo for at least 1 hour. In another embodiment, the Wnt antagonist is active in vivo for at least 5 hours. In another embodiment, the Wnt antagonist has an in vivo half-life of at least 1 day. In yet another embodiment, the Wnt antagonist has an in vivo half-life of at least 2 days.

In a further embodiment of this aspect, the Frizzled domain component comprises a minimal CRD (ECD) domain from a Frz polypeptide selected from the group consisting of hFrz1 (SEQ ID NO: 18), hFrz2 (SEQ ID NO: 19), hFrz3 (SEQ ID NO: 20), hFrz4 (SEQ ID NO: 21), hFrz5 (SEQ ID NO: 22), hFrz6 (SEQ ID NO: 23), hFrz7 (SEQ ID NO: 24), hFrz8 (SEQ ID NO: 25), hFrz9 (SEQ ID NO: 26), and hFrz10 (SEQ ID NO: 27), and active variants thereof. In yet a further embodiment, the Frizzled domain component comprises a minimal CRD (ECD) domain from a sFRP polypeptide selected from the group consisting of sFRP1 (SEQ ID NO: 28), sFRP2 (SEQ ID NO: 29), sFRP3 (SEQ ID NO: 30), sFRP4 (SEQ ID NO: 31), and sFRP5 (SEQ ID NO: 32), and active variants thereof. In yet a further embodiment, the Frizzled domain component comprises a minimal CRD (ECD) domain from a Ror polypeptide selected from the group consisting of hRor1 (SEQ ID NO: 33), and hRor2 (SEQ ID NO: 34), and active variants thereof.

In yet a further embodiment, the Frizzled domain component comprises a mature Frz polypeptide selected from the group consisting of: (SEQ ID NO: 50), hFrz2 (SEQ ID NO: 51), hFrz3 (SEQ ID NO: 52), hFrz4 (SEQ ID NO: 53), hFrz5 (SEQ ID NO: 54), hFrz6 (SEQ ID NO: 55), hFrz7 (SEQ ID NO: 56), hFrz8 (SEQ ID NO: 57), hFrz9 (SEQ ID NO: 58), and hFrz10 (SEQ ID NO: 59), and active variants thereof, or a mature sFrp polypeptide selected from the group consisting of sFRP1 (SEQ ID NO: 60), sFRP2 (SEQ ID NO: 61), sFRP3 (SEQ ID NO: 62), sFRP4 (SEQ ID NO: 63), and sFRP5 (SEQ ID NO: 64), and active variants thereof, or a mature Ror polypeptide selected from the group consisting of hRor1 (SEQ ID NO: 65), and hRor2 (SEQ ID NO: 66), and active variants thereof.

In a still further embodiment, the Frizzled domain component comprises a pro-Frz polypeptide selected from the group consisting of hFrz1 (SEQ ID NO: 35), hFrz2 (SEQ ID NO: 36), hFrz3 (SEQ ID NO: 37), hFrz4 (SEQ ID NO: 38), hFrz5 (SEQ ID NO: 39), hFrz6 (SEQ ID NO: 40), hFrz7 (SEQ ID NO: 41), hFrz8 (SEQ ID NO: 42), hFrz9 (SEQ ID NO: 43), and hFrz10 (SEQ ID NO: 44), and active variants thereof, or a pro-sFrp polypeptide selected from the group consisting of sFRP1 (SEQ ID NO: 45), sFRP2 (SEQ ID NO: 46), sFRP3 (SEQ ID NO: 47), sFRP4 (SEQ ID NO: 48), and sFRP5 (SEQ ID NO: 49), and active variants thereof.

In one embodiment, the Wnt antagonist comprises a Fc component derived from an immunoglobulin selected from the group consisting of IgG1, IgG2, IgG3 and IgG4. In another embodiment, the Fc is derived from an IgG1 immunoglobulin. In yet another embodiment the Fc sequence shown in SEQ ID NO: 67 or SEQ ID NO: 68.

In one embodiment, Wnt antagonist further comprises a linker connecting the Frizzled domain component to the Fc domain. In one embodiment, the linker is a peptide linker such as ESGGGGVT (SEQ ID NO: 69), LESGGGGVT (SEQ ID NO: 70), GRAQVT (SEQ ID NO: 71), WRAQVT (SEQ ID NO: 72), and ARGRAQVT (SEQ ID NO: 73).

In particular embodiments, the Wnt antagonist comprises a polypeptide selected from the group consisting of Frz8-Fc (SEQ ID NO: 74), Frz5-Fc (SEQ ID NO: 75), Frz1-Fc (SEQ ID NO: 76), Frz2-Fc (SEQ ID NO: 77), Frz3-Fc (SEQ ID NO: 78), Frz4-Fc (SEQ ID NO: 79), Frz6-Fc (SEQ ID NO: 80), Frz7-Fc (SEQ ID NO: 81), Frz9-Fc (SEQ ID NO: 82), Frz10-Fc (SEQ ID NO: 83), sFRP1-Fc (SEQ ID NO: 84), sFRP2 (SEQ ID NO: 85), sFRP3-Fc (SEQ ID NO: 86), sFRP4-Fc (SEQ ID NO: 87), and sFRP5-Fc (SEQ ID NO: 88).

In one embodiment of this method, the cell is contained within a mammal and the amount administered is a therapeutically effective amount. In another embodiment, the Wnt signaling results from activation of a Wnt signaling component through somatic mutation. In another embodiment, the inhibition of Wnt signaling results in the inhibition of growth of the cell. In yet another embodiment, the cell is a cancer cell.

Another aspect of the invention provides for a method of treating a Wnt-mediated disorder in a mammal suffering therefrom, comprising administering to the mammal a therapeutically effective amount of a Wnt antagonist comprising a Frizzled domain component and a Fc domain. The Frizzled domain component of the Wnt antagonist comprises a polypeptide derived from a Frz protein, a FRP protein, or a Ror protein. In one embodiment, the Wnt antagonist is active in vivo for at least 1 hour. In another embodiment, the Wnt antagonist is active in vivo for at least 5 hours. In another embodiment, the Wnt antagonist has an in vivo half-life of at least 1 day. In yet another embodiment, the Wnt antagonist has an in vivo half-life of at least 2 days.

In a further embodiment of this aspect, the Frizzled domain component comprises a minimal CRD (ECD) domain from a Frz polypeptide selected from the group consisting of hFrz1 (SEQ ID NO: 18), hFrz2 (SEQ ID NO: 19), hFrz3 (SEQ ID NO: 20), hFrz4 (SEQ ID NO: 21), hFrz5 (SEQ ID NO: 22), hFrz6 (SEQ ID NO: 23), hFrz7 (SEQ ID NO: 24), hFrz8 (SEQ ID NO: 25), hFrz9 (SEQ ID NO: 26), and hFrz10 (SEQ ID NO: 27), and active variants thereof. In yet a further embodiment, the Frizzled domain component comprises a minimal CRD (ECD) domain from a sFRP polypeptide selected from the group consisting of sFRP1 (SEQ ID NO: 28), sFRP2 (SEQ ID NO: 29), sFRP3 (SEQ ID NO: 30), sFRP4 (SEQ ID NO: 31), and sFRP5 (SEQ ID NO: 32), and active variants thereof. In yet a further embodiment, the Frizzled domain component comprises a minimal CRD (ECD) domain from a Ror polypeptide selected from the group consisting of hRor1 (SEQ ID NO: 33), and hRor2 (SEQ ID NO: 34), and active variants thereof.

In yet a further embodiment, the Frizzled domain component comprises a mature Frz polypeptide selected from the group consisting of: (SEQ ID NO: 50), hFrz2 (SEQ ID NO: 51), hFrz3 (SEQ ID NO: 52), hFrz4 (SEQ ID NO: 53), hFrz5 (SEQ ID NO: 54), hFrz6 (SEQ ID NO: 55), hFrz7 (SEQ ID NO: 56), hFrz8 (SEQ ID NO: 57), hFrz9 (SEQ ID NO: 58), and hFrz10 (SEQ ID NO: 59), and active variants thereof, or a mature sFrp polypeptide selected from the group consisting of sFRP1 (SEQ ID NO: 60), sFRP2 (SEQ ID NO: 61), sFRP3 (SEQ ID NO: 62), sFRP4 (SEQ ID NO: 63), and sFRP5 (SEQ ID NO: 64), and active variants thereof, or a mature Ror polypeptide selected from the group consisting of hRor1 (SEQ ID NO: 65), and hRor2 (SEQ ID NO: 66), and active variants thereof.

In still further embodiments, the Frizzled domain component comprises a pro-Frz polypeptide selected from the group consisting of hFrz1 (SEQ ID NO: 35), hFrz2 (SEQ ID NO: 36), hFrz3 (SEQ ID NO: 37), hFrz4 (SEQ ID NO: 38), hFrz5 (SEQ ID NO: 39), hFrz6 (SEQ ID NO: 40), hFrz7 (SEQ ID NO: 41), hFrz8 (SEQ ID NO: 42), hFrz9 (SEQ ID NO: 43), and hFrz10 (SEQ ID NO: 44), and active variants thereof, or a pro-sFrp polypeptide selected from the group consisting of sFRP1 (SEQ ID NO: 45), sFRP2 (SEQ ID NO: 46), sFRP3 (SEQ ID NO: 47), sFRP4 (SEQ ID NO: 48), and sFRP5 (SEQ ID NO: 49), and active variants thereof.

In one embodiment, the Wnt antagonist comprises a Fc component derived from an immunoglobulin selected from the group consisting of IgG1, IgG2, IgG3 and IgG4. In another embodiment, the Fc is derived from an IgG1 immunoglobulin. In yet another embodiment the Fc sequence shown in SEQ ID NO: 67 or SEQ ID NO: 68.

In one embodiment, Wnt antagonist further comprises a linker connecting the Frizzled domain component to the Fc domain. In one embodiment, the linker is a peptide linker such as ESGGGGVT (SEQ ID NO: 69), LESGGGGVT (SEQ ID NO: 70), GRAQVT (SEQ ID NO: 71), WRAQVT (SEQ ID NO: 72), and ARGRAQVT (SEQ ID NO: 73).

In particular embodiments, the Wnt antagonist comprises a polypeptide selected from the group consisting of Frz8-Fc (SEQ ID NO: 74), Frz5-Fc (SEQ ID NO: 75), Frz1-Fc (SEQ ID NO: 76), Frz2-Fc (SEQ ID NO: 77), Frz3-Fc (SEQ ID NO: 78), Frz4-Fc (SEQ ID NO: 79), Frz6-Fc (SEQ ID NO: 80), Frz7-Fc (SEQ ID NO: 81), Frz9-Fc (SEQ ID NO: 82), Frz10-Fc (SEQ ID NO: 83), sFRP1-Fc (SEQ ID NO: 84), sFRP2 (SEQ ID NO: 85), sFRP3-Fc (SEQ ID NO: 86), sFRP4-Fc (SEQ ID NO: 87), and sFRP5-Fc (SEQ ID NO: 88).

In one embodiment of this method, the disorder is a cell proliferative disorder associated with aberrant Wnt signaling activity. In another embodiment, the aberrant Wnt signaling activity results from increased expression of a Wnt protein. In yet another embodiment, the cell proliferative disorder is cancer, such as of colon cancer, colorectal cancer, breast cancer, leukemia, gliomas, or medulloblastomas.

Yet another aspect of the invention provides for a method for detecting the presence of a Wnt protein, comprising contacting the sample with a Wnt antagonist as described above, where the presence of a complex, or the binding level between the Wnt antagonist and Wnt protein is indicative of the presence of a Wnt protein and/or signaling. In one embodiment, the method further comprises determining if the level of Wnt signaling is aberrant, the method further comprising comparing the level of binding in the sample to the level in a second sample known to have physiologically normal Wnt signaling. A level of binding in the sample that is higher or lower than that of the second sample is indicative of aberrant Wnt signaling. In yet another embodiment, the aberrant Wnt signaling is further indicative of the presence of a Wnt-mediated disorder, such as cancer.

Another aspect of the invention provides for a method of modulating the expression of a Wnt target gene in a cell characterized by activated or excessive Wnt signaling, comprising contact the cell with an effective amount of a Wnt antagonist described above.

Yet another aspect of the invention provides for a method of therapeutically treating a Wnt-mediated cancer, comprising administering a therapeutically effective amount of a Wnt antagonist comprising a Frizzled domain component and a Fc domain. The Frizzled domain component of the Wnt antagonist comprises a polypeptide derived from a Frz protein, a FRP protein, or a Ror protein. In one embodiment, the Wnt antagonist is active in vivo for at least 1 hour. In another embodiment, the Wnt antagonist is active in vivo for at least 5 hours. In another embodiment, the Wnt antagonist has an in vivo half-life of at least 1 day. In yet another embodiment, the Wnt antagonist has an in vivo half-life of at least 2 days.

In a further embodiment of this aspect, the Frizzled domain component comprises a minimal CRD (ECD) domain from a Frz polypeptide selected from the group consisting of hFrz1 (SEQ ID NO: 18), hFrz2 (SEQ ID NO: 19), hFrz3 (SEQ ID NO: 20), hFrz4 (SEQ ID NO: 21), hFrz5 (SEQ ID NO: 22), hFrz6 (SEQ ID NO: 23), hFrz7 (SEQ ID NO: 24), hFrz8 (SEQ ID NO: 25), hFrz9 (SEQ ID NO: 26), and hFrz10 (SEQ ID NO: 27), and active variants thereof. In yet a further embodiment, the Frizzled domain component comprises a minimal CRD (ECD) domain from a sFRP polypeptide selected from the group consisting of sFRP1 (SEQ ID NO: 28), sFRP2 (SEQ ID NO: 29), sFRP3 (SEQ ID NO: 30), sFRP4 (SEQ ID NO: 31), and sFRP5 (SEQ ID NO: 32), and active variants thereof. In yet a further embodiment, the Frizzled domain component comprises a minimal CRD (ECD) domain from a Ror polypeptide selected from the group consisting of hRor1 (SEQ ID NO: 33), and hRor2 (SEQ ID NO: 34), and active variants thereof.

In yet a further embodiment, the Frizzled domain component comprises a mature Frz polypeptide selected from the group consisting of: (SEQ ID NO: 50), hFrz2 (SEQ ID NO: 51), hFrz3 (SEQ ID NO: 52), hFrz4 (SEQ ID NO: 53), hFrz5 (SEQ ID NO: 54), hFrz6 (SEQ ID NO: 55), hFrz7 (SEQ ID NO: 56), hFrz8 (SEQ ID NO: 57), hFrz9 (SEQ ID NO: 58), and hFrz10 (SEQ ID NO: 59), and active variants thereof, or a mature sFrp polypeptide selected from the group consisting of sFRP1 (SEQ ID NO: 60), sFRP2 (SEQ ID NO: 61), sFRP3 (SEQ ID NO: 62), sFRP4 (SEQ ID NO: 63), and sFRP5 (SEQ ID NO: 64), and active variants thereof, or a mature Ror polypeptide selected from the group consisting of hRor1 (SEQ ID NO: 65), and hRor2 (SEQ ID NO: 66), and active variants thereof.

In a still further embodiment, the Frizzled domain component comprises a pro-Frz polypeptide selected from the group consisting of hFrz1 (SEQ ID NO: 35), hFrz2 (SEQ ID NO: 36), hFrz3 (SEQ ID NO: 37), hFrz4 (SEQ ID NO: 38), hFrz5 (SEQ ID NO: 39), hFrz6 (SEQ ID NO: 40), hFrz7 (SEQ ID NO: 41), hFrz8 (SEQ ID NO: 42), hFrz9 (SEQ ID NO: 43), and hFrz10 (SEQ ID NO: 44), and active variants thereof, or a pro-sFrp polypeptide selected from the group consisting of sFRP1 (SEQ ID NO: 45), sFRP2 (SEQ ID NO: 46), sFRP3 (SEQ ID NO: 47), sFRP4 (SEQ ID NO: 48), and sFRP5 (SEQ ID NO: 49), and active variants thereof.

In one embodiment, the Wnt antagonist comprises a Fc component derived from an immunoglobulin selected from the group consisting of IgG1, IgG2, IgG3 and IgG4. In another embodiment, the Fc is derived from an IgG1 immunoglobulin. In yet another embodiment the Fc sequence shown in SEQ ID NO: 67 or SEQ ID NO: 68.

In one embodiment, Wnt antagonist further comprises a linker connecting the Frizzled domain component to the Fc domain. In one embodiment, the linker is a peptide linker such as ESGGGGVT (SEQ ID NO: 69), LESGGGGVT (SEQ ID NO: 70), GRAQVT (SEQ ID NO: 71), WRAQVT (SEQ ID NO: 72), and ARGRAQVT (SEQ ID NO: 73).

In particular embodiments, the Wnt antagonist comprises a polypeptide selected from the group consisting of Frz8-Fc (SEQ ID NO: 74), Frz5-Fc (SEQ ID NO: 75), Frz1-Fc (SEQ ID NO: 76), Frz2-Fc (SEQ ID NO: 77), Frz3-Fc (SEQ ID NO: 78), Frz4-Fc (SEQ ID NO: 79), Frz6-Fc (SEQ ID NO: 80), Frz7-Fc (SEQ ID NO: 81), Frz9-Fc (SEQ ID NO: 82), Frz10-Fc (SEQ ID NO: 83), sFRP1-Fc (SEQ ID NO: 84), sFRP2 (SEQ ID NO: 85), sFRP3-Fc (SEQ ID NO: 86), sFRP4-Fc (SEQ ID NO: 87), and sFRP5-Fc (SEQ ID NO: 88).

The administration of the antagonist arrests any subsequent increase in size or advancement in severity of the cancer. In one embodiment, the administration of the Wnt antagonist results in the reduction in size or severity of the cancer. In another embodiment, the administration of the Wnt antagonist reduces the tumor burden of the cancer. In yet another embodiment, the administration of the Wnt antagonist kills the cancer.

Another aspect of the invention provides for the use of a Wnt antagonist in the manufacture of a medicament for the treatment of a cell proliferative disorder. Wnt antagonist comprises a Frizzled domain component and a Fc domain. The Frizzled domain component of the Wnt antagonist comprises a polypeptide derived from a Frz protein, a FRP protein, or a Ror protein. In one embodiment, the Wnt antagonist is active in vivo for at least 1 hour. In another embodiment, the Wnt antagonist is active in vivo for at least 5 hours. In another embodiment, the Wnt antagonist has an in vivo half-life of at least 1 day. In yet another embodiment, the Wnt antagonist has an in vivo half-life of at least 2 days.

In a further embodiment of this aspect, the Frizzled domain component comprises a minimal CRD (ECD) domain from a Frz polypeptide selected from the group consisting of hFrz1 (SEQ ID NO: 18), hFrz2 (SEQ ID NO: 19), hFrz3 (SEQ ID NO: 20), hFrz4 (SEQ ID NO: 21), hFrz5 (SEQ ID NO: 22), hFrz6 (SEQ ID NO: 23), hFrz7 (SEQ ID NO: 24), hFrz8 (SEQ ID NO: 25), hFrz9 (SEQ ID NO: 26), and hFrz10 (SEQ ID NO: 27), and active variants thereof. In yet a further embodiment, the Frizzled domain component comprises a minimal CRD (ECD) domain from a sFRP polypeptide selected from the group consisting of sFRP1 (SEQ ID NO: 28), sFRP2 (SEQ ID NO: 29), sFRP3 (SEQ ID NO: 30), sFRP4 (SEQ ID NO: 31), and sFRP5 (SEQ ID NO: 32), and active variants thereof. In yet a further embodiment, the Frizzled domain component comprises a minimal CRD (ECD) domain from a Ror polypeptide selected from the group consisting of hRor1 (SEQ ID NO: 33), and hRor2 (SEQ ID NO: 34), and active variants thereof.

In yet a further embodiment, the Frizzled domain component comprises a mature Frz polypeptide selected from the group consisting of: (SEQ ID NO: 50), hFrz2 (SEQ ID NO: 51), hFrz3 (SEQ ID NO: 52), hFrz4 (SEQ ID NO: 53), hFrz5 (SEQ ID NO: 54), hFrz6 (SEQ ID NO: 55), hFrz7 (SEQ ID NO: 56), hFrz8 (SEQ ID NO: 57), hFrz9 (SEQ ID NO: 58), and hFrz10 (SEQ ID NO: 59), and active variants thereof, or a mature sFrp polypeptide selected from the group consisting of sFRP1 (SEQ ID NO: 60), sFRP2 (SEQ ID NO: 61), sFRP3 (SEQ ID NO: 62), sFRP4 (SEQ ID NO: 63), and sFRP5 (SEQ ID NO: 64), and active variants thereof, or a mature Ror polypeptide selected from the group consisting of hRor1 (SEQ ID NO: 65), and hRor2 (SEQ ID NO: 66), and active variants thereof.

In a still further embodiment, the Frizzled domain component comprises a pro-Frz polypeptide selected from the group consisting of hFrz1 (SEQ ID NO: 35), hFrz2 (SEQ ID NO: 36), hFrz3 (SEQ ID NO: 37), hFrz4 (SEQ ID NO: 38), hFrz5 (SEQ ID NO: 39), hFrz6 (SEQ ID NO: 40), hFrz7 (SEQ ID NO: 41), hFrz8 (SEQ ID NO: 42), hFrz9 (SEQ ID NO: 43), and hFrz10 (SEQ ID NO: 44), and active variants thereof, or a pro-sFrp polypeptide selected from the group consisting of sFRP1 (SEQ ID NO: 45), sFRP2 (SEQ ID NO: 46), sFRP3 (SEQ ID NO: 47), sFRP4 (SEQ ID NO: 48), and sFRP5 (SEQ ID NO: 49), and active variants thereof.

In one embodiment, the Wnt antagonist comprises a Fc component derived from an immunoglobulin selected from the group consisting of IgG1, IgG2, IgG3 and IgG4. In another embodiment, the Fc is derived from an IgG1 immunoglobulin. In yet another embodiment the Fc sequence shown in SEQ ID NO: 67 or SEQ ID NO: 68.

In one embodiment, Wnt antagonist further comprises a linker connecting the Frizzled domain component to the Fc domain. In one embodiment, the linker is a peptide linker such as ESGGGGVT (SEQ ID NO: 69), LESGGGGVT (SEQ ID NO: 70), GRAQVT (SEQ ID NO: 71), WRAQVT (SEQ ID NO: 72), and ARGRAQVT (SEQ ID NO: 73).

In particular embodiments, the Wnt antagonist comprises a polypeptide selected from the group consisting of Frz8-Fc (SEQ ID NO: 74), Frz5-Fc (SEQ ID NO: 75), Frz1-Fc (SEQ ID NO: 76), Frz2-Fc (SEQ ID NO: 77), Frz3-Fc (SEQ ID NO: 78), Frz4-Fc (SEQ ID NO: 79), Frz6-Fc (SEQ ID NO: 80), Frz7-Fc (SEQ ID NO: 81), Frz9-Fc (SEQ ID NO: 82), Frz10-Fc (SEQ ID NO: 83), sFRP1-Fc (SEQ ID NO: 84), sFRP2 (SEQ ID NO: 85), sFRP3-Fc (SEQ ID NO: 86), sFRP4-Fc (SEQ ID NO: 87), and sFRP5-Fc (SEQ ID NO: 88).

In one embodiment, the cell proliferative disorder is cancer such as colon cancer, colorectal cancer, breast cancer, leukemia, gliomas, or medulloblastomas.

DESCRIPTION OF THE FIGURES

FIG. 3A shows an alignment of the extracellular domains of the 10 pro-Frizzled proteins (SEQ ID NOs: 35-44) and the 5 pro-sFRP proteins (SEQ ID NOs: 45-49), while FIG. 3B shows an alignment of the extracellular domains of 10 mature Frizzled proteins (SEQ ID NOs: 50-59), and 5 mature sFRP proteins (SEQ ID NOs: 60-64), as well as the extracellular domains of the mature Ror proteins (SEQ ID NOs: 65-66). Similar residues are boxed in gray, identical residues are indicated by asterisks. Similar residues are grouped as acidic, basic, polar and non-polar. In FIG. 3B, the minimal CRD (ECD) domains are indicated between the two boxed arrowed lines (SEQ ID NOs: 18-34).

FIG. 4 shows the sequences of the Frz (156)-Fc and Frz (173)-Fc chimeric constructs. FIG. 4A shows the longer Frz (173)-Fc sequence (SEQ ID NO: 113). Shown in bold (i.e., first 24 N-terminal amino acid residues) is the leader signal sequence. Residues 25-27 are alanine residues that may be present or absent in the mature protein. Shown in boxed text (i.e., residues 157-173) are the additional sequences of the Frz8 receptors that distinguish the longer (Frz173) from the shorter (Frz156) chimeric constructs. The linker sequence (i.e., residues 174-182) is underlined, while the Fc domain sequence is shown in italics (i.e., residues 183-409). FIG. 4B shows the shorter Frz (156)-Fc (SEQ ID NO: 74). In bold (i.e., first 24 N-terminal amino acid residues) is the leader signal sequence. Residues 25-27 are alanine residues that may be present or absent in the mature protein. The linker sequence (i.e., residues 157-164) is underlined, while the Fc domain sequence is shown in italics (i.e., residues 165-391).

FIG. 5A-5H shows the nucleic acid sequence encoding several Wnt antagonist chimeric constructs (Frz1-Fc (SEQ ID NO: 115), Frz2-Fc (SEQ ID NO: 116), Frz3-Fc (SEQ ID NO: 117), Frz4-Fc (SEQ ID NO: 118), Frz5-Fc (SEQ ID NO: 119), Frz6-Fc (SEQ ID NO: 120), Frz7-Fc (SEQ ID NO: 121), Frz8-Fc (SEQ ID NO: 122), Frz9-Fc (SEQ ID NO: 123), Frz10-Fc (SEQ ID NO: 124), sFRP1-Fc (SEQ ID NO: 125), sFRP2-Fc (SEQ ID NO: 126), sFRP3-Fc (SEQ ID NO: 127), sFRP4-Fc (SEQ ID NO: 128), and sFRP5-Fc (SEQ ID NO:129)).

FIG. 6A-6E shows the full length amino acid sequences of the human Frz, sFRP, and Ror proteins.

FIGS. 7 (A, B, and C) shows the amino acid sequences of several Wnt antagonist chimeric constructs (Frz1-Fc (SEQ ID NO: 76), Frz2-Fc (SEQ ID NO: 77), Frz3-Fc (SEQ ID NO: 78), Frz4-Fc (SEQ ID NO: 79), Frz5-Fc (SEQ ID NO: 75), Frz6-Fc (SEQ ID NO: 80), Frz7-Fc (SEQ ID NO: 81), Frz8-Fc (SEQ ID NO: 74), Frz9-Fc (SEQ ID NO: 82), Frz10-Fc (SEQ ID NO: 83), sFRP1-Fc (SEQ ID NO: 84), sFRP2-Fc (SEQ ID NO: 85), sFRP3-Fc (SEQ ID NO: 86), sFRP4-Fc (SEQ ID NO: 87), and sFRP5-Fc (SEQ ID NO: 88)). The bold text for Frz1-Fc (first 28 N-terminal amino acid residues), Frz2-Fc (first 31 N-terminal amino acid residues), Frz3-Fc (first 31 N-terminal amino acid residues), Frz4-Fc (first 31 N-terminal amino acid residues) Frz5-Fc (first 31 N-terminal amino acid residues), and sFRP3-Fc (first 31 N-terminal amino acid residues) indicates a non-native leader sequence. The linker is underlined and the Fc domain, following the linker, is shown in italics.

FIG. 8 shows an alignment of Frizzled extracellular domains where black shows conserved residues across all receptors and gray represents residues conserved across homologous groups.

FIG. 11 show a comparison of serum stability of the two different Frz8-Fc chimeras Frz8(173)-Fc and Frz (156)-Fc.

FIG. 13 shows pharmacokinetic (PK) data for Frz8-Fc following administration of a single dose of the protein. FIG. 13A is an immunoblot of a neat serum from mice treated with Frz8-Fc showing detection in serum at 7 days and beyond from both 20 or 5 mg/kg I.V. or 20 mg/kg I.P. FIGS. 13B and 13C are a graphical summary of Frz8-Fc serum levels as determined from the pharmacokinetic study. FIG. 13D is a summary of the parameters for a biphasic model of Frz8-Fc pharmacokinetics.

FIG. 14 demonstrate the enhanced ability of Frz8-ECD to block Wnt3a signaling when linked to a dimeric Fc domain. FIG. 14B is a gel confirming the purity of the isolated Frz8(156) CRD (ECD). Shown are: (a) non-reduced Frz8 ECD (Lane 1); (b) molecular weight markers (Lane 2); and reduced Frz8 ECD (Lane 3).

FIG. 15 demonstrates direct binding of Wnt3a to the Frz8-Fc chimera. FIG. 15B is an immunoprecipitation of a purified soluble Wnt3a by immobilized Frz8-Fc.

FIG. 16 demonstrates direct binding of several Frz-Fc chimeras to Wnt ligands as measured using the OCTET™ system.

FIG. 19 shows the effect of Frz8-Fc on expression of Wnt-target genes in cultured teratoma cells and tumor xenografts.

FIG. 20 shows the accession number and sequence of primers and probes used for real-time quantitative PCR analysis of gene expression shown in FIG. 19 (Example 9).

FIG. 22 illustrates the efficacy of Frz8-Fc against MMTV-Wnt tumor transplants in athymic nude mice by intraperitoneal (IP) dosing.

FIG. 23 illustrates the efficacy of Frz8-Fc against MMTV-Wnt tumor transplant in athymic nude mice by intravenous (IV) dosing. FIG. 23B is a tabular summary of mean tumor volume and mean % change in tumor volume over time in the four treatment groups.

FIG. 26 demonstrates the anti-tumor efficacy of Frz8 (156)-Fc treatment on the growth of NTera2 tumor xenografts in athymic nude mice. FIG. 26A is procedural flow chart, while FIGS. 26D and 26E are tabular summaries of mean tumor volume and mean % change in tumor volume, respectively.

FIG. 28 shows the anti-tumor efficacy of Frz8 (156)-Fc treatment on the growth of PA-1 tumor xenografts in athymic nude mice. FIG. 28A is a procedural flow chart, while FIGS. 28D and 28E are tabular summaries of mean tumor volume and mean % change in tumor volume, respectively.

FIG. 31 shows immunohistochemistry (IHC) photomicrographs for IHC staining of β-catenin and demonstrate that Frz8-Fc treatment on regenerative tissues such as intestine and skin appear normal.

FIG. 32 is an illustration of active Wnt signaling in human breast cancer.

DETAILED DESCRIPTION OF THE INVENTION

I. Definitions

Figure 1:
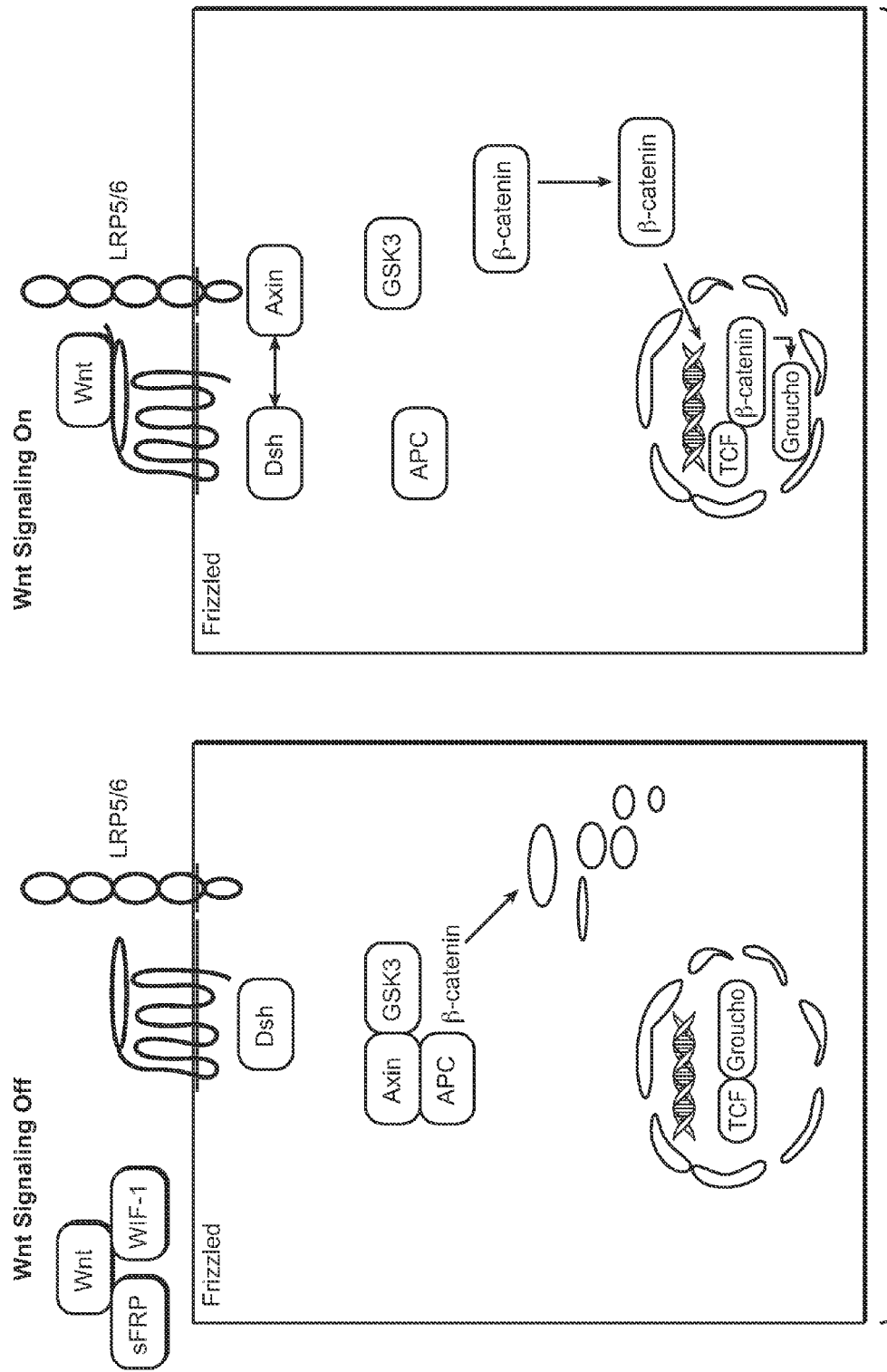
FIG. 1 is an abbreviated summary of the canonical Wnt signaling pathway both in the "off" or inactive state as well as the "on" or active state.
Figure 2:
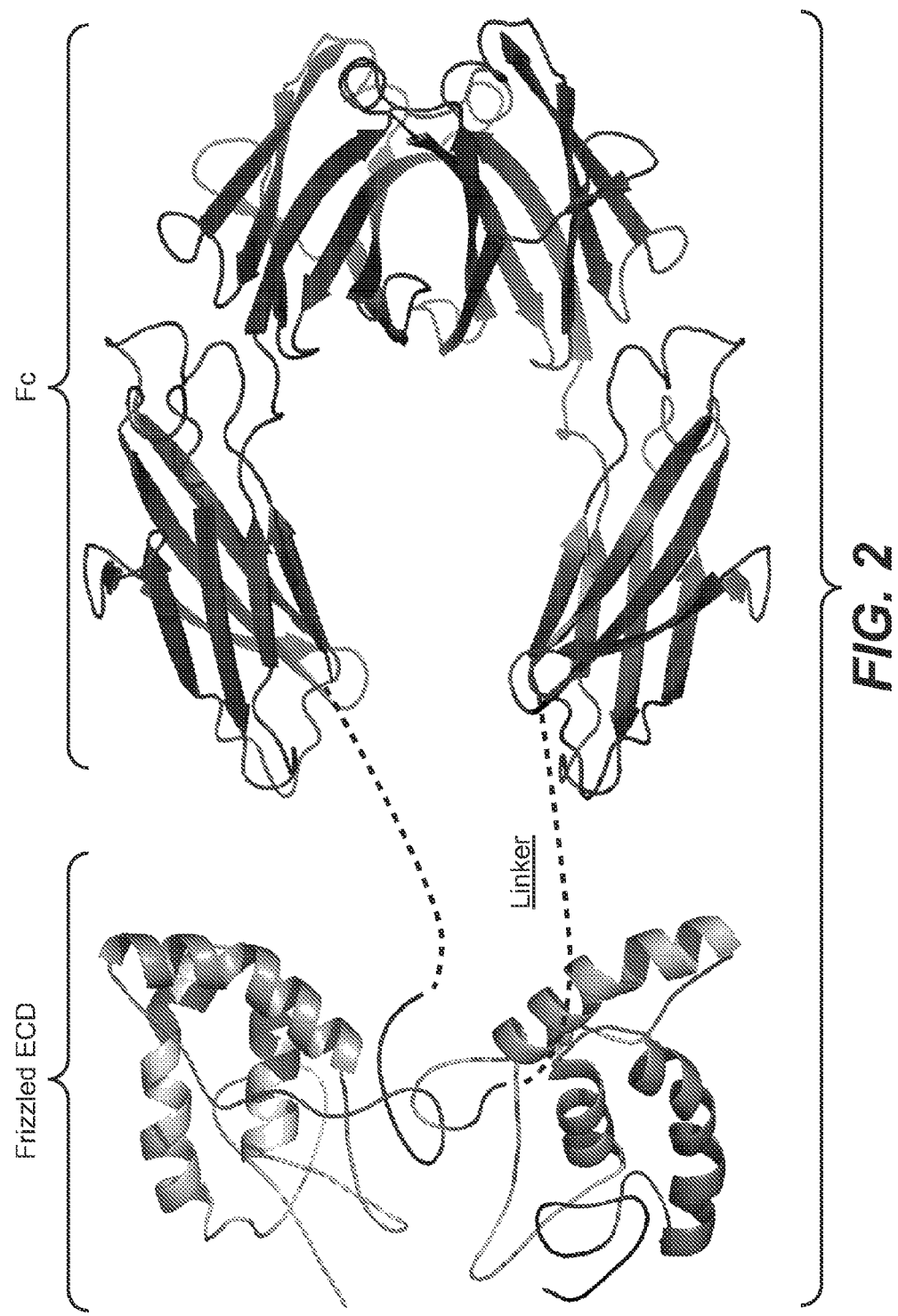
FIG. 2 is a schematic diagram representing a Frizzled extracellular domain linked to the Fc region of a human immunoglobulin domain.

A "Wnt protein" is a ligand of the Wnt signaling pathway component which binds to a Frizzled receptor so as to activate Wnt signaling. Specific examples of Wnt proteins include at least 19 members, including: Wnt-1 (RefSeq.: NM_005430), Wnt-2 (RefSeq.: NM_003391), Wnt-2B (Wnt-13) (RefSeq.: NM_004185), Wnt-3 (ReSeq.: NM_030753), Wnt3a (RefSeq.: NM_033131), Wnt-4 (RefSeq.: NM_030761), Wnt-5A (RefSeq.: NM_003392), Wnt-5B (RefSeq.: NM_032642), Wnt-6 (RefSeq.: NM_006522), Wnt-7A (RefSeq.: NM_004625), Wnt-7B (RefSeq.: NM_058238), Wnt-8A (RefSeq.: NM_058244), Wnt-8B (RefSeq.: NM_003393), Wnt-9A (Wnt-14) (RefSeq.: NM_003395), Wnt-9B (Wnt-15) (RefSeq.: NM_003396), Wnt-10A (RefSeq.: NM_025216), Wnt-10B (RefSeq.: NM_003394), Wnt-11 (RefSeq.: NM_004626), Wnt-16 (RefSeq.: NM_016087)). While each member has varying degrees of sequence identity, each contain 23-24 conserved cysteine residues which show highly conserved spacing. McMahon, A P et al, Trends Genet. 8: 236-242 (1992); Miller J R., *Genome Biol.* 3(1): 3001.1-3001.15 (2002). For purposes of this invention, a Wnt protein and active variants thereof is a protein that binds to a Frizzled ECD or the CRD component of such an Frz ECD.

A "Frizzled" (Frz) protein is a Wnt signaling pathway component that is a seven-pass transmembrane receptors that binds to a Wnt protein, and further complexes with other membrane—associated Wnt signaling components, so as to transmit Wnt signaling to downstream intracellular components. Frz proteins include Frz1, Frz2, Frz3, Frz4, Frz5, Frz6, Frz7, Frz8, Frz9, and Frz10. Examples of human full length Frz proteins are hFrz1 (NP_003496) (SEQ ID NO: 1), hFrz2 (NP_001457) (SEQ ID NO: 2), hFrz3 (NP_059108) (SEQ ID NO: 3), hFrz4 (NP_036325) (SEQ ID NO: 4), hFrz5 (NP_003459) (SEQ ID NO: 5), hFrz6 (NP_003497) (SEQ ID NO: 6), hFrz7 (NP_003498) (SEQ ID NO: 7), hFrz8 (NP_114072) (SEQ ID NO: 8), hFrz9 (NP_003499) (SEQ ID NO: 9), and hFrz10 (NP_009128) (SEQ ID NO: 10) (FIGS. 6A-6C).

A "secreted Frizzled related protein" (sFRP) is a Wnt signaling pathway component that is a secreted extracellular polypeptide that binds to a Wnt protein. sFRP proteins include sFRP1, sFRP2, sFRP3, sFRP4, and sFRP5. Examples of human full length sFRP proteins are sFRP1 (NP_003003) (SEQ ID NO: 11), sFRP2 (NP_003004) (SEQ ID NO: 12), sFRP3 (NP_001454) (SEQ ID NO: 13), sFRP4 (NP_003005) (SEQ ID NO: 14), and sFRP5 (NP_003006) (SEQ ID NO: 15) (FIGS. 6C-6D).

The "Ror" protein, includes the mammalian homologs, Ror1 and Ror2, which are characterized by extracellular Frizzled-like cysteine-rich domains (CRDs) as well as membrane proximal kringle domains. Ror proteins play crucial roles in developmental morphogenesis and are associated with different components of the cytoskeleton. Ror1 co-localizes with F-actin along stress fibers, while Ror2 partially colocalizes with microtubules. Ror1 and Ror2 share about 58% overall sequence identity. Ror2 associates with the melanoma-associated antigen (MAGE) family protein Dlxin-1 and regulates its intracellular distribution. Ror1 proteins include Ror1 and Ror2. Examples of human full length Ror proteins are hRor1 (NP_005003) (SEQ ID NO: 16), and hRor2 (NP_004551) (SEQ ID NO: 17) (FIGS. 6D-6E).

A "Frz domain component" is a polypeptide derived from a Frz protein, a sFRP protein, a Ror protein, or other protein, that is capable of binding with a Wnt protein. A polypeptide "derived from" a protein means a polypeptide that has an amino acid sequence that can be found within the reference protein sequence or within the sequence of active variants of the protein. Examples of a Frz domain component include a minimal cysteine rich domain (CRD) of an extracellular domain "CRD (ECD)" of a Frz protein, a sFRP protein, or a Ror protein, such as the CRD (ECD) of Frz1, Frz2, Frz3, Frz4, Frz5, Frz6, Frz7, Frz8, Frz9, Frz10, sFRP1, sFRP2, sFRP3, sFRP4, sFRP5, Ror1, or Ror2, and active variants thereof. The CRD (ECD) is a conserved structural motif of 100 to 250 amino acids and is defined by 10 highly conserved cysteines. Particular examples of human CRD (ECD)s are shown in boxed text in FIG. 3B and presented as SEQ ID NOs: hFrz1 (SEQ ID NO: 18), hFrz2 (SEQ ID NO: 19), hFrz3 (SEQ ID NO: 20), hFrz4 (SEQ ID NO: 21), hFrz5 (SEQ ID NO: 22), hFrz6 (SEQ ID NO: 23), hFrz7 (SEQ ID NO: 24), hFrz8 (SEQ ID NO: 25), hFrz9 (SEQ ID NO: 26), hFrz10 (SEQ ID NO: 27), sFRP1 (SEQ ID NO: 28), sFRP2 (SEQ ID NO: 29), sFRP3 (SEQ ID NO: 30), sFRP4 (SEQ ID NO: 31), sFRP5 (SEQ ID NO: 32), hRor1 (SEQ ID NO: 33), and hRor2 (SEQ ID NO: 34).

Figures 3A, 3A-1:
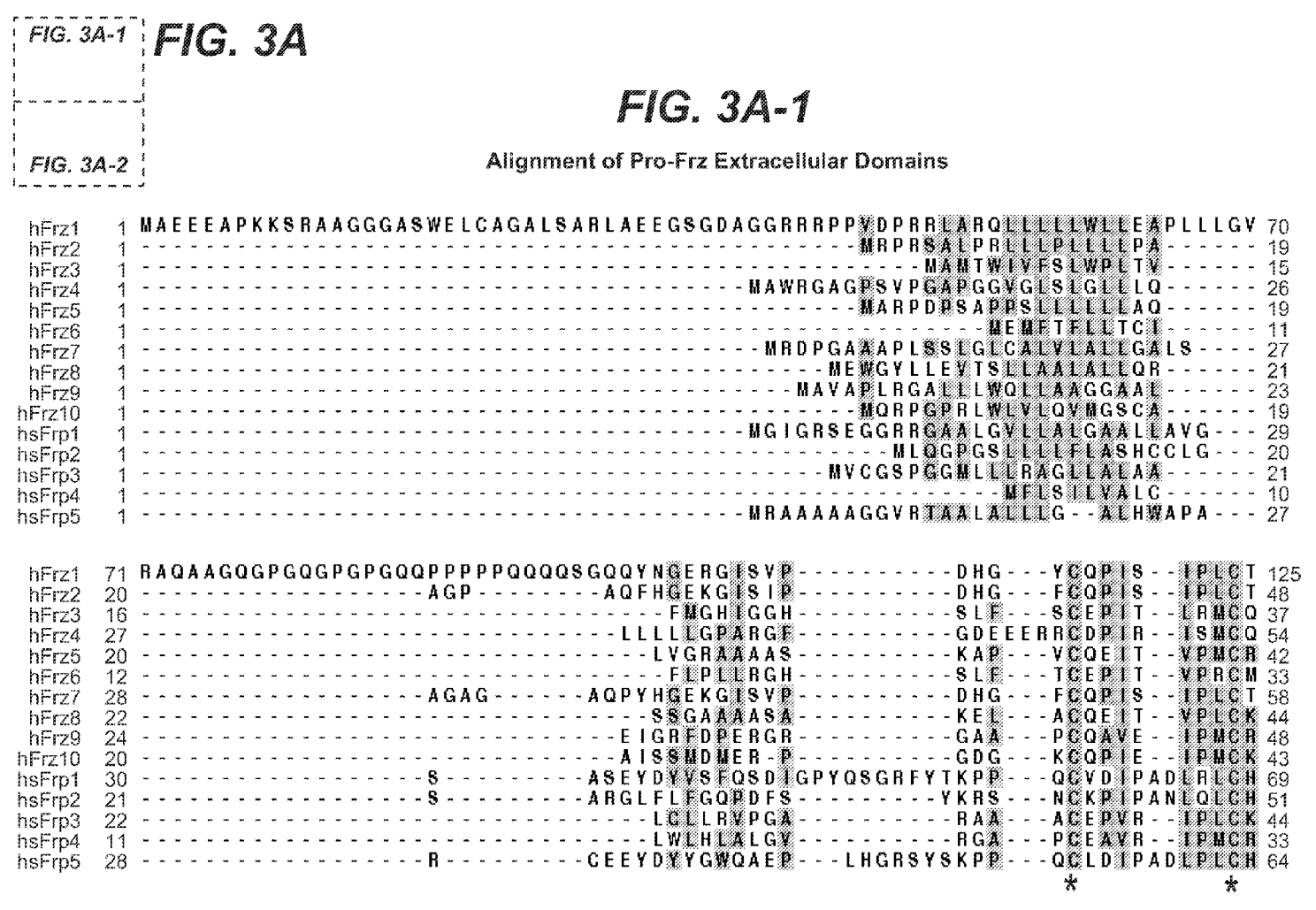
Figure 3A-2:
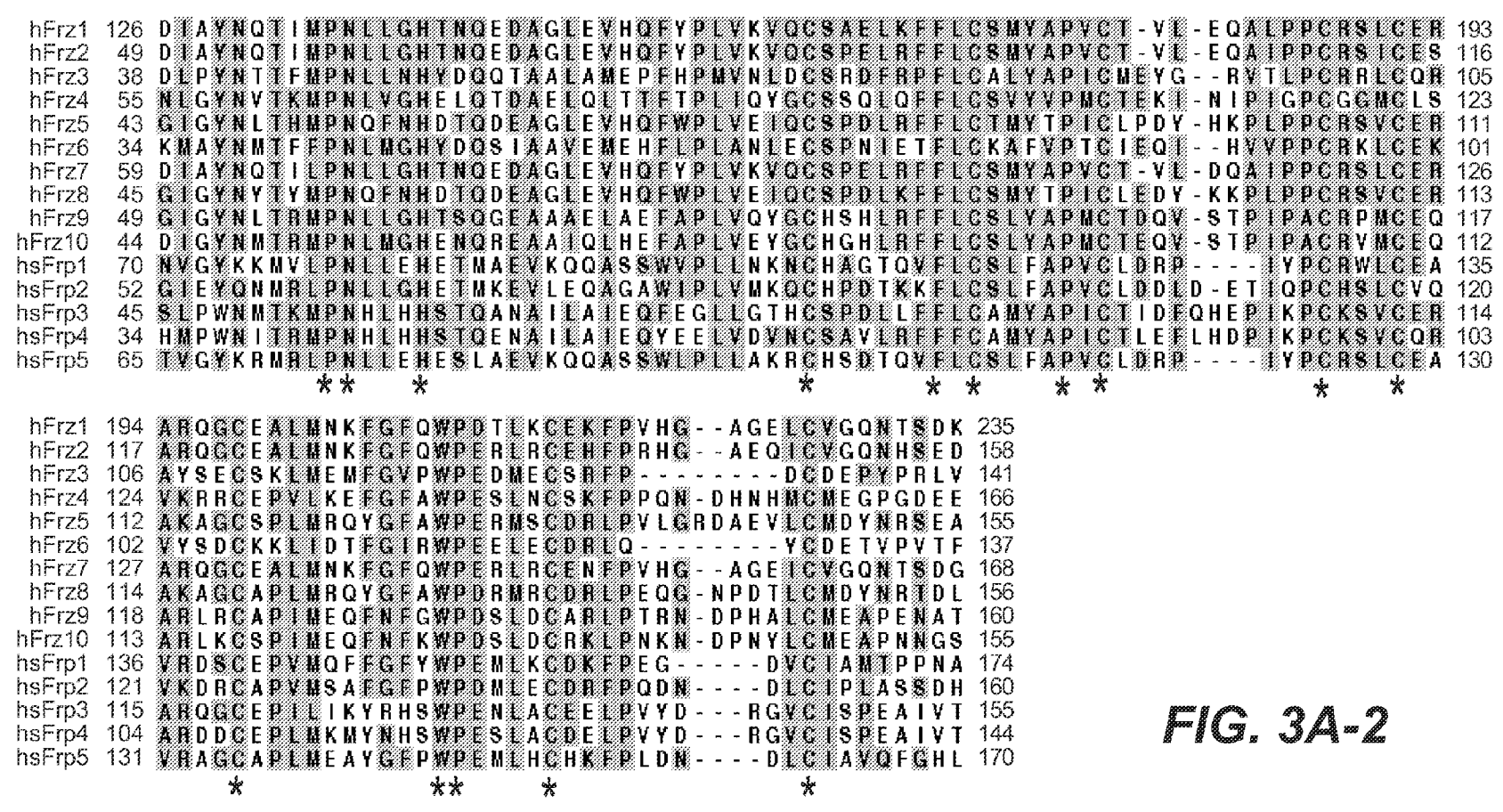
Figure 3B-2:
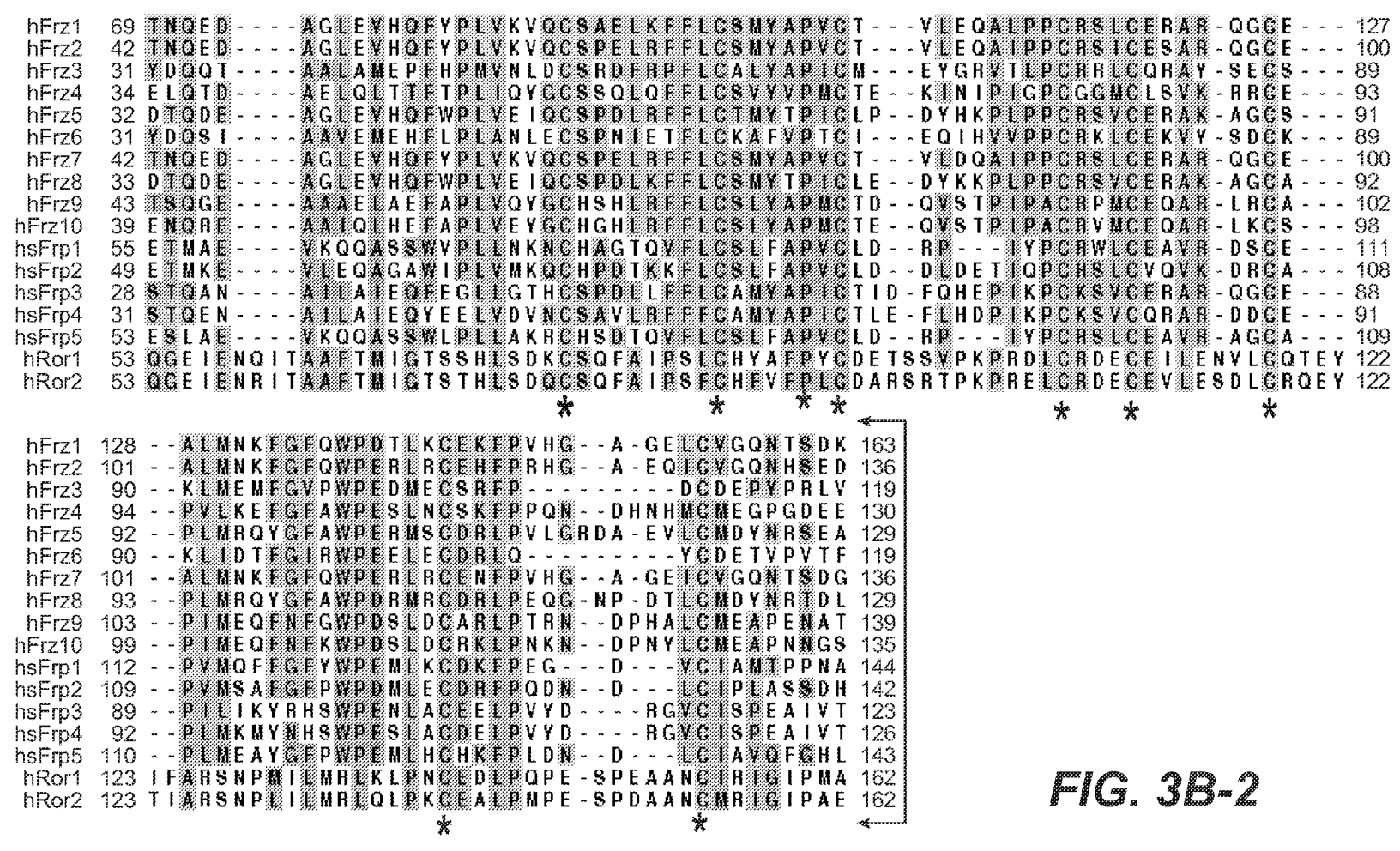
Figures 1, 31A:
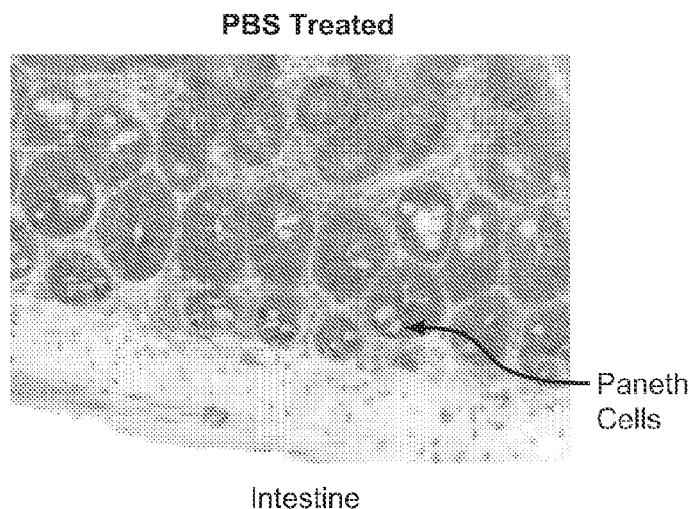
FIG. 31A shows IHC for β-catenin in small intestine of PBS (A-1) control protein (A-2) and Frz8-Fc (A-3) treated mice.
Figures 2, 31A:
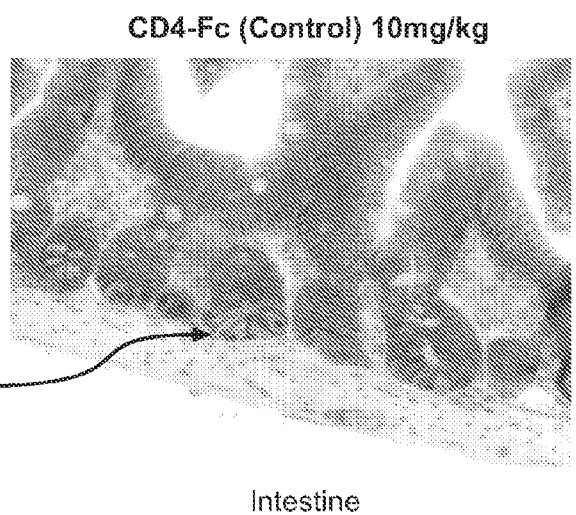
Figures 3, 31A:
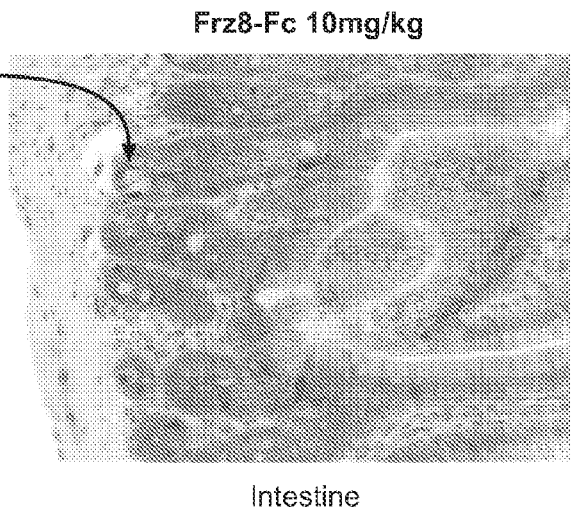
FIG. 3 is an alignment of the 17 known Frizzled protein extracellular domains.

Additional examples of a Frz domain component include a pro-Frz domain derived from a pro-Frz or pro-sFRP protein such as Frz1, Frz2, Frz3, Frz4, Frz5, Frz6, Frz7, Frz8, Frz9, Frz10, sFRP1, sFRP2, sFRP3, sFRP4, or sFRP5, and active variants thereof. Particular examples of human pro-Frz domains are shown in FIG. 3A and presented as SEQ ID NOs: hFrz1 (SEQ ID NO: 35), hFrz2 (SEQ ID NO: 36), hFrz3 (SEQ ID NO: 37), hFrz4 (SEQ ID NO: 38), hFrz5 (SEQ ID NO: 39), hFrz6 (SEQ ID NO: 40), hFrz7 (SEQ ID NO: 41), hFrz8 (SEQ ID NO: 42), hFrz9 (SEQ ID NO: 43), hFrz10 (SEQ ID NO: 44), sFRP1 (SEQ ID NO: 45), sFRP2 (SEQ ID NO: 46), sFRP3 (SEQ ID NO: 47), sFRP4 (SEQ ID NO: 48), and sFRP5 (SEQ ID NO: 49).

Additional examples of a Frz domain component include a mature Frz domain derived from a mature Frz, sFRP, or Ror protein, such as Frz1, Frz2, Frz3, Frz4, Frz5, Frz6, Frz7, Frz8, Frz9, Frz10, sFRP1, sFRP2, sFRP3, sFRP4, sFRP5, Ror1, or Ror2 and active variants thereof. Particular examples of human mature Frz domains are shown in FIG. 3B and presented as SEQ ID NOs: hFrz1 (SEQ ID NO: 50), hFrz2 (SEQ ID NO: 51), hFrz3 (SEQ ID NO: 52), hFrz4 (SEQ ID NO: 53), hFrz5 (SEQ ID NO: 54), hFrz6 (SEQ ID NO: 55), hFrz7 (SEQ ID NO: 56), hFrz8 (SEQ ID NO: 57), hFrz9 (SEQ ID NO: 58), hFrz10 (SEQ ID NO: 59), sFRP1 (SEQ ID NO: 60), sFRP2 (SEQ ID NO: 61), sFRP3 (SEQ ID NO: 62), sFRP4 (SEQ ID NO: 63), sFRP5 (SEQ ID NO: 64), hRor1 (SEQ ID NO: 65), and hRor2 (SEQ ID NO: 66).

A "Wnt antagonist" is a chimeric polypeptide comprising a Frz domain component and an immunoglobulin Fc domain that binds to a Wnt protein and is active by attenuating cellular Wnt signaling, or a physiological symptom resulting therefrom.

In certain embodiments, the Fc domain is a human IgG1, IgG2, IgG3 or IgG4 Fc domain. In one embodiment, the Fc domain is a human IgG1 Fc domain. Specific examples of Fc domains are shown in FIGS. 4, 5, and FIG. 7 and in SEQ ID NO: 67 and SEQ ID NO: 68.

In some embodiments, the Frz domain component and the Fc domain are fused by a linker. The term "linker" refers to a component that tethers together the Frz domain component to the Fc domain. Linkers that are suitable for use in the invention exhibit minimal or no interference with expression, secretion and folding of the protein domains of the Wnt antagonist molecules and provide minimal or no interference with either the effector function of the Fc domain or Wnt protein interaction function of the Frz domain (e.g., binding to a Wnt protein) through steric or other means. In particular embodiments, the linker is short peptide sequence. A linker sequence may also include additional amino acid residues from either the Frz domain component or Fc domain outside the minimal residues needed for activity. Preferred linkers will also provide for good serum stability and are resistant to protease cleavage. Specific examples of useful linkers appear in FIG. 4, FIG. 5, and FIG. 7, including the sequences ESGGGGVT (SEQ ID NO: 69), LESGGGGVT (SEQ ID NO: 70), GRAQVT (SEQ ID NO: 71), WRAQVT (SEQ ID NO: 72), and ARGRAQVT (SEQ ID NO: 73). As noted above, these linkers may include additional amino acid residues from either the Frz domain component or the Fc domain outside the minimal residues needed for activity. These linkers may also comprise additional amino acid residues other than those from the Frz domain component or Fc domain component.

A "Wnt signaling pathway component" is a component that transduces a signal originating from an interaction between a Wnt protein and an Frz receptor. As the Wnt signaling pathway is complex, and involves extensive feedback regulation, there are numerous and likely not yet discovered members of the Wnt signaling pathway. Example Wnt signaling pathway components include the membrane associated proteins LRP5 and LRP6, Axin, and Dishevelled, the extracellular Wnt interactive proteins sFRP, WIF-1, the LRP inactivating proteins Dkk and Krn, the cytoplasmic protein β-catenin, members of the β-catenin "degradation complex" APC, GSK3β, CKIα and PP2A, the nuclear transport proteins APC, pygopus and bcl9/legless, and the transcription factors TCF/LEF, Groucho and various histone acetylases such as CBP/p300 and Brg-1.

A "Wnt-mediated disorder" is a disorder, condition, or disease state characterized by aberrant Wnt signaling. In a specific aspect, the aberrant Wnt signaling is a level of Wnt signaling in a cell or tissue suspected of being diseased that exceeds the level of Wnt signaling in a similar non-diseased cell or tissue. In a specific aspect, a Wnt-mediated disorder includes cancer.

The term "cancer" refers to the physiological condition in mammals that is typically characterized by unregulated cell growth/proliferation. Examples of cancer include, but are not limited to: carcinoma, lymphoma, blastoma, and leukemia. More particular examples of cancers include, but are not limited to: chronic lymphocytic leukemia (CLL), lung, including non small cell (NSCLC), breast, ovarian, cervical, endometrial, prostate, colorectal, intestinal carcinoid, bladder, gastric, pancreatic, hepatic (hepatocellular), hepatoblastoma, esophageal, pulmonary adenocarcinoma, mesothelioma, synovial sarcoma, osteosarcoma, head and neck squamous cell carcinoma, juvenile nasopharyngeal angiofibromas, liposarcoma, thyroid, melanoma, basal cell carcinoma (BCC), medulloblastoma and desmoid.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

An "active" polypeptide, variant polypeptide, or fragments thereof, retain a biological activity of native or naturally-occurring component of the active polypeptide. Biological activity refers to a function mediated by the native or naturally-occurring counterpart of the active polypeptide. For example, binding or a protein-protein interaction constitutes a biological activity. In a specific sense, an active Wnt signaling pathway component is one which can effectively transduce a signal through interaction with other Wnt signaling pathway components. In another specific sense, an active Wnt antagonist is one which detectably attenuates Wnt signaling or a physiological condition resulting therefrom, relative to the level prior to administration of the Wnt antagonist.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"High stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" refers to a polypeptide that is fused to a "tag polypeptide." The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues). Example epitope tag sequences include HA, GD, c-myc, poly-His and FLAG.

"Treating" or "treatment" or "alleviation" refers to both therapeutic treatment and prophylactic or preventative measures, wherein the object is to prevent or slow down (lessen) the targeted pathologic disease or condition or disorder. Those in need of treatment include those already with the disorder as well as those prone to having the disorder or those in whom the disorder is to be prevented (prophylaxis). When the Wnt-mediated disorder is cancer, a subject or mammal is successfully "treated" or shows a reduced tumor burden if, after receiving a therapeutic amount of a Wnt antagonist according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the Wnt antagonist may prevent growth and/or kill existing cancer cells, it may be cytostatic and/or cytotoxic. Reduction of these signs or symptoms may also be felt by the patient.

The above parameters for assessing successful treatment and improvement in the disorder are readily measurable by routine procedures familiar to a physician. For cancer therapy, efficacy can be measured, for example, by assessing the time to disease progression (TDP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

"Chronic" administration refers to administration of the agent(s) in a continuous mode as opposed to an acute mode, so as to maintain the initial therapeutic effect (activity) for an extended period of time. "Intermittent" administration is treatment that is cyclic, or subject to periodic interruptions, as opposed to continuous or consecutive.

"Mammal" refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

An "effective amount" of a Wnt antagonist is an amount sufficient to carry out a specifically stated purpose. An "effective amount" may be determined empirically and in a routine manner, in relation to the stated purpose.

The term "therapeutically effective amount" refers to an amount of a Wnt antagonist effective to "treat" a Wnt-mediated disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

A "growth inhibitory amount" of a Wnt antagonist is an amount capable of inhibiting the growth of a cell, especially tumor, e.g., cancer cell, either in vitro or in vivo. A "growth inhibitory amount" of a Wnt antagonist for purposes of inhibiting neoplastic cell growth may be determined empirically and in a routine manner.

A "cytotoxic amount" of a Wnt antagonist is an amount capable of causing the destruction of a cell, especially tumor, e.g., cancer cell, either in vitro or in vivo. A "cytotoxic amount" of a Wnt antagonist for purposes of inhibiting neoplastic cell growth may be determined empirically and in a routine manner.

The terms "antibody" and "immunoglobulin" are used interchangeably, and in the broadest sense, including monoclonal antibodies (e.g., full length or intact monoclonal antibodies), polyclonal antibodies, multivalent antibodies, multispecific antibodies (e.g., bispecific antibodies exhibiting the desired biological activity) and may also include certain antibody fragments, as described herein in greater detail. An antibody can be chimeric, human, humanized or affinity matured.

The light chain from any vertebrate species can be assigned to one of two clearly distinct types, called kappa (κ) and lambda (λ), based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2. The subunit structures and three-dimensional configurations of different classes of immunoglobulins are well known and described generally in, for example, Abbas et al, Cellular and Molecular Biology, 4$^{th}$ Ed. (2000). An antibody may be part of a larger fusion molecule, formed by covalent or non-covalent associated of the antibody with one or more other proteins or peptides.

"Antibody fragments" comprise a portion of an intact antibody, preferably the antigen binding or variable region of the intact antibody. Examples of antibody fragments include Fab, Fab', F(ab')$_2$ and Fv fragments, diabodies, linear antibodies (U.S. Pat. No. 5,641,870); Zapata et al., *Protein Eng.* 8(10): 1057-1062 (1995), single chain antibody molecules and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire light chain along with the variable region domain of the heavy chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both heavy chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association.

The term "monoclonal antibody" as used herein refers to an antibody obtained from a population of substantially homogenous antibodies, i.e. the individual antibodies comprising the population are identical except for possible naturally occurring mutations that may be present in minor amounts. Monoclonal antibodies are highly specific, being directed against a single antigen. In contract to polyclonal antibody preparations that typically include different antibodies directed against different determinants (epitopes), each monoclonal antibody is directed against a single determinant on the antigen.

The term "chimeric" antibody, specifically included within the definition of monoclonal antibody, means antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences derived from another species or belonging to another antibody class or subclass, as well as fragment of such antibodies, so long as they exhibit the desired biological activity U.S. Pat. No. 4,816,567; Morrison et al, *P.N.A.S. USA* 81: 6851-6855 (1984).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al, *Nature* 321:522-525 (1986); Riechmann et al, *Nature* 332: 323-329 (1988); and Presta, *Curr. Op. Struct. Biol* 2:593-596 (1992). See also, Vaswani and Hamilton, *Ann. Allergy, Asthma & Immunol* 1:105-115 (1998); Harris, *Biochem. Soc. Trans.* 23: 1035-1038 (1995); Hurle and Gross, *Curr. Op. Biotech.* 5: 428-433 (1994).

"Polynucleotide" or "nucleic acid" are used interchangeably herein, and refer to polymers of nucleotides of any length, including, but are not limited to DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imported before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example: uncharged linkages (e.g., methyl phosphonates, phosphotriesters, phosphoamidates, carbamates, etc.); charged linkages (e.g., phosphorothioates, phosphorodithioates, etc.); pendant moieties, such as, for example, proteins (e.g., nucleases, toxins, antibodies, signal peptides, poly-L-lysine, etc.); intercalators (e.g., acridine, psoralen, etc.); chelators (e.g., metals, radioactive metals, boron, oxidative metal, etc.), alkylators, modified linkages (e.g., alpha anomeric nucleic acids, etc.). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl, 2'-O-allyl, 2'-fluoro- or 2'-azido-ribose, carbocyclic sugar analogs, α-anomeric sugars, epimeric sugars such as arabinose, xylose or lyxose, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replace by P(O)—S-(thioate), P(S)—S-(dithioate)-, (O)NR$_2$-amidate, P(O)R, P(O)OR', CO or CH$_2$-(formacetal), in which each R or R' is independently H or substituted or unsubstituted C$_{1-20}$ alkyl, optionally containing an ether, aryl, alkenyl, cycloalkenyl or aralkyl linkage. Not all linkages in a polynucleotide need be identical. The preceding description applies to all polynucleotides referred to herein, including RNA and DNA.

The term "peptide" generally refers to a contiguous and relatively short sequence of amino acids linked by peptidyl bonds. Typically, but not necessarily, a peptide has length of about 2 to 50 amino acids, 4-40 amino acids or 10-30 amino acids. Although the term "protein" generally refers to longer forms of a "polypeptide," the two terms can be and are used interchangeably in some contexts herein, and refer to amino acid sequences that are generally longer and perhaps more complex (e.g., multiple sequence, secondary and higher structure).

A "region" of a polypeptide is a contiguous sequence of 2 or more amino acid residues. In alternative embodiments, a region is at least about 3, 5, 10, 15 or more contiguous amino acid residues.

"C-terminal region", "C-terminal sequence" and variations thereof, as used herein, refer to an amino acid sequence that is located at or in close proximity to the C-terminal (generally 3') end. Generally, the sequence includes an amino acid that has a free carboxyl group. In one embodiment, a C-terminal regions or sequence refers to a region of a polypeptide that includes about 1-15 residues located closest to the C-terminus.

"N-terminal region", "N-terminal sequence", and variations thereof, as used herein, refer to an amino acid sequence that is located at or in close proximity to the N-terminal (generally 5') end. Generally, the sequence includes an amino acid that has free amino group. In one embodiment, an N-terminal region or sequence refers to a region of a polypeptide that includes about 1-15 residues located closest to the N terminus of the polypeptide.

"Internal region" or "internal sequence", and variations thereof, refer to an amino acid sequence that is located within a polypeptide and is flanked on both its N- and C-termini by one or more amino acids that are not part of the sequence. Generally, the sequence does not include an amino acid with either a free carboxyl or amino group.

A "ligand" refers to a naturally-occurring or synthetic molecule or moiety that is capable of a binding interaction with a specific site on a protein or other molecule, such as a receptor. A Wnt ligand is a molecule that specifically interacts with a Frizzled receptor. A "receptor" is often, but need not be located on the cell surface or membrane.

A "fusion protein" refers to a polypeptide having two portions covalently linked together, where each of the portions is derived from different proteins. The two portions may be linked directly by a single peptide bond or through a peptide linker containing one or more amino acid residues. Generally, the two portions and the linker will be in reading frame with each other and are produced using recombinant techniques.

A Wnt antagonist that "inhibits the growth of tumor cells" or a "growth inhibitory" Wnt antagonist is one which results in measurable growth inhibition of tumor cells having aberrant Wnt signaling activity. Preferred growth inhibitory Wnt antagonists inhibit growth of tumor cells having aberrant Wnt signaling activity by greater than 20%, preferably from about 20% to about 50%, and even more preferably, by greater than 50% (e.g., from about 50% to about 100%) as compared to the appropriate control, the control typically being cancer cells not treated with the Wnt antagonist molecule being tested. In one embodiment, growth inhibition can be measured at a Wnt antagonist concentration of about 0.1 to 30 µg/ml or about 0.5 nM to 200 nM in cell culture, where the growth inhibition is determined 1-10 days after exposure of the tumor cells to the Wnt antagonist. Growth inhibition of tumor cells in vivo can be determined in various ways such as is described in the Experimental Examples section below. The Wnt antagonist is growth inhibitory in vivo if administration of the Wnt antagonist at about 1 µg/kg to about 100 mg/kg body weight results in reduction in tumor size or cell proliferation within about 5 days to 3 months from the first administration of the antibody, preferably within about 5 to 30 days. In a specific aspect, the tumor size is reduced relative to its size at the start of therapy.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all precancerous and cancerous cells and tissues.

A Wnt antagonist molecule which "induces cell death" is one which causes a viable cell to become nonviable. The cell is one having aberrant Wnt signaling activity as compared to a normal cell of the same tissue type. Preferably, the cell is a cancer cell, as defined herein. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the Wnt antagonist is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells. Preferred cell death-inducing antibodies, oligopeptides or other organic molecules are those which induce PI uptake in the PI uptake assay in BT474 cells.

The word "label" when used herein refers to a detectable compound or composition which is conjugated directly or indirectly to the antibody, oligopeptide or other organic molecule so as to generate a "labeled" antibody, oligopeptide or other organic molecule. The label may be detectable by itself (e.g. radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell, especially a cancer cell having Wnt signaling activity, either in vitro or in vivo. Thus, the growth inhibitory agent may be one which significantly reduces the percentage of such cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3, 6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "package insert" is used to refer to instructions customarily included in commercial packages of therapeutic products, that contain information about the indications, usage, dosage, administration, contraindications and/or warnings concerning the use of such therapeutic products.

II. Description of Specific Embodiments

The Wnt antagonists described herein are capable of binding to Wnt ligands in vitro and are capable of inhibiting or suppressing Wnt stimulated cell signaling. Additionally, the Wnt antagonists have a long in vivo half life and exhibit anti-tumor activity in vivo, inhibiting the growth of Wnt-1 driven tumors in a mouse MMTV breast tumor model. The Wnt antagonists are also capable of inhibiting the growth in mice of tumor xenografts derived from human teratoma cell lines. Regenerative tissues taken from mice that were treated with a Wnt antagonist appear to be within physiological norms. The Wnt antagonists are also capable of inhibiting autocrine Wnt signaling in human tumor cell lines in vitro.

Figure 8:
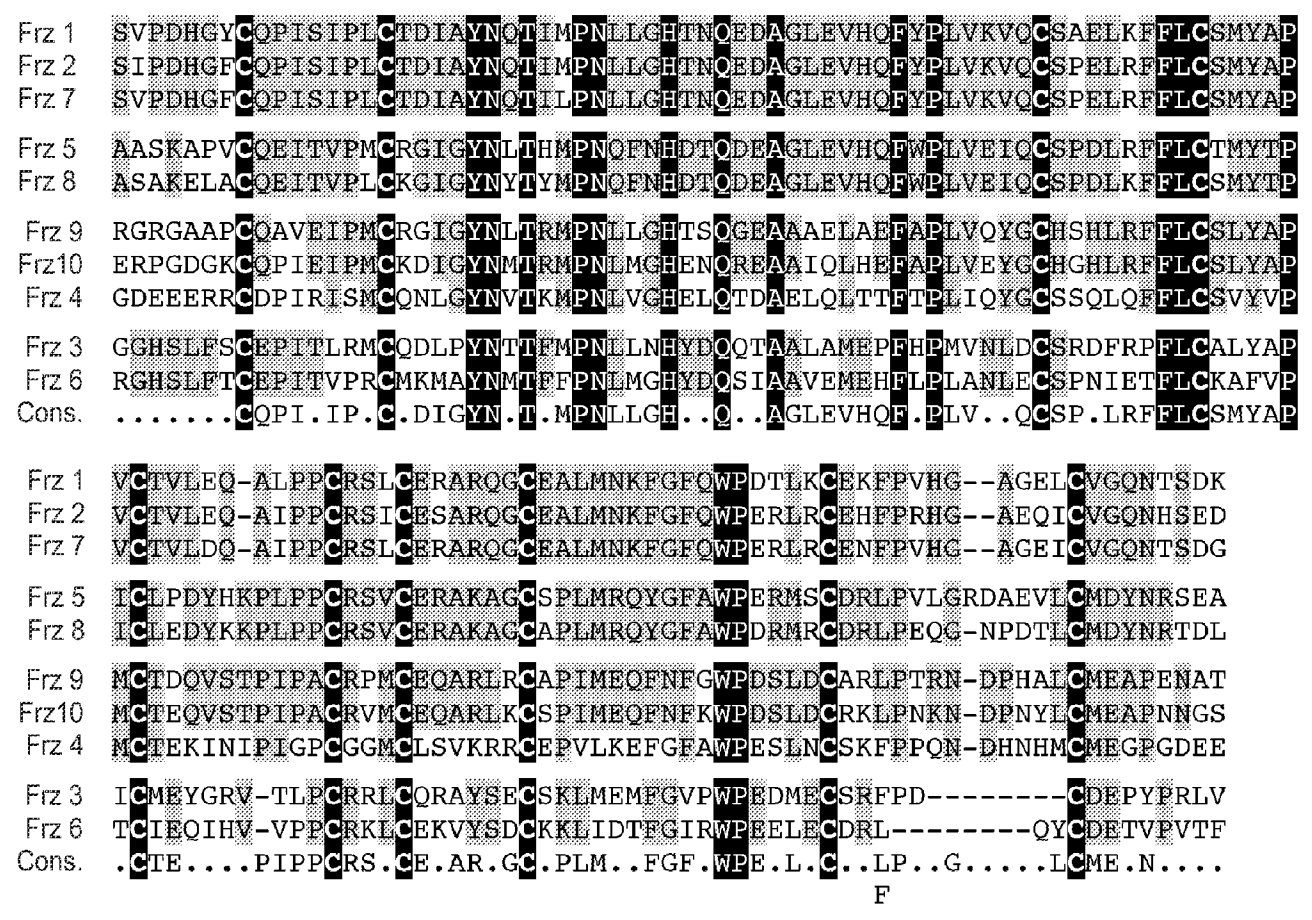
Figure 9:
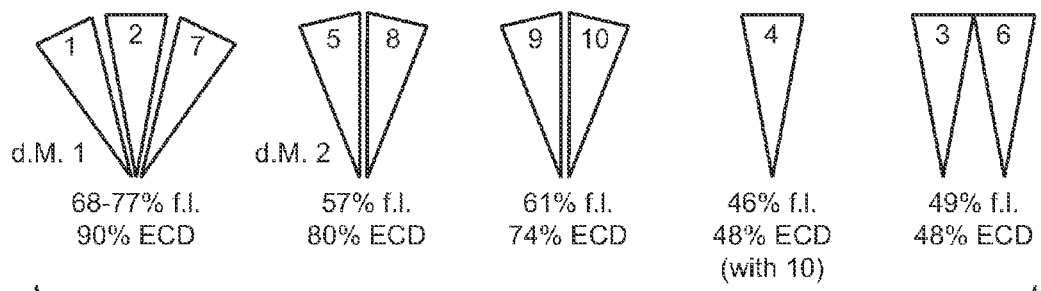
FIG. 9 shows Frizzleds grouped into families based on both full-length and extracellular domain sequence identities.

The Frizzled receptor proteins can be grouped into families based on both full-length and extracellular domain sequence identities. This grouping is illustrated in the alignments shown in FIGS. 8 and 9. The underlined residues in this figure are conserved across all the Frz receptors and the shadowed residues are conserved across homologous groupings. The Frz proteins can be grouped into the following families 1) Frz1, Frz2, and Frz7 having a shared homology of 68-77% for the full length sequence and 90% for the ECD; 2) Frz5 and Frz8 having a shared homology of 57% for the full length sequence and 80% for the ECD; 3) Frz9 and Frz10 having a shared homology of 61% for the full length sequence and 74% for the ECD; 4) Frz3 and Frz6 having a shared homology of 49% for the full length sequence and 50% for the ECD; and 5) Frz4 (which exhibits a shared homology of 46% for the full length sequence and 48% for the ECD with Frz10). The family of Frz1, Frz2, and Frz7 also has significant homology to *Drosophila* Frz1 and the family of Frz5 and Frz8 has significant homology to *Drosophila* Frz2, shown to be responsible for planar cell polarity and Wnt signaling, respectively.

Wnt ligand-Frizzled binding behavior appears to cluster within Frizzled families. Both Wnt3a and Wnt5a bind Frz5, Frz8, and Frz4 fastest relative to the other Frz proteins while Wnt3a binds Frz1, Frz 2, and Frz7 at a slower rate. The amplitude and linear nature of Wnt5a binding behavior is indicative of lower binding affinity, relative to Wnt3a binding, as determined by the OCTET™ binding assay. The presence of both high affinity and low affinity receptors may confer ability for acute and long term signaling.

The ability of the Wnt antagonists to inhibit Wnt ligand induced signaling also appears to cluster within Frizzled families. Both Frz5 and Frz8 show complete inhibition of the Wnt3a signal and significant inhibition of the Wnt5a signal in a cell-based assay (Example 7). Frz4, Frz2, and Frz7 show significant inhibition of the Wnt3a signal. This finding mirrors the observation in *Drosophila* that dFrz2 (with homology to Frz 5 and Frz 8) strongly activates and dFrz1 (with homology to Frz 1, Frz2, and Frz7) can weakly activate the Wnt pathway.

While not being bound to a particular theory of action, the data presented herein indicate that cell-based Wnt signaling inhibition data generated using the Wnt antagonists correlates with data obtained by measuring the direct binding of Wnt ligands to the Wnt antagonists, indicating that the Wnt antagonists bind directly to Wnt ligands thus blocking them from binding the full-length Frizzled receptors on the cell. The data presented herein further provides validation that in vitro activity can be used to predict in vivo Wnt signaling blocking activity of the Wnt antagonists.

As indicated in the studies with Fz8-Fc set forth in the Examples, the Wnt antagonists comprising both a Frizzled domain and an immunoglobulin FC domain surprisingly exhibit increased binding affinity to Wnt ligand over the Frizzled domain alone. For example, FIG. 14 shows that binding affinity increased over two orders of magnitude when the Fz ECD domain was converted to the Fz (156)-Fc construct. The finding of the Fz(156)-Fc construct as a stable and highly efficacious Wnt signaling inhibitor, in which conjugation to Fc resulted in a two order of magnitude increase in binding affinity, was greatly unexpected and non-obvious.

A. Compositions and Methods of the Invention

1. Polypeptides

The present invention is directed toward compositions and methods for the treatment of Wnt-mediated disorders, including cancer, and for inhibiting cellular Wnt signaling. One aspect of the invention provides Wnt antagonists that are chimeric molecules comprising a Frizzled (Frz) domain component and an immunoglobulin Fc domain. In particular embodiments of this aspect, the Frz domain component and Fc domain are fused through a linker. Another aspect provides for use of these Wnt antagonists for inhibiting cellular Wnt signaling and for treatment of Wnt-mediated disorders, such as cancer.

In one aspect, the invention provides for Wnt antagonists that are chimeric molecules with a Frz domain component comprising a minimal cysteine rich domain (CRD) of an extracellular domain "CRD (ECD)". The CRD (ECD) is a conserved structural motif of 100 to 250 amino acids and is defined by 10 highly conserved cysteines. This protein domain appears in two classes of the Wnt signaling family—the integral membrane Wnt receptor proteins known as Frizzled, and the secreted extracellular proteins known as the Frizzled related protein (sFrp).

In one aspect, the invention provides for Wnt antagonists that are chimeric molecules having a Frz domain component comprising a CRD (ECD) of a Frizzled protein such as Frz1, Frz2, Frz3, Frz4, Frz5, Frz6, Frz7, Frz8, Frz9, or Frz10. Examples of such CRD (ECD)s are provided in FIG. 3B. In specific embodiments, the Frz domain component is selected from the group consisting of CRD (ECD)s of hFrz1 (SEQ ID NO: 18), hFrz2 (SEQ ID NO: 19), hFrz3 (SEQ ID NO: 20), hFrz4 (SEQ ID NO: 21), hFrz5 (SEQ ID NO: 22), hFrz6 (SEQ ID NO: 23), hFrz7 (SEQ ID NO: 24), hFrz8 (SEQ ID NO: 25), hFrz9 (SEQ ID NO: 26), and hFrz10 (SEQ ID NO: 27), and active variants thereof.

Alternatively, the Frz domain component comprises, for example, a CRD (ECD) from a secreted Frizzled related protein (sFRP) such as sFRP1, sFRP2, sFRP3, sFRP4, or sFRP5. Examples of such CRD (ECD)s are provided in FIG. 3B. In specific embodiments, the Frz domain component is selected from the group consisting CRD (ECD)s of sFRP1 (SEQ ID NO: 28), sFRP2 (SEQ ID NO: 29), sFRP3 (SEQ ID NO: 30), sFRP4 (SEQ ID NO: 31), sFRP5 (SEQ ID NO: 32), and active variants thereof.

Alternatively, the Frz domain component comprises, for example, a CRD (ECD) of the receptor tyrosine kinases Ror1 and Ror2. Examples of such CRD (ECD)s are provided in FIG. 3B. In specific embodiments, the Frz domain component is selected from the group consisting of CRD (ECD)s of hRor1 (SEQ ID NO: 33), and hRor2 (SEQ ID NO: 34), and active variants thereof.

In another aspect, the Frz domain component is a pro-Frz or pro-sFrp sequence, examples of which are shown in FIG. 3A. In specific embodiments, the Frz domain component is selected from the group consisting of hFrz1 (SEQ ID NO: 35), hFrz2 (SEQ ID NO: 36), hFrz3 (SEQ ID NO: 37), hFrz4 (SEQ ID NO: 38), hFrz5 (SEQ ID NO: 39), hFrz6 (SEQ ID NO: 40), hFrz7 (SEQ ID NO: 41), hFrz8 (SEQ ID NO: 42), hFrz9 (SEQ ID NO: 43), hFrz10 (SEQ ID NO: 44), sFRP1 (SEQ ID NO: 45), sFRP2 (SEQ ID NO: 46), sFRP3 (SEQ ID NO: 47), sFRP4 (SEQ ID NO: 48), and sFRP5 (SEQ ID NO: 49), and active variants thereof.

In yet another aspect, the Frz domain component is derived from a mature Frz, sFRP or hRor sequence, examples of which are shown in FIG. 3B. In specific embodiments, the Frz domain component is selected from the group consisting of hFrz1 (SEQ ID NO: 50), hFrz2 (SEQ ID NO: 51), hFrz3 (SEQ ID NO: 52), hFrz4 (SEQ ID NO: 53), hFrz5 (SEQ ID NO: 54), hFrz6 (SEQ ID NO: 55), hFrz7 (SEQ ID NO: 56), hFrz8 (SEQ ID NO: 57), hFrz9 (SEQ ID NO: 58), hFrz10 (SEQ ID NO: 59), sFRP1 (SEQ ID NO: 60), sFRP2 (SEQ ID NO: 61), sFRP3 (SEQ ID NO: 62), sFRP4 (SEQ ID NO: 63), sFRP5 (SEQ ID NO: 64), hRor1 (SEQ ID NO: 65), and hRor2 (SEQ ID NO: 66), and active variants thereof.

In particular embodiments, the Frz domain component and the immunoglobulin Fc domain of the chimeric Wnt antagonist molecules are fused through a linker. In one embodiment, the linker is a peptide linker. In another embodiment, the linker is selected from the group consisting of ESGGGGVT (SEQ ID NO: 69), LESGGGGVT (SEQ ID NO: 70), GRAQVT (SEQ ID NO: 71), WRAQVT (SEQ ID NO: 72), and ARGRAQVT (SEQ ID NO: 73). Optionally, the linkers may include additional amino acid residues from either the Frz domain component or the Fc domain outside the minimal residues needed for activity. These linkers may also comprise additional amino acid residues other than those from the Frz domain component or Fc domain component.

In one embodiment, the Wnt antagonist is Frz8-Fc chimera comprising a Frz8 CRD (ECD) and a Fc domain. In some embodiments, the Frz8-Fc chimera further comprises a linker, such as a peptide linker. In a further embodiment, the Frz8-Fc further comprises a leader sequence. In a particular embodiment, the Frz domain component comprises amino acids 1-156 of the Frz8 protein (SEQ ID NO: 8). In another embodiment, the Fc component is a human Fc. In a further embodiment, the Fc component is a human IgG Fc. In yet a further embodiment, the Frz8-Fc has a Frz domain component comprising amino acids 1-156 of the Frz8 protein fused with a linker to a human IgG Fc. In a further embodiment, the Frz8-Fc is a chimera with the amino acid sequence as shown in FIG. 4B (SEQ ID NO: 74). As used in the Examples and accompanying Figures, unless otherwise noted, "Frz8-Fc" refers to the chimera shown in FIG. 4B (SEQ ID NO: 74).

In a further embodiment, the Wnt antagonist is Frz5-Fc chimera comprising a Frz5 CRD (ECD) and a Fc domain. In some embodiments, the Frz5-Fc chimera further comprises a linker, such as a peptide linker. In a further embodiment, the Frz5-Fc further comprises a leader sequence. In a particular embodiment, the Frz domain component comprises amino acids 27-155 of the Frz5 protein (SEQ ID NO: 5). In another embodiment, the Fc component is a human Fc. In a further embodiment, the Fc component is a human IgG Fc. In yet a further embodiment, the Frz5-Fc has a leader sequence and a Frz domain component comprising amino acids 27-155 of a mature Frz5 protein fused with a linker to a human IgG Fc. In a further embodiment, the Frz5-Fc is a chimera with the amino acid sequence as shown in FIG. 7A (SEQ ID NO: 75). As used in the Examples and accompanying Figures, unless otherwise noted, "Frz5-Fc" refers to the chimera shown in FIG. 7A (SEQ ID NO: 75).

Similarly, further embodiments include Frz1-Fc, Frz2-Fc, Frz3-Fc, Frz4-Fc, Frz6-Fc, Frz7-Fc, Frz9-Fc, Frz-10-Fc, sFRP1-Fc, sFRP2-Fc, sFRP3-Fc, sFRP4-Fc and sFRP5-Fc chimeras comprising a Frz domain component comprising a Frz CRD (ECD) from each respective Frz or sFRP protein and a Fc component. In some embodiments, the Frz-Fc chimera further comprises a linker, such as a peptide linker. In further embodiments, these chimeras comprise a leader sequence. In some embodiments, the Fc component is a human Fc. In further embodiments, the Fc component is a human IgG Fc. In yet further embodiments, these chimeras have a leader sequence and a Frz CRD (ECD) fused with a linker to a human IgG Fc. In further embodiment, these chimeras have the amino acid sequences as shown in FIGS. 7A, 7B and 7C (SEQ ID NOs: 76-88). As used in the Examples and accompanying Figures, unless otherwise noted, "Frz1-Fc, Frz2-Fc, Frz3-Fc, Frz4-Fc, Frz6-Fc, Frz7-Fc, Frz9-Fc, Frz-10-Fc, sFRP1-Fc, sFRP2-Fc, and sFRP4-Fc" refer to the respective chimeras shown in FIGS. 7A, 7B and 7C (SEQ ID NOs: 76-85, and 87).

The Wnt antagonists are stable in vivo. Prior constructs utilizing a Frizzled domain attached to a Fc component were rapidly degraded in vivo making them unsuitable for use as therapeutic compounds (Hsieh, J.-C. et al., PNAS, 96: 3546-3551 (1999)). The Wnt antagonists described herein remain stable in vivo for substantially longer than the prior constructs. As shown in Example 4 (FIG. 13), the Frz8-Fc Wnt antagonist displayed an in vivo half-life of about 4 days. Accordingly, the invention provides for Wnt antagonists that have an in vivo half-life of at least 1 day, 2 days, 3 days, or 4 days after being administered to a mammal.

Furthermore, as shown in Example 3 (FIG. 11), the Wnt antagonists retain activity in vivo for substantially longer than the prior constructs. In one embodiment, the Wnt antagonist is active for at least 30 minutes, 1 hour, 2 hours, 3 hours, 4 hours, 5 hours, 6 hours, 8 hours, 10 hours, 12 hours, 14 hours, 16 hours, 18 hours, 20 hours, 22 hours, 24 hours, 30 hours, 36 hours, 40 hours, 44 hours, 48 hours, 52 hours, 56 hours, 60 hours, 64 hours, 68 hours, 72 hours, 80 hours, 90 hours, or 100 hours after being administered to a mammal. Activity is measured, for example, by testing the serum of the mammal administered the Wnt antagonist for the ability to inhibit Wnt signaling as set forth in Examples 3 and 11, or by using other methods known in the art.

2. Nucleic Acids

One aspect of the invention provides for a nucleic acid encoding the Wnt antagonists described herein. In specific embodiments, the nucleic acid encodes a Wnt antagonist comprising a CRD (ECD)s of hFrz1 (SEQ ID NO: 18), hFrz2 (SEQ ID NO: 19), hFrz3 (SEQ ID NO: 20), hFrz4 (SEQ ID NO: 21), hFrz5 (SEQ ID NO: 22), hFrz6 (SEQ ID NO: 23), hFrz7 (SEQ ID NO: 24), hFrz8 (SEQ ID NO: 25), hFrz9 (SEQ ID NO: 26), hFrz10 (SEQ ID NO: 27), sFRP1 (SEQ ID NO: 28), sFRP2 (SEQ ID NO: 29), sFRP3 (SEQ ID NO: 30), sFRP4 (SEQ ID NO: 31), sFRP5 (SEQ ID NO: 32), hRor1 (SEQ ID NO: 33), or hRor2 (SEQ ID NO: 34).

In other embodiments, the nucleic acid encodes a Wnt antagonist comprising a pro-Frz or pro-sFrp proteins selected from among hFrz1 (SEQ ID NO: 35), hFrz2 (SEQ ID NO: 36), hFrz3 (SEQ ID NO: 37), hFrz4 (SEQ ID NO: 38), hFrz5 (SEQ ID NO: 39), hFrz6 (SEQ ID NO: 40), hFrz7 (SEQ ID NO: 41), hFrz8 (SEQ ID NO: 42), hFrz9 (SEQ ID NO: 43), hFrz10 (SEQ ID NO: 44), sFRP1 (SEQ ID NO: 45), sFRP2 (SEQ ID NO: 46), sFRP3 (SEQ ID NO: 47), sFRP4 (SEQ ID NO: 48), and sFRP5 (SEQ ID NO: 49).

In still other embodiments, the nucleic acid encodes a Wnt antagonist comprising a mature Frz, sFRP or hRor proteins selected from among hFrz1 (SEQ ID NO: 50), hFrz2 (SEQ ID NO: 51), hFrz3 (SEQ ID NO: 52), hFrz4 (SEQ ID NO: 53), hFrz5 (SEQ ID NO: 54), hFrz6 (SEQ ID NO: 55), hFrz7 (SEQ ID NO: 56), hFrz8 (SEQ ID NO: 57), hFrz9 (SEQ ID NO: 58), hFrz10 (SEQ ID NO: 59), sFRP1 (SEQ ID NO: 60), sFRP2 (SEQ ID NO: 61), sFRP3 (SEQ ID NO: 62), sFRP4 (SEQ ID NO: 63), sFRP5 (SEQ ID NO: 64), hRor1 (SEQ ID NO: 65), and hRor2 (SEQ ID NO: 66).

In still other embodiments, the nucleic acid encodes a Wnt antagonist comprising a Frz8-Fc (SEQ ID NO: 74), Frz5-Fc (SEQ ID NO: 75), Frz1-Fc (SEQ ID NO: 76), Frz2-Fc (SEQ ID NO: 77), Frz3-Fc (SEQ ID NO: 78), Frz4-Fc (SEQ ID NO: 79), Frz6-Fc (SEQ ID NO: 80), Frz7-Fc (SEQ ID NO: 81), Frz9-Fc (SEQ ID NO: 82), Frz10-Fc (SEQ ID NO: 83), sFRP1-Fc (SEQ ID NO: 84), sFRP2 (SEQ ID NO: 85), sFRP3-Fc (SEQ ID NO: 86), sFRP4-Fc (SEQ ID NO: 87), or sFRP5-Fc (SEQ ID NO: 88).

In one particular embodiment, the nucleic acid encodes a Frz8-Fc and comprises the nucleic acid sequence shown in SEQ ID NO: 122 (FIG. 5D). In another embodiment, the nucleic acid encodes a Frz5-Fc and comprises the nucleic acid sequence shown in SEQ ID NO: 119 (FIG. 5C). In yet further embodiment, the nucleic acid encodes a Frz1-Fc, Frz2-Fc, Frz3-Fc, Frz4-Fc, Frz6-Fc, Frz7-Fc, Frz9-Fc, Frz10-Fc, sFRP1-Fc, sFRP2, sFRP3-Fc, sFRP4-Fc, or sFRP5-Fc and comprises a nucleic acid sequence shown in FIG. 5 (A-H). For example, the nucleic acid comprises a Frz1-Fc (SEQ ID NO: 115), Frz2-Fc (SEQ ID NO: 116), Frz3-Fc (SEQ ID NO: 117), Frz4-Fc (SEQ ID NO: 118), Frz5-Fc (SEQ ID NO: 119), Frz6-Fc (SEQ ID NO: 120), Frz7-Fc (SEQ ID NO: 121), Frz8-Fc (SEQ ID NO: 122), Frz9-Fc (SEQ ID NO: 123), Frz10-Fc (SEQ ID NO: 124), sFRP1-Fc (SEQ ID NO: 125), sFRP2-Fc (SEQ ID NO: 126), sFRP3-Fc (SEQ ID NO: 127), sFRP4-Fc (SEQ ID NO: 128), or sFRP5-Fc (SEQ ID NO:129).

Another aspect of the invention provides for nucleic acids that hybridize under high stringency conditions to the nucleic acids described above.

3. Wnt Antagonist Variants

In addition to the Wnt antagonist polypeptides described herein, it is contemplated that Wnt antagonist variants can be prepared. Such variants can be prepared by introducing appropriate nucleotide changes into the encoding DNA, and/or by synthesis of the desired variant. Those skilled in the art will appreciate that amino acid changes may alter post-translational processes of the Wnt antagonist, such as changing the number or position of glycosylation sites or altering the membrane anchoring characteristics.

A Wnt antagonist variant includes, for example, a mutation or amino acid variant in an amino acid residue in one or more domains, while still retaining biological activity. A Wnt antagonist variant also includes Wnt antagonists having at least one amino acid deletion or addition, while still retaining biological activity. The addition or deletion of the amino acid residues can particularly occur in the region surrounding the amino acid sequence where the Frz domain component and Fc domain are connected, whether or not such region contains a linker. Wnt antagonist variants have at least 70%, 75%, 80%, 85%, 86%, 87%, 88%, 89%, 90%, 91%, 92%, 93%, 94%, 95%, 96%, 97%, 98% or 99% amino acid sequence identity with a reference Wnt antagonist polypeptide sequence. In general such variants exhibit substantially the same or greater binding affinity to a Wnt protein than the reference sequence, e.g., at least 0.75×, 0.8×, 0.9×, 1.0×, 1.25× or 1.5×, based on an art-accepted binding assay quantitation unit/metric.

In specific embodiments, the Wnt antagonist variant is a chimeric molecule comprising a Frz domain component having at least 70%, 75%, 80%, 85%, 86%, 87%, 88%, 89%, 90%, 91%, 92%, 93%, 94%, 95%, 96%, 97%, 98% or 99% amino acid sequence identity with the CRD (ECD)s of hFrz1 (SEQ ID NO: 18), hFrz2 (SEQ ID NO: 19), hFrz3 (SEQ ID NO: 20), hFrz4 (SEQ ID NO: 21), hFrz5 (SEQ ID NO: 22), hFrz6 (SEQ ID NO: 23), hFrz7 (SEQ ID NO: 24), hFrz8 (SEQ ID NO: 25), hFrz9 (SEQ ID NO: 26), hFrz10 (SEQ ID NO: 27), sFRP1 (SEQ ID NO: 28), sFRP2 (SEQ ID NO: 29), sFRP3 (SEQ ID NO: 30), sFRP4 (SEQ ID NO: 31), sFRP5 (SEQ ID NO: 32), hRor1 (SEQ ID NO: 33), or hRor2 (SEQ ID NO: 34).

In other embodiments, the Wnt antagonist variant is a chimeric molecule comprising a Frz domain component having at least 70%, 75%, 80%, 85%, 86%, 87%, 88%, 89%, 90%, 91%, 92%, 93%, 94%, 95%, 96%, 97%, 98% or 99% amino acid sequence identity with a pro-Frz or pro-sFrp proteins selected from among hFrz1 (SEQ ID NO: 35), hFrz2 (SEQ ID NO: 36), hFrz3 (SEQ ID NO: 37), hFrz4 (SEQ ID NO: 38), hFrz5 (SEQ ID NO: 39), hFrz6 (SEQ ID NO: 40), hFrz7 (SEQ ID NO: 41), hFrz8 (SEQ ID NO: 42), hFrz9 (SEQ ID NO: 43), hFrz10 (SEQ ID NO: 44), sFRP1 (SEQ ID NO: 45), sFRP2 (SEQ ID NO: 46), sFRP3 (SEQ ID NO: 47), sFRP4 (SEQ ID NO: 48), and sFRP5 (SEQ ID NO: 49).

In still other embodiments, the Wnt antagonist variant is a chimeric molecule comprising a Frz domain component having at least 70%, 75%, 80%, 85%, 86%, 87%, 88%, 89%, 90%, 91%, 92%, 93%, 94%, 95%, 96%, 97%, 98% or 99% amino acid sequence identity with mature Frz, sFRP or hRor proteins selected from among hFrz1 (SEQ ID NO: 50), hFrz2 (SEQ ID NO: 51), hFrz3 (SEQ ID NO: 52), hFrz4 (SEQ ID NO: 53), hFrz5 (SEQ ID NO: 54), hFrz6 (SEQ ID NO: 55), hFrz7 (SEQ ID NO: 56), hFrz8 (SEQ ID NO: 57), hFrz9 (SEQ ID NO: 58), hFrz10 (SEQ ID NO: 59), sFRP1 (SEQ ID NO: 60), sFRP2 (SEQ ID NO: 61), sFRP3 (SEQ ID NO: 62), sFRP4 (SEQ ID NO: 63), sFRP5 (SEQ ID NO: 64), hRor1 (SEQ ID NO: 65), and hRor2 (SEQ ID NO: 66).

In still other embodiments, the Wnt antagonist variant is a chimeric molecule comprising a Frz domain component having at least 70%, 75%, 80%, 85%, 86%, 87%, 88%, 89%, 90%, 91%, 92%, 93%, 94%, 95%, 96%, 97%, 98% or 99% amino acid sequence identity with Frz8-Fc (SEQ ID NO: 74), Frz5-Fc (SEQ ID NO: 75), Frz1-Fc (SEQ ID NO: 76), Frz2-Fc (SEQ ID NO: 77), Frz3-Fc (SEQ ID NO: 78), Frz4-Fc (SEQ ID NO: 79), Frz6-Fc (SEQ ID NO: 80), Frz7-Fc (SEQ ID NO: 81), Frz9-Fc (SEQ ID NO: 82), Frz10-Fc (SEQ ID NO: 83), sFRP1-Fc (SEQ ID NO: 84), sFRP2 (SEQ ID NO: 85), sFRP3-Fc (SEQ ID NO: 86), sFRP4-Fc (SEQ ID NO: 87), and sFRP5-Fc (SEQ ID NO: 88).

"Percent (%) amino acid sequence identity" is defined as the percentage of amino acid residues that are identical with amino acid residues in a reference (parent) polypeptide sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences. Those skilled in the art can determine appropriate parameters for measuring alignment, including any algorithms needed to achieve maximal alignment over the full length of the sequences being compared.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

$$\% \text{ amino acid sequence identity} = X/Y \times 100$$

where

X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A.

An "isolated" or "purified" peptide, polypeptide, protein or biologically active fragment is separated and/or recovered from a component of its natural environment. Contaminant components include materials that would typically interfere with diagnostic or therapeutic uses for the polypeptide, and may include enzymes, hormones, and other proteinaceous or non-proteinaceous materials. Preparations having preferably less than 30% by dry weight of non-desired contaminating material (contaminants), preferably less than 20%, 10%, and preferably less than 5% contaminants are considered to be substantially isolated. An isolated, recombinantly-produced peptide/polypeptide or biologically active portion thereof is preferably substantially free of culture medium, i.e., culture medium represents preferably less than 20%, preferably less than about 10%, and preferably less than about 5% of the volume of a peptide/polypeptide preparation. Examples of contaminants include cell debris, culture media, and substances used and produced during in vitro synthesis of the peptide/polypeptide.

Variations in the Wnt antagonist described herein, can be made, for example, using any of the techniques and guidelines for conservative and non-conservative mutations set forth, for instance, in U.S. Pat. No. 5,364,934. Variations may be a substitution, deletion or insertion of one or more codons encoding the antibody or polypeptide that results in a change in the amino acid sequence as compared with the native sequence antibody or polypeptide. Optionally the variation is by substitution of at least one amino acid with any other amino acid in one or more of the domains Wnt antagonist. Guidance in determining which amino acid residue may be inserted, substituted or deleted without adversely affecting the desired activity may be found by comparing the sequence of the Wnt antagonist with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions, deletions or substitutions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Wnt antagonists may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR.

In particular embodiments, conservative substitutions of interest are shown in Table A under the heading of preferred substitutions. If such substitutions result in a change in biological activity, then more substantial changes, denominated exemplary substitutions in Table A, or as further described below in reference to amino acid classes, are introduced and the products screened.

TABLE A

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr; cys | cys |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the Wnt antagonist are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: Norleucine, Met, Ala, Val, Leu, Ile;
(2) neutral hydrophilic: Cys, Ser, Thr; Asn; Gln
(3) acidic: Asp, Glu;
(4) basic: His, Lys, Arg;
(5) residues that influence chain orientation: Gly, Pro; and
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al, *Nucl. Acids Res.*, 13:4331 (1986); Zoller et al, *Nucl. Acids Res.*, 10:6487 (1987)], cassette mutagenesis [Wells et al, *Gene*, 34:315 (1985)], restriction selection mutagenesis [Wells et al, *Philos. Trans. R. Soc. London SerA*, 317:415 (1986)] or other known techniques can be performed on the cloned DNA to produce the Wnt antagonists of the invention.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244:1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

Any cysteine residue not involved in maintaining the proper conformation of the Wnt antagonist may also be substituted, generally with serine, to improve the oxidative stability of the molecule and prevent aberrant crosslinking. Conversely, cysteine bond(s) may be added to the Wnt antagonist to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the Wnt antagonist and Wnt protein. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Covalent modifications of Wnt antagonists are included within the scope of this invention. One type of covalent modification includes reacting targeted amino acid residues of a Wnt antagonist with an organic derivatizing agent that is capable of reacting with selected side chains or the N- or C-terminal residues of the Wnt antagonist. Derivatization with bifunctional agents is useful, for instance, for crosslinking the Wnt antagonist to a water-insoluble support matrix or surface for use in the method for purifying Wnt antagonists. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the Wnt antagonist included within the scope of this invention comprises altering the native glycosylation pattern of the Frz, Wnt or sFRP polypeptide domains of the Wnt antagonist. "Altering the native glycosylation pattern" is defined as deleting one or more carbohydrate moieties found in native sequence of the component domains (either by removing the underlying glycosylation site or by deleting the glycosylation by chemical and/or enzymatic means), and/or adding one or more glycosylation sites that are not present in the native sequence component domain. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the Wnt antagonist is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the sequence of the original (i.e., pre-variant) Wnt antagonist. This sequence may optionally be altered through changes at the DNA level, particularly by mutating the DNA encoding the sequence at preselected bases such that codons are generated that will translate into the desired amino acids.

Another means of increasing the number of carbohydrate moieties on the Wnt antagonist is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the Wnt antagonist may be accomplished chemically or enzymatically or by mutational substitution of codons encoding for amino acid residues that serve as targets for glycosylation. Chemical deglycosylation techniques are known in the art and described, for instance, by Hakimuddin, et al, *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of Wnt antagonist comprises linking the sequence to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337. The antibody or polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington: The Science and Practice of Pharmacy*, 20th edition, Gennaro, A., Ed., (2000).

The Wnt antagonists of the present invention may also be modified in a way to form molecules having additional chimeric nature, comprising a Wnt antagonist (i.e., Frz-, sFRP- or Ror-Fc chimera) fused to another, heterologous polypeptide or amino acid sequence.

In one embodiment, such a chimeric molecule comprises a fusion of the Wnt antagonist with a tag polypeptide which provides an epitope to which an anti-tag antibody can selectively bind. The epitope tag is generally placed at the amino- or carboxyl-terminus of the Wnt antagonist. The presence of such epitope-tagged forms of the Wnt antagonist can be detected using an antibody against the tag polypeptide. Also, provision of the epitope tag enables the Wnt antagonist to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al, *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al, *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In alternative embodiments, the Wnt antagonists comprise a variant Fc component. For example, the Fc region may comprise a human Fc region sequence (e.g., a human IgG1, IgG2, IgG3 or IgG4 Fc region) comprising an amino acid modification (e.g, a substitution) at one or more amino acid positions including that of a hinge cysteine. In one embodiment, such variants have at least 70%, 75%, 80%, 85%, 86%, 87%, 88%, 89%, 90%, 91%, 92%, 93%, 94%, 95%, 96%, 97%, 98% or 99% amino acid sequence identity with a reference Fc polypeptide sequence.

In one embodiment, the Fc region variant may display altered neonatal Fc receptor (FcRn) binding affinity. Such variant Fc regions may comprise an amino acid modification oat any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447 of the Fc region, wherein the numbering of the residues in the Fc region is that of the EU index as in Kabat. Fc region variants with reduced binding to an FcRn may comprise an amino acid modification at any one or more of amino acid positions 252, 253, 254, 255, 288, 309, 386, 388, 400, 415, 433, 435, 436, 439 or 447 of Fc region (EU index/Kabat numbering). Alternatively, variants displaying increased binding to FcRn may comprise an amino acid modification at any one or more of amino acid positions 238, 256, 265, 272, 286, 303, 305, 307, 311, 312, 317, 340, 356, 360, 362, 376, 378, 380, 382, 413, 424 or 434 of the Fc region (EU index/Kabat numbering).

In another embodiment, the Fc region variant may display reduced binding to an FcγR, and comprises amino acid modifications at positions 238, 239, 248, 249, 252, 254, 265, 268, 269, 270, 272, 278, 289, 292, 293, 294, 295, 296, 298, 301, 303, 322, 324, 327, 329, 333, 335, 338, 340, 373, 376, 382, 388, 389, 414, 416, 419, 434, 435, 437, 438 or 439 of the Fc region (EU index/Kabat numbering).

In yet another embodiment, the Fc region variant may display reduced binding to FcγRII and comprises amino acid modifications at any one or more of amino acid positions 238, 265, 269, 270, 292, 294, 295, 298, 303, 324, 327, 329, 333, 335, 338, 373, 376, 414, 416, 419, 435, 438 or 439 of the Fc region (EU index/Kabat numbering).

In a further embodiment, the Fc region variant may display enhanced binding to FcγRII, and comprises an amino acid modification at any one or more of amino acid positions 238, 265, 269, 270, 292, 294, 295, 298, 303, 324, 327, 329, 333, 338, 373, 376, 414, 416, 419, 435, 438 or 439 of the Fc region (EU index/Kabat numbering).

In a still further embodiment, the Fc region variant of interest may display reduced binding to an FcγRIII, and comprises an amino acid modification at one or more amino acid positions 238, 239, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 of the Fc region (EU index/Kabat numbering).

In a still further embodiment, Fc region variants with altered (i.e, improved or diminished) C1q binding and/or complement dependent cytotoxicity (CDC) are described in WO99/51642. Such variants may comprise an amino acid substitution at one or more of amino acid positions 270, 322, 326, 327, 329, 331, 333 or 334 of the Fc region. See also, Duncan and Winter, Nature 322: 738-40 (1988); U.S. Pat. No. 5,648,260; U.S. Pat. No. 5,624,821 and WO94/29351 concerning Fc region variants.

B. Preparation of Wnt Antagonists

The description below relates primarily to production of Wnt antagonist polypeptides by culturing cells transformed or transfected with a vector containing Wnt antagonist polypeptide-encoding nucleic acid. It is, of course, contemplated that alternative methods, which are well known in the art, may be employed to prepare such Wnt antagonists. For instance, the appropriate amino acid sequence, or portions thereof, may be produced by direct peptide synthesis using solid-phase techniques [see, e.g., Stewart et al, *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the Wnt antagonist polypeptide may be chemically synthesized separately and combined using chemical or enzymatic methods to produce the desired sequence.

1. Isolation of DNA Encoding Wnt Antagonist Polypeptide

DNA encoding the sequence of the antagonists or any desired component domains of the Wnt antagonist, such as an Frz, or sFRP may be obtained from a cDNA library prepared from tissue believed to possess such sequence and to express it at a detectable level. Accordingly, a human Frz or sFRP sequence DNA can be conveniently obtained from a cDNA library prepared from human tissue. The desired DNA sequence gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding Wnt antagonist polypeptide and components thereof is to use PCR methodology [Sambrook et al, supra; Dieffenbach et al, *PCR Primer: A Laboratory Manual* (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

DNA sequence encoding Fc immunoglobulin domains may be derived from hybridoma cells secreting mAbs of the desired Fc subtype.

Nucleic acid having protein coding sequence may be obtained by screening selected cDNA or genomic libraries using the deduced amino acid sequence disclosed herein for the first time, and, if necessary, using conventional primer extension procedures as described in Sambrook et al, supra, to detect precursors and processing intermediates of mRNA that may not have been reverse-transcribed into cDNA.

2. Selection and Transformation of Host Cells

Host cells are transfected or transformed with expression or cloning vectors described herein for Wnt antagonist polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al, supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al, *J. Bact.*, 130:946 (1977) and Hsiao et al, *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al, *Methods in Enzymology*, 185:527-537 (1990) and Mansour et al, *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac) 169 degP ompT kan$^r$; *E. coli* W3110 strain 37D6, which has the complete genotype tonA ptr3 phoA E15 (argF-lac) 169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789, 199 (Joly et al), and U.S. Pat. No. 5,840,523 (Simmons et al) which describes translation initiation regio (TIR) and signal sequences for optimizing expression and secretion, these patents are incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for Wnt antagonist polypeptide-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139, 383 published 2 May 1985); *Kluyveromyces* hosts (U.S. Pat. No. 4,943,529; Fleer et al, *Bio/Technology*, 9:968-975 (1991)) such as, e.g., *K. lactis* (MW98-8C, CBS683, CBS4574; Louvencourt et al., *J. Bacteriol.*, 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus; yarrowia* (EP 402,226); *Pichia pastoris* (EP 183, 070; Sreekrishna et al., *J. Basic Microbiol.*, 28:265-278 [1988]); *Candida; Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrohs*, 269 (1982).

Suitable host cells for the expression of glycosylated Wnt antagonist polypeptide are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/–DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for Wnt antagonist polypeptide production and cultured in conventional nutrient media modified as appropriate for inducing promoters, selecting transformants, or amplifying the genes encoding the desired sequences.

3. Selection and Use of a Replicable Vector

One aspect of the invention provides for the nucleic acid (e.g., cDNA or genomic DNA) encoding a Wnt antagonist polypeptide inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The Wnt antagonist may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the Wnt antagonist polypeptide-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the Wnt antagonist-encoding nucleic acid, such as DHFR or thymidine kinase. An appropriate host cell when wild-type DHFR is employed is the CHO cell line deficient in DHFR activity, prepared and propagated as described by Urlaub et al, *Proc. Natl. Acad. Sci. USA,* 77:4216 (1980). A suitable selection gene for use in yeast is the trp1 gene present in the yeast plasmid YRp7 [Stinchcomb et al, *Nature,* 282:39 (1979); Kingsman et al, *Gene,* 7:141 (1979); Tschemper et al, *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the Wnt antagonist-encoding nucleic acid sequence to direct mRNA synthesis. Promoters recognized by a variety of potential host cells are well known. Promoters suitable for use with prokaryotic hosts include the β-lactamase and lactose promoter systems [Chang et al, *Nature,* 275:615 (1978); Goeddel et al, *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al, *Proc. Natl. Acad. Sci. USA,* 80:21-25 (1983)]. Promoters for use in bacterial systems also will contain a Shine-Dalgarno (S.D.) sequence operably linked to the DNA encoding the Wnt antagonist polypeptide.

Examples of suitable promoting sequences for use with yeast hosts include the promoters for 3-phosphoglycerate kinase [Hitzeman et al, *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Wnt antagonist polypeptide transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the Wnt antagonist polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the Wnt antagonist polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding Wnt antagonist.

Still other methods, vectors, and host cells suitable for adaptation to the synthesis of Wnt antagonist polypeptide in recombinant vertebrate cell culture are described in Gething et al., Nature, 293:620-625 (1981); Mantei et al, *Nature,* 281:40-46 (1979); EP 117,060; and EP 117,058.

4. Culturing the Host Cells

One aspect of the invention provides for a host cell comprising the nucleic acid encoding the Wnt antagonists. The host cells used to produce the Wnt antagonist polypeptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a Frz, sFRP or Ror sequence identified herein or against a synthetic peptide based on the DNA sequences provided herein or against exogenous sequence fused to the Wnt antagonist and encoding a specific antibody epitope.

6. Purification of Wnt Antagonist

Forms of Wnt antagonist polypeptide may be recovered from culture medium or from host cell lysates. If membrane-bound, it can be released from the membrane using a suitable detergent solution (e.g. Triton-X 100) or by enzymatic cleavage. Cells employed in expression of Wnt antagonist polypeptide can be disrupted by various physical or chemical means, such as freeze-thaw cycling, sonication, mechanical disruption, or cell lysing agents.

It may be desired to purify Wnt antagonist polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the Wnt antagonist. Various methods of protein purification may be employed and such methods are known in the art and described for example in Deutscher, *Methods in Enzymology,* 182 (1990); Scopes, *Protein Purification Principles and Practice*, Springer-Verlag, New York (1982). The purification step(s) selected will depend, for example, on the nature of the production process used and the particular Wnt antagonist polypeptide produced.

When using recombinant techniques, the Wnt antagonist polypeptide can be produced intracellularly, in the periplasmic space, or directly secreted into the medium. If the Wnt antagonist polypeptide is produced intracellularly, as a first step, the particulate debris, either host cells or lysed fragments, are removed, for example, by centrifugation or ultrafiltration. Carter et al, *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the Wnt antagonist polypeptide is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The Wnt antagonist polypeptide composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the Wnt antagonist polypeptide comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

C. Pharmaceutical Formulations

One aspect of the invention provides for a composition comprising a Wnt antagonist and at least one pharmaceutically acceptable carrier or excipient. Therapeutic formulations of the Wnt antagonists used in accordance with the present invention are prepared for storage by mixing the Wnt antagonists having the desired degree of purity with optional pharmaceutically acceptable carriers, excipients or stabilizers (*Remington: The Science and Practice of Pharmacy*, 20th edition, A. Gennaro, Ed. (2000)), in the form of lyophilized formulations or aqueous solutions. A "pharmaceutically acceptable carrier" includes any and all solvents, dispersion media, coatings, antibacterial and antifungal agents, isotonic and absorption delaying agents, and the like, compatible with pharmaceutical administration. Additional examples of suitable carriers or diluents include, but are not limited to, water, saline, Finger's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions.

Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as poly sorbate; salt-forming counter-ions such as sodium; metal complexes (e.g., Zn-protein complexes); and/or nonionic surfactants such as TWEEN®, PLURONICS® or polyethylene glycol (PEG). The antibody preferably comprises the antibody at a concentration of between 5-200 mg/ml, preferably between 10-100 mg/ml.

The formulations herein may also contain more than one active compound as necessary for the particular indication being treated, preferably those with complementary activities that do not adversely affect each other. For example, in addition to a particular Wnt antagonist, it may be desirable to include in the one formulation, an additional antibody, e.g., which binds a different epitope on the Wnt protein, to a different Wnt protein entirely, or an antibody to some other target such as a growth factor that affects the growth of the Wnt mediated disorder. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington: The Science and Practice of Pharmacy*, 20th edition, A. Gennaro, Ed. (2000).

The formulations to be used for in vivo administration must be sterile. This is readily accomplished by filtration through sterile filtration membranes.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics", In Toxicokinetics and New Drug Development, Yacobi et al., Eds., Pergamon Press, New York 1989, pp. 42-96.

When in vivo administration of a substance or molecule of the invention is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a substance or molecule is desired in a formulation with release characteristics suitable for the treatment of any disease or disorder requiring administration of the substance or molecule, microencapsulation of the substance or molecule is contemplated. Suitable examples of sustained-release preparations include semi-permeable matrices of solid hydrophobic polymers containing the antibody, which matrices are in the form of shaped articles, e.g., films, or microcapsules. Microencapsulation of recombinant proteins for sustained release has been successfully performed with human growth hormone (rhGH), interferon-$\alpha$,$\gamma$ (rhIFN-$\alpha$, -$\gamma$), interleukin-2, and MN rgp120. Johnson et al., Nat. Med., 2:795-799 (1996); Yasuda, *Biomed. Ther.*, 27:1221-1223 (1993); Hora et al., *Bio/Technology*, 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins may be developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

Additional examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and $\gamma$ ethyl-L-glutamate, non-degradable ethylene-vinyl acetate, degradable lactic acid-glycolic acid copolymers such as the LUPRON DEPOT®, (injectable microspheres composed of lactic acid-glycolic acid copolymer and leuprolide acetate), and poly-D-(-)-3-hydroxybutyric acid.

D. Methods of Treating Wnt Mediated Disorder

The invention provides for methods of treating a Wnt-mediated disorder in a mammal suffering therefrom, comprising administering to the mammal a therapeutically effective amount of a Wnt antagonist. In one embodiment, the disorder is a cell proliferative disorder associated with aberrant, e.g., increased, expression of activity of Wnt signaling. In another embodiment, the disorder results from increased expression of a Wnt protein. In yet another embodiment, the cell proliferative disorder is cancer, such as for example, colon cancer, colorectal cancer, breast cancer, cancer associated with various disorders relating to HSC's, such as leukemias and various other blood related cancers, and cancer related to neuronal proliferative disorders, including brain tumors, such as gliomas, astrocytomas, meningiomas, Schwannomas, pituitary tumors, primitive neuroectodermal tumors (PNET), medulloblastomas, craniopharyngioma, and pineal region tumors.

Treatment of the cell proliferative disorder by administration of a Wnt antagonist results in an observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the Wnt antagonist may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TDP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

In a specific embodiment, the administration of Wnt antagonist decreases tumor burden (e.g., reduces size or severity of the cancer). In yet another specific embodiment, the administration of Wnt antagonist kills the cancer.

E. Methods of Inhibiting Wnt-Signaling in a Cell

The invention provides for a method of inhibiting Wnt-signaling in a cell comprising contacting the cell with an effective amount of a Wnt antagonist. In one embodiment, the cell is contained within a mammal, preferably a human, and the administered amount is a therapeutically effective amount. In yet another embodiment, the inhibition of Wnt signaling further results in the inhibition of the growth of the cell. In a further embodiment, the cell is a cancer cell.

Inhibition of cell proliferation is measured using methods known to those skilled in the art. For example, a convenient assay for measuring cell proliferation is the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al (1993) *J. Immunol. Meth.* 160: 81-88, U.S. Pat. No. 6,602,677. The assay may be conducted in 96- or 384-well format, making it amenable to automated high-throughput screening (HTS). See Cree et al (1995) *Anti-Cancer Drugs* 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

F. Methods of Modulating the Expression of a Wnt Target Gene

The invention provides for a method of modulating the expression of a Wnt target gene in a cell characterized by activated or excessive Wnt signaling, comprising contacting the cell with an effective amount of a Wnt antagonist. In one embodiment, the Wnt target gene is overexpressed as a result of the Wnt signaling, and the result of the contact with the Wnt antagonist reduces expression of the Wnt target gene. In another embodiment, the Wnt target gene is selected from the group consisting of: Axin2, APCDD1, Gad1, Sax1, c-myc, cyclin D1, PPARdelta, gastrin, clusterin, survivin, cyclooxygenase, fra-1, osteopontin, uPAR, claudin-1, CD44, MMP-7/9/11/14/26, IGFBP-4, Met, BMP4, sox-9, histone deacetylase 2, VEGF. In yet another embodiment, the Wnt target gene is underexpressed as a result of the Wnt signaling, and the result of contact with the Wnt antagonist restores expression of the Wnt target gene. In a further embodiment, the Wnt target gene is selected from the group consisting of: Lefty1, Lefty2, sFRP1, Fzd5, fas antigen, caspase 3, integrin $\beta$7, alpha e integrin, hath 1, fatty acid binding protein 2, muc-2, kruppel like factor-4, carbonic anhydrase-11, EphrinB1, EphB2R, EphB3R, muc-3, histocompatibility 2, Q region locus 1, $\beta$2-microglobulin.

Expression of the target genes is determined using methods known to those of skill in the art, including those described herein and set forth in the Examples below.

G. Methods of Detecting the Presence of a Wnt Protein

The invention provides for a method of detecting the presence of a Wnt protein in a sample, comprising contacting the sample with a Wnt antagonist, wherein the presence of a complex or the level of binding between the Wnt antagonist and the Wnt protein is indicative of the presence of Wnt protein and/or Wnt signaling. In one embodiment, the method further comprises determining if the level of Wnt signaling is aberrant. In this embodiment, the level of Wnt protein binding in the sample is compared with the level in a second sample in which Wnt protein expression and/or Wnt signaling is known to be physiologically normal. The level of binding in the suspect sample compared to the second sample that is higher or lower than the physiologically normal sample is indicative of aberrant Wnt signaling. In another embodiment, the presence of Wnt signaling or aberrant Wnt signaling is indicative of the presence of a Wnt-mediated disorder, such as cancer.

H. The Wnt Pathway and Disorders Associated Therewith

1. The Wnt Signaling Pathway:

The Wnt signaling pathway is an unusually complex signaling process involving multiple proteins which exert varying levels of control in the pathway. This multi-level, tight regulation of the pathway is indicative of its importance in cellular biology. Despite the complicated regulatory mechanisms, the initial signal of the pathway is generated by the binding of a Wnt to the Frizzled (Frz) receptors. Effective signal further requires the presence of an additional single pass transmembrane molecule of the LRP (LDL receptor related protein) class, specifically LRP 5 and LRP 6. Wnt may further bind with LRP to form a trimeric complex with Frizzled. The cytoplasmic tail of LRP in turn interacts with Axin, another downstream component. Dishevelled, a cytoplasmic component that interacts directly with Frizzled, may also directly interact with Axin, thus forming a tetra-plex complex of Frizzled, LRP, Dsh and Axin. This interaction with Axin releases $\beta$-catenin from the "degradation complex" (discussed infra) for subsequent downstream activity in the Wnt signaling pathway.

Outside the cell, Wnt signaling is inhibited by various proteins that can bind to Wnt thereby sequestering it from its receptor. Included in this group are the secreted Frizzled related proteins (sFRPs, Jones et al., *Bioessays* 2002; 24: 811-820) and Wnt inhibitory factor-1 (WIF-1, Hsieh, J. C. et al., *Nature* 1999; 398: 431-436). In humans, the sFRP family consists of five members (e.g., sFRP-1, sFRP-2 . . . sFRP-5), each containing a cysteine-rich domain (CRD) which shares 30-50% sequence homology with the CRD of Frz receptors. (Melkonyan, H. S. et al., *Proc. Natl. Acad. Sci. USA* 1997; 94: 13636-13641). sFRPs are believed to form function-inhibiting complexes with Frz receptors, and therefore are natural antagonists, but the biology is complex, and in some cases, may even act to agonize Wnt activity. (Uren, A. et al., *J. Biol. Chem.* 2000; 275: 4374-4382).

Another class of extracellular Wnt inhibitor is Dickkopf (Dkk). [Brott, B. K. et al., *Mol. Cell Biol.* 2002; 22: 6100-6110; Fedi, P. et al., *J. Biol. Chem.* 1999; 274: 19465-19472] The three members of the Dkk family (e.g., Dkk-1, Dkk-2 and Dkk-4) can antagonize Wnt signaling through inactivation of the cell surface receptor LRP-5 and LRP-6, essential components of the canonical pathway. [Mao, J. H. et al., *Mol. Cell* 2001; 7: 801-809; Pinson, K. I. et al., *Nature* 2000; 407: 535-538]. Dkk forms a ternary complex with LRP5/6 and the single pass transmembrane receptors Kremen 1 (Krm-1) or Kremen 2 (Krm-2) [Mao et al., *Gene* 2003; 302: 179-183; Mao et al., *Nature* 2002; 417: 664-667; Mao et al., *Nature* 2001; 411: 321-325]. This complex in turn undergoes endocytosis, thereby removing LRP5/6 receptors from the cell surface. As a result, Dkks can selectively antagonize canonical Wnt signaling, while not affecting non-canonical signaling.

The hallmark of canonical Wnt signaling activation is elevated levels of the protein $\beta$-catenin. $\beta$-catenin is constitutively produced and is present in the cytoplasm as pools of monomeric protein. [Papkoff, J. et al., *Mol. Cell Biol.* 1996; 16: 2128-2134]. The primary mechanism for controlling cytoplasmic levels of $\beta$-catenin is through direct physical degradation upon recruitment into a large multi-protein complex ("degradation complex"). The central scaffolding of this complex is provided by Axin, as well as binding sites for $\beta$-catenin, adenomatous polyposis coli (APC), glycogen synthase kinase 3$\beta$ (GSK3$\beta$), casein kinase I$\alpha$ (CKI$\alpha$) and protein phophatase 2A (PP2A) [Hinoi, T. et al., *J. Biol. Chem.* 2000; 275: 34399-34406; Ikeda et al., *Oncogene* 2000; 19: 537-545; Yamamoto et al., *J. Biol. Chem.* 1999; 274: 10681-10684; Kishida et al., *J. Biol. Chem.* 1998; 273: 10823-10826; Ikeda et al., *EMBO J.* 1998; 17: 1371-1384. After formation, the complex is stabilized by the GSK3$\beta$-mediated phosphorylation of Axin and APC, as well as PP2A. GSK3$\beta$-then phosphorylates $\beta$-catenin thereby allowing it be recognized by $\beta$-transducin repeat containing protein ($\beta$-TrCP), thereby targeting it for ubiquitination and proteosomic degradation. [Aberle et al., *EMBO J.* 1997; 16: 3797-804; Latres et al., *Oncogene* 1999; 18: 849-54; Liu et al., *Proc. Natl. Acad. Sci. USA* 1999; 96: 6273-8].

Although complexation with Axin/APC/GSK3$\beta$ is the primary mechanism for degradation of $\beta$-catenin, an alternative degradation pathway has been shown involving ubiquitination induced by complexation with Siah-1 and the C-terminus of APC. [Matsuzawa et al., *Mol Cell* 2001; 7: 915-926; Liu et al., *Mol. Cell* 2001; 7: 927-936]. In addition to its role as a transcription factor, $\beta$-catenin further is involved in cellular adhesion. [Nelson et al., *Science* 2004; 303: 1483-1487; Ilyas et al., *J. Pathol.* 1997; 182: 128-137. $\beta$-catenin can be found at the cell surface sites of intercellular contact known as adherens junctions, where it is complexed with E-cadherin and $\beta$-catenin. Thus, any increase in E-cadherin expression will direct $\beta$-catenin to the cell membrane, thereby depleting cytoplasmic levels, and in turn inhibit Wnt signaling. Moreover, the breakdown of the E-cadherin-catenin complex can increase cytoplasmic levels of free $\beta$-catenin, thereby stimulating transcriptional activity. [Nelson et al, supra.]. Thus, activation of the cell surface receptors cRON, epidermal growth factor receptor (EGFR) and c-ErbB2, by liberating β-catenin, can also stimulate canonical Wnt signaling. Other signaling pathways that can either activate or facilitate the effects of Wnt signaling. For example, integrin signaling can result in nuclear transportation of β-catenin [Eger et al., *Oncogene* 2004; 23: 2672-2680], while signaling through insulin-like growth factor (IGF) can activate Wnt signaling by "soaking up" available GSK3β—thereby preventing formation of the "degradation complex."

In canonical signaling, an initial step involves the binding of Wnt to Frz in the presence of LRP5/6. [Mao et al., *Mol. Cell* 2001; 7: 801-809; Pinson et al., Nature 2000; 407: 535-538]. The formation of this trimeric complex has two downstream consequences. First is the recruitment of Dishevelled (Dsh) to the cell surface and its phosphorylation by casein kinase Iε (CIε) [Kishida et al., *J. Biol. Chem.* 2001; 276: 33147-33155]. The phosphorylated Dsh can form a complex with Frat 1 and GSK3β, which in turn can inhibit the activity of GSK3β. Second, the Wnt/Frz/LRP5/6 tri-plex facilitates the LRP5/6 mediated degradation of Axin. The net effect of this is the destabilization of the degradation complex responsible for phosphorylating β-catenin. In the absence of phosphorylation, β-catenin is not ubiquinated, thereby escaping degradation, thus increasing intracellular levels and availability for translocation to the nucleus.

The manner in which β-catenin is transported to the nucleus is not entirely clear, but interaction with the nuclear transport proteins APC [Rosin-Arbesfeld et al., *Nature* 2000; 406: 1009-1012; Neufeld et al., *Proc. Natl. Acad. Sci. USA* 2000; 97: 12085-12090], as well as pygopus and Bcl9/legless have been implicated. [Townsley et al., *Nature Cell Biol* 2004; 6: 626-633].

Once in the nucleus, β-catenin displaces the transcriptional repressor Groucho for binding with T-cell-specific transcription factor/lymphoid enhancer-binding factor-1 (TCF/LEF) DNA binding proteins. In the absence of displacement by β-catenin, TCF/LEF complexes with Groucho to repress expression of the Wnt "target genes". The inhibitory effect of Groucho is further mediated by interactions with various histone deacetylases (HDAC), which are believed to make DNA refractive to transcriptional activation. [Cavallo et al., *Nature* 1998; 395: 604-8; Chen et al., *Genes Dev.* 1999; 13: 2218-30]. The conversion of the TCF transcriptional repressor complex into a transcriptional activation complex further involves recruitment of histone acetylases such as Creb binding protein (CBP)/p300 as well as other activating factors such as Brg-1. [Takemaru et al., *J. Cell Biol.* 2000; 149: 249-54; Barker et al., Cell 2002; 109: 47-60; Brantjes et al., *Biol. Chem.* 2002; 383: 255-261; Roose et al., *Biochim. Biophys Acta—Rev. Cancer* 1999; 1424: M23-M37]. The interactions between the β-catenin-TCF complex and chromatin also may be mediated by Legless (Bcl9) and Pygopus. Kramps et al., *Cell* 2002; 109: 47-60; Thompson et al., *Nat. Cell Biol.* 2002; 4: 367-73; Parker et al., *Development* 2002; 129: 2565-76.

An abbreviated summary of the canonical Wnt signaling pathway both in the "off" or inactive state as well as the "on" or active state is depicted in FIG. 1.

2. Disorders Associated with Wnt Signaling Activity:

Deregulation of the Wnt signaling pathway may be caused by somatic mutations in genes encoding various Wnt signaling pathway components. For example, aberrant Wnt signaling activity has been associated with Wnt ligand overexpression in non small cell lung cancer (NSCLC) [You et al., *Oncogene* 2004; 23: 6170-6174], chronic lymphocytic leukemia (CLL) [Lu et al., *Proc. Natl. Acad. Sci. USA* 2004; 101: 3118-3123], gastric cancer [Kim et al., *Exp. Oncol.* 2003; 25: 211-215; Saitoh et al., *Int. J. Mol. Med.* 2002; 9: 515-519], head and neck squamous cell carcinoma (HNSCC) [Rhee et al., *Oncogene* 2002; 21: 6598-6605], colorectal cancer [Holcombe et al., *J. Clin. Pathol—Mol. Pathol.* 2002; 55: 220-226], ovarian cancer [Ricken et al., Endocrinology 2002; 143: 2741-2749], basal cell carcinoma (BCC) [Lo Muzio et al., *Anticancer Res.* 2002; 22: 565-576] and breast cancer. Moreover, the reduction of various Wnt ligand regulatory molecules such as sFRP and WIF-1 have been associated with breast cancer [Klopocki et al., *Int. J. Oncol.* 2004; 25: 641-649; Ugolini et al., *Oncogene* 2001; 20: 5810-5817; Wissmann et al., *J. Pathol* 2003; 201: 204-212], bladder cancer [Stoehr et al., *Lab Invest.* 2004; 84: 465-478; Wissmann et al., supra], mesothelioma [Lee et al., *Oncogene* 2004; 23: 6672-6676], colorectal cancer [Suzuki et al., *Nature Genet.* 2004; 36: 417-422; Kim et al., *Mol. Cancer Ther.* 2002; 1: 1355-1359; Caldwell et al., *Cancer Res.* 2004; 64: 883-888], prostate cancer [Wissman et al., supra], NSCLC [Mazieres et al., *Cancer Res.* 2004; 64: 4717-4720], and lung cancer [Wissman et al., supra]. Antagonizing Wnt signaling with the Wnt antagonist molecules of the invention is expected to therapeutically treat these cancers.

Continuing, aberrant Wnt signaling resulting from overexpression of various components of the Frz-LRP receptor complex have also been associated with certain cancers. For example, LRP5 overexpression has been associated with osteosarcoma [Hoang et al., *Int. J. Cancer* 2004; 109: 106-111], while Frz overexpression has been associated with cancers such as prostate [Wissmann et al., supra], HNSCC [Rhee et al., *Oncogene* 2002; 21: 6598-6605], colorectal [Holcombe et al., supra], ovarian cancer [Wissmann et al., supra], esophageal [Tanaka et al., *Proc. Natl. Acad. Sci. USA* 1998; 95: 10164-10169] and gastric [Kirikoshi et al., *Int. J. Oncol.* 2001; 19: 111-115]. Additionally, overexpression of Wnt signaling pathway components such as Dishevelled have been associated with cancers such as prostate [Wissman et al, supra], breast [Nagahata et al., *Cancer Sci.* 2003; 94: 515-518], mesothelioma [Uematsu et al., *Cancer Res.* 2003; 63: 4547-4551] and cervical [Okino et al, *Oncol Rep.* 2003; 10: 1219-1223]. Frat-1 overexpression has been associated with cancers such as pancreatic, esophageal, cervical, breast and gastric. [Saitoh et al., *Int. J. Oncol.* 2002; 20: 785-789; Saitoh et al., *Int. J. Oncol* 2001; 19: 311-315]. Axin loss of function (LOF) mutations have been associated with hepatocellular cancer [Satoh et al., *Nature Genet.* 2000; 24: 245-250; Taniguchi et al., *Oncogene* 2002; 21: 4863-4871] and medulloblastoma [Dahmen et al., *Cancer Res.* 2001; 61: 7039-7043; Yokota et al., *Int. J. Cancer* 2002; 101: 198-201]. The blocking of Wnt-Frz interactions with the Wnt antagonists of the present invention is expected to alleviate cancers associated with overexpression of Frz or LRPs.

Finally, a multitude of cancers has been associated with activating β-catenin through disruption of the "degradation complex" such as gain-of-function mutations in β-catenin or loss-of-function mutations in APC. A reduction in the degradation of β-catenin results in greater amounts of functional β-catenin in the cell, which then causes increased transcription of the target genes, resulting in aberrant cell proliferation. For example, mutations in the gene encoding β-catenin (i.e., CTNNB1) have been associated with cancers such as gastric [Clements et al., *Cancer Res.* 2002; 62: 3503-3506; Park et al., *Cancer Res.* 1999; 59: 4257-4260], colorectal [Morin et al., *Science* 1997; 275: 1787-1790; Ilyas et al., *Proc. Natl. Acad. Sci. USA* 1997; 94: 10330-10334], intestinal carcinoid [Fujimori et al., *Cancer Res.* 2001; 61: 6656-6659], ovarian [Sunaga et al., *Genes Chrom. Cancer* 2001; 30: 316-321], pulmonary adenocarcinoma [Sunaga et al., supra], endometrial [Fukuchi et al., *Cancer Res.* 1998; 58: 3526-3528; Kobayashi et al., *Japan. J. Cancer Res.* 1999; 90: 55-59; Mirabelli-Primdahl et al., *Cancer Res.* 1999; 59: 3346-3351], hepatocellular [Satoh et al., supra.; Wong et al., *Cancer* 2001; 92: 136-145], hepatoblastoma [Koch et al., *Cancer Res.* 1999; 59: 269-273], medulloblastoma [Koch et al., *Int. J. Cancer* 2001; 93: 445-449], pancreatic [Abraham et al., *Am. J. Pathol* 2002; 160: 1361-1369], thyroid [Garcia-Rostan et al., *Cancer Res.* 1999; 59: 1811-1815; Garcia-Rostan et al., *Am. J. Pathol* 2001; 158: 987-996], prostate [Chesire et al., *Prostate* 2000; 45: 323-334; Voeller et al., *Cancer Res.* 1998; 58: 2520-2523], melanoma [Reifenberger et al., *Int. J. Cancer* 2002; 100: 549-556], pilomatricoma [Chan et al., *Nature Genet.* 1999; 21: 410-413], Wilms' tumor [Koesters et al., *J. Pathol* 2003; 199: 68-76], pancreatoblastomas [Abraham et al., *Am. J. Pathol* 2001; 159: 1619-1627], liposarcomas [Sakamoto et al., *Arch. Pathol. Lab Med.* 2002; 126: 1071-1078], juvenile nasopharyngeal angiofibromas [Abraham et al., *Am. J. Pathol.* 2001; 158: 1073-1078], desmoid [Tejpar et al., *Oncogene* 1999; 18: 6615-6620; Miyoshi et al., *Oncol. Res.* 1998; 10: 591-594], synovial sarcoma [Saito et al., *J. Pathol* 2000; 192: 342-350]. While loss-of-function mutations have been associated with cancers such as colorectal [Fearon et al., *Cell* 1990; 61: 759-767; Rowan et al., *Proc. Natl. Acad. Sci. USA* 2000; 97: 3352-3357], melanoma [Reifenberger et al., *Int. J. Cancer* 2002; 100: 549-556; Rubinfeld et al., *Science* 1997; 275: 1790-1792], medulloblastoma [Koch et al., *Int. J. Cancer* 2001; 93: 445-449; Huang et al., *Am. J. Pathol* 2000; 156: 433-437] and desmoids [Tejpar et al., *Oncogene* 1999; 18: 6615-6620; Alman et al., *Am J. Pathol.* 1997; 151: 329-334]. Cancers that result from aberrant activity of β-catenin thereby activating the Wnt pathway are suitable for treatment with the Wnt antagonists of the present invention.

3. Wnt Signaling and Carcinogenesis

The Wnt pathway has many transcriptional endpoints or target genes. The majority of these are specific to certain types—which is not unusual in developmental signaling pathways. This is consistent with a fundamental mechanism of gene control by extracellular signals in which the cell rather than the signal determines the nature of the response. However, in addition to cell type specific genes, Wnt signaling also controls genes that are more widely induced, including components of the Wnt signaling pathway and genes that are most likely activated by the Wnt-β-catenin-TCF cascade.

The transition of normal cellular physiology into one characterized by neoplastic change has been the object of intense study in an effort to better understand the events underlying the development of cancer. The inappropriate activation of the target genes by β-catenin thus can result in a disease state in the organism even though there may not be any somatic mutation in the target genes themselves. Ilyas has generated a modification of the Hanahan and Weinberg list of phenotypes that are acquired by most malignancies; including "Inappropriate stem cell phenotype/limitless replicative potential", "evasion of apoptosis," "tissue invasion and metastasis," "self sufficiency of growth signals," "insensitivity to growth inhibitors," "failure of terminal differentiation," "evasion of immune response," and "sustained angiogenesis." Ilyas, *J. Pathol* 2005; 205: 130-144; Hanahan and Weinberg, *Cell* 2000; 100: 57-70. Analysis of the genes modulated by Wnt signaling, including target genes of β-catenin or altered expression as shown by microarray analysis shows that the perturbations from aberrant Wnt signaling either directly or through the effect on target genes can impart nearly all of these "neoplastic phenotypes." Ilyas, M., *J. Pathol* 2005; 205: 130-144. A list of example targets of Wnt signaling is given in Table 1. Gene targets that are upregulated appear in boldface, while those which are downregulated are italicized. Aberrant expression of such target genes due to the result of activated and/or excessive Wnt signaling may be remedies upon application of the Wnt antagonists of the invention.

TABLE 1

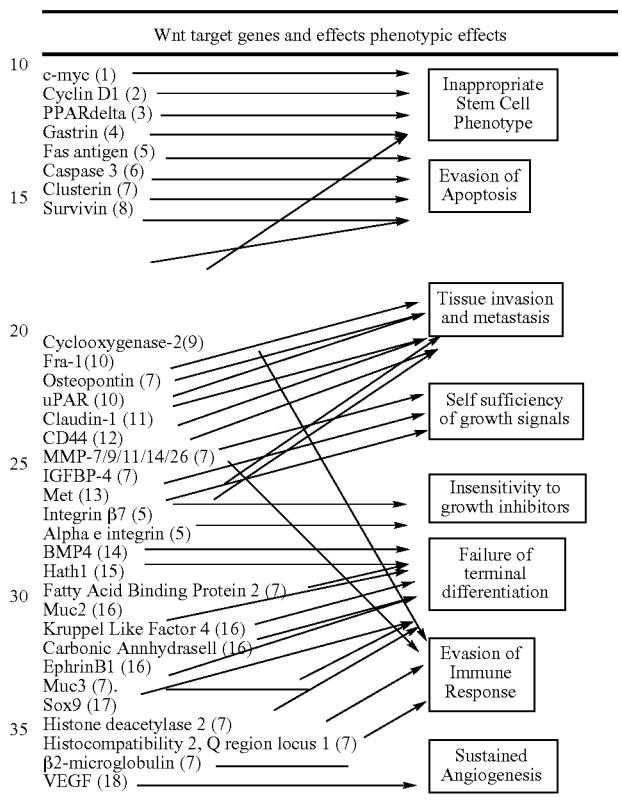

Increasingly, cancer is being viewed as a "stem cell" disease (Taipale et al, *Nature* 2001; 411: 349-54—that is, an inappropriate activation and/or maintenance of stem cells. Wnt signaling has been shown to be essential for the maintenance of stem cells [He et al., *Nature Genet.* 2004; 36: 1117-1121; Reya et al., *Nature* 2003; 423: 409-414; Willert et al., *Nature* 2003; 423: 448-452]. In the intestine, TCF4 is the main nuclear binding factor for β-catenin and the failure of TCF4 knock out mice to develop stem cells in the small intestine further supports the role of canonical Wnt signaling in stem cell maintenance [Korinek et al., *Nat. Genet.* 1998; 19: 379-83; Pinto et al., *Genes Dev.* 2003; 17: 1709-13; Kuhnert et al., *Proc. Natl. Acad. Sc. USA* 2004; 101: 66-71].

The effect of Wnt signaling on multiple biological processes is illustrated by the matrix metalloproteinase genes (MMPs). MMP7, MMP14 and MMP26 have been shown to direct targets of β-catenin [Marchenko et al., *Int. J. Biochem. Cell Biol.* 2004; 36: 942-956; Takahashi et al., *Oncogene* 2002; 21: 5861-5867; Brabletz et al., *Am. J. Pathol* 1999; 155: 1033-1038], while other MMPs were found expressed directly by intestinal adenomas [Paoni et al., *Physiol Genomics* 2003; 15: 228-235]. The MMPs are proteolytic enzymes that breakdown stromal collagen thereby allowing tumor cells to acquire the phenotype "tissue invasion and metastasis." The enzymatic activity also allows the release of latent growth factors in the stroma, which together with other growth factors secreted by the tumor cells themselves will contribute to "self sufficiency of growth signals." [Coussens et al., *Science* 2002; 295: 2387-2392; Egeblad et al., *Nature Rev. Cancer* 2002; 2: 161-174]. MMPs can also act on osteopontin (a secondary Wnt-induced target [Paoni et al., supra], to release fragments which together with vascular endothelial growth factor (VEGF), a direct target of β-catenin, contributes to the feature of "sustained angiogenesis." [Zhang et al., *Cancer Res.* 2001; 61: 6050-6054; Agnihotri et al., *J. Bio. Chem.* 2001; 276: 28261-28267].

While the Wnt signaling pathway can be activated at levels downstream of the ligand receptor interaction, there is strong evidence to suggest inhibition of the extracellular ligand-receptor interaction component is effective in reducing the tumorigenicity, even though the event initiating the Wnt signaling may have occurred downstream. For example, Ilyas reports in a recent review that the inhibition of Wnt signals in several colorectal cancer cell lines results in reduced tumorigenicity. [Ilyas, supra.]. Moreover, the transfection of inoperative frizzled receptor (Frz7 ectodomain) into carcinoma cell line (SK-CO-1) restored a normal β-catenin phenotype. This cell line has active Wnt signaling due to a homozygous $APC^{-/-}$ mutation. Moreover, such cells also did not demonstrate tumor formation when transferred in vivo. Vincan et al., *Differentiation* 2005; 73: 142-153. This demonstrates that the inhibition of Wnt signaling at the extracellular level can downregulate Wnt signaling resulting from activation of a downstream intracellular Wnt signaling pathway component. This further suggests that inhibitors such as the Wnt antagonists of the present invention, which inhibit Wnt-Frz interactions, have therapeutic benefit for any Wnt-mediated disorder, regardless of the particular manner in which Wnt signaling has been activated.

4. Aberrant Wnt Signaling in Colon Cancer:

Defects in the Wnt signaling component APC was originally discovered to be the key in the hereditary cancer syndrome familial adenomatous polyposis (FAP). FAP patients who inherit one defective APC allele develop large number of colon polyps, or adenomas, in the early years of their life. Such polyps develop as clonal outgrowths of epithelial cells in which the second APC allele is inactivated. The cumulative effect of these FAP adenomas inevitably results in the appearance of adenocarcinomas, evident as a more or less ordered accumulation of mutations in additional oncogenes or tumor suppressor genes, such as K-Ras, p53 and Smad4. Moreover, the loss of APC also occurs in most sporadic colorectal cancers. Kinzler et al., *Cell* 87: 159-170 (1996). The mutational inactivation of APC, by resulting in the stabilization of, and eventual nuclear transport of β-catenin, and Wnt signaling, thereby transforms epithelial cells. Interestingly, reporter plasmids containing concatemerized TCF binding sites such as the pTOPFLASH, normally transcribed only upon Wnt signaling, are inappropriately transcribed in APC mutant cancer cells through constitutive activation of β-catenin/TCF-4 transcription complexes. In other examples of colorectal cancer in which APC in not mutated, the scaffolding protein Axin-2 is mutated [Liu et al., *Nature Genet.* 26: 146-147 (2000) or β-catenin is mutated so as to remove the N-terminal Ser/Thr destruction motif. [Morin et al., *Science* 275: 1787-1790 (1997). Thus, colorectal cancer is linked not only to defects in APC, but to the inappropriate persistence of β-catenin/TCF-4 transcriptional activation. It has further been reported that TCF-4 mutations result in activation of the same target genes (as shown by microarray analysis) in colorectal cancers, as is observed through defective APC expression in crypt stem and progenitor cells. Van de Wetering et al., *Cell* 111: 241-250 (2002). Once the Wnt cascade is activated, the APC-adenoma cells maintain their progenitor status indefinitely. As a result, it is likely that the activation of Wnt signaling is a necessary precursor in the carcinogenesis of colorectal cancer, and the inhibition of Wnt signaling could be an effective means to treat and/or prevent the onset of this disorder.

5. Wnt Signaling in Hematopoietic Stem Cells

Hematopoietic stem cells give rise to the adult blood cells of the circulatory system in a process of lineage-committed progenitor cells from multipotential hematopoietic stem cells (HSC). It is also apparent that Wnt signaling contributes to the self-renewal and maintenance of HSC's, and that dysfunctional Wnt signaling is responsible for various disorders resulting from HSC's, such as leukemias and various other blood related cancers. Reya et al., *Nature* 434: 843-850 (2005); Baba et al., *Immunity* 23: 599-609 (2005); Jamieson et al., *N. Engl. J. Med.* 351(7): 657-667 (2004). Wnt signaling is normally reduced as stem cells convert to committed myeloid progenitor cells. Reya et al., *Nature* 423: 409-414 (2003).

Not only are Wnt ligands themselves produced by HSC's, but Wnt signaling is also active, thereby suggesting autocrine or paracrine regulation. Rattis et al., *Curr. Opin. Hematol.* 11: 88-94 (2004); Reya et al., *Nature* 423: 409-414 (2003). Additionally, both β-catenin and Wnt3a promote self renewal of murine HSCs and progenitor cells, while application of Wnt-5A to human hematopoietic progenitors promotes the expansion of undifferentiated progenitors in vitro. Reya et al., supra.; Willert et al., *Nature* 423: 448-452 (2003); Van Den Berg et al., *Blood* 92: 3189-3202 (1998).

In addition to HSC's, it is apparent that embryonic stem cells, epidermal stem cells and epithelial stem cells are responsive or dependent on Wnt signaling for maintenance in an undifferentiated, proliferating state. Willert et al., supra; Korinek et al., *Nat. Genet.* 19: 379-383 (1998); Sato et al., *Nat. Med.* 10: 55-63 (2004); Gat et al., *Cell* 95: 605-614 (1998); Zhu et al., *Development* 126: 2285-2298 (1999). Therefore the inhibition of Wnt signaling with the Wnt antagonists of the present invention may be a therapeutic in the treatment of disorders resulting from dysfunctional hematopoieses, such as leukemias and various blood related cancers, such as acute, chronic, lymphoid and myelogenous leukemias, myelodysplastic syndrome and myeloproliferative disorders. These include myeloma, lymphoma (e.g., Hodgkin's and non-Hodgkin's) chronic and nonprogressive anemia, progressive and symptomatic blood cell deficiencies, polycythemia vera, essential or primary thrombocythemia, idiopathic myelofibrosis, chronic myelomonocytic leukemia (CMML), mantle cell lymphoma, cutaneous T-cell lymphoma, Waldenstrom macroglobinemia, 6. Wnt Signaling in Leukemia Unregulated activation of the Wnt signaling pathway is a precursor to the development of leukemia. Reya et al., supra. Experimental evidence exists supporting the oncogenic growth of both myeloid and lymphoid lineages as dependent on Wnt signaling. Wnt signaling has been implicated in regulating both the chronic and acute forms of myeloid leukemia. Granulocyte-macrophage progenitors (GMPs) from chronic myelogenous leukemia patients and blast crisis cells from patients resistant to therapy display activated Wnt signaling. Jamieson, et al., supra. Moreover, inhibition of β-catenin through ectopic expression of Axin decreases the replating capacity of leukemic cells in vitro, suggesting that chronic myelogenous leukemia precursors are dependent on Wnt signaling for growth and renewal. Also, Wnt overexpression caused GMPs to acquire stem-cell-like properties of long-term self renewal. Jamieson et al., supra. This finding further support the hypothesis that Wnt signaling is necessary for the normal development of blood lineages, but that aberrant Wnt signaling results in the transformation of progenitor cells. The Wnt antagonists of the present invention would be useful to treat these types of leukemias.

Recent studies also suggest that lymphoid neoplasias may also be influenced by Wnt signaling. Wnt-16 is overexpressed in pre-B-cell leukemia cell lines carrying the E2A-PbX translocation, suggesting that autocrine Wnt activity may contribute to oncogenesis. McWhirter, et al., *Proc. Natl. Acad. Sci. USA* 96: 11464-11469 (1999). The role of Wnt signaling in the growth and survival of normal B-cell progenitors further supports this notion. Reya et al., *Immunity* 13: 15-24 (2000); Ranheim et al., *Blood* 105: 2487-2494 (2005). Autocrine dependence on Wnt has also been proposed for regulating the growth of multiple myeloma, a cancer of terminally differentiated B-cells. Derksen et al., *Proc. Natl. Acad. Sci. USA* 101: 6122-6127 (2004). Primary myelomas and myeloma cell lines were also found to express stabilized (i.e., independent of degradation complex). Although no mutations in Wnt signaling components was present, the overexpression of several components, including Wnt-5A and Wnt-10B suggest that tumor dependency and cancer self-renewal is not necessarily dependent on mutations appearing in Wnt signaling pathway components, but rather only upon constitutive activation of the pathway itself. Reya et al., supra. Through binding overexpressed Wnt, the Wnt antagonists of the present invention would be an effective therapeutic in treating B-cell leukemias.

The transition of self-renewing, pluripotent stem cells to myeloid progenitors is accompanied by the downregulation of Wnt signaling. Reya et al, *Nature* 423: 409-414 (2003). Similarly, the stable expression of β-catenin in lymphoid progenitors restored multiple differentiation options, albeit such cells lacked markers typically associated with either cell type. Baba et al, *Immunity* 23: 599-609 (2005). Thus, it is strongly suggested that the inhibition of Wnt signaling by the Wnt antagonists of the invention could be an effective therapeutic in treating leukemia, such as myeloid and lymphoid leukemia, including acute and chronic myelogenous leukemia as well as acute and chronic lymphoid leukemias.

7. Aberrant Wnt Signaling in Neural Disorders

It has also been observed that the activation of Wnt signaling through β-catenin can increase cycling and expansion of neural progenitors, and that loss of such signaling can result in a loss of progenitor compartment. Chenn et al., *Science* 297: 365-369 (2002); Zechner et al., *Dev. Biol.* 258: 406-418 (2003). Just as normal activation of Wnt signaling may promote self-renewal of neuronal stem cells, aberrant Wnt pathway activation may be tumorigenic in the nervous system. Experimental evidence supporting this conclusion is the discovery that medulloblastoma, a pediatric brain tumor of the cerebellum, contains mutations in both β-catenin and Axin—thereby suggesting that medulloblastomas arise from primitive progenitors that become transformed in response to uncontrolled Wnt signaling. Zurawel et al., *Cancer Res.* 58: 896-899 (1998); Dahmen et al., *Cancer Res.* 61: 7039-7043 (2001); Baeza et al., *Oncogene* 22: 632-636 (2003). Thus, it is strongly suggested that the inhibition of Wnt signaling by the Wnt antagonists of the invention may be an effective therapeutic in the treatment of various neuronal proliferative disorders, including brain tumors, such as gliomas, astrocytomas, meningiomas, Schwannomas, pituitary tumors, primitive neuroectodermal tumors (PNET), medulloblastomas, craniopharyngioma, pineal region tumors, and non cancerous neurofibromatoses.

8. Aberrant Wnt Signaling in Breast Cancer.

In mammary tissues where stem cells have yet to be definitively isolated, a controlling role for Wnt in progenitor cell fate or maintenance is suggested by studies of Wnt transgenic mice develop mammary tumors. These tumors have an increased frequency of individual cells with stem and progenitor properties, in stark contrast to tumors from mice overexpressing other oncogenes. [Liu et al., *Proc. Natl. Acad. Sci. USA* 101: 4158-4163 (2004); Li et al., *Proc. Natl. Acad. Sci. USA* 100: 15853-15858 (2003)]. This suggests that the Wnt pathway may be unique in its ability to target stem and progenitor cells for transformation, and suggests a key role in the self-renewal of normal breast epithelium. Thus the inhibition of Wnt signaling by the Wnt antagonists of the invention is likely an effective therapeutic in the treatment of breast cancer.

FIG. 32 is an illustration of active Wnt signaling in human breast cancer. FIG. 32A shows Wnt-1 expression (as shown by in vitro hybridization) in normal (A-1), low grade (A-2) and high grade (A-3) human breast tumor initially reported in Wong et al., *J. Pathol* 196: 145 (2002). FIG. 32B shows nuclear (B-1) and cytoplasmic (B-2) localization (as shown by IHC) of β-catenin in breast cancer patients. Also shown is a Kaplan-Meier survival plot (B-3) showing patient survival probability that correlates with the indicated β-catenin expression pattern. This data was initially reported in Lin et al., *P.N.A.S.* (*USA*) 97(8): 4262-66 (2000). FIG. 32C is a microarray analysis of Wnt-1 expression in a normal breast from a patient without cancer in comparison with tissue isolated from a patient with infiltrating ductal carcinoma, her-2 negative.

9. Wnt Signaling in Aging

The Wnt signaling pathway may also play a critical role in aging and age-related disorders.

As reported in Brack A S, et al., *Science,* 317(5839):807-10 (2007), muscle stem cells from aged mice were observed to convert from a myogenic to a fibrogenic lineage as they begin to proliferate. This conversion is associated with an increase in canonical Wnt signaling pathway activity in aged myogenic progenitors and can be suppressed by Wnt inhibitors. Additionally, components of serum from aged mice bind to the Frizzled proteins and may account for the elevated Wnt signaling in aged cells. Injection of Wnt3A into young regenerating muscle reduced proliferation and increased deposition of connective tissue.

The Wnt signaling pathway has been further implicated in aging process in studies using the Klotho mouse model of accelerated aging in which it was determined that the Klotho protein physically interacted with and inhibited Wnt proteins. Liu H, et al., Science, 317(5839):803-6 (2007). In a cell culture model, the Wnt-Klotho interaction resulted in the suppression of Wnt biological activity while tissues and organs from Klotho-deficient animals showed evidence of increased Wnt signaling.

Accordingly, Wnt antagonists could find use as therapeutics to reduce the effects of aging and to treat age-related diseases.

I. Modes of Administration Specific Formulations

1. General Considerations

A pharmaceutical composition is formulated to be compatible with its intended route of administration, including intravenous, intradermal, subcutaneous, oral (e.g., inhalation), transdermal (i.e., topical), transmucosal, and rectal administration. Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

2. Injectable Formulations

Pharmaceutical compositions suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL (BASF, Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a solvent or dispersion medium containing, for example, water, ethanol, polyol (such as glycerol, propylene glycol, and liquid polyethylene glycol), and suitable mixtures. Proper fluidity can be maintained, for example, by using a coating such as lecithin, by maintaining the required particle size in the case of dispersion and by using surfactants. Various antibacterial and antifungal agents; for example, parabens, chlorobutanol, phenol, ascorbic acid, and thimerosal, can contain microorganism contamination. Isotonic agents; for example, sugars, polyalcohols such as manitol, sorbitol, and sodium chloride can be included in the composition. Compositions that can delay absorption include agents such as aluminum monostearate and gelatin.

Sterile injectable solutions can be prepared by incorporating the active compound (e.g., any modulator substance/molecule of the invention) in the required amount in an appropriate solvent with one or a combination of ingredients as required, followed by sterilization. Generally, dispersions are prepared by incorporating the active compound into a sterile vehicle that contains a basic dispersion medium, and the other required ingredients. Sterile powders for the preparation of sterile injectable solutions, methods of preparation include vacuum drying and freeze-drying that yield a powder containing the active ingredient and any desired ingredient from a sterile solutions.

3. Systemic Administration

Systemic administration can also be transmucosal or transdermal. For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the active compounds are formulated into ointments, salves, gels, or creams.

The compounds can also be prepared in the form of suppositories (e.g., with bases such as cocoa butter and other glycerides) or retention enemas for rectal delivery.

4. Carriers

In one embodiment, the active compounds are prepared with carriers that protect the compound against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Such materials can be obtained commercially from ALZA Corporation (Mountain View, Calif.) and NOVA Pharmaceuticals, Inc. (Lake Elsinore, Calif.), or prepared by one of skill in the art. Liposomal suspensions can also be used as pharmaceutically acceptable carriers. These can be prepared according to methods known to those skilled in the art, such as in (Eppstein et al., U.S. Pat. No. 4,522,811, 1985).

5. Unit Dosage

Oral formulations or parenteral compositions in unit dosage form can be created to facilitate administration and dosage uniformity. Unit dosage form refers to physically discrete units suited as single dosages for the subject to be treated, containing a therapeutically effective quantity of active compound in association with the required pharmaceutical carrier. The specification for the unit dosage forms are dictated by, and directly dependent on, the unique characteristics of the active compound and the particular desired therapeutic effect, and the inherent limitations of compounding the active compound.

6. Gene Therapy Compositions

The nucleic acid molecules can be inserted into vectors and used as gene therapy vectors. Gene therapy vectors can be delivered to a subject by, for example, intravenous injection, local administration (Nabel and Nabel, U.S. Pat. No. 5,328,470, 1994), or by stereotactic injection (Chen et al., *Proc Natl Acad Sci USA*. 91:3054-7 (1994)). The pharmaceutical preparation of a gene therapy vector can include an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

7. Dosage

The pharmaceutical composition and method may further comprise other therapeutically active compounds that are usually applied in the administration of the Wnt antagonists.

In the treatment or prevention of conditions which require administration of Wnt antagonists, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

However, the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

8. Kits for Compositions

The compositions (e.g., pharmaceutical compositions) can be included in a kit, container, pack, or dispenser together with instructions for administration. When supplied as a kit, the different components of the composition may be packaged in separate containers and admixed immediately before use. Such packaging of the components separately may permit long-term storage without losing the active components' functions.

Kits may also include reagents in separate containers that facilitate the execution of a specific test, such as diagnostic tests or tissue typing.

(a) Containers or Vessels

The reagents included in kits can be supplied in containers of any sort such that the life of the different components are preserved and are not adsorbed or altered by the materials of the container. For example, sealed glass ampules may contain lyophilized modulator substance/molecule and/or buffer that have been packaged under a neutral, non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include simple bottles that may be fabricated from similar substances as ampules, and envelopes, that may consist of foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

(b) Instructional Materials

Kits may also be supplied with instructional materials. Instructions may be printed on paper or other substrate, and/or may be supplied as an electronic-readable medium, such as a floppy disc, CD-ROM, DVD-ROM, Zip disc, videotape, laserdisc, audio tape, etc. Detailed instructions may not be physically associated with the kit; instead, a user may be directed to an internet web site specified by the manufacturer or distributor of the kit, or supplied as electronic mail.

9. Combination Therapy

In certain embodiments, a pharmaceutical formulation comprising a Wnt antagonist is administered in combination with at least one additional therapeutic agent and/or adjuvant. In certain embodiments, the additional therapeutic agent is a chemotherapeutic agent, growth inhibitory agent, or cytotoxic agent like a toxin, such as a maytansinoid, calicheamicin, antibiotic, radioactive isotope, nucleolytic enzyme or the like.

Such combination therapies noted above encompass combined administration (where two or more therapeutic agents are included in the same or separate formulations), and separate administration, in which case, administration of a Wnt antagonist can occur prior to, simultaneously, and/or following, administration of the additional therapeutic agent and/or adjuvant. A Wnt antagonist can also be used in combination with radiation therapy.

10. Medicaments

The invention provides a Wnt antagonist for a use in the preparation of a medicament useful for treating a Wnt-mediated disorder. In a specific aspect, the Wnt-mediated disorder is cancer.

The following examples are included to demonstrate preferred embodiments of the present invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention. All references cited throughout the specification are expressly incorporated by reference in their entirety herein.

Example 1

General Protocols

Mammalian Cell Culture.

Human kidney epithelial (HEK) 293 cells (ATCC # CRL-1573), human ovarian PA1 cells (ATCC # CRL-1572) were grown in 50/50 Dulbecco modified Eagle high glucose medium, Ham's F12 which has been supplemented with 10% fetal bovine serum. Human teratoma derived NTer2 (ATCC #CRL-1973) and Tera2 (ATCC#HTB-106) cells were maintained in McCoy's medium supplemented with 15% fetal bovine serum and NCCIT cells (ATCC # CRL-2073) were maintained in RPMI supplemented with 10% fetal bovine serum. All cell lines were further supplemented with 2 mM glutamine, and 1% penicillin-streptomycin at 37° C. in 5% $CO_2$.

Transfection and Luciferase Assays

In preparation for transfection, (1) 500,000 HEK293 and (2) 100,000 PA1 cells (ATCC # CRL-1572), NCCIT, NTera2 or Tera2 cells were plated into each well of a 12-well dish (Nuc) 24 hours before transfections. Cells were transfected with 0.375 μg TOPglow (Upstate, Cat # 21-204), 0.05 mg LEF1, 0.01 mg SV40 RL with Fugene (Roche) and at 24 hours post transfection. Media was changed and cells were untreated or treated with Wnt3a alone, Wnt-5a alone, or with serum samples for an additional 20-24 hours before harvesting. All dilutions were made in complete media for the indicated cell lines. Cells were harvested in 50-100 μl of 1×SJC lysis buffer (20 mM Tris pH 8.0, 137 mM NaCl, 1 mM EGTA, 1% Triton X-100, 10% Glycerol, 1.5 mM $MgCl_2$, 1 mM DTT, 50 mM NaF, 1 mM $NaVO_4$ and protease inhibitors) and duplicate 10 μl were assayed using Dual-Glo™ luciferase assay kit (Promega, Part # TM058) and detected in an Envision Luminometer (Perkin Elmer). Luciferase activity was normalized against *Renilla* activity.

Example 2

Construction of Frz-Fc Chimeric Molecules

Cloning and Expression
Frz8(173)-Fc and Frz8(156)-Fc

FIGS. 4A and B show the sequences of the Frz8 (156)-Fc and Frz8 (173)-Fc chimeric constructs. FIG. 4A shows the longer Frz8(173) sequence. Shown in gray (i.e., first 24 N-terminal amino acid residues) is the leader signal sequence. Shown in underline (i.e., residues 25-27) are alanine residues that may be present or absent in the mature protein. Shown in boxed text (i.e., residues 157-173) are the additional sequences of the Frz8 receptors that distinguish the longer Frz8 (173) from the shorter Frz8(156) chimeric constructs. Shown in bold (i.e., residues 174-182) is the linker sequence, while the sequence in italics (i.e., residues 183-409) is the Fc region. FIG. 4B shows the shorter Frz (156) minimal CRD (ECD) domain sequence. In gray (i.e., first 24 N-terminal amino acid residues) is the leader signal sequence. Shown in underline (i.e., residues 25-27) are alanine residues that may be present or absent in the mature protein. Shown in bold (i.e., residues 157-164) is the linker sequence, while the sequence in italics (i.e., residues 165-391) is the Fc region.

The Frz8(156)-Fc construct was constructed as follows. cDNA encoding Frizzled 8 residues 1-156 were sub-cloned into the EcoR1 and XhoI sites of a pRK-derived plasmid. While native human cDNA is preferred, alternative sequence encoding identical protein sequence (e.g., murine) may also be used. In this cloning procedure, the carboxyl terminus of the Frz8 was fused to the amino terminus of a human IgG effector domain (Fc) via a short linker region (e.g., residues LESGGGGVT) (SEQ ID NO: 70), to create an Frz8-Fc fusion. A final construct encodes 156 residues of Frz8. The cloning was performed using standard molecular biology techniques (Ausubel et al (eds.), 2003, *Current Protocols in Molecular Biology*, 4 Vols., John Wiley & Sons). Protein was expressed in Chinese Hamster Ovary (CHO) cells.

Alternatively, the cDNA encoding a length of Frz8 of a length different than described previously (e.g., 1-173) may be used. In addition, an alternative linker sequence (e.g., ESGGGGVT) (SEQ ID NO: 69) may also be used.

Frz-Fc and sFrp-Fc Constructs

The constructs for the Wnt antagonists with a Frizzled domain component comprising Frz1, Frz2, Frz3, Frz4, Frz5, Frz6, Frz7, Frz9, Frz10, sFRP1, sFRP2, sFRP3, sFRP4, or sFRP5 were constructed in a manner similar to the procedure described for Frz8. Frz2, Frz3, Frz4, Frz5, and sFRP3 were subcloned into a pRK-derived plasmid using XhoI and AscI. Frz1, Frz6, Frz7, Frz9, Frz10, and sFRP4 were subcloned into a pRK-derived plasmid using ClaI and XhoI and sFrp1, sFrp2, and sFRP5 were subcloned into a pRK-derived plasmid using ClaI and AscI. As with the Frz8 constructs, the carboxyl terminus of the Frz domains were fused to the amino terminus of a human IgG effector domain (Fc) via a short linker region to create the chimeric Wnt antagonists. FIGS. 7 (A, B, and C) shows exemplary amino acid sequences for these constructs. The leader signal sequence is shown in bold with italics indicating a non-native leader sequence. The linker is underlined and the Fc component is shown in italics.

FIG. 5 (A-H) (SEQ ID NOs: 115-129) provides exemplary nucleic acid sequences for these Wnt antagonist constructs.

Alternative constructs can be made to optimize in vivo activity or stability or to provide other beneficial characteristics, such as, for example, increased solubility, improved binding characteristics. These constructs may include linkers that are different than the linkers of the above-described Wnt antagonists. For example, an alternative construct of the Frz3-Fc chimeric protein (SEQ ID NO: 114) has been made by subcloning a Frz3 domain into a pRK-derived plasmid using BstXI and XhoI and using the LESGGGGVT (SEQ ID NO: 70) peptide linker to fuse the Frz3 domain to the Fc domain.

Protein Isolation

Figure 10:
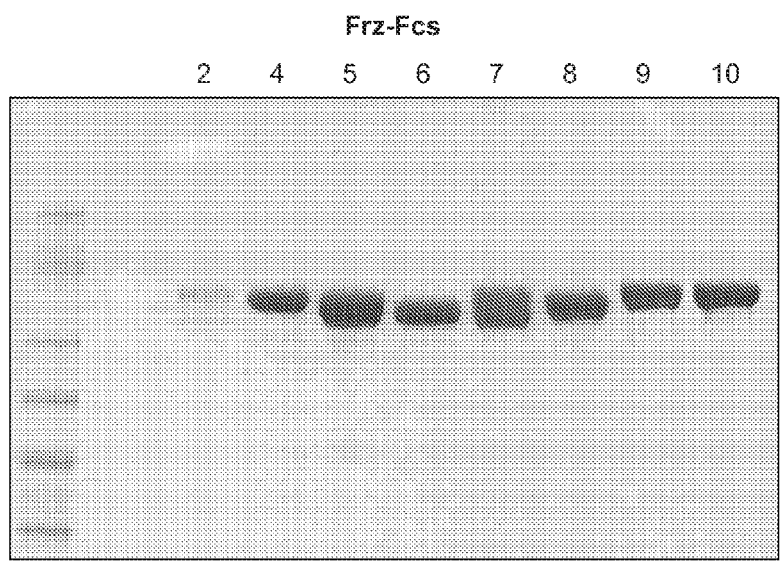
FIG. 10 depicts samples of purified Frizzled-Fc fusion proteins expressed and purified from CHO cells. Samples were separated on non-reducing SDS-PAGE gels and imaged by Coomassie staining.

The Wnt antagonist chimeric proteins were isolated to >90% purity by affinity capture using a PROSEP® (Millipore) protein-A conjugated resin. Higher order aggregates were separated from dimers by passage over a Superdex 200® (GE-Healthcare) gel-filtration column. Protein identity and processing of the amino terminus to remove the signal sequence were confirmed by Edmund degradation. Purity of the final protein is estimated to be greater than 98% (FIG. 10). Endotoxin levels of the material after purification is complete and less than 1.0 EU/mg.

Example 3

Serum Stability of Frz8-Fc Chimeric Molecules

Figure 11A:
FIG. 11A is an immunoblot for human FC used to detect the chimeric proteins present at increasing time points in serum of athymic nude mice injected with the chimeras.

Initial studies of the serum stability of the Frz8(173)-Fc chimeric constructs indicated that the construct had a limited in vivo half-life. The in vivo instability was likely due to the presence of protease cleavage sites in the EC domain (ECD) of the Frizzled receptor component. The Frz8(156)-Fc construct described in Example 2 exhibited increased serum stability over the Frz8(173)-Fc. Athymic nude mice were injected i.v. with 10 mg/kg of either Frz8(173)-Fc or Frz8 (156)-Fc. Serum was collected at specified time points and analyzed for total and active protein. FIG. 11A shows an immunoblot for human Fc used to detect the protein present in 1 µL of serum and compared with 25 µg of the respective purified protein (P). Frz8(156)-Fc was detectable in serum 72 h after administration, whereas Frz8(173)-Fc was not detectable beyond 30 minutes.

Figure 11B:
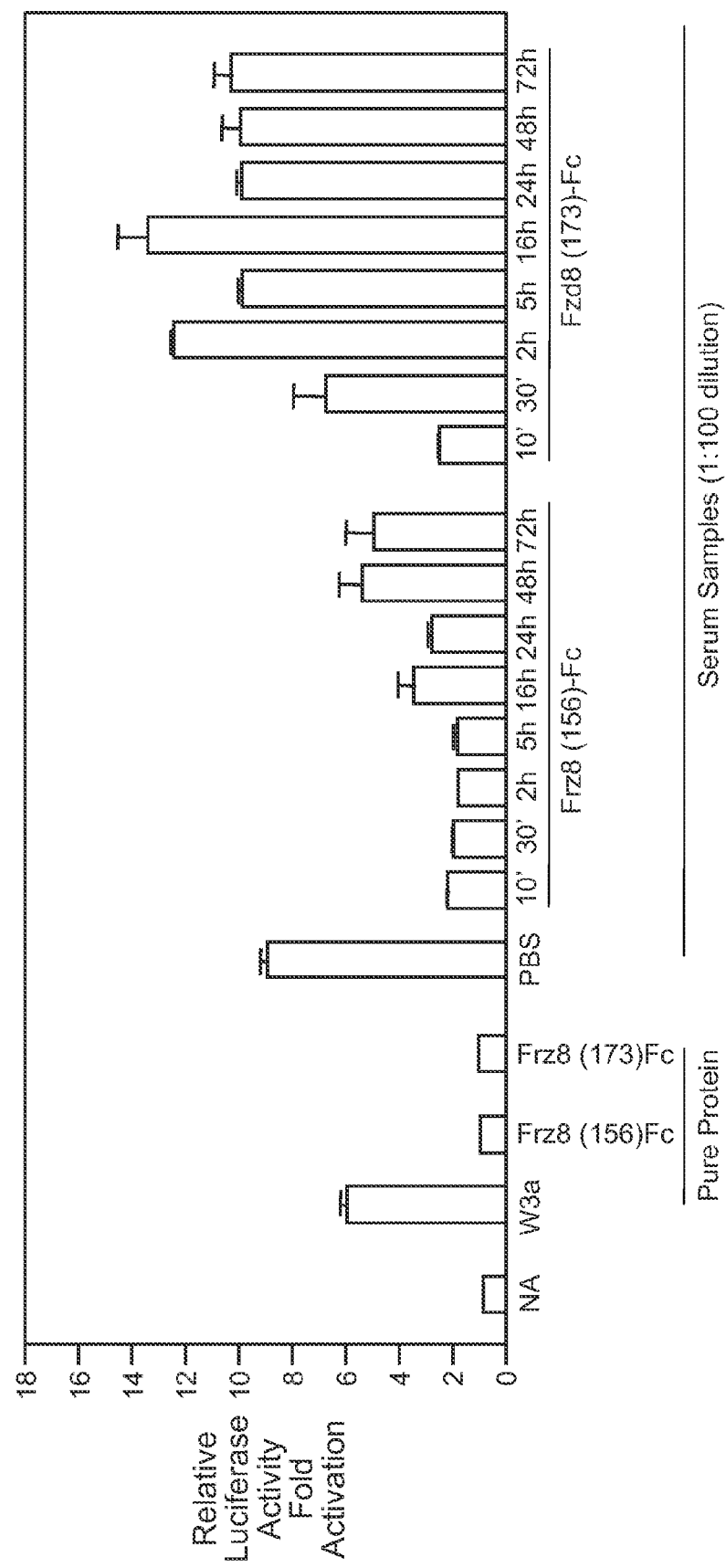
FIG. 11B shows the Wnt inhibitory activity of the chimeric proteins assayed by measuring TOPglow activity shown on the Y axis as relative luciferase activity.

The activity of Frz8(156)-Fc and Frz8(173)-Fc in the collected serum was assayed by measuring the inhibition of Wnt3a-dependent TOPglow reporter activity in HEK293 cells. Although comparable in vitro potency was observed on treatment with purified Frz8(156)-Fc and Frz8(173)-Fc at 2.5 µg/mL, only partial inhibitory activity was recovered from the serum of Frz8(173)-Fc-treated mice collected 30 minutes after protein administration. In contrast, more potent inhibitory activity could be recovered from the serum of Frz8(156)-Fc treated mice for up to 24 hours after administration, with detectable levels of inhibition for at least 72 hours (FIG. 11B). These studies demonstrate that the Frz8(156) molecule is more stable in vivo than the molecule based on Frz8(173).

Figure 12:
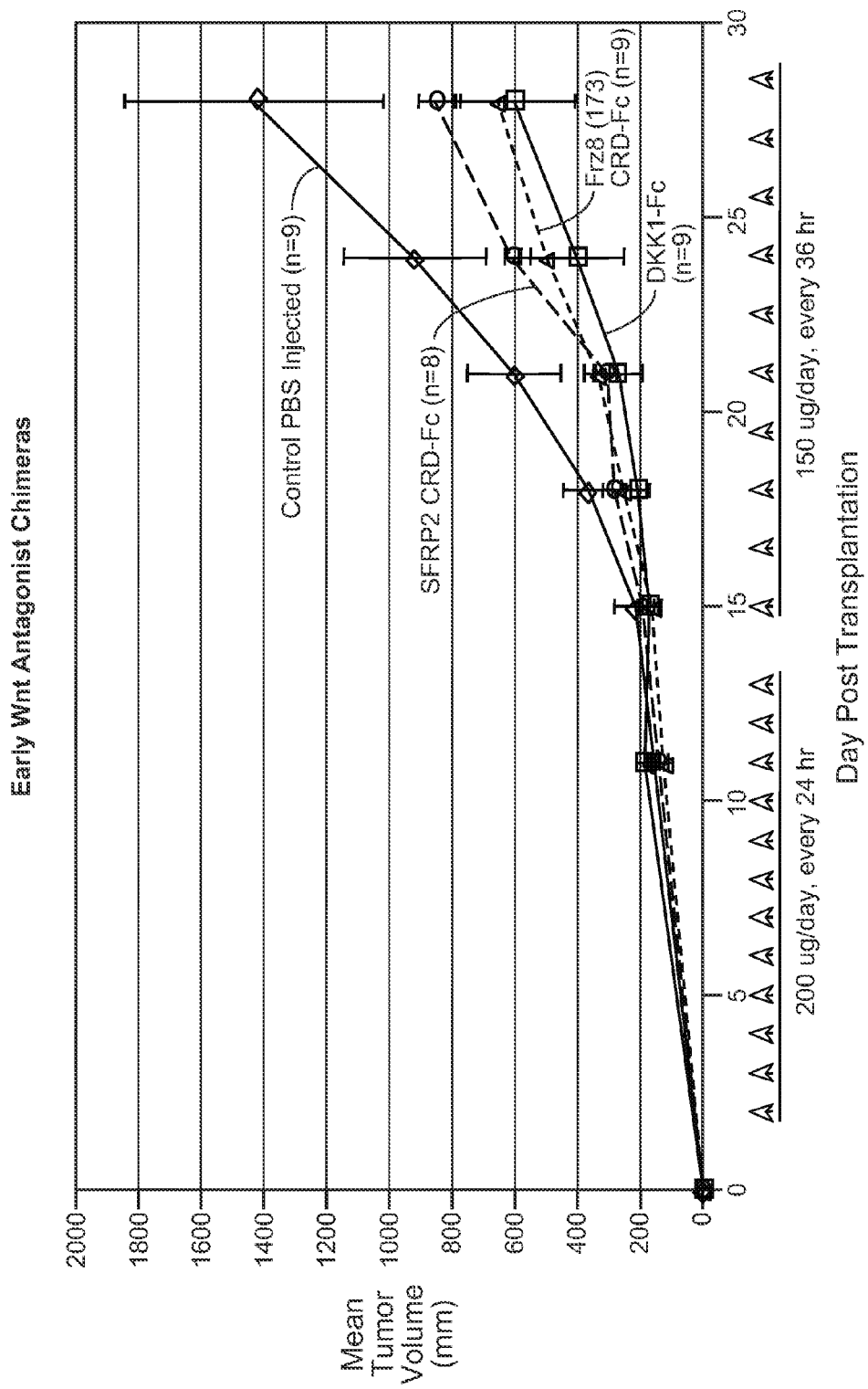
FIG. 12 is a graph of tumor volume over time resulting from treatment with Frz8(173)-Fc chimera.

Additionally, the Frz8(173)-FC had suboptimal efficacy and acted only to reduce the rate of increase in tumor volume, as opposed to shrinking starting tumor volume. This suboptimal efficacy is illustrated in FIG. 12, showing a graph of tumor volume over time resulting from treatment with various Wnt signaling component-Fc chimeric antagonists, including the Frz8(173)-FC molecule. In this assay, the MMTV-WNT-1 tumors were transplanted into the mammary fat pad of athymic nude mice, and drug was administered IV at the time points indicated by the arrows on the X-axis.

Example 4

In Vivo Pharmacokinetics of Frz8(156)-FC

The in vivo pharmacokinetics of Frz8(156)-FC were tested by administration of a single dose of this protein at 1, 5, or 20 mg/kg i.v. or at 20 mg/kg i.p. into nude mice. As reported in FIG. 13 and discussed further in this Example below, the Frz8-Fc reagent displayed biphasic elimination in nude mice at all doses. After a single IV or IP dose, Frz8-Fc displays: (1) dose proportional increase in exposure; (2) rapid absorption after IP dosing; (3) clearance of about 25-30 ml/day; and (4) a half life of about 4 days. Bioavailability coefficient, $AUC_{IP}/AUC_{IV}$=92%.

Animal Protocol

Female athymic nude mice are separated into 4 groups of 12, on the basis of quantity of drug administered and manner of administration. Group 1: Frz8-Fc 1 mg/kg, intravenous (IV); Group 2: Frz8-Fc, 5 mg/kg, IV; Group 3: Frz8-Fc 20 mg/kg, IV; and Group 4: Frz8-Fc, 20 mg/kg, interperitoneal (IP). Each animal received an IV or IP bolus dose of Frz8-Fc according to the group designation. The dose volume administered (5-10 mL/kg) varies depending upon the concentration of the dosing solution and the weight of each animal. IV dosing is administered via the tail vein.

About 125 µl of blood is collected from each animal according to the following procedure. Serum is stored at −70° C. until assayed by ELISA. Sample are drawn such that n=3 animals/timepoint. Extra animals are used for predose sample collection and/or collection of blank mouse serum. Blood is collected with a retroorbital bleed for the first two timepoints for each animal, using alternative eyes. For the final timepoint, blood is collected via a cardiac stick and about 1 ml is aliquoted into 2 tubes. One sample will be used to determine Frz8-Fc concentration and the other will be reserved for research use. Each animal receives an IP bolus of 10 ml saline as fluid replacement after each blood collection timepoint. Retroorbital bleeds are performed under isoflorane anesthesia and terminal bleeds occur under a ketamine/xylazine cocktail. Animals are euthanized via cervical dislocation under anesthesia after the final blood draw.

Results

FIG. 13A is an immunoblot of a neat serum from mice treated with Frz8-Fc showing detection in serum at 7 days and beyond from both 20 or 5 mg/kg I.V. or 20 mg/kg I.P. Samples were taken from individual mice at 4, 7, 10 or 14 days. For controls, serum samples were taken from untreated mice, Frz8-Fc protein was added to 20 μg/ml and the samples incubated for 2 hours at 37° C. and the sample was then treated with SDS loading buffer (labeled as 2 h); neat serum from untreated mice was also run as a negative control (labeled as S).

FIGS. 13B and 13C are a graphical summary of Frz8-Fc serum levels as determined from the pharmacokinetic study. Specific periods of time include evaluation over 16 days (FIG. 13B) and 2 days (FIG. 13C). Frz8-Fc displayed biphasic elimination administration in nude mice at all doses. Curves represent the predicted concentrations, while individual data points represent the average serum levels of Frz8-Fc protein from individual mice as determined by ELISA. FIG. 13D is a summary of the parameters for a biphasic model of Frz8-Fc pharmacokinetics. When dosed at 20 mg/kg by either the i.p. or i.v. route, comparable serum levels of protein were achieved within a day of injection and the protein was detectable in serum up to 7 days. After i.p. dosing at 20 mg/kg, protein was rapidly absorbed with a $T_{max}$ of 8 h and bioavailability ($AUC_{IP}/AUC_{IV}$) of 92%. The clearance of the protein was ~25 to 30 mL/d/kg with a half-life of about 4 days Example 5

Binding Affinity of Frz-FC Molecules

Figure 14A:
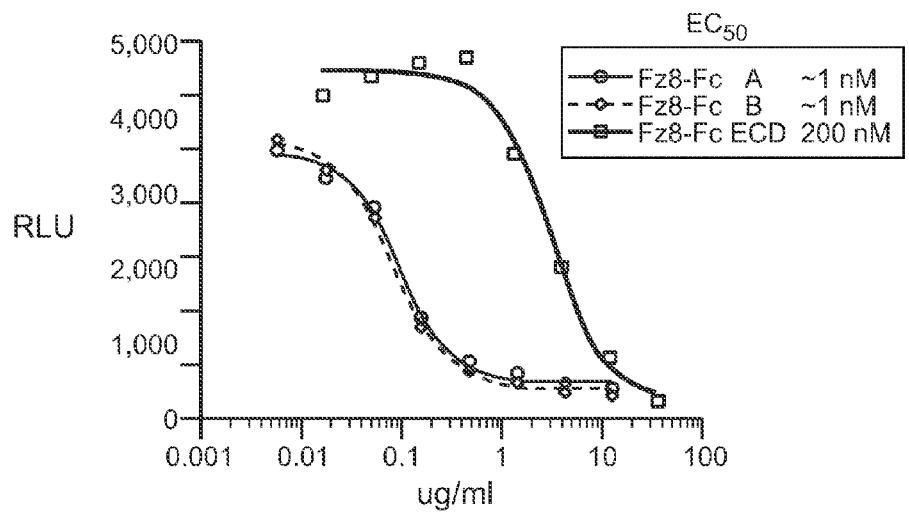
FIG. 14A is an $IC_{50}$ graph of a Wnt3a inhibition assay of two different preparations of Frz8(156)-FC.

The addition of the FC domain to the Frz8(156) domains results in an increase in binding affinity for Wnt3a of over two magnitudes. FIG. 14 demonstrates the enhanced ability of Frz8-ECD to block Wnt3a signaling when linked to a dimeric Fc domain. FIG. 14A is an $IC_{50}$ graph of a Wnt3a inhibition assay of two different preparations of Frz8(156)-FC. FIG. 14B is a gel confirming the purity of the isolated Frz8(156) CRD (ECD). Shown are: (a) non-reduced Frz8(156) ECD (Lane 1); (b) molecular weight markers (Lane 2); and reduced Frz8 ECD (156) (Lane 3). This gel indicates that the Frz8 ECD used in the binding assay is intact and runs at approximately the expected molecular weight.

Example 6

Binding Activity of Frz-FC Chimeras

ELISA

For PK evaluation of the Wnt antagonist, the wells of a 384-well ELISA micro titer plate (Nunc Maxisorp, Rochester, N.Y.) were coated with the rabbit anti-human Fc (Jackson Immuno Research, Westgrove, Pa.) at a concentration of 1 μg/ml in PBS (25 μg/well). After an overnight incubation at 4° C., the rabbit anti-human Fc solution was decanted, and the plates were blocked with 40 μl/well of block buffer (PBS containing 0.5% BSA and 10 ppm proclin). After a 60 minute incubation at room temperature with gentle agitation, the rabbit anti-human Fc coated plates were washed three times with wash buffer (PBS 0.05% Tween 20® and 10 ppm proclin). The Frizzled-Fc standards (a dilution series with a concentration range of 0.78-100 ng/ml), and the samples diluted into assay range in assay buffer (PBS containing 0.5% BSA, 0.05% Tween 20® and 10 ppm proclin) were added to the assay plate (25 μl/well). After a 120 minute incubation at room temperature with gentle agitation, the assay plates were washed six times with wash buffer. The remaining bound Frz-Fc was detected using a horse radish peroxidase (HRP) conjugated goat anti-human IgG-Fc (Jackson Immuno Research) diluted into assay diluent (25 μl/well). After appropriate color development (10-25 minutes) the enzymatic reaction was stopped with 1M phosphoric acid (25 μl/well). The assay plates were read at a wavelength of 450 nm with a reference wavelength of 630 nm. Sample concentrations were determined by comparing the sample OD against the standard curve fit using a 4-parameter algorithm.

BIAcore

Figure 15A:
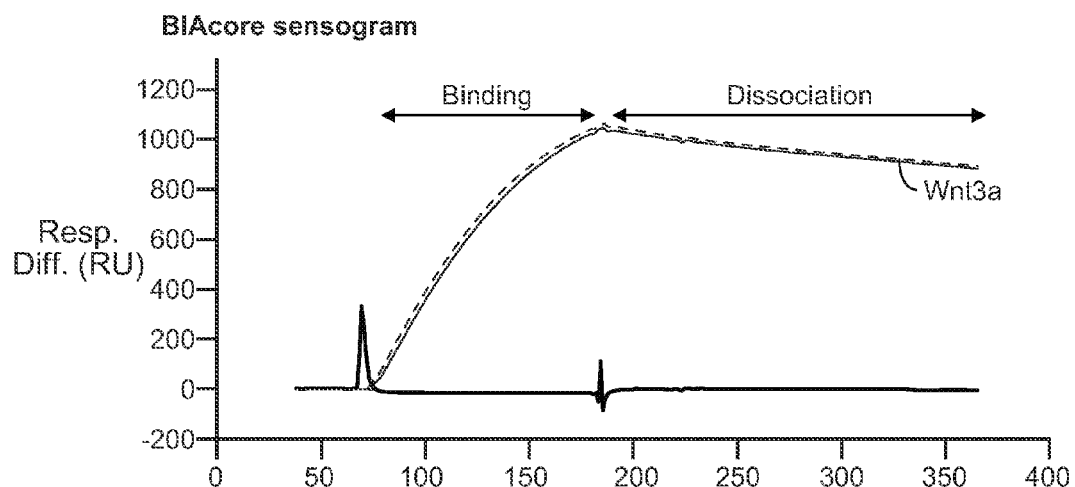
FIG. 15A is BIAcore sensogram demonstrating binding of purified soluble Wnt3a to immobilized Frz8-Fc.

FIG. 15 demonstrates direct binding by Wnt3a to the Frz8 (1-156)-Fc chimera. This chimera protein was amine coupled to a Biocore™ (BIAcore, Inc. Piscataway, N.J.) CM5 sensor chip at approximately 1700 response units as described generally in Chen, Y. et al, *J. Mol. Biol.* 293: 865-881 (1999). Briefly, carboxymethylated dextran biosensor chips (CM5, BIAcore™ Inc.) were activated with N-ethyl-N'-(3-dimethylaminopropyl)-carbodiimide hydrochloride (EDC) and N-hydroxysuccinimide (NHS) according to the supplier's instructions. An injection of 1M ethanolamine was done to block unreacted groups. Wnt3a was then injected at an estimated concentration of 0.5 μg/ml and binding was assessed by the change in response units as a function of time. Wnt3a was found to bind Frz8-Fc. As shown in FIG. 15, the association of Wnt3a and Frz-Fc results in a highly significant increase of 1000 response units over control protein (*E. coli* expressed non-native Wnt3a.)

OCTET

Figure 16A:
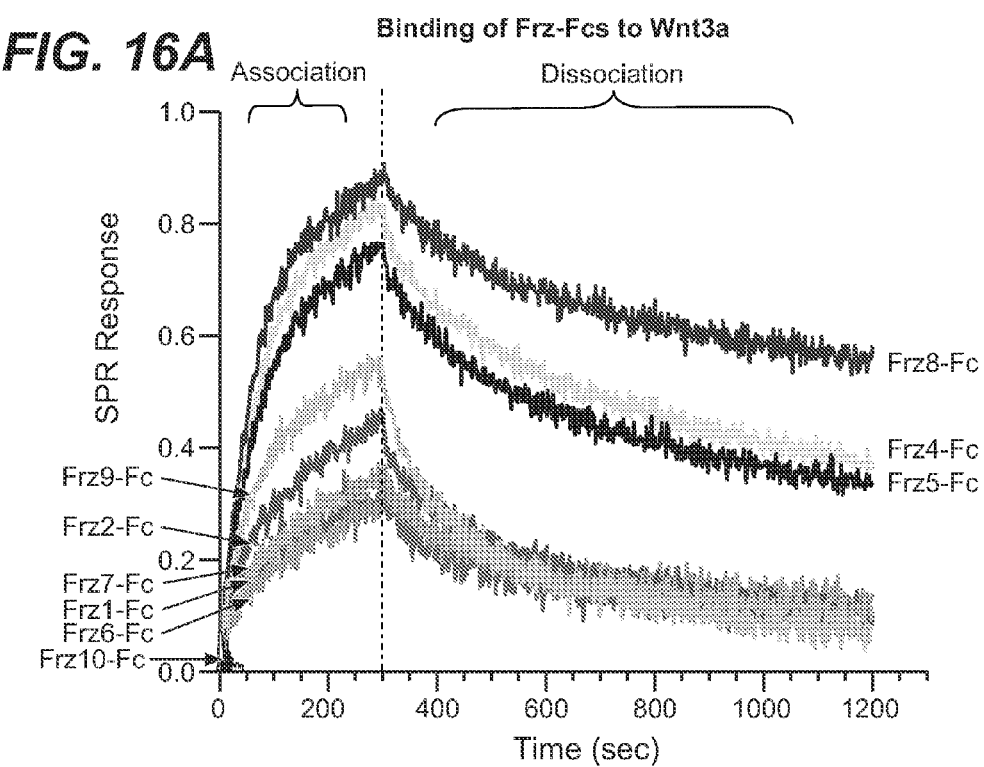
FIG. 16A shows data from the binding of Wnt3a to the Frz1-Frz10-Fc chimeras.
Figure 16B:
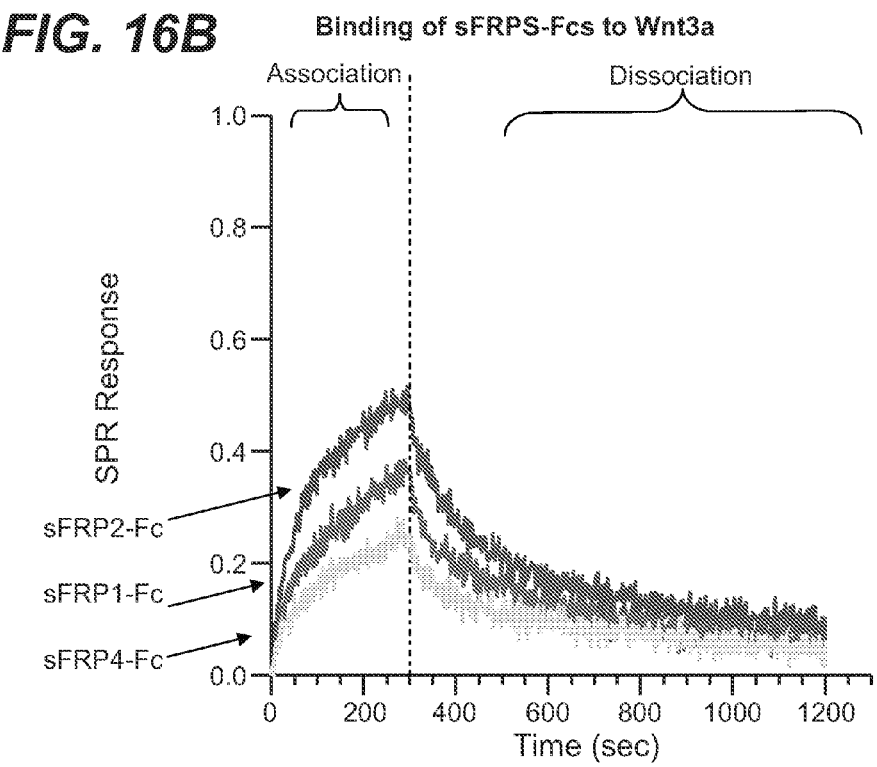
FIG. 16B shows data from the binding of Wnt3a to sFRP-Fc chimeras.
Figure 16C:
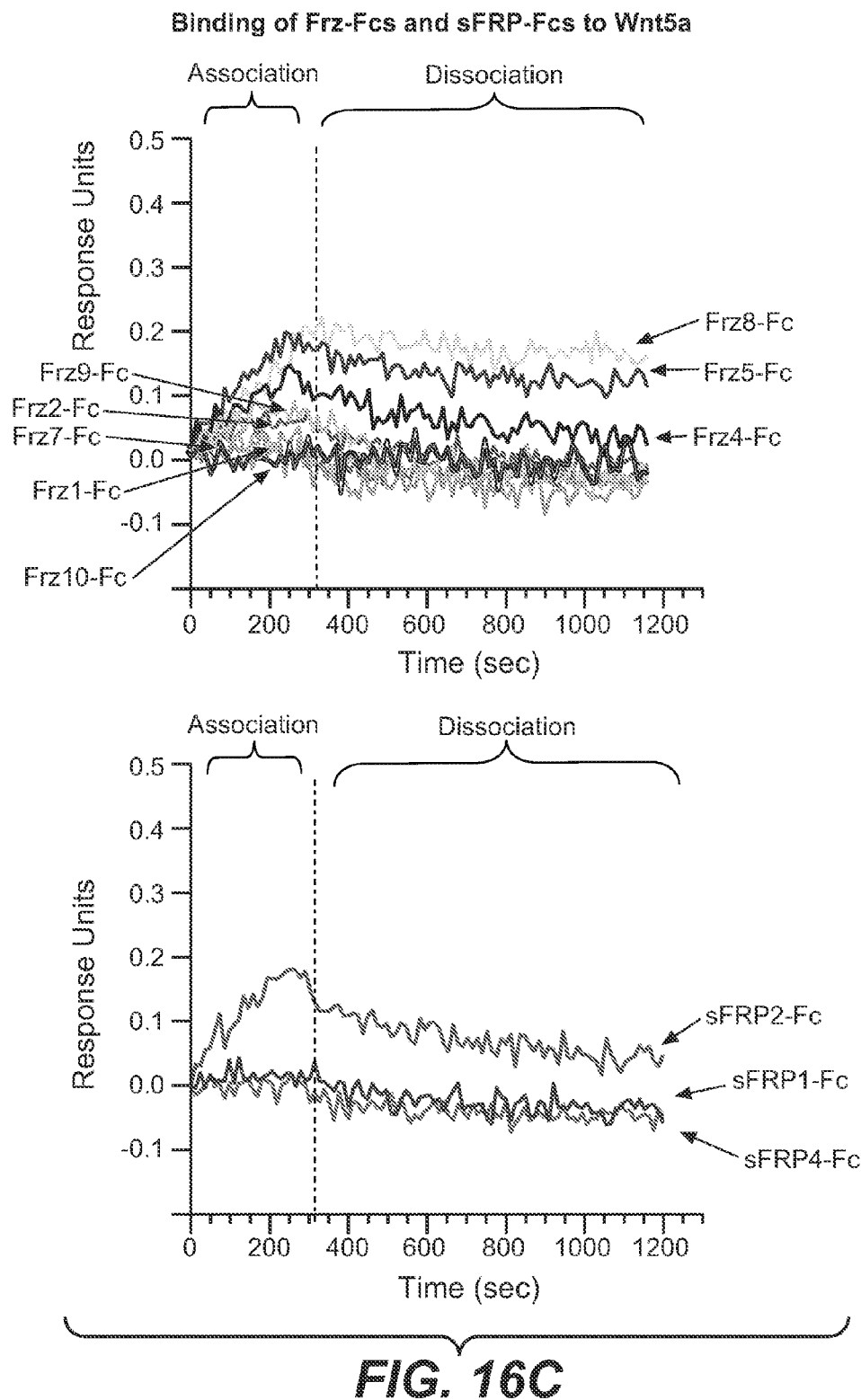
FIG. 16C shows data from the binding of Wnt5a to the Frz1-Frz10-Fc chimeras and sFRP-Fc chimeras.

The ability of the Wnt antagonists to interact with the Wnt ligands Wnt3a and Wnt5a was measured using the OCTET™-QK system. (FortéBio, Inc., Menlo Park, Calif.). This system allows for the measurement of protein binding at a biosensor surface. The assays were conducted by first incubating one of the Wnt antagonist molecules (20 ug/mL) with anti-human IgG Fc-specific biosensors for 10 minutes in phosphate buffered saline (PBS) with 0.5% CHAPS. The unbound Wnt antagonist was removed by washing for 1.5 minutes in PBS 0.5% CHAPS. Either Wnt3a or Wnt5a (5.0 ug/mL) was then added to the assay and incubated with the Wnt antagonist molecules bound to the biosensor surface for 5 minutes in PBS with 0.5% CHAPS. The interaction between the Wnt antagonist molecules and Wnt ligand was monitored in the same buffer. All assay steps were performed at room temperature in a volume of 150 uL. FIG. 16 shows the result of this binding assay with FIG. 16A showing data from the binding of Wnt3a to the Frz1-Frz10-Fc chimeras, FIG. 16B showing data from the binding of Wnt3a to sFRP-Fc chimeras, and FIG. 16C showing data from the binding of Wnt5a to the Frz1-Frz10-Fc chimeras and sFRP-Fc chimeras.

The OCTET™ assay indicates that both Wnt3a and Wnt-5a bind Fz8-Fc, Fz5-Fc, and Fz4-Fc the fastest, relative to the other Frz proteins, with Wnt3a binding Fz1-Fc, Fz2-Fc, and Fz7-Fc at a slower rate. The amplitude and linear nature of Wnt-5a binding curves suggest a lower binding affinity relative to Wnt3a binding, as determined by this binding assay. The amplitude of the OCTET™ binding data suggest that the sFRP-Fc proteins have an affinity for Wnt3a similar that observed for Frz1, Frz2, and Frz7, and somewhat lower that observed for Frz5 and Frz8.

Example 7

Inhibition of Wnt Signaling by the Wnt Antagonists

Cellular Assays

Cellular assays were performed using 293 (human kidney) cells transfected with the TOPglow reporter plasmid. In preparation for transfection approximately 500,000 HEK293 were plated into a well of a 12-well dish (Nuc) 24 hours before transfections. Cells were transfected with 0.375 µg TOPglow (Upstate, Cat # 21-204), 0.05 mg LEF1, 0.01 mg SV40 RL with Fugene (Roche) and at 24 hours post transfection. Media was changed and cells were untreated or treated with Wnt3a alone, Wnt-5a alone, or with a Wnt antagonist for an additional 20-24 hours before harvesting. All dilutions were made in complete media for the indicated cell lines. Cells were harvested in 50-100 µl of 1×SJC lysis buffer (20 mM Tris pH 8.0, 137 mM NaCl, 1 mM EGTA, 1% Triton X-100, 10% Glycerol, 1.5 mM $MgCl_2$, 1 mM DTT, 50 mM NaF, 1 mM $NaVO_4$ and protease inhibitors) and duplicate 10 µl were assayed using Dual-Glo™ luciferase assay kit (Promega, Part # TM058) and detected in an Envision Luminometer (Perkin Elmer). Luciferase activity was normalized against *Renilla* activity.

Cells to be treated with Wnt5a were transfected with Frz4 and Lrp5 in addition to the reporter. The presence of these additional components allows Wnt pathway activation by Wnt5a to proceed as per the canonical pathway. Mikels A J, and Nusse R., *PLOS Biol.* 4:e115 (2006). Wnt3a activated cells were treated with 100 ng/ml Wnt3a and Wnt5a activated cells were treated with 1 ug/ml Wnt5a.

Figure 17A:
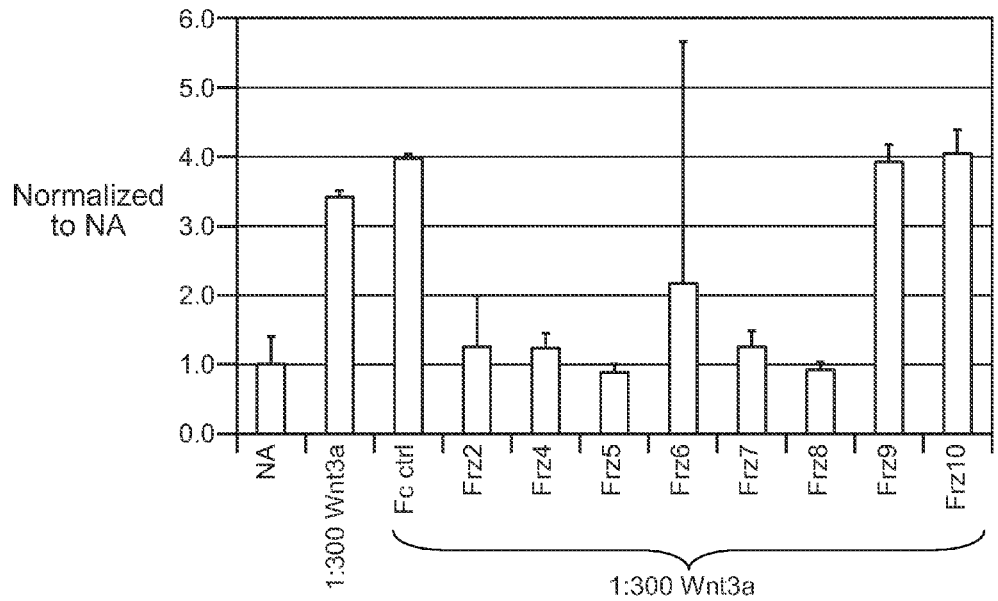
FIG. 17A shows cells stimulated with Wnt3a and FIG. 17B shows cells stimulated with Wnt-5a. Cells to be treated with Wnt5a were transfected with Frz4 and Lrp5 in addition to the reporter. 293 (human kidney) cells were activated with 100 ng/ml Wnt3a or 1 ug/ml Wnt5a. Cells then left untreated, treated with control Fc, or treated with purified Frz-Fc protein in PBS and assayed for luciferase response.
Figure 17B:
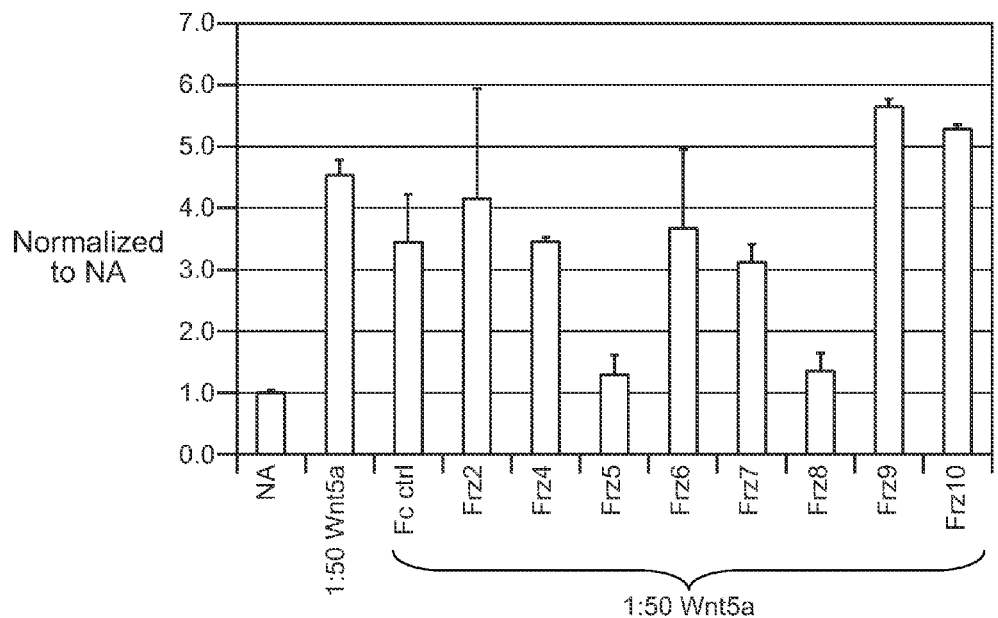
FIG. 17 shows the effect of the Wnt antagonists on Wnt-stimulated cells transiently transfected with TOPglow luciferase TCF reporter plasmid.

As shown in FIGS. 17A and B, the Frz-Fc antagonist inhibited Wnt signaling to varying degrees. Both Frz5-Fc and Frz8-Fc showed complete inhibition of the Wnt3a signal and significantly inhibited the Wnt5a signal. Frz4-Fc, Frz2-Fc, and Frz7-Fc showed significant inhibition of the Wnt3a signal.

Example 8

Relative $IC_{50}$s of the Wnt Antagonists

Figure 18:
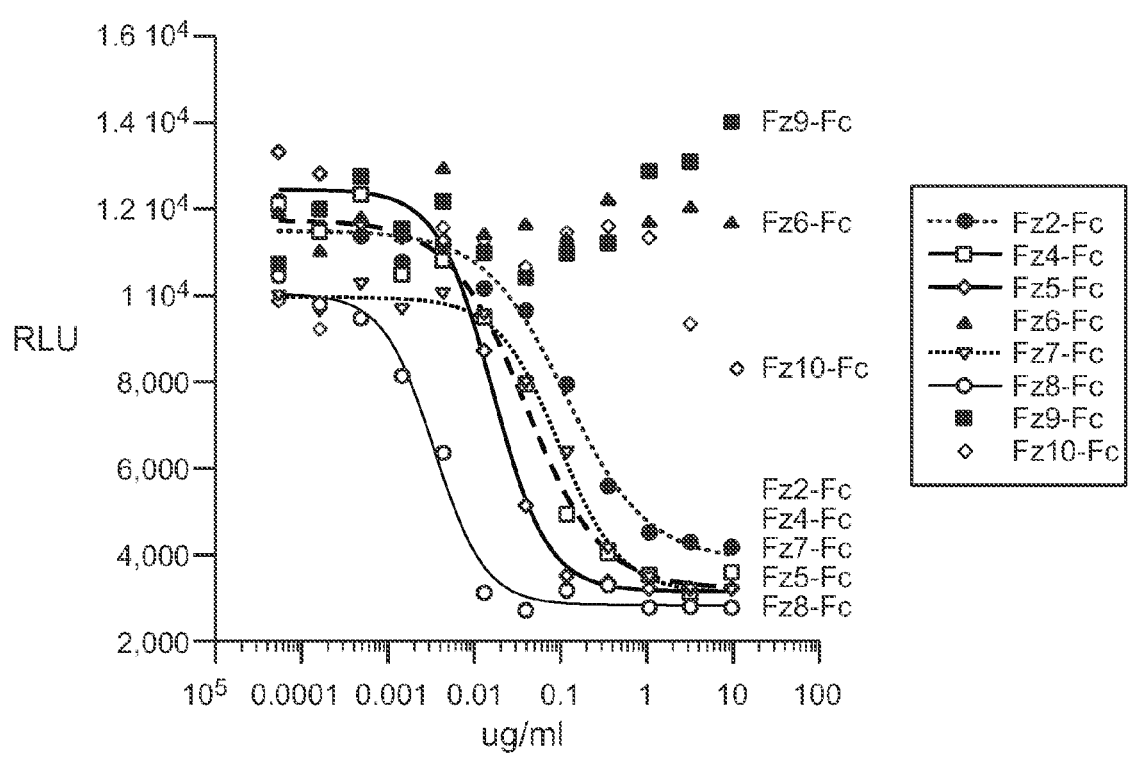
FIG. 18 shows inhibition of Wnt signaling by the Wnt antagonists in U2OS (human osteosarcoma) cells stably transfected with a luciferase TCF reporter plasmid. Initial Wnt signaling in cells was obtained with Wnt3a activation.

The relative $IC_{50}$s of the Wnt antagonists were determined by measuring inhibition of Wnt signaling by the Wnt antagonists in U20S (human osteosarcoma) cells stably transfected with TOPglow luciferase TCF reporter plasmid as described in Example 7. Initial Wnt signaling in cells was obtained with Wnt3a activation. A 3-fold dilution series of Frz-Fcs was applied to cells overnight. (FIG. 18). As determined by this assay, Wnt3a binds to Frz8-Fc, Frz5-Fc, and Frz4-Fc with sub-nanomolar IC50 (with Frz8-Fc having an IC50 of 0.04 nM, Frz-5Fc having an IC50 of 0.20 nM, and Frz-4 having an IC50 of 0.48 nM) and to Frz2-Fc and Frz7-Fc with nanomolar IC50 (with Frz2-Fc having an IC50 of 1.2 nM and Frz2-Fc having an IC50 of 1.4 nM.

Example 9

Wnt Target Genes as Pharmacodynamic Markers of Drug Response

As an alternative to immunohistochemical analysis of B-catenin, transcriptional targets of Wnt were used to monitor inhibition of Wnt signaling activity. The cell lines that had autocrine Wnt signaling showed increased expression of known Wnt target genes and this expression was regulated by in vitro treatment with Wnt3a as well as by Frz8-Fc. RNA analysis of NTera-2 cells indicated that Frz8-Fc treatment affects expression of the Wnt target genes tested. Thus, the expression of these genes can be followed as an indicator of treatment efficacy. As an extension of these observations, expression of these Wnt target genes can be used as a diagnostic tool to identify cancers that are driven by Wnt signaling and are likely candidates for anti-Wnt therapeutic agents.

In Vitro

In vitro comparative gene expression analysis on PA-1 cells treated with purified Wnt3a, Fz8 CRD-Fc, or a control protein was performed to determine the suitability of Wnt target genes to indicate in vivo inhibition of Wnt signaling in teratoma cells. RNA isolated from PA-1 cells that were treated with Wnt3a, Frz8-Fc, or control Fc protein was subject to microarray analysis and the change in expression levels of the indicated genes in response to exogenously added Wnt3a, Frz8-Fc, and control Fc protein was determined. For microarray analysis, cells were treated with the indicated proteins in triplicate and total RNA was isolated using the RNAeasy kit (Qiagen). Array analysis was done on the Affymetrix Human Genome U133 Gene Chip set (Rubinfeld B, et al., *Nat Biotechnol* 2006; 24:205-9). The specific probes and primer sets are shown in FIG. 20.

Figure 19A:
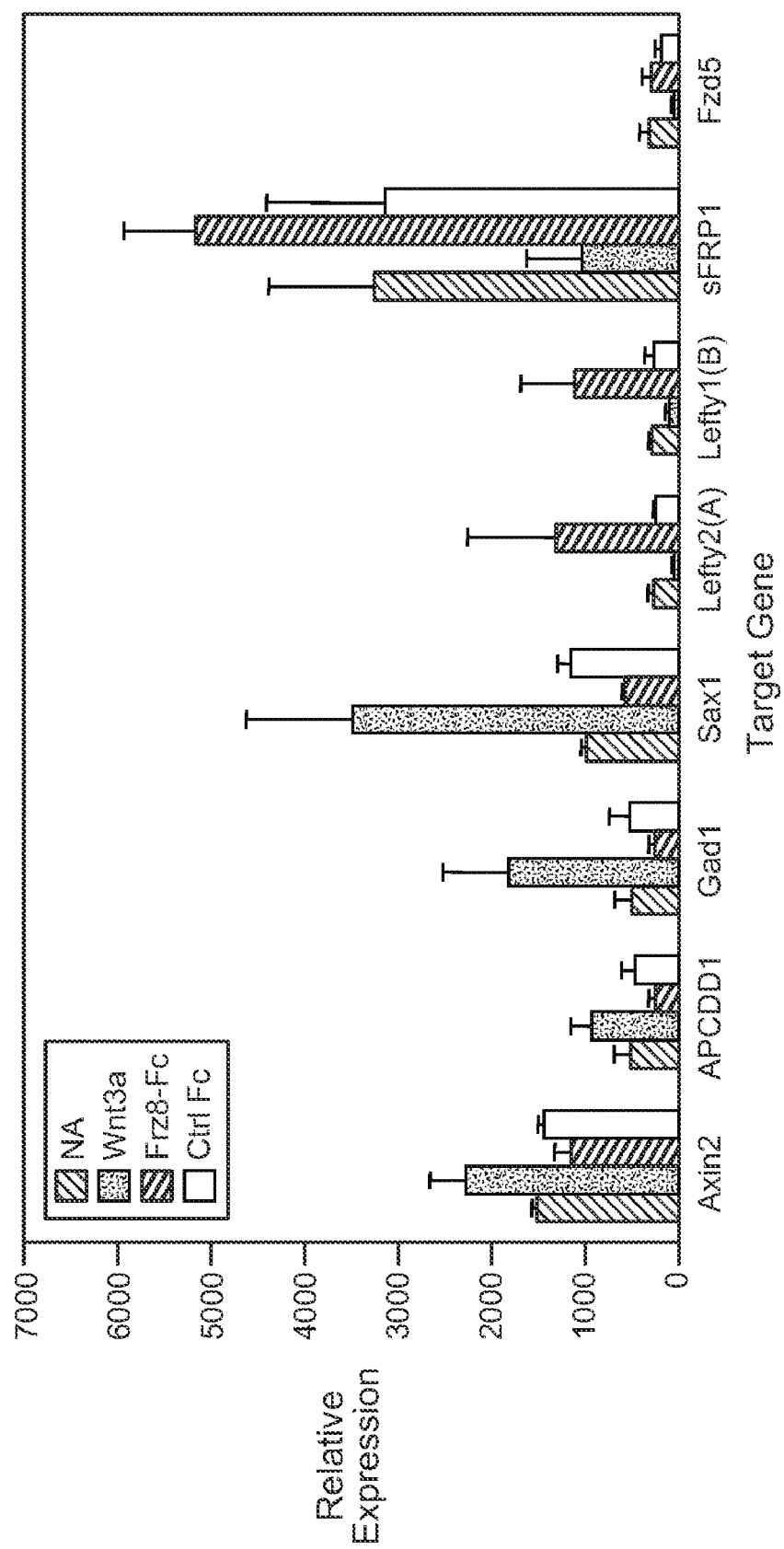
FIG. 19A shows expression of Wnt-target genes in PA-1 cell lines treated with Wnt3a and Frz8-Fc. RNA isolated from PA-1 cells that were treated with Wnt3a, Frz8-Fc, or control Fc protein was subject to microarray analysis and the change in expression levels of the indicated genes in response to exogenously added Wnt3a, Frz8-Fc, and control Fc protein was plotted. Columns, mean expression level from three wells; bars, standard error (S).

The expression levels of previously identified targets of Wnt signaling such as Axin2, APCDD1, and Gad1 were up-regulated by Wnt3a treatment or down-regulated by Frz8-Fc treatment (FIG. 19A). Moreover, some genes such as Lefty2 (A), Lefty1 (B), sFRP1, and Fzd5 were down-regulated by Wnt3a and up-regulated by inhibition of Wnt signaling with Frz8-Fc (FIG. 19A). Subsequent gene expression analysis by qRT-PCR showed that these transcripts were similarly regulated by Wnt3a and Fz8 CRD-Fc in NTera-2, Tera-2, and NCCIT cells as well.

In Vivo

APCDD1, Gad1, and Fzd5 were among the most consistently modulated genes in above described in vitro analyses and were therefore selected as potential markers of Wnt responsiveness for in vivo tumor xenograft studies.

Tumor tissue RNA was purified from xenograft specimens collected at the end of the efficacy study and quantitative reverse transcription-PCR (qRT-PCR) analysis of Wnt-responsive transcripts carried out as previously described Rubinfeld B, et al., *Nat Biotechnol* 2006; 24:205-9). Fold induction for each gene was determined using the ΔΔCt method and the result presented relative to glyceraldehyde-3-phosphate dehydrogenase. The specific probes and primer sets are shown in FIG. 20. All reactions were done in duplicate and the average of at least two assays ±SEM was plotted.

Figure 19B:
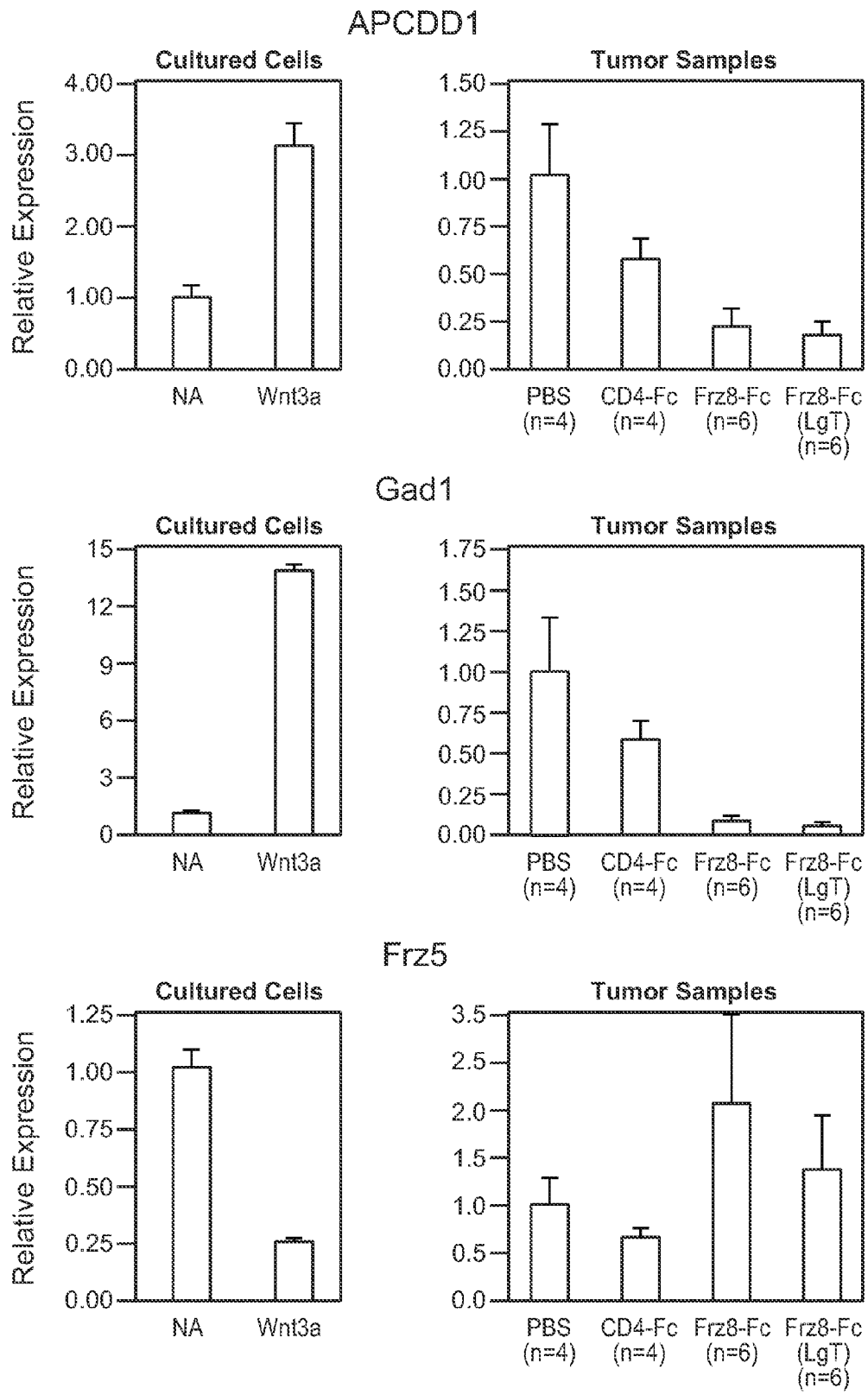
FIG. 19B shows the relative expression of Wnt target genes APCDD1, Gad-1, and Fzd5 in NTera-2 tumors from mice given PBS, CD4-Fc, or Frz8-Fc relative to PBS control. The data represents the mean expression level from the indicated number of tumors and is representative of at least two independent qRT-PCR experiments done in duplicate. Regulation of expression of each gene by the addition of purified Wnt3a to the corresponding cultured cells is also presented.

Similar to the effects seen in vitro, treatment with therapeutic doses of Frz8-Fc reduced the expression of genes for APCDD1 and Gad1 and increased the expression of Fzd5 in tumors from the NTera-2 xenografts (FIG. 19B). Although there is a general nonspecific down-regulation of all genes following CD4hFc treatment, these changes were not statistically significant compared with those seen in Frz8-Fc-treated tumors. These observations show that the antitumorigenic effects of Frz8-Fc in vivo are on target genes and that the expression levels of these genes can be used to monitor the efficacy of potential anti-Wnt therapeutic agents.

Example 10

Inhibitory Effect of Wnt Antagonists on Growth of Tumors in Mice with Allografts and Human Xenografts The studies set forth in this Example indicate that the Wnt antagonists are useful in treating Wnt expressing tumors. The largely complete tumor regression in the case of Wnt-1-MMTV model illustrate the effect of the Wnt antagonists on tumors that are strongly Wnt driven. However, the significant effect of the Wnt antagonist on the PA-1 and NTer2 tumors also reflects the strong therapeutic potential to treat tumors that may not be entirely Wnt driven.

Animals

Female C57B16 mice (The Jackson Laboratory) were used for the passaging of MMTV-Wnt1 tumors. Maintenance of mice and in vivo procedures were carried out using Institutional Animal Care and Use Committee-approved protocols.

MMTV-Wnt Model-Allografts

Figures 21, 22B:
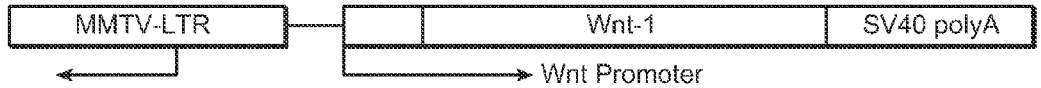
FIG. 21 is a linear schematic describing the vector construct used in the transfection to create the Wnt animal model.
FIG. 22B is tabular summary of mean tumor volume and mean % change in tumor volume over time in the four treatment groups.

FIG. 21 is a linear schematic describing the vector construct used in the transfection to create the Wnt animal model. This construct mimics the constitutive Wnt signaling activation observed with MMTA viral insertion, as described in Tsujomoto et al., *Cell* 55: 619-625 (1988) and Li et al., *Oncogene* 19: 1002-1009 (2000).

Passaging of MMTV-Wnt1 Transgenic Tumors in Mice.

The tumors from MMTV-Wnt1 transgenic mice were serially passaged in C57B16 mice for 6 to 10 passages by surgical implantation in the mammary fat pad. Tumor tissue was aseptically collected from the transgenic mouse, rinsed in HBSS and cut into small pieces. The recipient mice were anaesthetized with a mixture of ketamine (75-80 mg/kg) and xylazine (7.5-15 mg/kg), the tumor fragment inserted under the skin rostral to the third mammary fat pad, and the skin closed using wound clips. Tumors were passaged for a maximum of 10 passages, and after the first two passages, tumor tissue was examined histologically to confirm that it was of mammary origin and continues to express Wnt. Mammary adenocarcinomas develop in 6-12 months in the mice. Tumors isolated from these mice were used to create the transplant models described below.

In Vivo Studies.

For in vivo studies testing the efficacy of Wnt antagonists in the MMTV-Wnt model, the tumor cells were introduced by subcutaneous injection of cells obtained from macerated tumors tissue. Tumor tissue was aseptically collected from mice transplanted with tumors from Wnt transgenic mice (described above), rinsed in PBS or HBSS, cut into smaller pieces and macerated into HBSS using a cell dissociation kit (Sigma). The cells were washed twice in sterile HBSS and suspended in a 50% matrigel solution in HBSS. The cell suspension was inoculated subcutaneously into the mammary fat pad of athymic nude mice, with a volume not exceeding 150 µl/mouse.

For in vivo studies using the NTera2 or PA-1 animals models, cells were grown as described and harvested when growth is in the logarithmic phase. The cells were suspended in a 50% matrigel solution in HBSS and inoculated subcutaneously into athymic nude mice at a concentration of either 8 million cells/mouse (NTera2) or 10 million cells/mouse (PA-1).

Tumors were monitored daily and measured after 7-12 days of inoculation. Animals were separated into groups with identical mean tumor volumes in the range of 150-250 mm$^3$. Treatment with the Wnt antagonist started 1-2 days after grouping and the mice were dosed intraperitoneally (IP) or intravenously (IV) with 100-200 µl of Wnt antagonist, negative control protein CD4-Fc, or PBS negative control once daily. Subsequent drug treatments were repeated 2-3 times weekly and continued for 3-4 weeks. Tumor volume was measured twice weekly the animals were sacrificed when the tumor volume reached 2500 mm$^3$. Blood was collected during the study by an orbital vein bleed and the serum assayed for levels of therapeutic agent by SDS-PAGE followed by immunoblot and detection using HRP or fluorescent conjugated anti-human Fc, and for activity of the therapeutic agent by its ability to inhibit Wnt3a activation of TOPglow activity as described in Example 7.

Allograft Tumors

Inhibitory Effect of Wnt Antagonists on Growth of Tumor Allografts

Treatment with Frz8-Fc by either the i.p. or i.v. routed resulted in rapid tumor regression with sustained inhibition during the course of treatment, whereas the negative control protein CD4-Fc had no effect relative to the PBS treatment. The treated mice were monitored for three weeks after termination of treatment and regrowth of tumors was eventually observed.

Figure 22A:
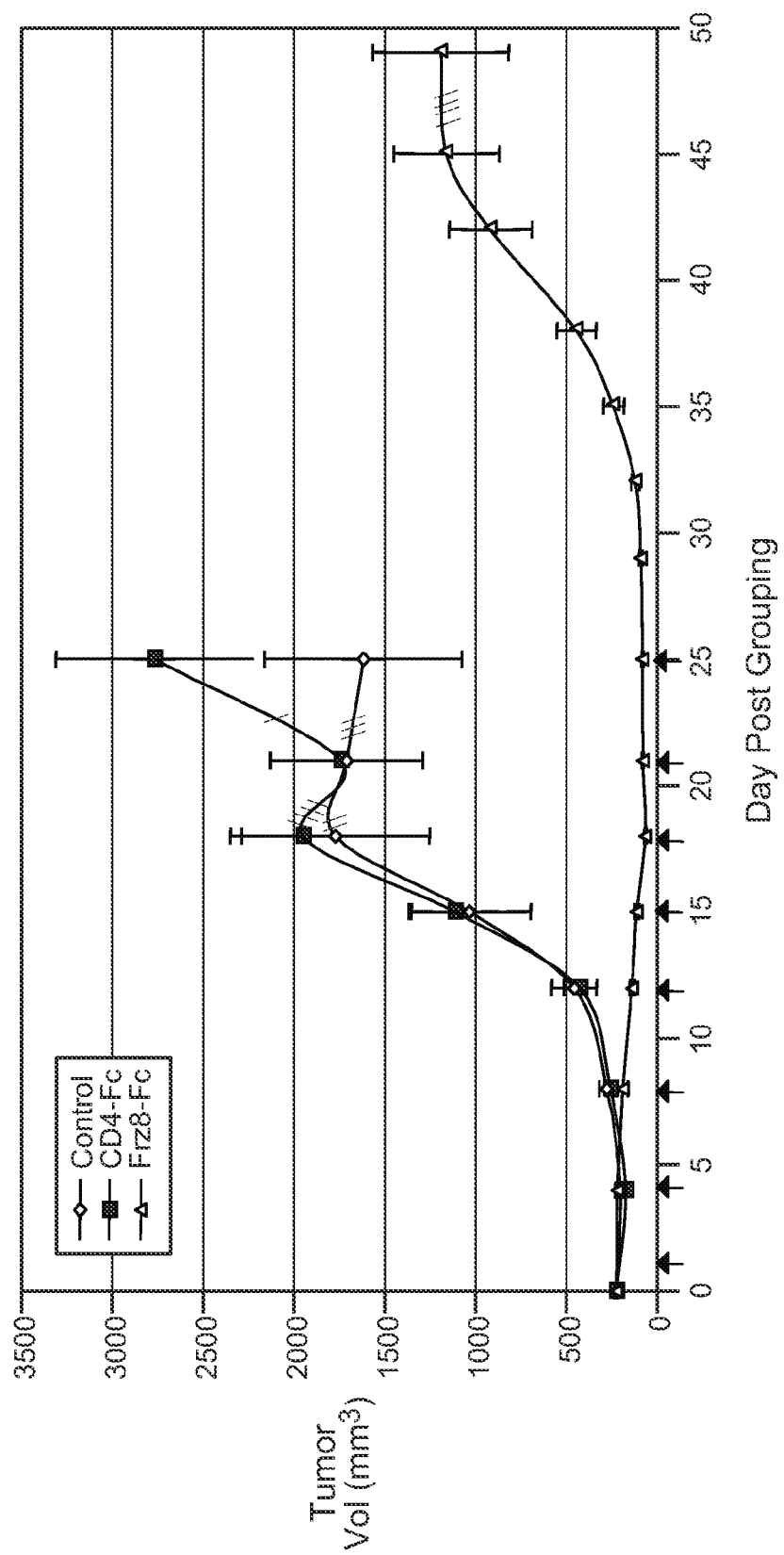
FIG. 22A is a graph showing data from nude mice hosting MMTV-Wnt-1 tumor transplants were administered PBS, CD4-Fc (10 mg/kg/day) or Frz8-Fc (10 mg/kg/day) by intraperitoneal injection twice weekly. Mean tumor volume is plotted over time and the treatment days are indicated by arrows on the X-axis.

FIG. 22 illustrates the efficacy of Frz8-Fc against MMTV-Wnt tumor transplants in athymic nude mice by intraperitoneal (IP) dosing. FIG. 22A is a graph showing that nude mice hosting MMTV-Wnt-1 tumor transplants were administered PBS, CD4-Fc (10 mg/kg/day) or Frz8-Fc (10 mg/kg/day) by intraperitoneal injection twice weekly. Each group had 11 mice and the average tumor volume for the group was 226 mm$^3$ before the start of treatments. Mean tumor volume is plotted over time and the treatment days are indicated by arrows on the X-axis. On day 25, the control groups were sacrificed and the drug administration to the treatment group stopped. FIG. 22B is tabular summary of mean tumor volume and mean % change in tumor volume over time in the four treatment groups. Note that in FIG. 22B, the mean tumor volume after treatment with Frz8-Fc antagonist results in a reduction in tumor volume from 226 mm to about 219 mm$^3$ on the fifth day after start of treatment, and about 67 mm$^3$ on the 18$^{th}$ day. This represents a 4% and 70%, respectively, reduction in tumor size. In this study, tumors administered the Frz-Fc antagonist showed regression in tumor size compared with control animals. This demonstrates that Frz-Fc antagonists of the invention are tumoricidal as a single agent and are useful as anti-cancer therapeutics.

Figure 23A:
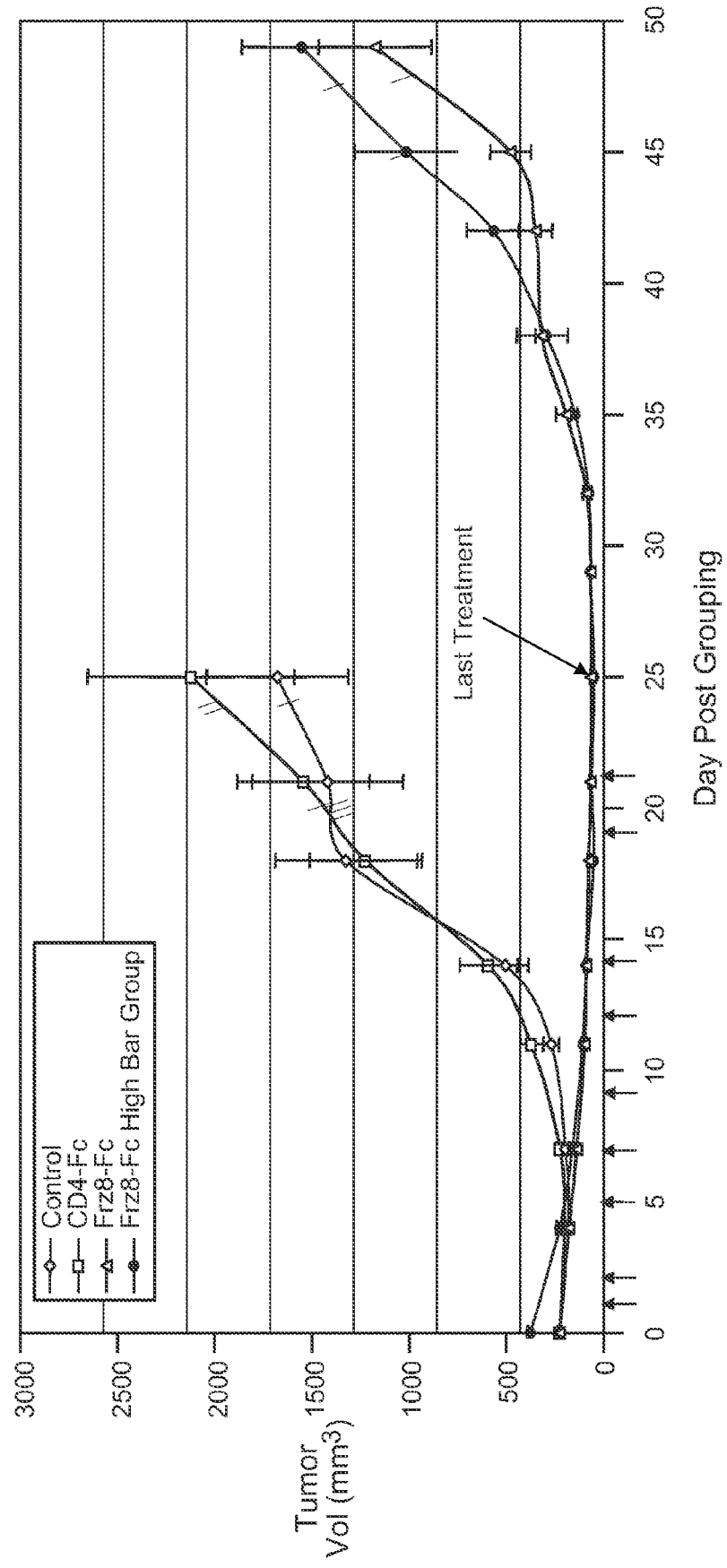
FIG. 23A is a graph showing data from nude mice hosting MMTV-Wnt-1 tumor transplants were administered PBS, CD4-Fc (10 mg/kg/day) or Frz8-Fc (10 mg/kg/day) by intravenous injection three times weekly. Mean tumor volume is plotted over time and the treatment days are indicated by arrows on the X-axis.

FIG. 23 illustrates the efficacy of Frz8-Fc against MMTV-Wnt tumor transplant in athymic nude mice by intravenous (IV) dosing. FIG. 23A is a graph showing that nude mice hosting MMTV-Wnt-1 tumor transplants were administered PBS, CD4-Fc (10 mg/kg/day) or Frz8-Fc (10 mg/kg/day) by intravenous injection three times weekly. Each group had 11 mice and the average tumor volume for the group was 226 mm$^3$ before the start of treatments. The fourth group (high bar) in this study included 10 mice with a mean tumor volume of 375 mm$^3$ at the start of the study that were treated with Frz8-Fc (10 mg/kg/day) by intravenous injection three times weekly. Mean tumor volume is plotted over time and the treatment days are indicated by arrows on the X-axis. On day 25, the control group animals were sacrificed and drug administration to the treatment group stopped. FIG. 23B is a tabular summary of mean tumor volume and mean % change in tumor volume over time in the four treatment groups. Note that in all mice treated with Frz-Fc that the tumor burden was reduced from an average of 226 mm$^3$ to an average volume of 179 mm$^3$ on the 4$^{th}$ day after start of treatment, and to 73 mm$^3$ after the 18$^{th}$ day. This represents a 21% and 67% reduction, respectively, in tumor volume. For the high bar group, tumor volume was reduced from an average of 376 mm³ to 225 mm³ on the 4 µl day of treatment, and to 53 m³ on the 18$^{th}$ day. This represents a 39% and 86% reduction, respectively, in tumor volume.

Inhibitory Effect of Serum Obtained from Treated Mice on Wnt Signaling

Figure 24A:
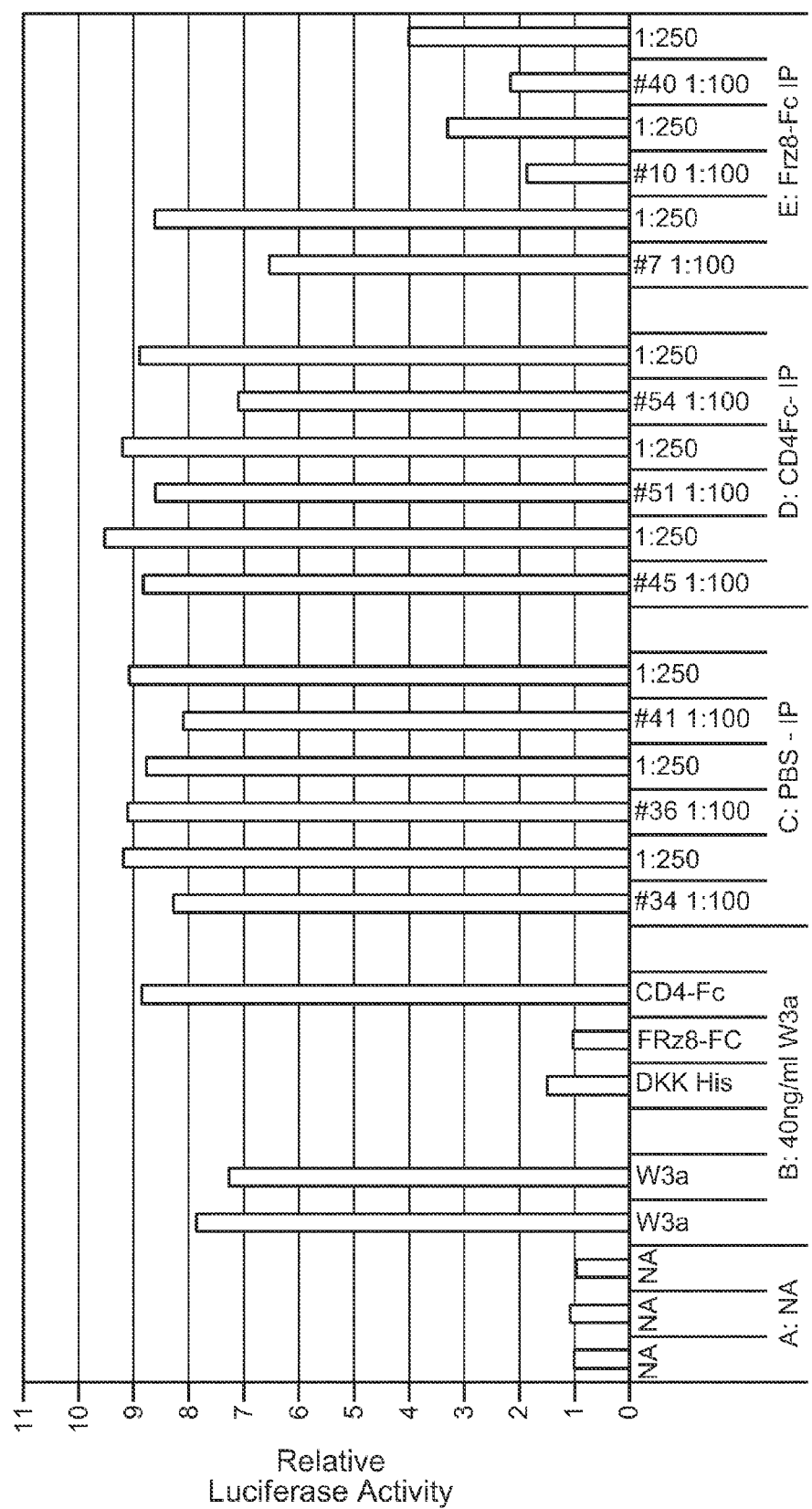
FIG. 24A shows the testing results of serum isolated from IP treated mice, while the IV treated ones appear in FIG. 24B.
Figure 24B:
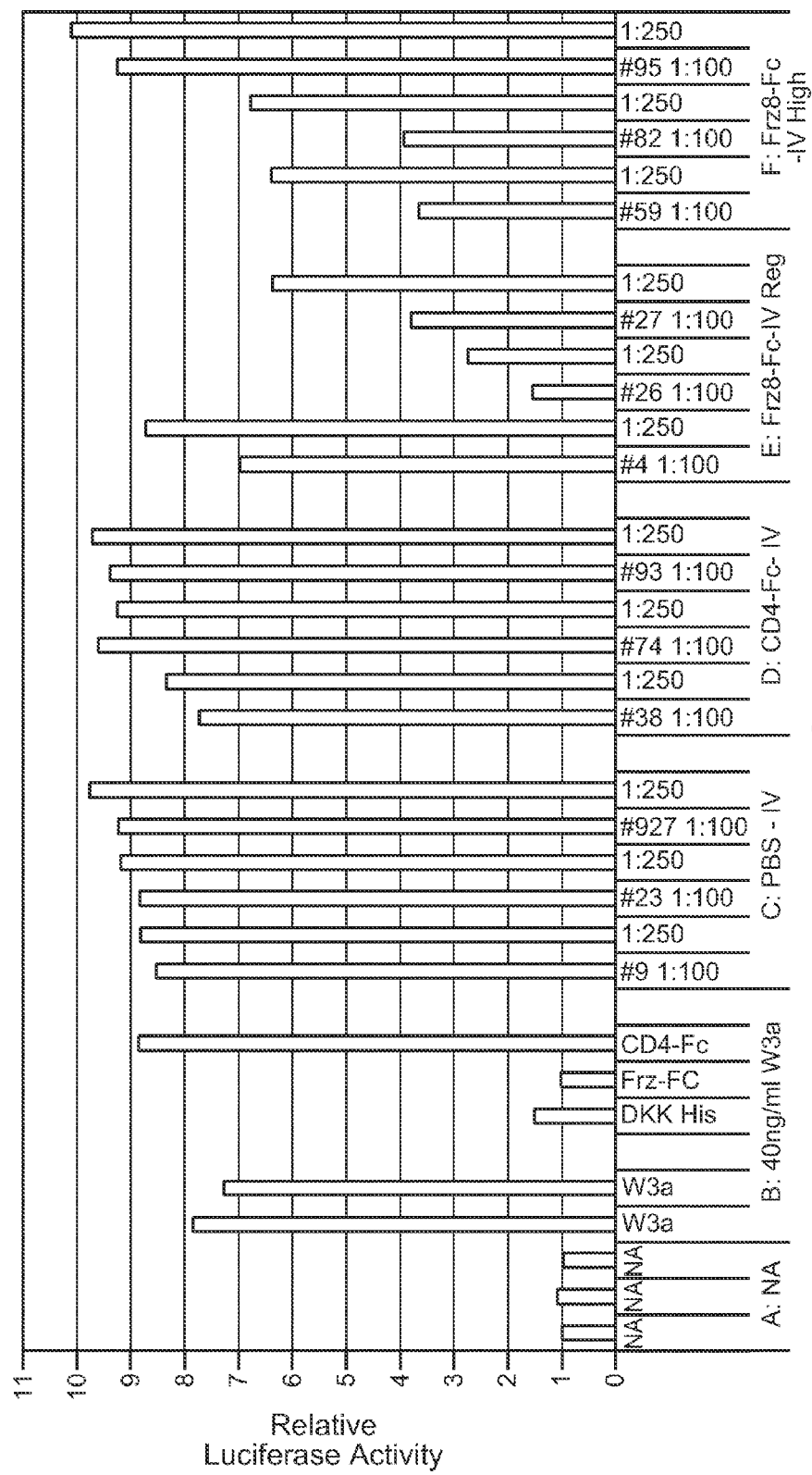
FIG. 24 is a bar graph showing the Wnt signaling antagonist activity in the TOPglow assay of various Wnt antagonists in serum isolated from the MMTV Wnt tumor study. The X-axis samples appear in groups A-E (FIG. 24A) or A-F (FIG. 24B) according to treatment, mouse study number and dilution. The relative luciferase activity in the TOPGLOW gene reporter assay is shown on the Y-axis. All samples are treated with ~40 ng/ml purified Wnt3a except for NA (control). All other protein controls are present in the medium at 5 μg/ml.

Inhibition of Wnt signaling from serum isolated from the treated mice is reported in FIG. 24, with FIG. 24A showing the results of serum isolated from IP treated mice, while the IV treated ones appear in FIG. 24B. The data is presented as a bar graph showing the Wnt signaling antagonist activity in the TOPglow assay (as described in Example 7). The samples appear in groups according to treatment, mouse study number and dilution. The relative luciferase activity in the TOPglow gene reporter assay is shown on the Y-axis. All samples are treated with ~40 ng/ml purified Wnt3a except for NA (control). All other protein controls are present in the medium at 5 µg/ml.

Human Xenograft Tumors

Figure 25A:
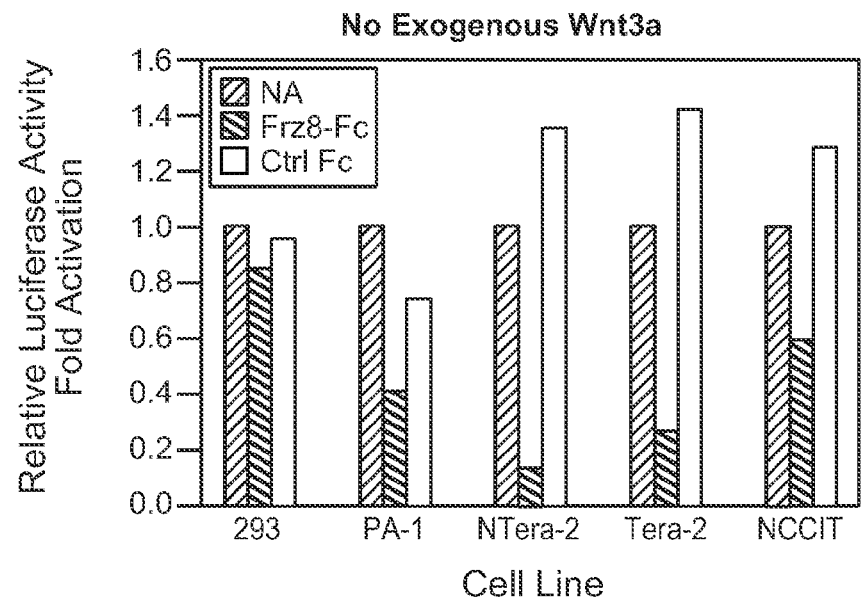
FIG. 25 shows Wnt signaling antagonist activity in the TOPglow assay of various Wnt antagonists in the indicated teratacarcinoma cell lines in the absence (FIG. 25A) or presence (FIG. 25B) of exogenously added Wnt3a. For each cell line, activity was expressed relative to that observed in the absence of any treatment (NA); representative of at least two independent experiments. Relative luciferase activity (Y-axis) were measured from TOPglow assays from various cancer cell lines in the presence or absence or Wnt inhibitors.
Figure 25B:
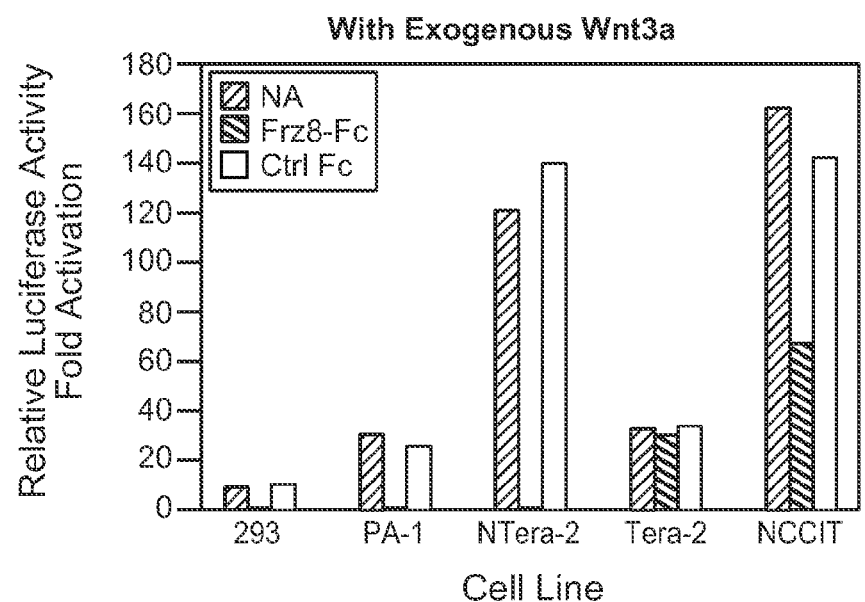

Inhibition of naturally derived human tumor models by the Wnt antagonists would serve as a further indicator of their usefulness in treating human cancer. Human tumor-derived cell lines were tested for evidence of autocrine wnt signaling, similar to that seen in the PA-1 teratoma cell line, as an indication of usefulness in testing Wnt antagonist activity. The teratoma-derived NTera-2, Tera-2, and NCCIT cell lines exhibited basal Wnt signaling that could be inhibited by Frz8-Fc, in contrast with 293 cells that exhibited low basal signaling that was not inhibited by Frz8-Fc (FIG. 25A). Nevertheless, all four teratoma cell lines seemed to express Wnt receptors, as signaling was further stimulated by Wnt3a treatment, which could be blocked by Frz8-Fc (FIG. 25B). These results indicate that the teratoma cell lines express Wnt(s), which might contribute to their tumorigenicity. These lines were therefore evaluated for tumor formation in athymic nude mice and based on consistency of tumor formation, NTera-2 and PA-1 were selected for in vivo efficacy studies.

Inhibitory Effect of Wnt Antagonists on Growth of NTera2 Tumor Xenografts

Treatment of mice exhibiting NTera2 tumor xenografts with the Wnt antagonist Frz8-Fc resulted in a reduction of tumor volume by approximately 50% and reduction tumor mass by approximately 70%, relative to the control mice.

Figure 26A:
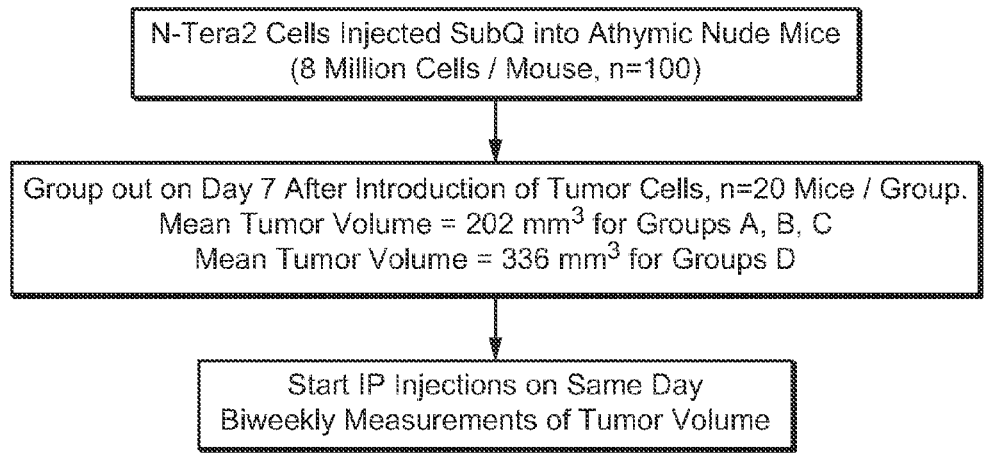
Figure 26B:
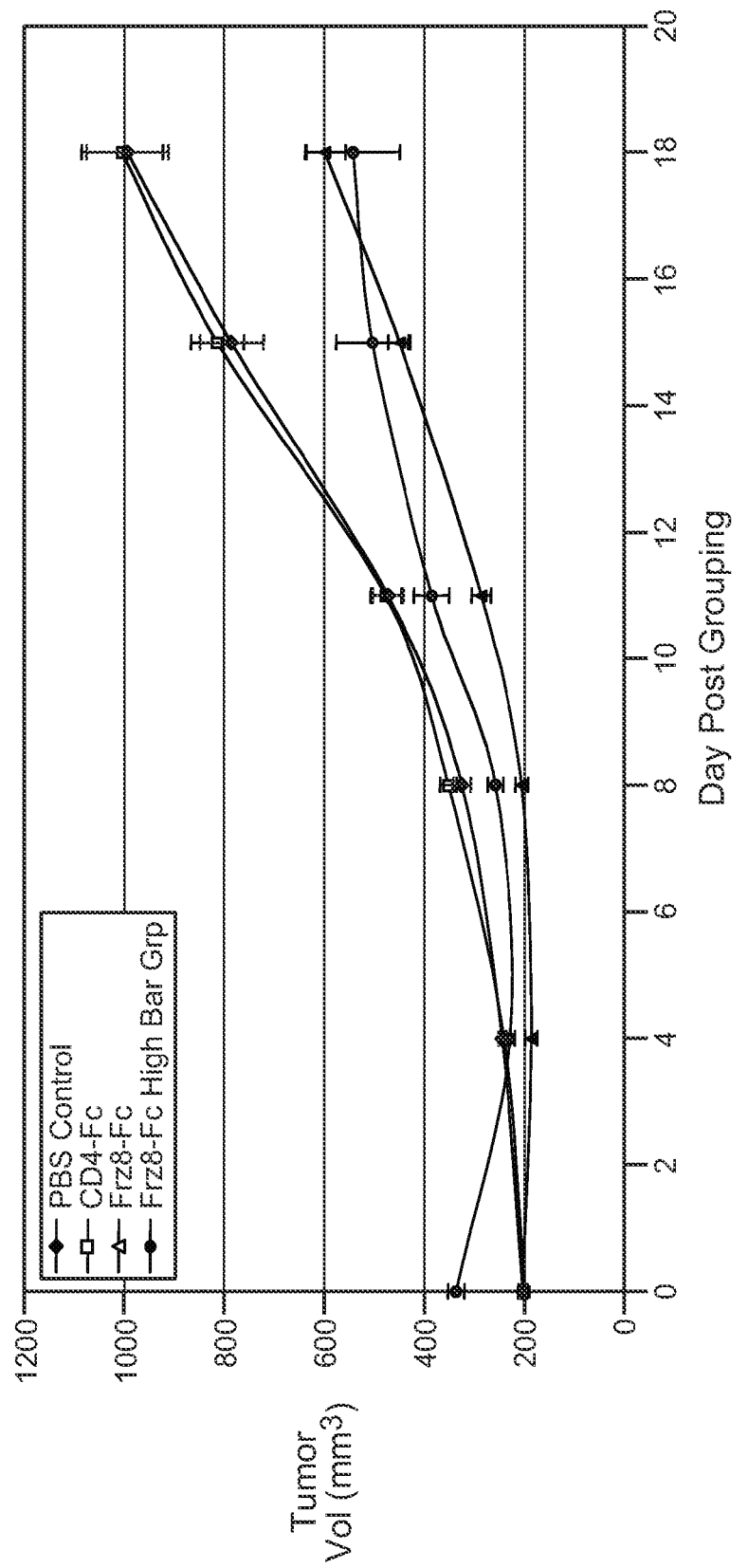
FIG. 26B is a graph plotting mean tumor volume over time, wherein the treatment days are indicated by arrows on the X-axis.
Figure 26C:
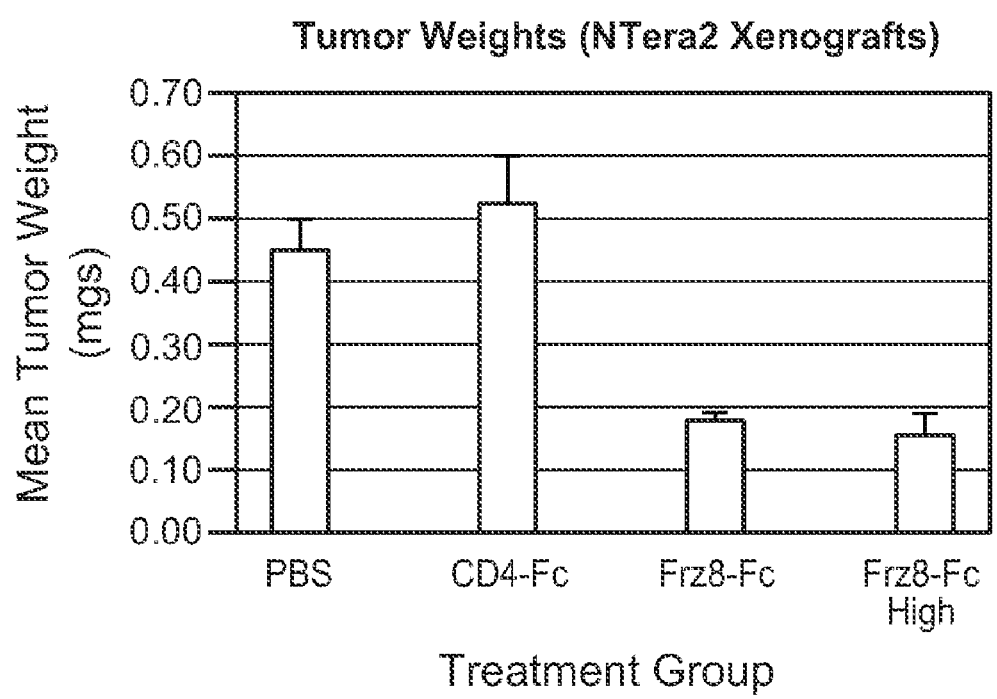
FIG. 26C is a bar graph plotting the mean tumor weights at sacrifice of all animals in the group at day 20 of the study.

FIG. 26 shows the anti-tumor efficacy of Frz8-Fc treatment on the growth of NTera2 tumor xenografts in athymic nude mice. Athymic nude mice bearing NTera2 tumor xenografts were administered an initial dose of PBS, CD4-Fc and Frz8-Fc at 15 mg/kg/day, followed by subsequent doses of 10 mg/kg/day by intraperitoneal injection three times weekly. Each group had 20 mice and the average tumor volume for the group was 200 mm³ before the start of treatments. The fourth group of the study included 10 mice with a mean tumor volume of 336 mm³ at the start of the study that were treated with Frz8-Fc (10 mg/kg/day) by intraperitoneal injection three times weekly. FIG. 26A is an exemplary procedural flow chart, while FIG. 26B is a graph plotting mean tumor volume over time, wherein the treatment days are indicated by arrows on the X-axis. FIG. 26C is a bar graph plotting the mean tumor weights at sacrifice of all animals in the group at day 20 of the study. FIGS. 26D and 26E are tabular summaries of mean tumor volume and mean % change in tumor volume, respectively.

Figure 27:
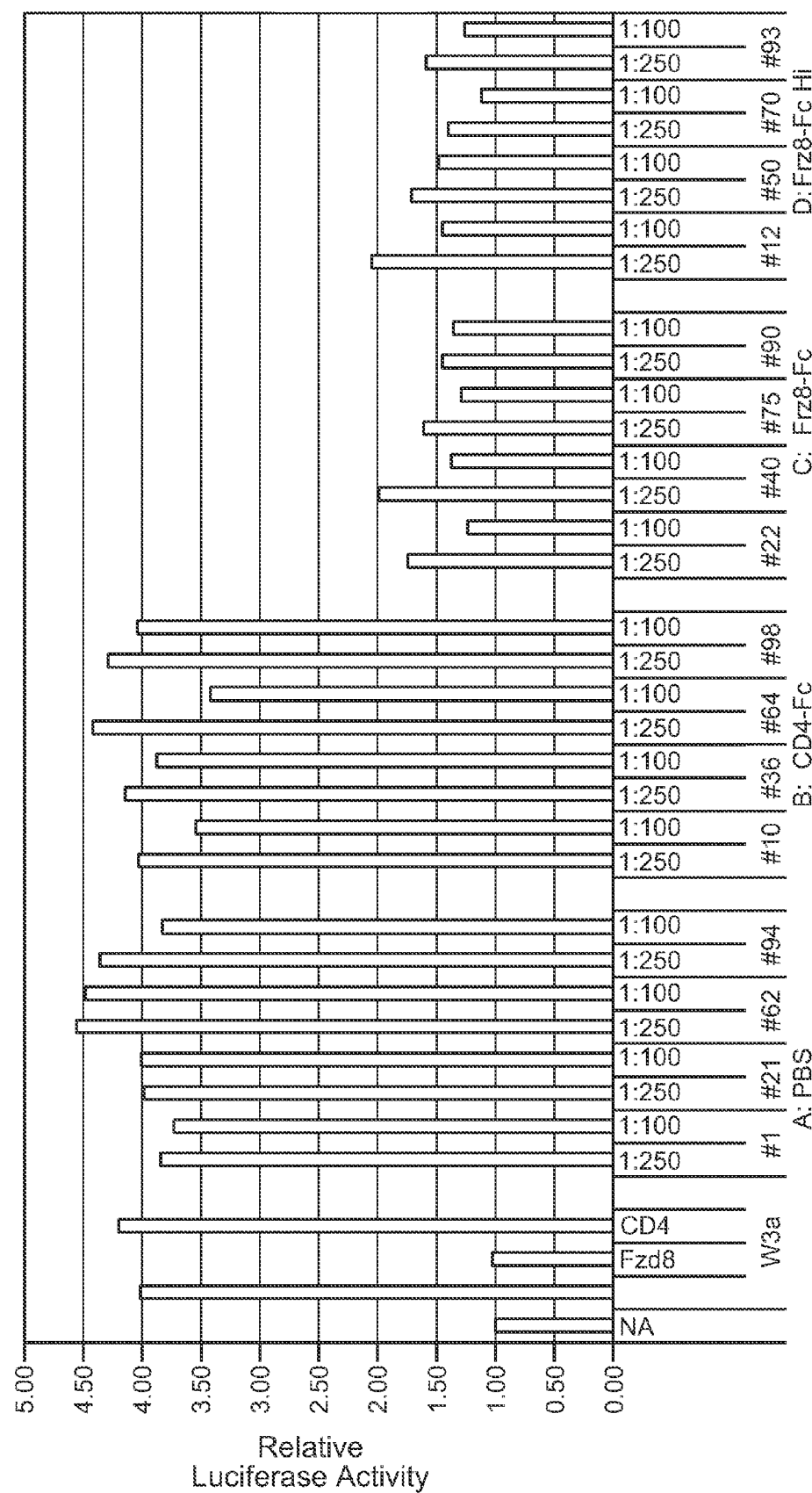
FIG. 27 is a bar graph showing Wnt signaling antagonist activity of serum isolated from various animals in the NTera2 tumor study as determined by the TOPglow assay. The Y-axis shows relative luciferase activity (Y-axis) from the TOPglow assay for the controls and Frz8-Fc Wnt antagonist. No additional purified Wnt or Wnt conditioned media was added to the cells.

Inhibitory Effect of Serum Obtained from Mice with NTera2 Tumor Xenografts on Wnt Signaling FIG. 27 is a bar graph showing Wnt signaling antagonist activity in the TOPglow assay of the Frz8-Fc Wnt antagonist of serum isolated from various animals in the NTera2 tumor study. Relative luciferase activity (Y-axis) as measured from TOPglow assay from the controls and Frz8-Fc Wnt antagonist. No additional purified Wnt or Wnt conditioned media was added to the cells. These results demonstrate that reduced Wnt signaling is associated with reduction in tumor size in these mice treated with Frz8-Fc Wnt antagonist.

Inhibitory Effect of Wnt Antagonists on Growth of PA-1 Tumor Xenografts

Treatment of mice exhibiting PA-1 tumor xenografts with the Wnt antagonist Frz8-Fc resulted in a significant reduction in tumor growth within 12 days of treatment. In this model, the tumors were approximately 50% smaller, with significantly smaller mass than tumors in the control mice at the end of the treatment period.

Figure 28A:
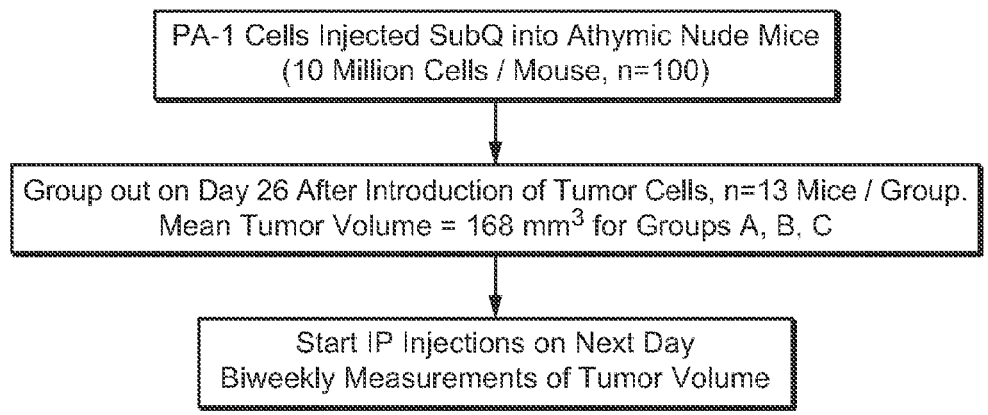
Figure 28B:
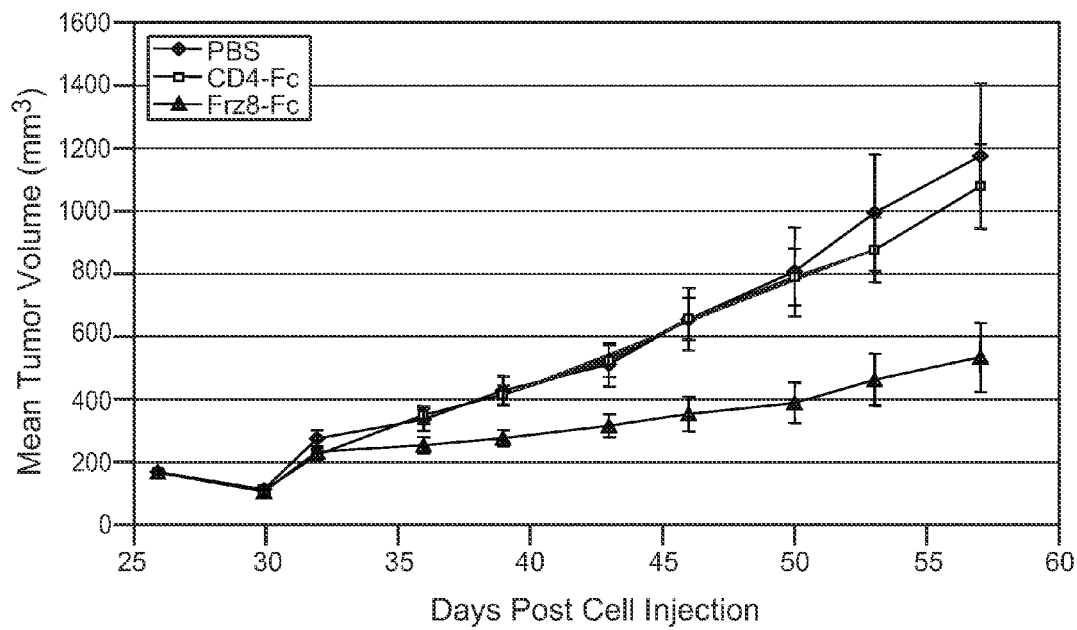
FIG. 28B is a graph plotting mean tumor volume over time.
Figure 28C:
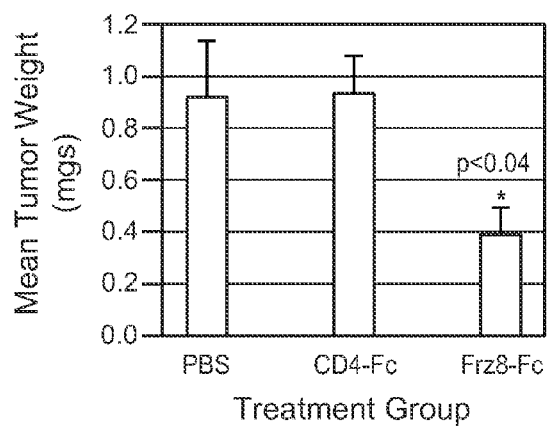
FIG. 28C is a graph of mean tumor weight at sacrifice. The mean tumor weight±SEM is plotted as a function of the group.

FIG. 28 demonstrates the anti-tumor efficacy of Frz8-Fc treatment on the growth of PA-1 tumor xenografts in athymic nude mice. Athymic nude mice bearing PA-1 tumors xenografts were administered PBS, CD4-Fc or Frz-Fc at 15 mg/kg/day, followed by subsequent doses of 10 mg/kg/day by intraperitoneal injection three times weekly. Each group had 13 mice and the average tumor volume for the group was 168 mm³ before the start of treatments. FIG. 28A is an exemplary procedural flow chart, while FIG. 28B is a graph plotting mean tumor volume over time, wherein the treatment days are indicated by arrows on the X-axis. FIG. 28C is a graph of mean tumor weight at sacrifice. The mice were sacrificed on day 58 after cell inoculation (day 32 after start of treatments) and tumors were excised and weighed. The mean tumor weight ±SEM is plotted as a function of the group. FIGS. 28D and 28E are tabular summaries of mean tumor volume and mean % change in tumor volume, respectively.

Example 11

Wnt Signaling in Mice Transplanted with MMTV Tumors and Treated with Frz8-Fc and Frz5-Fc Wnt Antagonists Effect of Frz8-Fc and Frz5-Fc Wnt Antagonists on Wnt Signaling Frz5-Fz inhibits Wnt3a induced signaling as effectively as Frz8-Fc.

Figure 29:
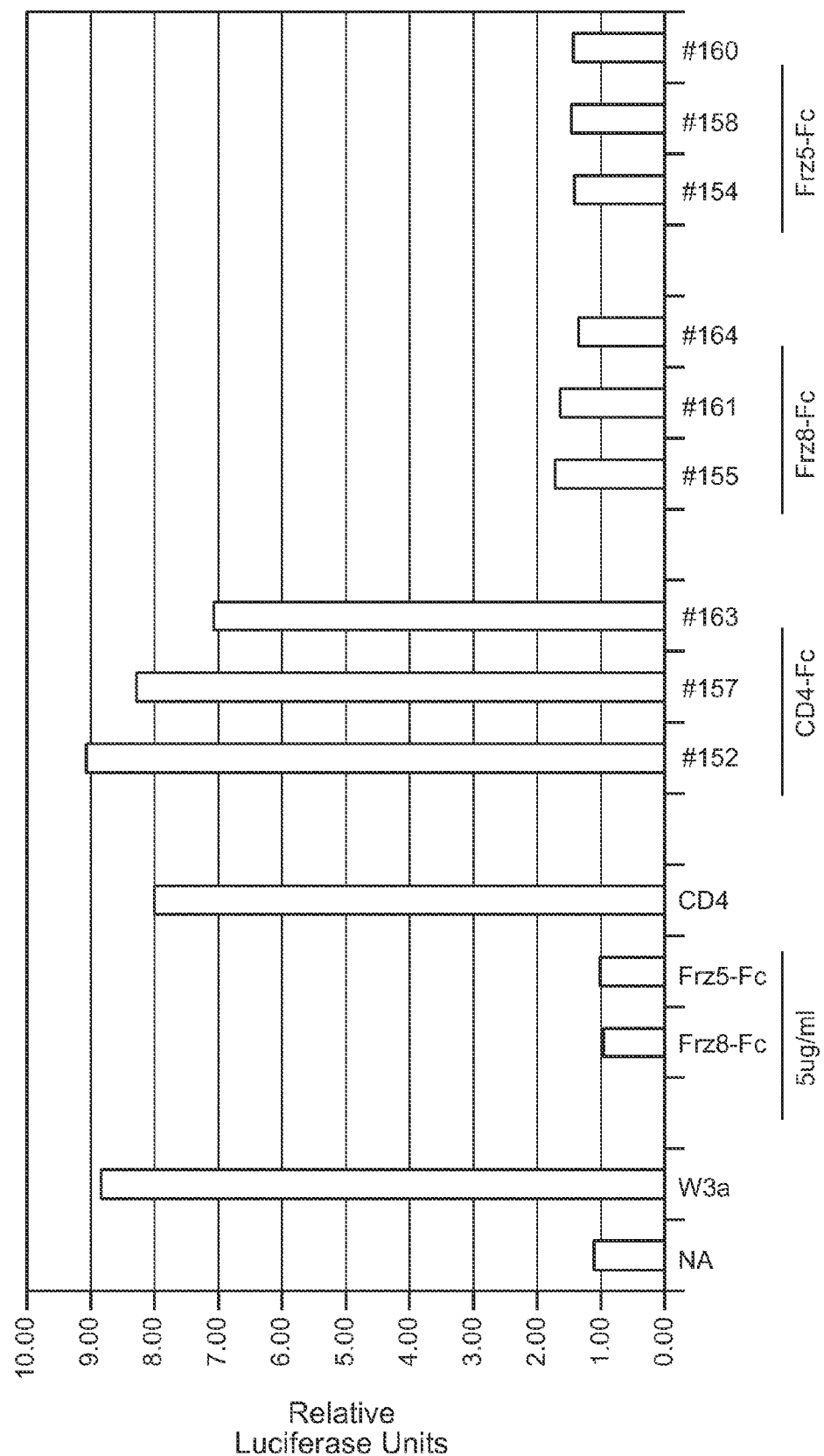
FIG. 29 shows Wnt signaling inhibition in mice treated with Frz8-Fc or Frz5-Fz as determined by the TOPglow assay. The Y-axis shows relative luciferase activity (Y-axis) from the TOPglow assay for the controls and Frz8-Fc and Frz5-Fc Wnt antagonists.

Athymic nude mice with MMTV tumors (approximately 400-800 cubic millimeters in size) were treated with Frz8-Fc, Frz5-Fz, or CD4-Fc, as a negative control, at 10 mg/kg. Five hours after treatment, serum was collected by cardiac puncture from the mice and analyzed for Wnt inhibiting effect on 293 cells activated with Wnt3a and transfected with TOPglow as described in Example 7. All samples are treated with ~40 ng/ml purified Wnt3a except for NA (control). All other protein controls are present in the medium at 5 µg/ml. FIG. 29 shows the level of inhibition in mice treated with Frz8-Fc or Frz5-Fz. Treatment with Frz8-Fc or Frz5-Fz resulted in similar levels of inhibition of Wnt 3a induced signaling.

Effect of Frz8-Fc and Frz5-Fc Wnt Antagonists on Axin2 Expression

Frz8-Fc and Frz5-Fz compounds inhibit in vivo Wnt signaling as determined by modulation of the Wnt target gene Axin2.

Figure 30A:
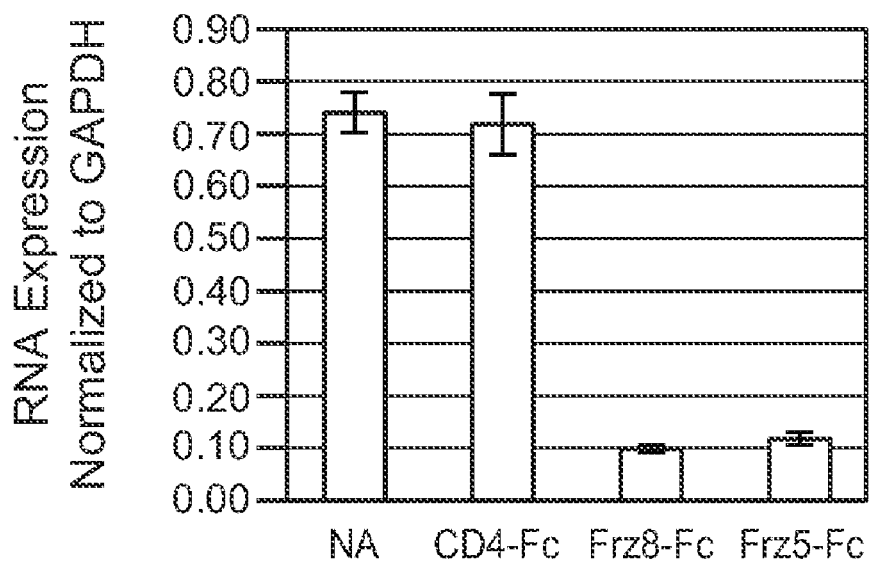
FIG. 30 shows the reduced Axin2 expression in Frz8-Fc and Frz5-Fz treated tumor with FIG. 30A showing expression normalized to expression of GAPDH and FIG. 30B showing expression normalized to expression of rpl19.
Figure 30B:
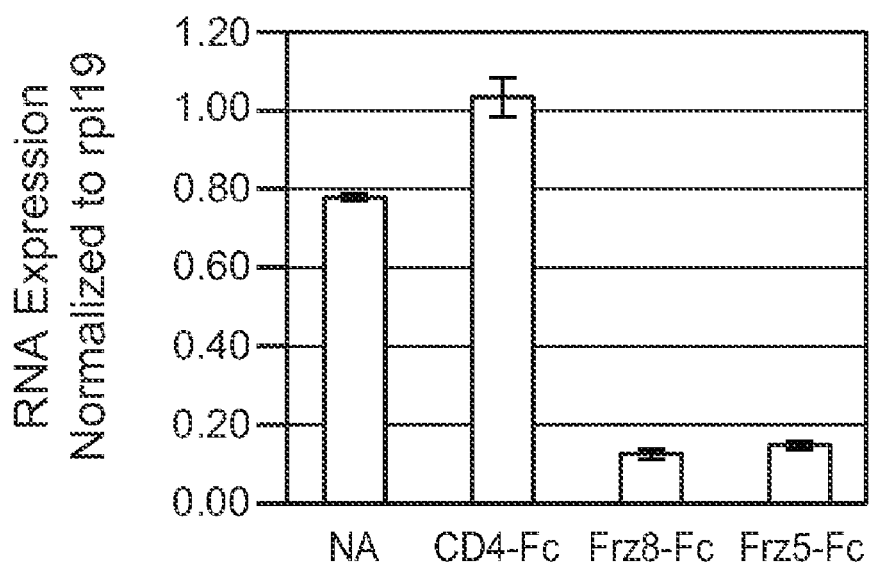

Athymic nude mice with MMTV tumors (approximately 400-800 cubic millimeters in size) were treated with Frz8-Fc, Frz5-Fz, or CD4-Fc, as a negative control, at 10 mg/kg. Five hours after treatment, serum was collected by cardiac puncture from the mice. RNA was extracted from the tumor cells using the QIAGEN RNAEASY kit (Qiagen, Valencia, Calif.) and analyzed for expression of Axin2 as described in Example 9. Reduced levels of Axin2 was observed in samples obtained from mice treated with Frz8-Fc or Frz5-Fz indicating that these compounds are able to inhibit in vivo Wnt signaling. FIG. 30 shows the reduced Axin2 expression in Frz8-Fc and Frz5-Fz treated tumor with FIG. 30A showing expression normalized to expression of GAPDH and FIG. 30B showing expression normalized to expression of rpl19.

Example 12

Regenerative Tissue Treated with Wnt Antagonist

Figures 1, 31B:
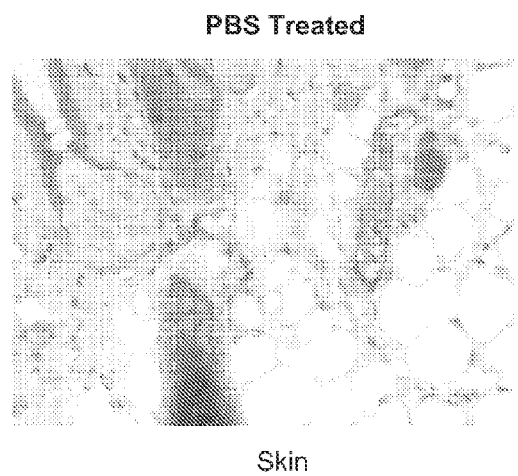
FIG. 31B shows IHC for β-catenin in skin of PBS (B-1) control protein (B-2) and Frz8-Fc (B-3) treated mice.
Figures 2, 31B:
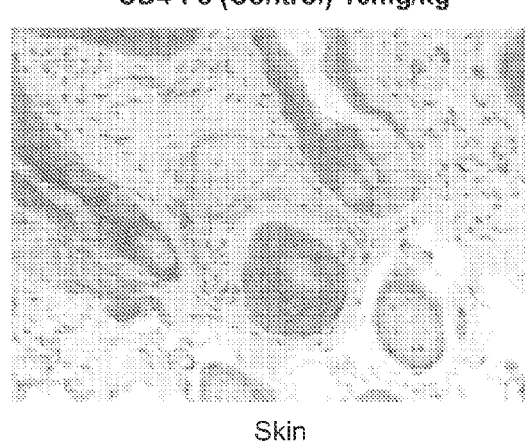
Figures 3, 31B:
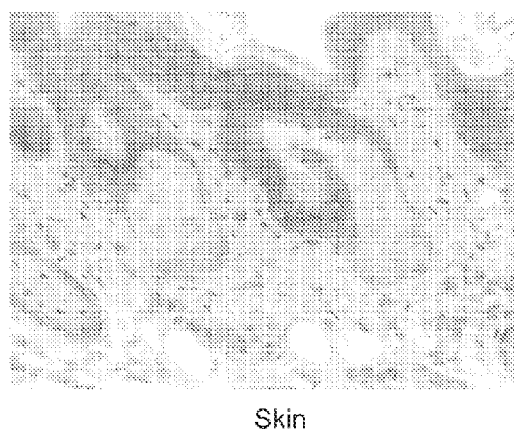
Figures 1, 32A:
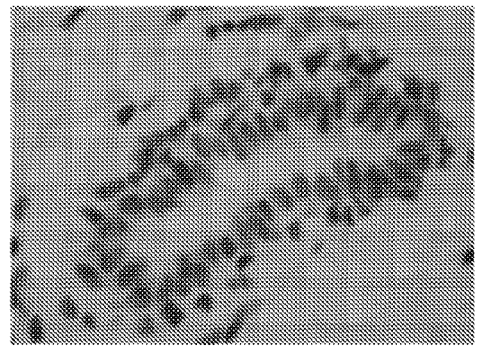
FIG. 32A shows Wnt-1 expression (as shown by in vitro hybridization) in normal (A-1), low grade (A-2) and high grade (A-3) human breast tumor initially reported in Wong et al., J. Pathol. 196: 145 (2002).
Figures 2, 32A:
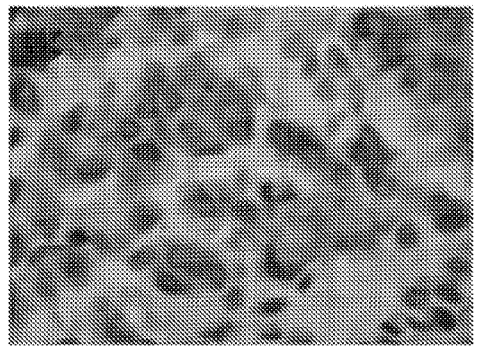
Figures 3, 32A:
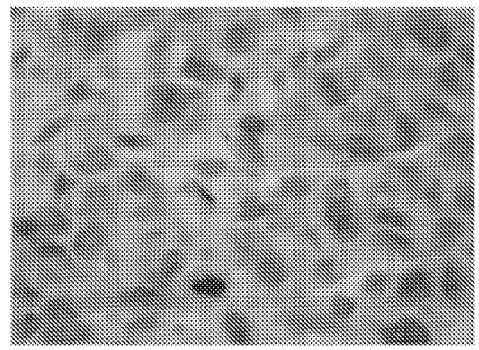
Figures 1, 32B:
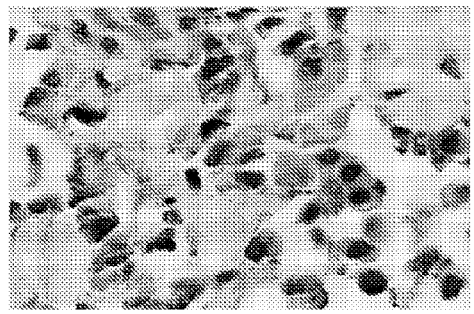
FIG. 32B shows nuclear (B-1) and cytoplasmic (B-2) localization (as shown by IHC) of β-catenin in breast cancer patients. Also shown is a Kaplan-Meier survival plot (B-3) showing patient survival probability that correlates with the indicated β-catenin expression pattern. This data was initially reported in Lin et al., P.N.A.S. (USA) 97(8): 4262-66 (2000).
Figures 2, 32B:
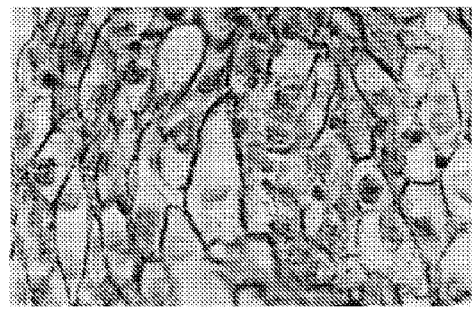
Figures 3, 32B:
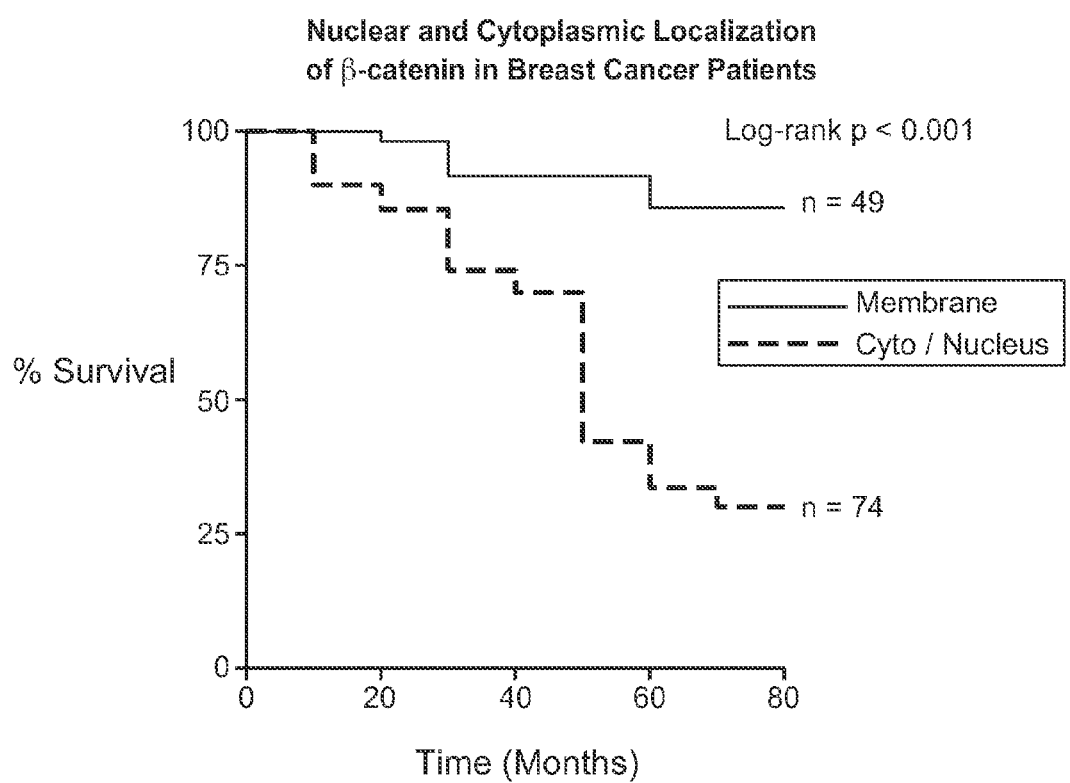
Figure 32C:
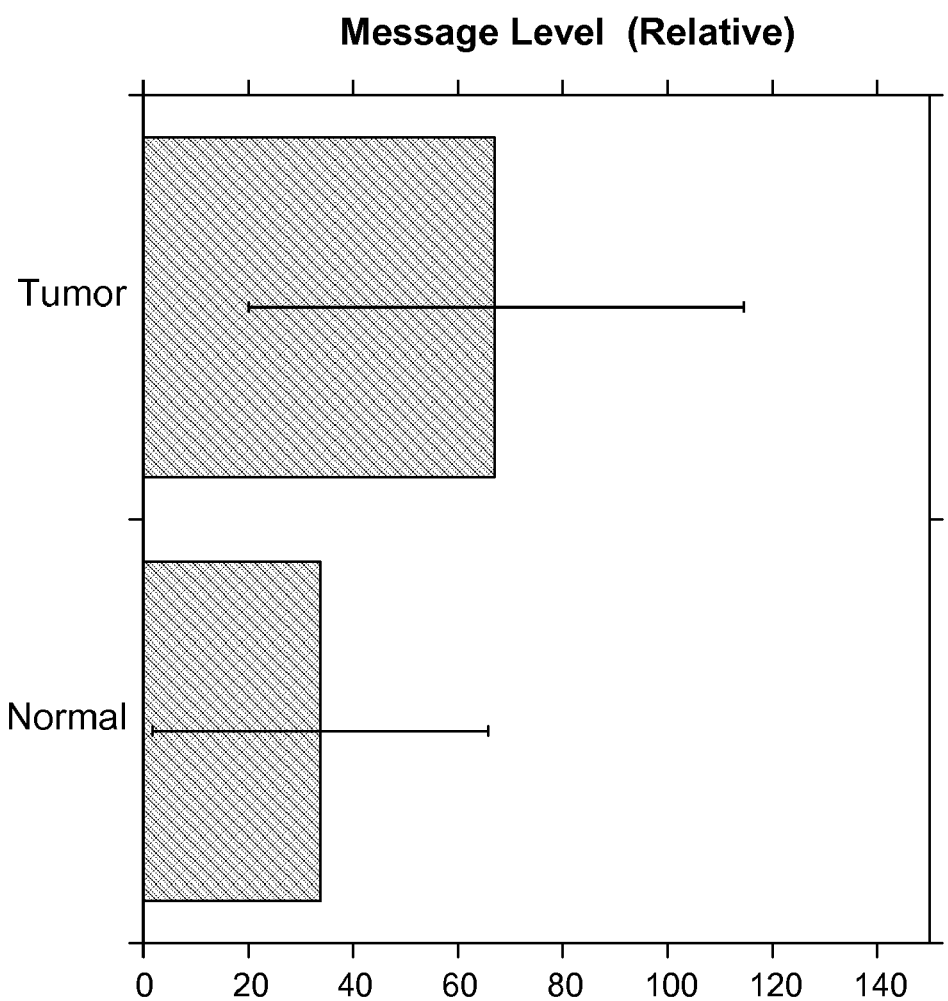
FIG. 32C is a graphical representation of a microarray analysis of Wnt-1 expression in a normal breast from a patient without cancer in comparison with tissue isolated from a patient with infiltrating ductal carcinoma, her-2 negative.

Wnt signaling plays a critical role in self-renewal of regenerating tissue such as skin, intestine, and hematopoietic cells, and inhibition of Wnt signaling by Dkk1 can adversely affect the architecture of these tissues in adult mice. The following Example examines whether exposure to Frz8-Fc under the same conditions used to obtain antitumor efficacy had any effect on intestine and skin in the mice. Tissues were collected from mice that were treated in the MMTV-Wnt1 tumor model (described in Example 10) after 14 treatments, thrice a week, and sections were stained for β-catenin protein by immunohistochemistry. Analysis of skin and various intestinal compartments revealed that the architecture of these tissues appeared morphologically normal in treated mice of all groups, with typical patterns of cytoplasmic and nuclear B-catenin staining in intestinal Paneth cells (FIG. 31A) and skin hair follicles (FIG. 31B). Furthermore, histologic and immunohistochemical analysis of skin and intestine collected from animals using the NTera-2 model, after nine treatments, thrice a week also revealed no differences between control and treated groups. This suggests that treatment with Frz8-Fc with the therapeutic regimen that can inhibit tumor growth does not have adverse effects on tissue renewal of skin and intestine.

Example 13

This Example describes various methods of producing the Wnt antagonists.
Expression of Wnt Antagonist in *E. coli*
This example illustrates preparation of an unglycosylated form of Wnt antagonist by recombinant expression in *E. coli*.

The DNA sequence encoding Wnt antagonist is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al, *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the Wnt antagonist coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized Wnt antagonist protein can then be purified using a metal chelating column under conditions that allow tight binding of the protein.

Wnt antagonist may be expressed in *E. coli* in a poly-His tagged form, using the following procedure. The DNA encoding Wnt antagonist is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. Coli* host based on strain 52 (W3110 fuhA (tonA) lon galE rpoHts (htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate.2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. Coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentrifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded Wnt antagonist polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Expression of Wnt Antagonist in Mammalian Cells

This example illustrates preparation of a potentially glycosylated form of Wnt antagonist by recombinant expression in mammalian cells.

The vector, pRK5 (see EP 307,247, published Mar. 15, 1989), is employed as the expression vector. Optionally, the Wnt antagonist DNA is ligated into pRK5 with selected restriction enzymes to allow insertion of the Wnt antagonist DNA using ligation methods such as described in Sambrook et al, supra. For purposes of this example, the resulting vector is referred to as pRK5-WA.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-WA DNA is mixed with about 1 μg DNA encoding the VA RNA gene [Thimmappaya et al., Cell, 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of Wnt antagonist polypeptide. The cultures containing transfected cells may undergo further incubation (in serum free medium) and the medium is tested in selected bioassays.

In an alternative technique, Wnt antagonist may be introduced into 293 cells transiently using the dextran sulfate method described by Somparyrac et al, Proc. Natl. Acad. Sci., 12:7575 (1981). 293 cells are grown to maximal density in a spinner flask and 700 μg pRK5-WA DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed Wnt antagonist can then be concentrated and purified by any selected method, such as dialysis and/or column chromatography.

In another embodiment, Wnt antagonist can be expressed in CHO cells. The pRK5-WA can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of Wnt antagonist polypeptide, the culture medium may be replaced with serum free medium. Preferably, the cultures are incubated for about 6 days, and then the conditioned medium is harvested. The medium containing the expressed Wnt antagonist can then be concentrated and purified by any selected method.

Epitope-tagged Wnt antagonist may also be expressed in host CHO cells. The Wnt antagonist may be subcloned out of the pRK5 vector. The subclone insert can undergo PCR to fuse in frame with a selected epitope tag such as a poly-his tag into a Baculovirus expression vector. The poly-his tagged Wnt antagonist insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged Wnt antagonist can then be concentrated and purified by any selected method, such as by $Ni^{2+}$-chelate affinity chromatography.

Wnt antagonist may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., Current Protocols of Molecular Biology, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., Nucl. Acids Res. 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents SUPERFECTt®

(Quiagen), DOSPER® or FUGENE® (Boehringer Mannheim). The cells are grown as described in Lucas et al., supra. Approximately $3 \times 10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/mL. On day 0, the cell number pH is determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Expression of Wnt Antagonist in Yeast

The following method describes recombinant expression of Wnt antagonist in yeast.

First, yeast expression vectors are constructed for intracellular production or secretion of Wnt antagonist from the ADH2/GAPDH promoter. DNA encoding Wnt antagonist and the promoter is inserted into suitable restriction enzyme sites in the selected plasmid to direct intracellular expression of Wnt antagonist. For secretion, DNA encoding Wnt antagonist can be cloned into the selected plasmid, together with DNA encoding the ADH2/GAPDH promoter, a native Wnt antagonist signal peptide or other mammalian signal peptide, or, for example, a yeast alpha-factor or invertase secretory signal/leader sequence, and linker sequences (if needed) for expression of Wnt antagonist.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant Wnt antagonist can subsequently be isolated and purified by removing the yeast cells from the fermentation medium by centrifugation and then concentrating the medium using selected cartridge filters. The concentrate containing Wnt antagonist may further be purified using selected column chromatography resins.

Expression of Wnt Antagonist in Baculovirus-Infected Insect Cells

The following method describes recombinant expression of Wnt antagonist in Baculovirus-infected insect cells.

The sequence coding for Wnt antagonist is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding Wnt antagonist or the desired portion of the coding sequence of Wnt antagonist such as the sequence encoding an extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BACULOGOLD™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al, *Baculovirus expression vectors: A Laboratory Manual*, Oxford: Oxford University Press (1994).

Expressed poly-his tagged Wnt antagonist can then be purified, for example, by $Ni^{2+}$-chelate affinity chromatography as follows. Extracts are prepared from recombinant virus-infected Sf9 cells as described by Rupert et al, *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged Wnt antagonist are pooled and dialyzed against loading buffer.

Alternatively, purification of the IgG tagged (or Fc tagged) Wnt antagonist can be performed using known chromatography techniques, including for instance, Protein A or protein G column chromatography.

Purification of Wnt Antagonist Polypeptides Using Affinity Chromatography

Native or recombinant Wnt Antagonist polypeptides may be purified by a variety of standard techniques in the art of protein purification. For example, pro-, mature, or pre-Wnt antagonist polypeptide is purified by immunoaffinity chromatography using antibodies specific for the Wnt antagonist polypeptide of interest. In general, an immunoaffinity column is constructed by covalently coupling the Wnt antagonist polypeptide to an activated chromatographic resin. Alternatively, Wnt antagonist which contain an Fc domain may be purified directly from media using a immobilized protein A resin such as ProSepA (Millipore).

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column may be utilized in the purification of Wnt antagonist polypeptide by preparing a fraction from cells containing Wnt antagonist in a soluble form. This preparation is derived by solubilization of the whole cell or of a subcellular fraction obtained via differential centrifugation by the addition of detergent or by other methods well known in the art. Alternatively, soluble Wnt antagonist polypeptide containing a signal sequence may be secreted in useful quantity into the medium in which the cells are grown.

A soluble Wnt antagonist polypeptide-containing preparation is passed over the immunoaffinity column, and the column is washed under conditions that allow the preferential absorbance of Wnt antagonist polypeptide (e.g., high ionic strength buffers in the presence of detergent). Then, the column is eluted under conditions that disrupt antibody/Wnt antagonist binding (e.g., a low pH buffer such as approximately pH 2-3, or a high concentration of a chaotrope such as urea or thiocyanate ion), and Wnt antagonist polypeptide is collected.

BIBLIOGRAPHY

1. He T C, Sparks A B, Rago C, et al. Identification of c-MYC as a target of the APC pathway. *Science* 1998; 281: 1509-1512.
2. Tetsu O, McCormick F. Beta-catenin regulates expression of cyclin D1 in colon carcinoma cells. *Nature* 1999; 398: 422-426
3. He T C, Chan T A, Vogelstein B, Kinzler K W. PPAR delta is an APC-regulated target of nonsteroidal anti-inflammatory drugs. *Cell* 1999; 99: 335-345.
4. Koh T J, Bulitta C J, Fleming J V, Dockray G J, Varro A, Wang T C. Gastrin is a target of the beta-catenin/TCF-4 growth-signaling pathway in a model of intestinal polyposis. *J Clin Invest* 2000; 106: 533-539.
5. Sanson O J, Reed K R, Hayes A J, et al. Loss of Apc in vivo immediately perturbs Wnt signaling, differentiation, and migration. *Genes Dev* 2004; 18: 1385-1390.
6. Chen T A, Yang I, Irby R, et al. Regulation of caspase expression and apoptosis by adenomatous polyposis coli. *Cancer Res* 2003; 63: 4368-4374.
7. Paoni N F, Feldman M W, Gutierrez L S, Ploplis V A, Castellino F J. Transcriptional profiling of the transition from normal intestinal epithelia to adenomas and carcinomas in the APC (Min/+) mouse. *Physiol Genomics* 2003; 15: 228-235.
8. Zhang T, Otevrel T, Gao Z Q, et al. Evidence that APC regulates survivin expression: a possible mechanism contributing to the stem cell origin of colon cancer. *Cancer Res* 2001; 61: 8664-8667.
9. Howe L R, Subbaramaiah K, Chung W J, Dannenberg A J, Brown A M C. Transcriptional activation of cyclooxygenase-2 in Wnt-1-transformed mouse mammary epithelial cells. *Cancer Res* 1999; 59: 1572-1577.
10. Mann B, Gelos M, Siedow A, et al. Target genes of beta-catenin-T Cell-factor lymphoid-enhancer-factor signaling in human colorectal carcinomas. *Proc Natl Acad Sci USA* 1999; 96: 1603-1608
11. Miwa N, Furuse M, Tsukita S, Niikawa N, Nakamura Y, Furukawa Y. Involvement of claudin-1 in the beta-catenin/Tcf signaling pathway and its frequent upregulation in human colorectal cancers. *Oncol Res* 2001; 12: 469-476.
12. Wielenga V J M, Smits R, Korinek V, et al. Expression of CD44 in Apc and Tcf mutant mice implies regulation by the WNT pathway. *Am J Pathol* 1999; 154: 515-523
13. Boon E M J, van der Neut R, van de Wetering M, Clevers H, Pals S T. Wnt signaling regulates expression of the receptor tyrosine kinase Met in colorectal cancer. *Cancer Res* 2002; 62: 5126-5128.
14. Kim J S, Crooks H, Dracheva T, et al. Oncogenic beta-catenin is required for bone morphogenetic protein 4 expression in human cancer cells. *Cancer Res* 2002; 62: 2744-2748.
15. Leow C C, Romero M S, Ross S, Polakis P, Gao W Q. Hath1, down-regulated in colon adenocarcinomas, inhibits proliferation and tumorigenesis of colon cancer cells. *Cancer Res* 2004; 64: 6050-6057.
16. Batlle E, Henderson J T, Beghtel H, et al. Beta-catenin and TCF mediate cell positioning in the intestinal epithelium by controlling the expression of EphB/EphrinB. *Cell* 2002; 111: 251-263.
17. Blanche P, van de Wetering M, Duluc I, et al. SOX9 is an intestine crypt transcription factor, is regulated by the Wnt pathway, and represses the CDX2 and MUC2 genes. *J Cell Biol* 2004; 166: 37-47.
18. Zhang X B, Gaspard J P, Chung D C. Regulation of vascular endothelial growth factor by the Wnt and K-ras pathways in colonic neoplasia. *Cancer Res* 2001; 61: 6050-6054.
19. DeAlmeida, V L., Miao L, Ernst J A, Koeppen H., Polakis P., Rubinfeld, B, The soluble Wnt receptor Frizzled8CRD-hFc inhibits the growth of teratocarcinomas in vivo, *Cancer Res* 2007; 67: 5371-5379.

The invention claimed is:

1. A Wnt antagonist comprising:
   (a) a Frizzled domain component,
   (b) a Fc domain, and
   (c) a linker component connecting the Frizzled domain component and Fc domain,
   wherein the Frizzled domain component comprises a polypeptide consisting of the minimal CRD (ECD) domain from hFrz8 (SEQ ID NO: 25) or a polypeptide that is at least 95% identical to the minimal CRD (ECD) domain from hFrz8 (SEQ ID NO: 25), and
further wherein the Wnt antagonist is active in vivo for at least 1 hour.

2. The Wnt antagonist of claim 1, wherein the Wnt antagonist is active in vivo for at least 5 hours.

3. The Wnt antagonist of claim 1, wherein the Fc component is selected from the group consisting of an IgG1 domain, IgG2 domain, IgG3 domain and IgG4 domain.

4. The Wnt antagonist of claim 3, wherein the Fc is an IgG1.

5. A Wnt antagonist comprising:
(a) a Frizzled domain component,
(b) a Fc domain, and
(c) a linker component,
wherein the Frizzled domain component consists of the minimal CRD (ECD) domain from hFrz8 (SEQ ID NO: 25) or a polypeptide that is at least 95% identical to the minimal CRD (ECD) domain from hFrz8 (SEQ ID NO: 25), and
further wherein the Wnt antagonist has an in vivo half-life of at least 1 day.

6. The Wnt antagonist of claim 5, wherein the Wnt antagonist has an in vivo half-life of at least 2 days.

7. A composition comprising at least one pharmaceutically acceptable carrier or excipient and the Wnt antagonist of claim 1.

8. A composition comprising at least one pharmaceutically acceptable carrier or excipient and the Wnt antagonist of claim 5.

9. The Wnt antagonist of claim 1, wherein the linker comprises the peptide LESGGGGVT (SEQ ID NO: 72).

10. The Wnt antagonist of claim 5, wherein the linker comprises the peptide LESGGGGVT (SEQ ID NO: 72).

11. A Wnt antagonist comprising an Frz8-Fc polypeptide consisting of the amino acid sequence of SEQ ID NO: 74.

12. A Wnt antagonist comprising an Frz8-Fc polypeptide consisting of a polypeptide that is at least 95% identical to the amino acid sequence of SEQ ID NO: 74,
wherein the Wnt antagonist is active in vivo for at least 1 hour.

13. A Wnt antagonist comprising an Frz8-Fc polypeptide consisting of a polypeptide that is at least 95% identical to the amino acid sequence of SEQ ID NO: 74,
wherein the Wnt antagonist has an in vivo half-life of at least 1 day.

* * * * *